(12) United States Patent
Heil et al.

(10) Patent No.: US 10,559,756 B2
(45) Date of Patent: Feb. 11, 2020

(54) MATERIALS FOR ELECTRONIC DEVICES

(71) Applicant: Merck Patent GmbH, Darmstadt (DE)

(72) Inventors: Holger Heil, Frankfurt am Main (DE);
Lara-Isabel Rodriguez, Darmstadt (DE); Beate Burkhart, Darmstadt (DE); Amandine Darsy, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 383 days.

(21) Appl. No.: 15/029,067

(22) PCT Filed: Apr. 29, 2014

(86) PCT No.: PCT/EP2014/001148
§ 371 (c)(1),
(2) Date: Apr. 13, 2016

(87) PCT Pub. No.: WO2014/111269
PCT Pub. Date: Jul. 24, 2014

(65) Prior Publication Data
US 2016/0254456 A1 Sep. 1, 2016

(30) Foreign Application Priority Data

Oct. 14, 2013 (EP) .................................... 13004921

(51) Int. Cl.
| | | |
|---|---|---|
| *H01L 51/00* | (2006.01) | |
| *C07C 1/30* | (2006.01) | |
| *C07C 211/61* | (2006.01) | |
| *C07C 255/52* | (2006.01) | |
| *C07C 13/62* | (2006.01) | |
| *C07C 22/08* | (2006.01) | |
| *C07C 25/22* | (2006.01) | |
| *C07C 13/72* | (2006.01) | |
| *C07C 17/20* | (2006.01) | |
| *C07C 209/10* | (2006.01) | |
| *C07C 253/14* | (2006.01) | |
| *C07C 255/51* | (2006.01) | |
| *C07D 209/80* | (2006.01) | |
| *C07D 209/86* | (2006.01) | |
| *C07D 213/06* | (2006.01) | |
| *C07D 307/77* | (2006.01) | |
| *C07D 307/91* | (2006.01) | |
| *C07D 311/78* | (2006.01) | |
| *C07F 7/08* | (2006.01) | |

(Continued)

(52) U.S. Cl.
CPC ............ *H01L 51/0056* (2013.01); *C07C 1/30* (2013.01); *C07C 13/62* (2013.01); *C07C 13/72* (2013.01); *C07C 17/206* (2013.01); *C07C 22/08* (2013.01); *C07C 25/22* (2013.01); *C07C 209/10* (2013.01); *C07C 211/61* (2013.01); *C07C 253/14* (2013.01); *C07C 255/51* (2013.01); *C07C 255/52* (2013.01); *C07D 209/80* (2013.01); *C07D 209/86* (2013.01); *C07D 213/06* (2013.01); *C07D 307/77* (2013.01); *C07D 307/91* (2013.01); *C07D 311/78* (2013.01); *C07F 7/083* (2013.01); *C07F 7/0807* (2013.01); *C09K 11/06* (2013.01); *H01L 51/006* (2013.01); *H01L 51/0058* (2013.01); *H01L 51/0061* (2013.01); *H01L 51/0067* (2013.01); *H01L 51/0072* (2013.01); *H01L 51/0073* (2013.01); *H01L 51/0094* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1088* (2013.01); *C09K 2211/1096* (2013.01); *H01L 51/0071* (2013.01); *H01L 51/5012* (2013.01)

(58) Field of Classification Search
CPC ....... H01L 51/0056; C07C 1/30; C07C 13/62; C07C 13/72; C07C 17/206; C07C 17/263; C07C 22/08; C07C 25/22; C07C 209/10
USPC .......................................................... 428/690
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 8,786,181 B2 | 7/2014 | Eberle et al. | |

(Continued)

FOREIGN PATENT DOCUMENTS

| | | |
|---|---|---|
| CN | 101460434 A | 6/2009 |
| CN | 101939279 A | 1/2011 |

(Continued)

OTHER PUBLICATIONS

Murayama et al., Synthesis of Triphenylene Derivatives by Rhodium-Catalyzed [2+2+2] Cycloaddition: Application to the Synthesis of Highly Fluorescent Triphenylene-Based Long Ladder Molecules, Journal of Organic Chemistry, vol./Issue 78, pp. 6202-6210, May 23, 2013.*

(Continued)

*Primary Examiner* — Jayne L Mershon
(74) *Attorney, Agent, or Firm* — Kim IP Law Group PLLC

(57) ABSTRACT

The invention relates to compounds with benzindenofluorene base bodies having a structure of formula (I):

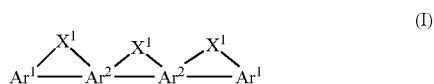

and to the use thereof in electronic devices, in particular in organic electroluminescent devices.

15 Claims, No Drawings

(51) Int. Cl.
    C09K 11/06    (2006.01)
    H01L 51/50    (2006.01)

(56) References Cited

U.S. PATENT DOCUMENTS

| | | | |
|---|---|---|---|
| 8,932,732 B2 | 1/2015 | Buesing et al. | |
| 8,993,123 B2 | 3/2015 | Buesing et al. | |
| 9,051,233 B2 | 6/2015 | Buesing et al. | |
| 2009/0066225 A1 | 3/2009 | Kimura et al. | |
| 2009/0261717 A1* | 10/2009 | Buesing ............ | C07C 13/62 313/504 |
| 2011/0114889 A1* | 5/2011 | Buesing ............ | C07C 13/62 252/301.16 |

FOREIGN PATENT DOCUMENTS

| | | |
|---|---|---|
| CN | 103228759 A | 7/2013 |
| JP | 2011529455 A | 12/2011 |
| KR | 2008/0109000 A | 12/2008 |
| WO | 2006100896 A1 | 9/2006 |
| WO | 2008022633 A2 | 2/2008 |

OTHER PUBLICATIONS

Gao et al., Conjugated Ladder-Type Heterocenes Bearing Pyrrole and Thiophene Ring Units: Facile Synthesis and Characterization, Journal of Organic Chemistry, vol./Issue 73, pp. 9207-9213 (Year: 2008).*

Murayama et al., "Synthesis of Triphenylene Derivatives by Rhodium-Catalyzed [2+2+2] Cycloaddition: Application to the Synthesis of Highly Fluorescent Triphenylene-Based Long Ladder Molecules", The Journal of Organic Chemistry, 2013, vol. 78, Issue 12, pp. 6202-6210.

Jacob et al., "Ladder-Type Pentaphenylenes and Their Polymers: Efficient Blue-Light Emitters and Electron-Accepting Materials via a Common Intermediate", Journal of the American Chemical Society, 2004, vol. 126, Issue 22, pp. 6987-6995.

Japanese Office Action for Japanese Application No. 2016-522757, dated Sep. 26, 2017, 6 pages.

Cocherel et al., "New 3π-2Spiro Ladder-Type Phenylene Materials: Synthesis, Physicochemical Properties and Applications in OLEDs", Chemical: A European Journal, 2008, vol. 14, pp. 11328-11342.

Poriel et al., "Incorporation of Spiroxanthene Units in Blue-Emitting Oligophenylene Frameworks: A New Molecular Design for OLED Applications", Chemical: A European Journal, 2011, vol. 17, pp. 12631-12645.

Jiang et al., "Bent Ladder-Type Hexaphenylene with Carbazole Core and Spiro Linkage as Stable and efficient Blue Emitter", Organic Letters, 2009, vol. 11, No. 18, pp. 4132-4135.

Database CA [Online], CAS, Kim et al., XP002684350; Accession No. 2012:893981; Jan. 5, 2011.

Database CA [Online], CAS Wang et al; XP002729020; Database accession No. 2012:350021; Jun. 20, 2012.

English Translation of Chinese Office Action for Chinese Application No. 201480055307.X, dated Apr. 28, 2017, 10 pages.

* cited by examiner

MATERIALS FOR ELECTRONIC DEVICES

RELATED APPLICATIONS

This application is a national stage entry, filed pursuant to 35 U.S.C. § 371, of PCT/EP2014/001148, filed Apr. 29, 2014, which claims the benefit of European Patent Application No. 13004921.6, filed Oct. 14, 2013, which is incorporated herein by reference in its entirety.

The present application relates to a compound of the formula (I) below and to the use thereof in electronic devices, in particular in organic electronic devices (OLEDs). The invention furthermore relates to certain embodiments of electronic devices comprising the compound of the formula (I), and to a process for the preparation of the compound of the formula (I).

In accordance with the present invention, the term electronic device is generally taken to mean electronic devices which comprise organic materials. It is preferably taken to mean OLEDs.

The general structure and functional principle of OLEDs are known to the person skilled in the art and are described, inter alia, in U.S. Pat. Nos. 4,539,507, 5,151,629, EP 0676461 and WO 1998/27136.

Further improvements are necessary with respect to the performance data of the electronic devices, in particular in view of broad commercial use, for example in displays or as light sources. Of particular importance in this connection are the lifetime, the efficiency and the operating voltage of the electronic devices and the colour values achieved. In particular in the case of blue-emitting OLEDs, there is potential for improvement with respect to the lifetime of the devices and the colour values achieved of the emitted light.

An important starting point for achieving the said improvements is the choice of the emitting compound employed in the electronic device. In the prior art, a multiplicity of compounds, in particular arylamines having an indenofluorene basic structure, are described as compounds which emit blue light. Examples thereof are benzindenofluorenamines, for example in accordance with WO 2008/006449 and WO 2007/140847.

As compounds for the emitting layer which do not emit light (matrix compounds), the prior art discloses, inter alia, anthracene compounds, as described, for example, in WO 2008/145239 and WO 2009/100925. Furthermore, benzindenofluorene compounds are described for this use, for example in the above-mentioned applications WO 2008/006449 and WO 2007/140847.

The prior art likewise describes, inter alia, compounds having an indenofluorene basic structure as compounds for use in hole-transporting or hole-injecting layers, for example in WO 2006/108497, WO 2006/122630, and WO 2009/141026.

However, there continues to be a demand for novel compounds for use in electronic devices. In particular, there is a demand for compounds with which excellent performance data for the electronic devices can be achieved. A particularly low operating voltage, long lifetime, high power efficiency and suitable colour coordinates of the emitted light should be emphasised here.

In investigations of novel compounds for use in electronic devices, it has now been found, unexpectedly, that compounds of a formula (I) having a bisindenofluorene basic structure are highly suitable for use in electronic devices.

These compounds preferably have one or more properties selected from low operating voltage, long lifetime, high power efficiency and suitable colour coordinates of the emitted light. In particular, they enable, on use in the emitting layer, an excellent lifetime to be achieved in combination with deep-blue colour coordinates of the emitted light.

The invention thus relates to a compound of a formula (I)

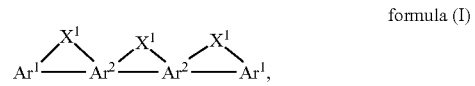

formula (I)

where:

Ar$^1$ is on each occurrence, identically or differently, an aryl or heteroaryl group having 6 to 18 aromatic ring atoms, which may be substituted by one or more radicals R$^1$;

Ar$^2$ is on each occurrence, identically or differently, an aryl or heteroaryl group having 6 aromatic ring atoms, which may be substituted by one or more radicals R$^2$;

X$^1$ is on each occurrence, identically or differently, BR$^3$, C(R$^3$)$_2$, —C(R$^3$)$_2$—C(R$^3$)$_2$—, —C(R$^3$)$_2$—O—, —C(R$^3$)$_2$—S—, —R$^3$C=CR$^3$—, —R$^3$C=N—, Si(R$^3$)$_2$, —Si(R$^3$)$_2$—Si(R$^3$)$_2$—, C=O, O, S, S=O, SO$_2$, NR$^3$, PR$^3$ or P(=O)R$^3$;

R$^1$, R$^2$, R$^3$ are on each occurrence, identically or differently, H, D, F, Cl, Br, I, C(=O)R$^4$, CN, Si(R$^4$)$_3$, N(R$^4$)$_2$, P(=O)(R$^4$)$_2$, OR$^4$, S(=O)R$^4$, S(=O)$_2$R$^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^4$ and where one or more CH$_2$ groups in the above-mentioned groups may be replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO or SO$_2$, or an aromatic or heteroaromatic ring system having 5 to 30 aromatic ring atoms, which may in each case be substituted by one or more radicals R$^4$, where two or more radicals R$^3$ may be linked to one another and may form a ring;

R$^4$ is on each occurrence, identically or differently, H, D, F, Cl, Br, I, C(=O)R$^5$, CN, Si(R$^5$)$_3$, N(R$^5$)$_2$, P(=O)(R$^5$)$_2$, OR$^5$, S(=O)R$^5$, S(=O)$_2$R$^5$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^5$ and where one or more CH$_2$ groups in the above-mentioned groups may be replaced by —R$^5$C=CR$^5$—, —C≡C—, Si(R$^5$)$_2$, C=O, C=NR$^5$, —C(=O)O—, —C(=O)NR$^5$—, NR$^5$, P(=O)(R$^5$), —O—, —S—, SO or SO$_2$, or an aromatic or heteroaromatic ring system having 5 to 30 aromatic ring atoms, which may in each case be substituted by one or more radicals R$^5$, where two or more radicals R$^4$ may be linked to one another and may form a ring;

R$^5$ is on each occurrence, identically or differently, H, D, F or an aliphatic, aromatic or heteroaromatic organic radical having 1 to 20 C atoms, in which, in addition, one or more H atoms may be replaced by D or F; two or more substituents R$^5$ here may be linked to one another and may form a ring;

where at east one of the two groups Ar$^1$ must contain 10 or more aromatic ring atoms; and where, if one of the two groups Ar$^1$ is a phenyl group, the other of the two groups Ar$^1$ must not contain more than 14 aromatic ring atoms.

For the formula (I), the bonds to adjacent groups Ar$^1$ or Ar$^2$ and to groups X$^1$ may each be present at any desired positions of the groups Ar$^2$ or Ar$^1$ respectively. In particular, the depiction of the formula (I) does not imply that the groups X$^1$ must be present in the cis-position to one another. The groups X$^1$ can be present in the cis- or trans-position to one another.

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is intended for the purposes of the present application to be taken to mean, inter glia, that the two radicals are linked to one another by a chemical bond. Furthermore, however, the above-mentioned formulation is also intended to be taken to mean that, in the case where one of the two radicals represents hydrogen, the second radical is bonded to the position to which the hydrogen atom was bonded, with formation of a ring.

The bonds from the groups $Ar^2$ to the adjacent group $Ar^1$ or $Ar^2$ are preferably each present in the para-position to one another.

$Ar^1$ is preferably selected on each occurrence, identically or differently, from aryl groups or heteroaryl groups having 6 to 14 aromatic ring atoms, particularly preferably 6 to 10 aromatic ring atoms, where $Ar^1$ may in each case be substituted by one or more radicals $R^1$.

$Ar^1$ is preferably selected on each occurrence, identically or differently, from aryl groups having 6 to 14 aromatic ring atoms, particularly preferably 6 to 10 aromatic ring atoms, where $Ar^1$ may in each case be substituted by one or more radicals R.

The groups $Ar^2$ are preferably phenyl groups, which may be substituted by one or more radicals $R^2$.

According to a particularly preferred embodiment, the groups $Ar^1$ are naphthyl groups, which may be substituted by one or more radicals $R^1$, and the groups $Ar^2$ are phenyl groups, which may be substituted by one or more radicals $R^2$.

According to an alternative particularly preferred embodiment, one of the two groups $Ar^1$ is a phenyl group, which may be substituted by one or more radicals $R^1$, and the other of the two groups $Ar^1$ is a naphthyl group, which may be substituted by one or more radicals $R^1$, and the groups $Ar^2$ are phenyl groups, which may be substituted by one or more radicals $R^2$.

It is preferred for $X^1$ to be selected on each occurrence, identically or differently, from $C(R^3)_2$, $—C(R^3)_2—C(R^3)_2—$, $—C(R^3)_2—O—$, $—R^3C=CR^3—$, $Si(R^3)_2$, $C=O$, $O$, $S$, $S=O$, $SO_2$ and $NR^3$, particularly preferably $C(R^3)_2$, $—C(R^3)_2—C(R^3)_2—$, $—C(R^3)_2—O—$, $Si(R^3)_2$, $O$, $S$ and $NR^3$, very particularly preferably $C(R^3)_2$.

$R^1$ and $R^2$ are preferably on each occurrence, identically or differently, H, D, F, CN, $Si(R^4)_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more $CH_2$ groups in the above-mentioned groups may be replaced by $—C≡C—$, $—R^4C=CR^4—$, $Si(R^4)_2$, $C=O$, $—NR^4—$, $—O—$ or $—S—$, or an aromatic or heteroaromatic ring system having 5 to 20 aromatic ring atoms, which may in each case be substituted by one or more radicals $R^4$.

$R^2$ is particularly preferably equal to H or D, particularly preferably equal to H.

$R^3$ is preferably on each occurrence, identically or differently, F, CN, $Si(R^4)_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^4$ and where one or more $CH_2$ groups in the above-mentioned groups may be replaced by $—C≡C—$, $—R^4C=CR^4—$, $Si(R^4)_2$, $C=O$, $—NR^4—$, $—O—$ or $—S—$, or an aromatic or heteroaromatic ring system having 5 to 20 aromatic ring atoms, which may in each case be substituted by one or more radicals $R^4$, where two or more radicals $R^3$ may be linked to one another and may form a ring.

According to a preferred embodiment, two radicals $R^3$ which are a constituent of a group $X^1$ which represents $C(R^3)_2$ or $Si(R^3)_2$ form a ring with one another, so that a spiro compound is formed. A five- or six-membered ring is preferably formed here. Furthermore, it is preferred in this case for the radicals $R^3$ to represent alkyl groups, so that a spirocyclic alkyl ring is formed, particularly preferably a spirocyclohexane ring or a spirocyclopentane ring.

$R^4$ is preferably on each occurrence, identically or differently, F, CN, $Si(R^5)_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^5$ and where one or more $CH_2$ groups in the above-mentioned groups may be replaced by $—C≡C—$, $—R^5C=CR^5—$, $Si(R^5)_2$, $C=O$, $—NR^5—$, $—O—$ or $—S—$, or an aromatic or heteroaromatic ring system having 5 to 20 aromatic ring atoms, which may in each case be substituted by one or more radicals $R^5$, where two or more radicals $R^4$ may be linked to one another and may form a ring.

According to a preferred embodiment of the invention, all groups $R^1$ and $R^2$ in formula (I) are equal to H or D, particularly preferably equal to H.

According to a further preferred embodiment of the invention, one or more groups $R^1$ are equal to CN, particularly preferably precisely two groups $R^1$ are equal to CN.

According to a further preferred embodiment of the invention, one or more groups $R^1$ are equal to an aromatic or heteroaromatic ring system having 6 to 20 aromatic ring atoms, which may be substituted by one or more radicals $R^4$, particularly preferably precisely two groups $R^1$ are equal to an aromatic or heteroaromatic ring system having 6 to 20 aromatic ring atoms, which may be substituted by one or more radicals $R^4$.

According to a particularly preferred embodiment, $R^1$ is a benzindenofluorene group, particularly preferably a monobenzindenofluorene group, which may in each case be substituted by radicals $R^4$.

According to a further preferred embodiment of the invention, none of the groups $R^1$ and $R^2$ are groups of the formula $N(R^4)_2$. In this case, the groups $X^1$ are preferably not equal to $NR^3$, the groups $X^1$ are in this case particularly preferably equal to $C(R^3)_2$.

According to a further preferred embodiment of the invention, one or more groups $R^1$ are equal to $N(R^4)_2$, particularly preferably precisely two groups $R^1$ are equal to $N(R^4)_2$.

A preferred embodiment of the compound conforms to the formula (I-1)

formula (I-1)

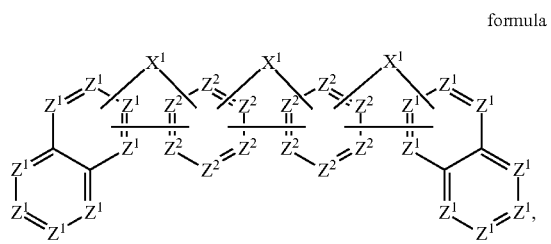

where:

$Z^1$ is on each occurrence, identically or differently, $CR^1$ or N, where $Z^1$ is equal to C if a group is bonded;

$Z^2$ is on each occurrence, identically or differently, $CR^2$ or N, where $Z^2$ is equal to C if a group is bonded; and the groups $X^1$ are defined as above.

An alternative preferred embodiment of the compound conforms to the formula (I-2)

formula (I-2)

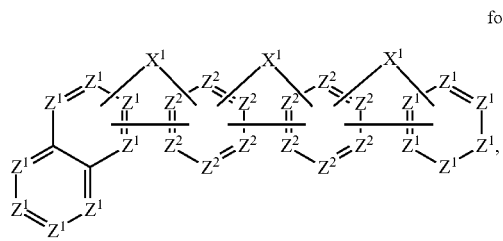

where:

$Z^1$ is on each occurrence, identically or differently, $CR^1$ or N, where $Z^1$ is equal to C if a group is bonded;

$Z^2$ is on each occurrence, identically or differently, $CR^2$ or N, where $Z^2$ is equal to C if a group is bonded; and the groups $X^1$ are defined as above.

For the formulae (I-1) and (I-2), the bonds to groups $X^1$ and the bonds between the aromatic rings may each be present at any desired positions of the aromatic rings, as can the bonds between the individual aromatic rings. In particular, the depiction of the formulae (I-1) and (I-2) does not imply that the groups $X^1$ must be present in the cis-position to one another. The groups $X^1$ can be present in the cis- or trans-position to one another.

It is preferred for a maximum of two groups $Z^1$ per aromatic ring to be equal to N, particularly preferably for a maximum of one group $Z^1$ per aromatic ring to be equal to N, and very particularly preferably for no group $Z^1$ in an aromatic ring to be equal to N.

It is generally preferred for $Z^1$ to be equal to $CR^1$.

It is preferred for a maximum of two groups $Z^2$ per aromatic ring to be equal to N, particularly preferably for a maximum of one group $Z^2$ per aromatic ring to be equal to N, and very particularly preferably for no group $Z^2$ in an aromatic ring to be equal to N.

It is generally preferred for $Z^2$ to be equal to $CR^2$.

Preferred embodiments of the formula (I-1) conform to the following formulae (I-1-1) to (I-1-11) and (I-2-1) to (I-2-8)

formula (I-1-1)

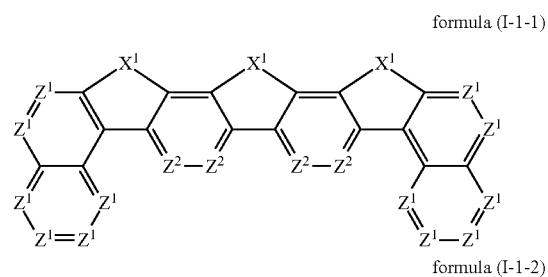

formula (I-1-2)

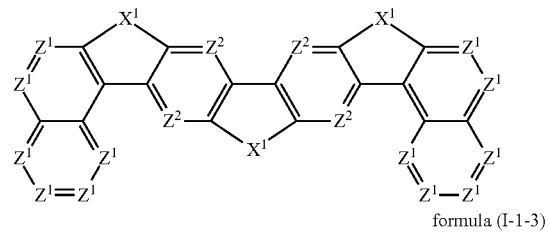

formula (I-1-3)

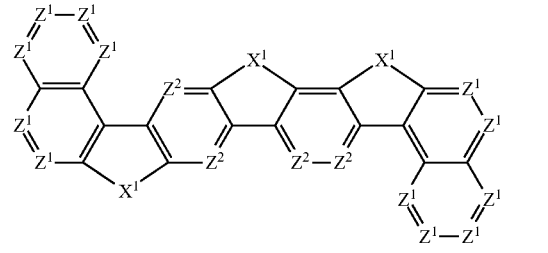

formula (I-1-4)

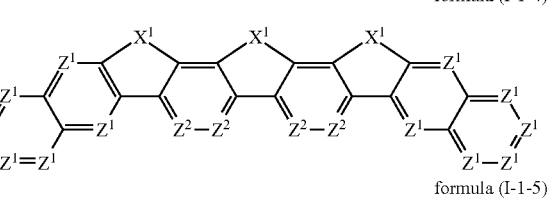

formula (I-1-5)

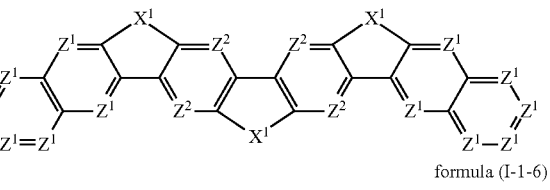

formula (I-1-6)

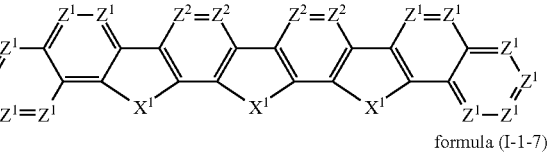

formula (I-1-7)

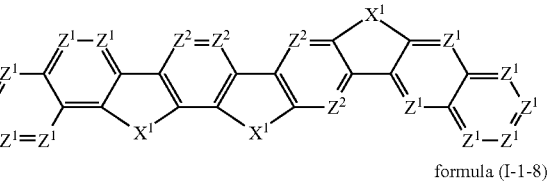

formula (I-1-8)

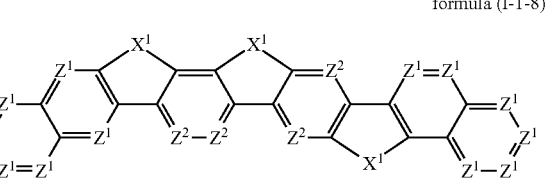

formula (I-1-9)
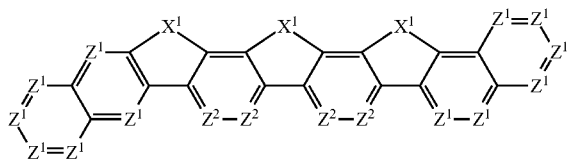

formula (I-1-10)
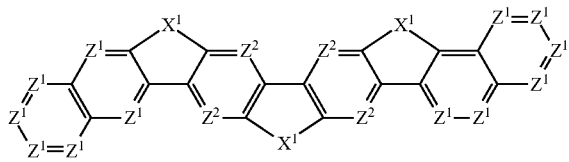

formula (I-1-11)
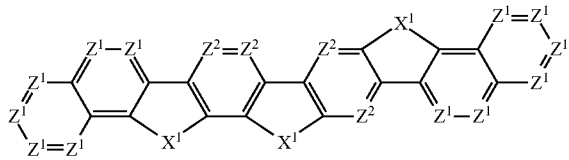

formula (I-2-1)
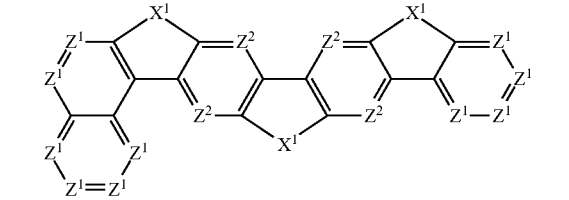

formula (I-2-2)
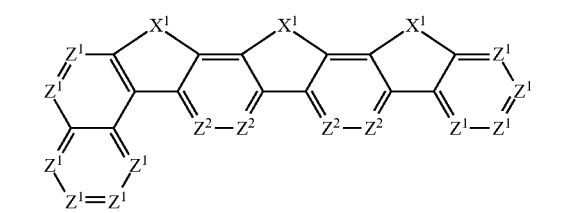

formula (I-2-3)
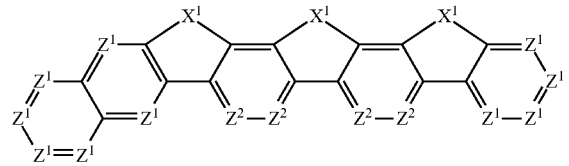

formula (I-2-4)
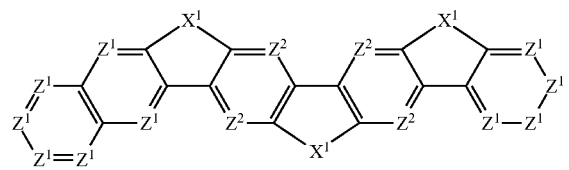

formula (I-2-5)
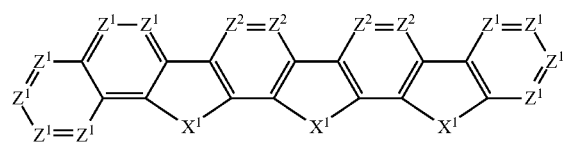

formula (I-2-6)
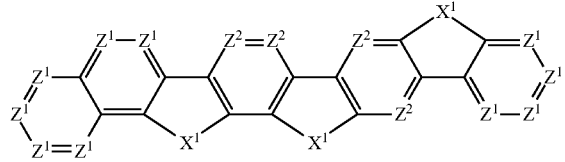

formula (I-2-7)
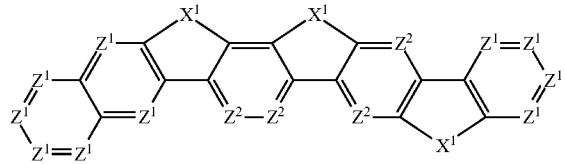

formula (I-2-8)
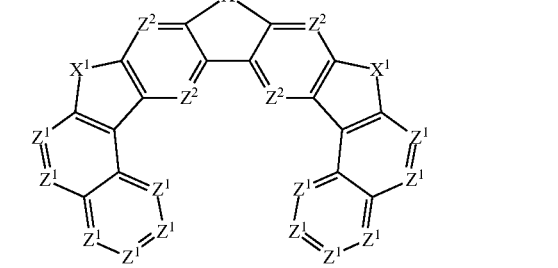

where:
$Z^1$ is on each occurrence, identically or differently, $CR^1$ or N;
$Z^2$ is on each occurrence, identically or differently, $CR^2$ or N; and
the groups $X^1$ are defined as above.

In particular for the groups $Z^1$, $Z^2$ and $X^1$, the preferred embodiments indicated above are also preferred for the above formulae.

It is again particularly preferred in the formulae (I-1-1) to (I-1-11) and (I-2-1) to (I-2-8) for $Z^1$ to be equal to $CR^1$, for $Z^2$ to be equal to $CR^2$, and for $X^1$ to be equal to $C(R^3)_2$.

Of the formulae (I-1-1) to (I-1-11) and (I-2-1) to (I-2-8) the formulae (I-1-2), (I-2-1) and (I-2-8) are particularly preferred, the formula (I-1-2) is most preferred.

Compounds of the formula (I) preferably conform to one of the formulae (I-1-2-1) and (I-2-1-1)

formula (I-1-2-1)
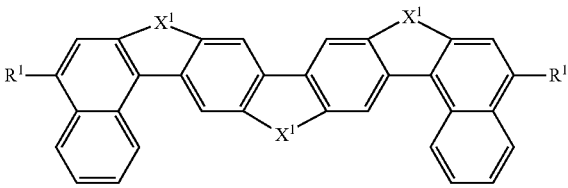

formula (I-2-1-1)
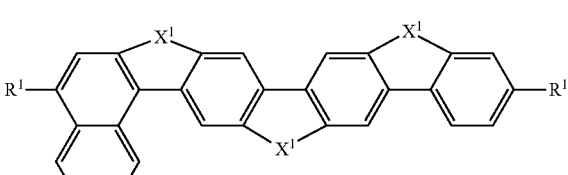

where $X^1$ and $R^1$ are as defined above.

$X^1$ in the formulae (I-1-2-1) and (I-2-1-1) is preferably selected on each occurrence, identically or differently, from $C(R^3)_2$, $-C(R^3)_2-C(R^3)_2-$, $-C(R^3)_2-O-$, $Si(R^3)_2$, O, S, and $NR^3$, $X^1$ is particularly preferably equal to $C(R^3)_2$.

$R^1$ in the formulae (I-1-2-1) and (I-2-1-1) is preferably on each occurrence, identically or differently, H, D, F, CN, $Si(R^4)_3$, or an aromatic or heteroaromatic ring system having 5 to 20 aromatic ring atoms, which may in each case be substituted by one or more radicals $R^4$.

According to a particularly preferred embodiment, $R^1$ in the formulae (I-1-2-1) and (I-2-1-1) is a benzindenofluorene group, particularly preferably a monobenzindenofluorene group, which may in each case be substituted by radicals $R^4$.

Very particularly preferred embodiments of the compounds of the formula (I) conform to the following formulae, where the following preferably applies: $Z^1$ is $CR^1$ and $Z^2$ is $CR^2$:

| | Basic structure of | $X^1$ (left) | $X^1$ (middle) | $X^1$ (right) |
|---|---|---|---|---|
| 1 | formula (i-1-1) | $C(R^3)_2$ | $C(R^3)_2$ | $C(R^3)_2$ |
| 2 | " | " | $-C(R^3)_2-C(R^3)_2-$ | " |
| 3 | " | " | $-C(R^3)_2-O-$ | " |
| 4 | " | " | $Si(R^3)_2$ | " |
| 5 | " | " | O | " |
| 6 | " | " | S | " |
| 7 | " | " | $NR^3$ | " |
| 8 | formula (i-1-2) | $C(R^3)_2$ | $C(R^3)_2$ | $C(R^3)_2$ |
| 9 | " | " | $-C(R^3)_2-C(R^3)_2-$ | " |
| 10 | " | " | $-C(R^3)_2-O-$ | " |
| 11 | " | " | $Si(R^3)_2$ | " |
| 12 | " | " | O | " |
| 13 | " | " | S | " |
| 14 | " | " | $NR^3$ | " |
| 15 | formula (i-1-3) | $C(R^3)_2$ | $C(R^3)_2$ | $C(R^3)_2$ |
| 16 | " | " | $-C(R^3)_2-C(R^3)_2-$ | " |
| 17 | " | " | $-C(R^3)_2-O-$ | " |
| 18 | " | " | $Si(R^3)_2$ | " |
| 19 | " | " | O | " |
| 20 | " | " | S | " |
| 21 | " | " | $NR^3$ | " |
| 22 | formula (i-1-4) | $C(R^3)_2$ | $C(R^3)_2$ | $C(R^3)_2$ |
| 23 | " | " | $-C(R^3)_2-C(R^3)_2-$ | " |
| 24 | " | " | $-C(R^3)_2-O-$ | " |
| 25 | " | " | $Si(R^3)_2$ | " |
| 26 | " | " | O | " |
| 27 | " | " | S | " |
| 28 | " | " | $NR^3$ | " |
| 29 | formula (i-1-5) | $C(R^3)_2$ | $C(R^3)_2$ | $C(R^3)_2$ |
| 30 | " | " | $-C(R^3)_2-C(R^3)_2-$ | " |
| 31 | " | " | $-C(R^3)_2-O-$ | " |
| 32 | " | " | $Si(R^3)_2$ | " |
| 33 | " | " | O | " |
| 34 | " | " | S | " |
| 35 | " | " | $NR^3$ | " |
| 36 | formula (i-1-6) | $C(R^3)_2$ | $C(R^3)_2$ | $C(R^3)_2$ |
| 37 | " | " | $-C(R^3)_2-C(R^3)_2-$ | " |
| 38 | " | " | $-C(R^3)_2-O-$ | " |
| 39 | " | " | $Si(R^3)_2$ | " |
| 40 | " | " | O | " |
| 41 | " | " | S | " |
| 42 | " | " | $NR^3$ | " |
| 43 | formula (i-1-7) | $C(R^3)_2$ | $C(R^3)_2$ | $C(R^3)_2$ |
| 44 | " | " | $-C(R^3)_2-C(R^3)_2-$ | " |
| 45 | " | " | $-C(R^3)_2-O-$ | " |
| 46 | " | " | $Si(R^3)_2$ | " |
| 47 | " | " | O | " |
| 48 | " | " | S | " |
| 49 | " | " | $NR^3$ | " |
| 50 | formula (i-1-8) | $C(R^3)_2$ | $C(R^3)_2$ | $C(R^3)_2$ |
| 51 | " | " | $-C(R^3)_2-C(R^3)_2-$ | " |
| 52 | " | " | $-C(R^3)_2-O-$ | " |
| 53 | " | " | $Si(R^3)_2$ | " |
| 54 | " | " | O | " |
| 55 | " | " | S | " |
| 56 | " | " | $NR^3$ | " |
| 57 | formula (i-1-9) | $C(R^3)_2$ | $C(R^3)_2$ | $C(R^3)2$ |
| 58 | " | " | $-C(R^3)_2-C(R^3)_2-$ | " |
| 59 | " | " | $-C(R^3)_2-O-$ | " |
| 60 | " | " | $Si(R^3)_2$ | " |
| 61 | " | " | O | " |
| 62 | " | " | S | " |
| 63 | " | " | $NR^3$ | " |
| 64 | formula (i-1-10) | $C(R^3)_2$ | $C(R^3)_2$ | $C(R^3)_2$ |
| 65 | " | " | $-C(R^3)_2-C(R^3)_2-$ | " |
| 66 | " | " | $-C(R^3)_2-O-$ | " |
| 67 | " | " | $Si(R^3)_2$ | " |
| 68 | " | " | O | " |
| 69 | " | " | S | " |
| 70 | " | " | $NR^3$ | " |
| 71 | formula (i-1-11) | $C(R^3)_2$ | $C(R^3)_2$ | $C(R^3)_2$ |
| 72 | " | " | $-C(R^3)_2-C(R^3)_2-$ | " |
| 73 | " | " | $-C(R^3)_2-O-$ | " |
| 74 | " | " | $Si(R^3)_2$ | " |
| 75 | " | " | O | " |
| 76 | " | " | S | " |
| 77 | " | " | $NR^3$ | " |
| 78 | formula (i-2-1) | $C(R^3)_2$ | $C(R^3)_2$ | $C(R^3)_2$ |
| 79 | " | " | $-C(R^3)_2-C(R^3)_2-$ | " |
| 80 | " | " | $-C(R^3)_2-O-$ | " |
| 81 | " | " | $Si(R^3)_2$ | " |
| 82 | " | " | O | " |
| 83 | " | " | S | " |
| 84 | " | " | $NR^3$ | " |
| 85 | formula (i-2-2) | $C(R^3)_2$ | $C(R^3)_2$ | $C(R^3)_2$ |
| 86 | " | " | $-C(R^3)_2-C(R^3)_2-$ | " |
| 87 | " | " | $-C(R^3)_2-O-$ | " |
| 88 | " | " | $Si(R^3)_2$ | " |
| 89 | " | " | O | " |
| 90 | " | " | S | " |
| 91 | " | " | $NR^3$ | " |
| 92 | formula (i-2-3) | $C(R^3)_2$ | $C(R^3)_2$ | $C(R^3)_2$ |
| 93 | " | " | $-C(R^3)_2-C(R^3)_2-$ | " |
| 94 | " | " | $-C(R^3)_2-O-$ | " |
| 95 | " | " | $Si(R^3)_2$ | " |
| 96 | " | " | O | " |
| 97 | " | " | S | " |
| 98 | " | " | $NR^3$ | " |
| 99 | formula (i-2-4) | $C(R^3)_2$ | $C(R^3)_2$ | $C(R^3)_2$ |
| 100 | " | " | $-C(R^3)_2-C(R^3)_2-$ | " |
| 101 | " | " | $-C(R^3)_2-O-$ | " |
| 102 | " | " | $Si(R^3)_2$ | " |
| 103 | " | " | O | " |
| 104 | " | " | S | " |
| 105 | " | " | $NR^3$ | " |
| 106 | formula (i-2-5) | $C(R^3)_2$ | $C(R^3)_2$ | $C(R^3)_2$ |
| 107 | " | " | $-C(R^3)_2-C(R^3)_2-$ | " |
| 108 | " | " | $-C(R^3)_2-O-$ | " |
| 109 | " | " | $Si(R^3)_2$ | " |
| 110 | " | " | O | " |
| 111 | " | " | S | " |
| 112 | " | " | $NR^3$ | " |
| 113 | formula (i-2-6) | $C(R^3)_2$ | $C(R^3)_2$ | $C(R^3)_2$ |
| 114 | " | " | $-C(R^3)_2-C(R^3)_2-$ | " |
| 115 | " | " | $-C(R^3)_2-O-$ | " |
| 116 | " | " | $Si(R^3)_2$ | " |
| 117 | " | " | O | " |
| 118 | " | " | S | " |
| 119 | " | " | $NR^3$ | " |
| 120 | formula (i-2-7) | $C(R^3)_2$ | $C(R^3)_2$ | $C(R^3)_2$ |
| 121 | " | " | $-C(R^3)_2-C(R^3)_2-$ | " |
| 122 | " | " | $-C(R^3)_2-O-$ | " |
| 123 | " | " | $Si(R^3)_2$ | " |
| 124 | " | " | O | " |
| 125 | " | " | S | " |
| 126 | " | " | $NR^3$ | " |
| 127 | formula (i-2-8) | $C(R^3)_2$ | $C(R^3)_2$ | $C(R^3)_2$ |
| 128 | " | " | $-C(R^3)_2-C(R^3)_2-$ | " |
| 129 | " | " | $-C(R^3)_2-O-$ | " |
| 130 | " | " | $Si(R^3)_2$ | " |
| 131 | " | " | O | " |
| 132 | " | " | S | " |
| 133 | " | " | $NR^3$ | " |

The following compounds are examples of compounds of the formula (I):

1
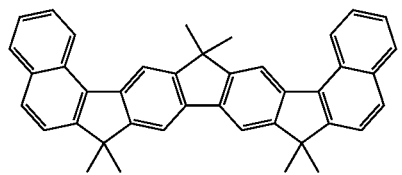
2
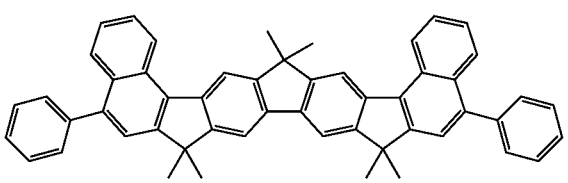
3
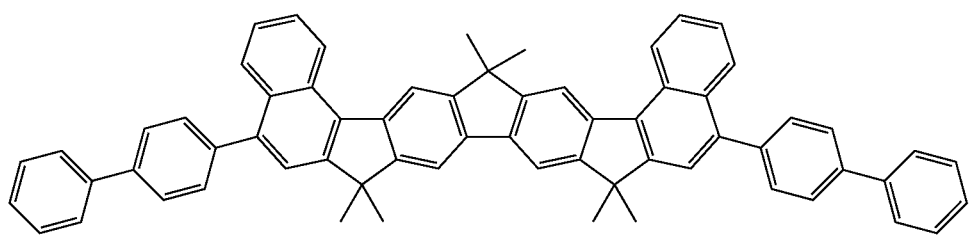
4
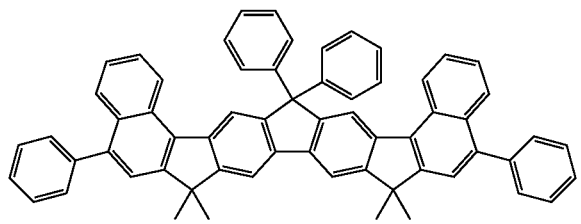
5
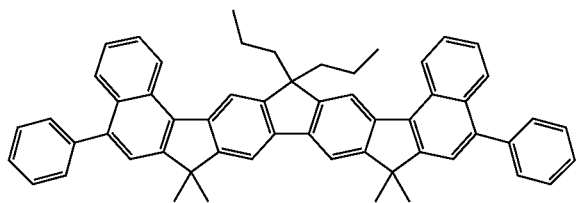
6
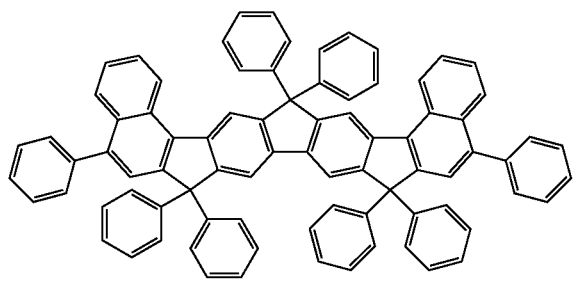
7
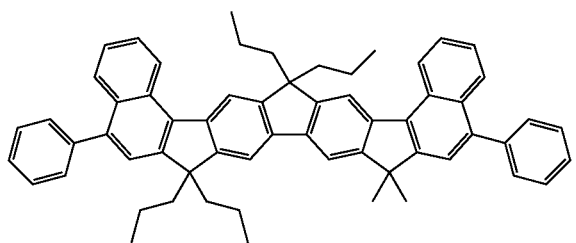
8
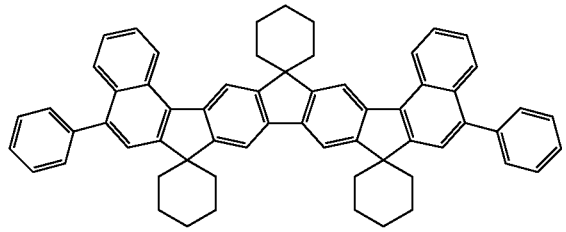
9
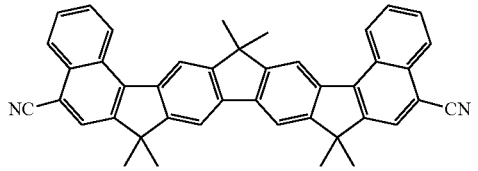
10
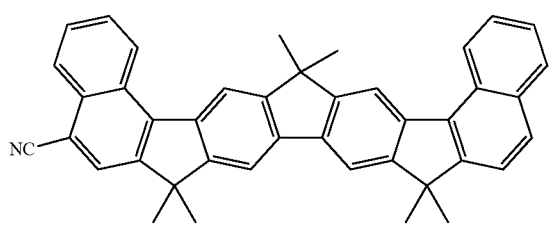

11
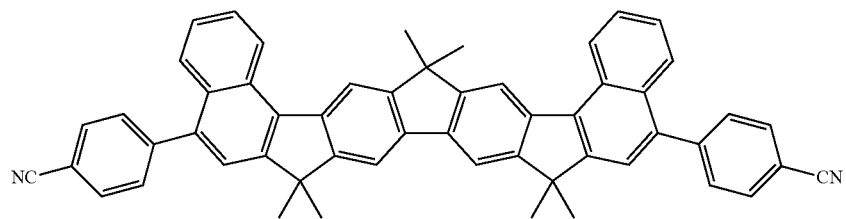
12
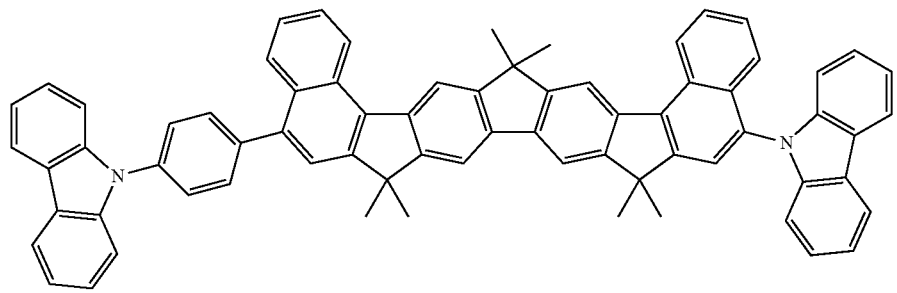
13
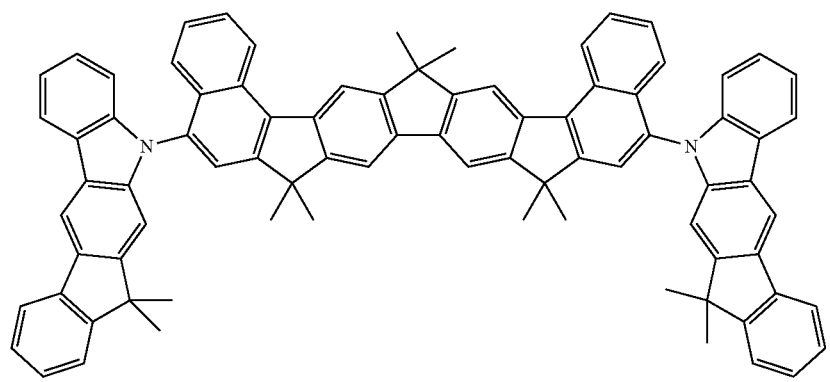
14
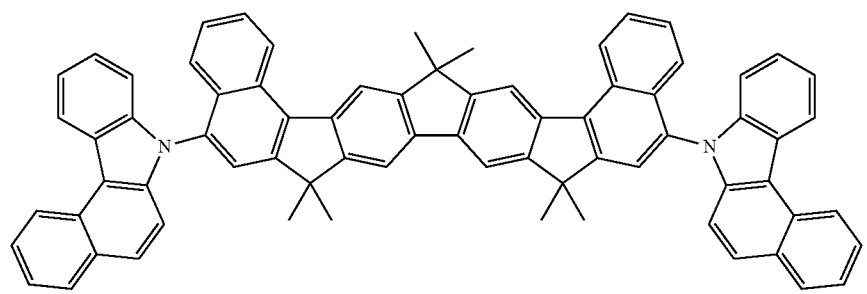
15
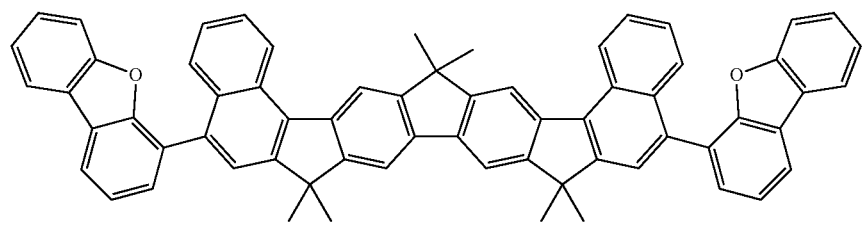
16
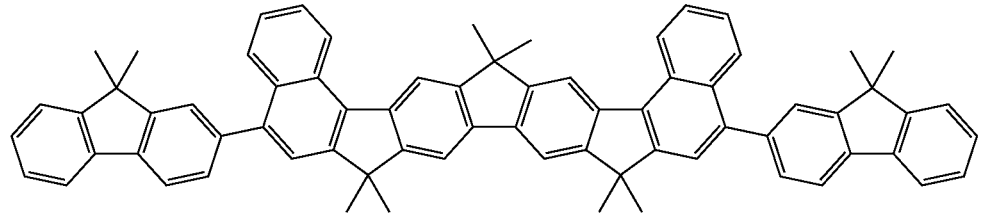

17
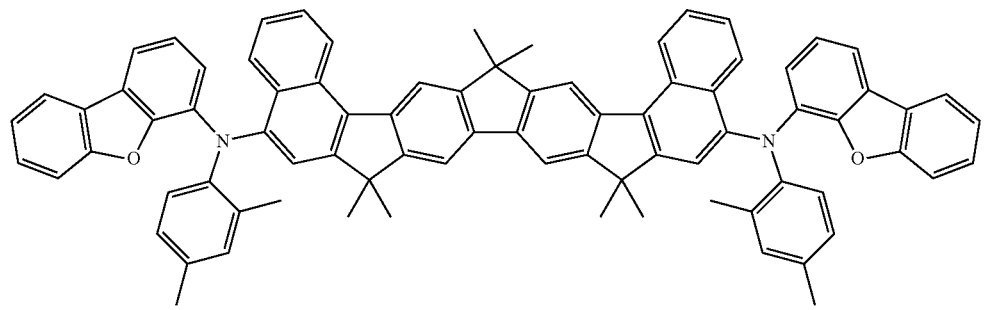
18
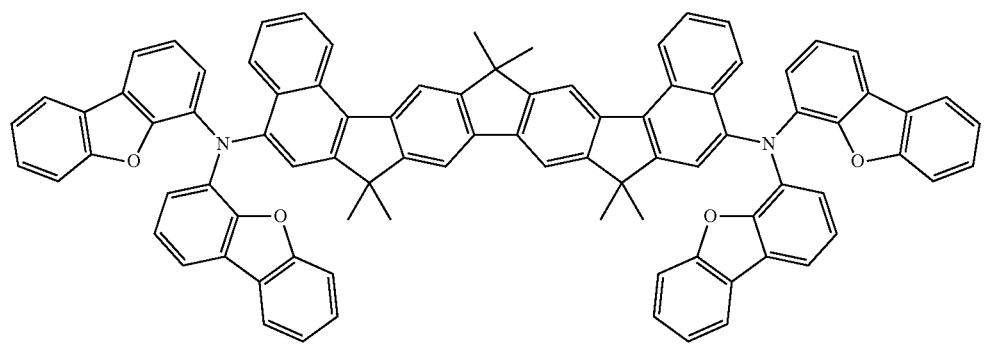
19
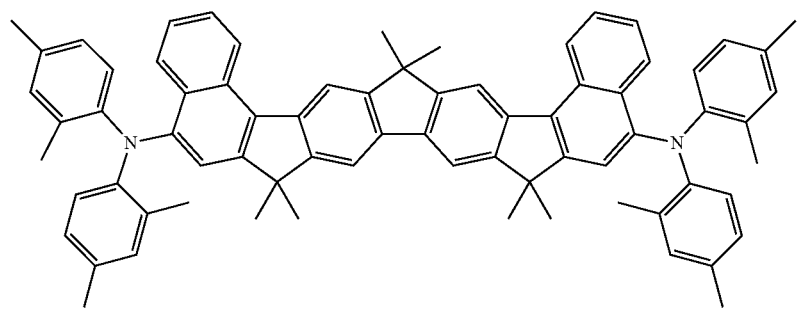
20
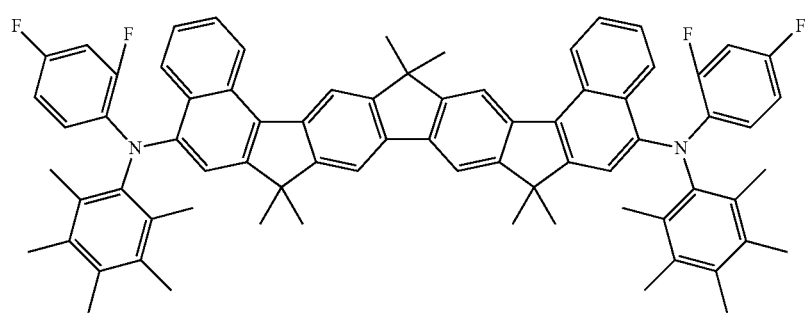
21
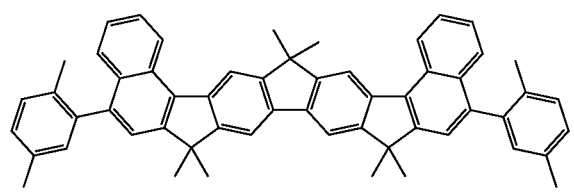
22
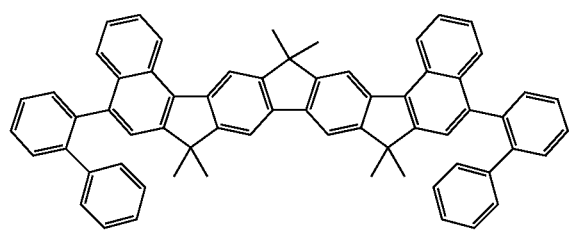

-continued
23
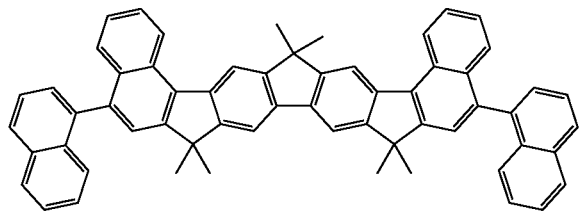
24
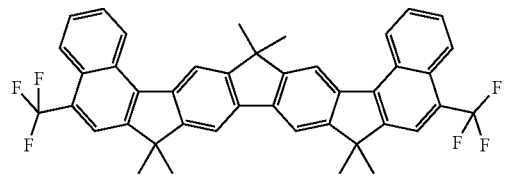
25
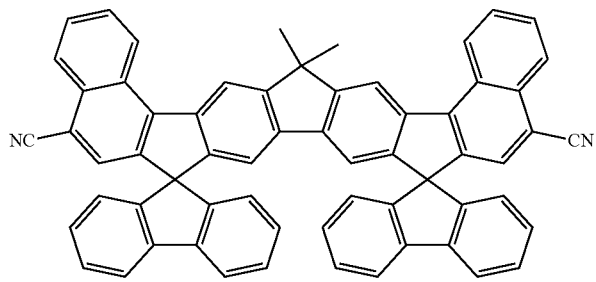
26
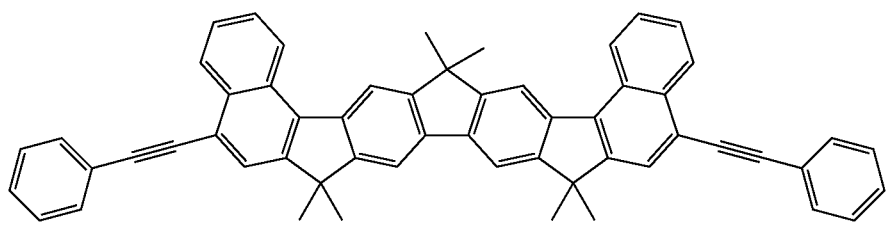
27
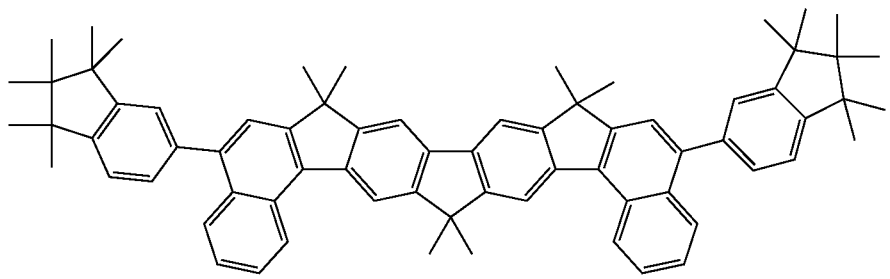
28
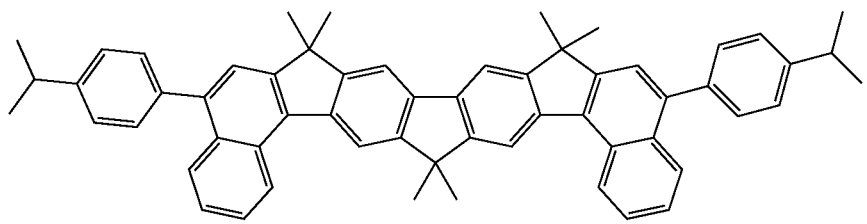
29
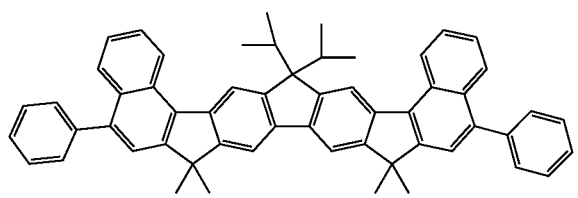
30
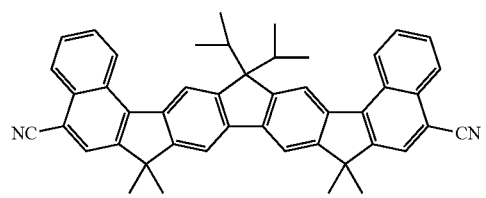

-continued
31
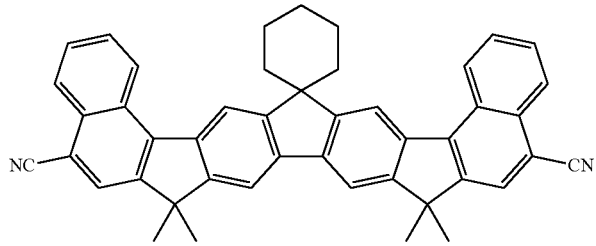
32
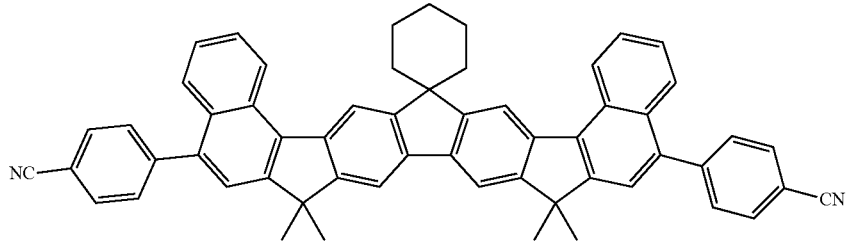
33
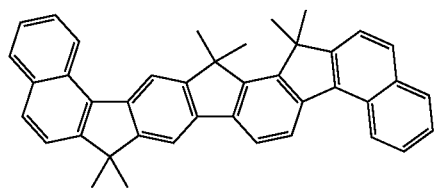
34
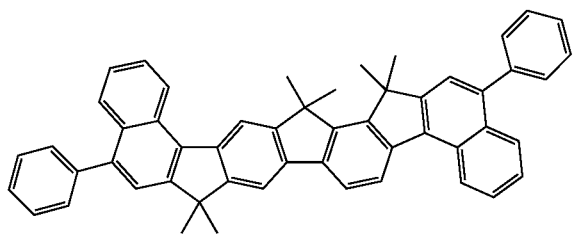
35
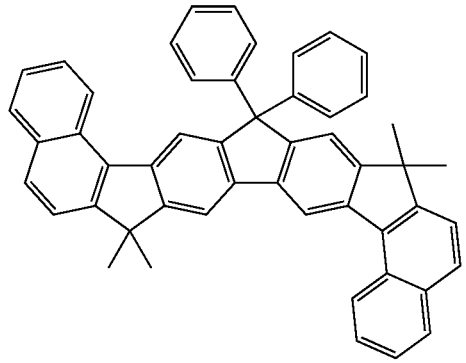
36
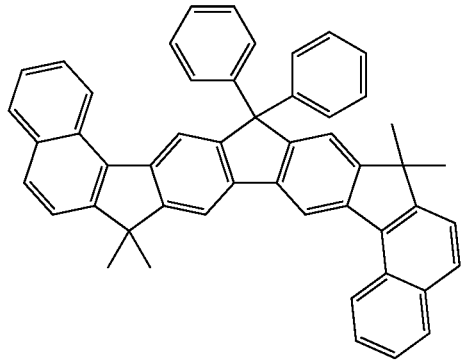
37
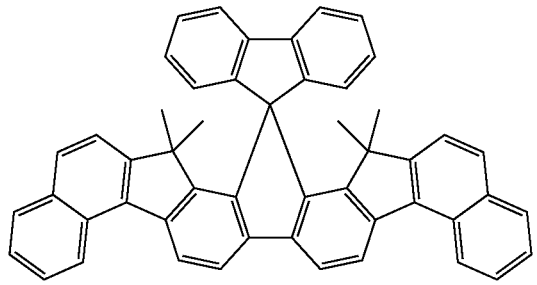
38
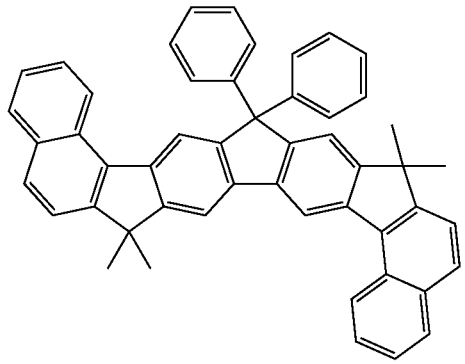

-continued
39
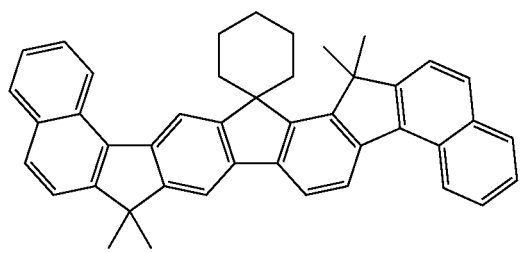
40
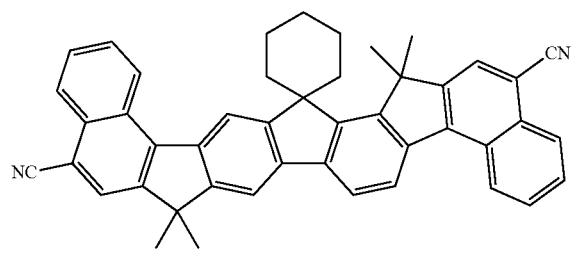
41
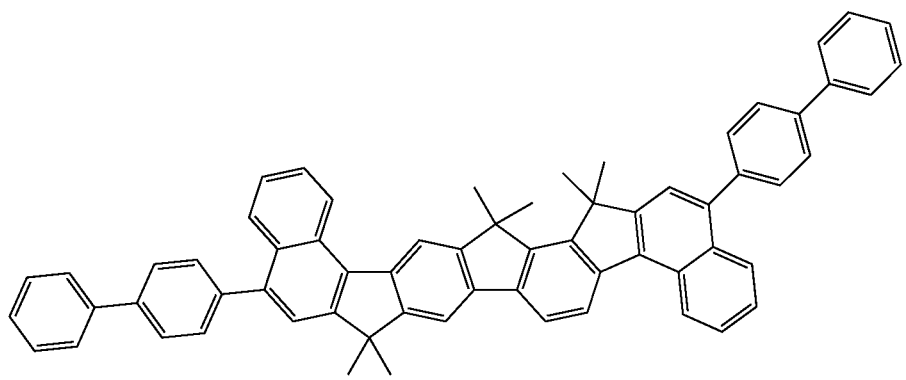
42
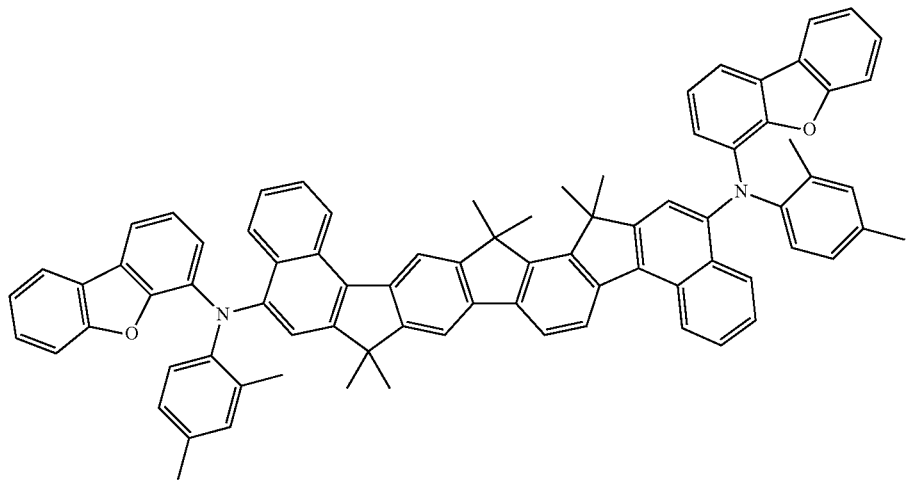
43
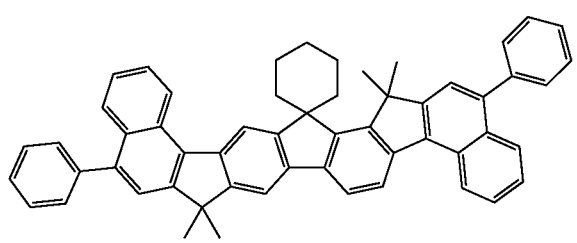
44
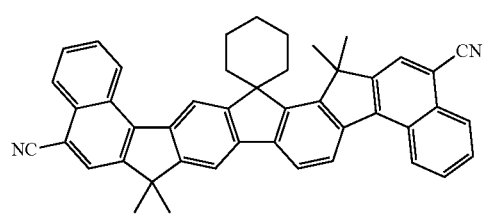

45
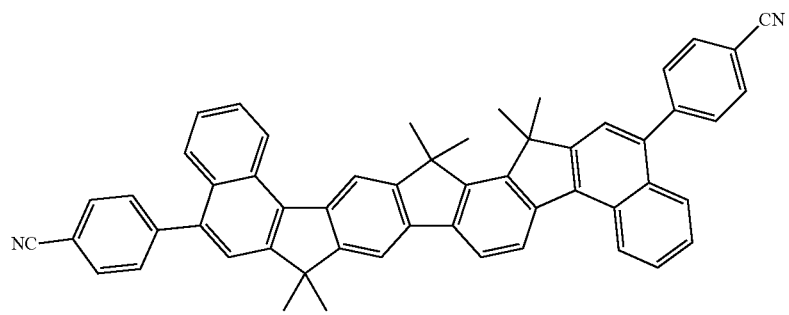
46
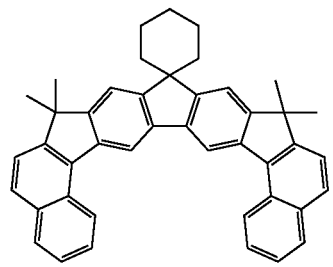
47
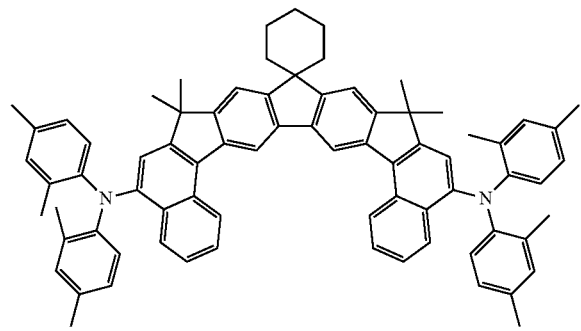
48
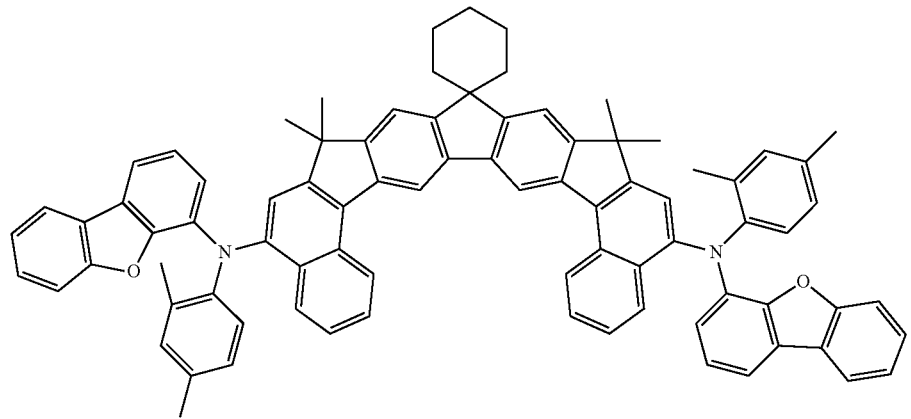
49
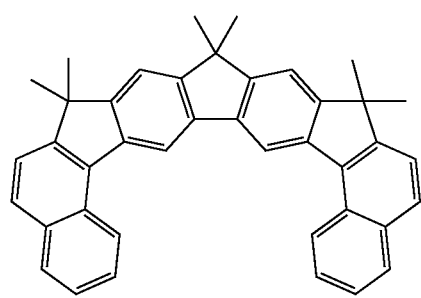
50
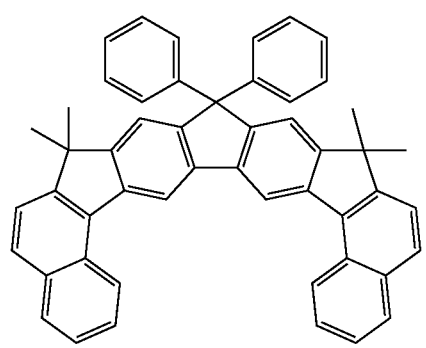

-continued
51
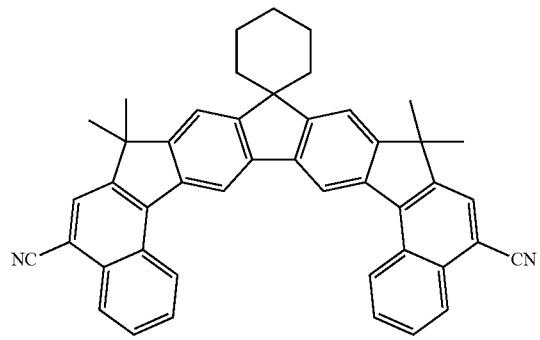
52
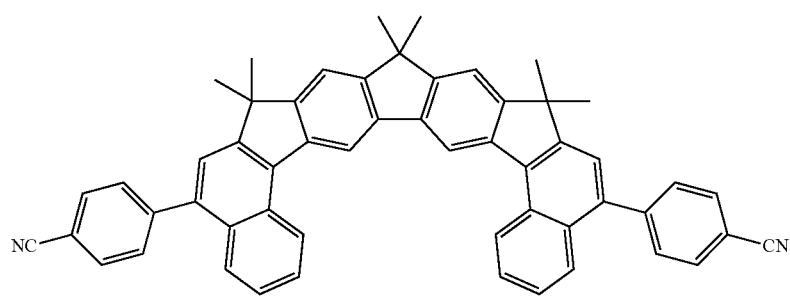
53
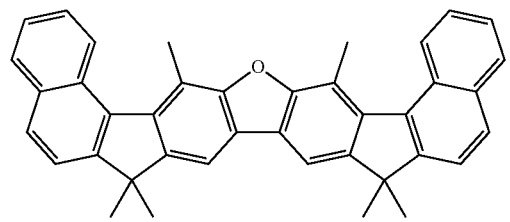
54
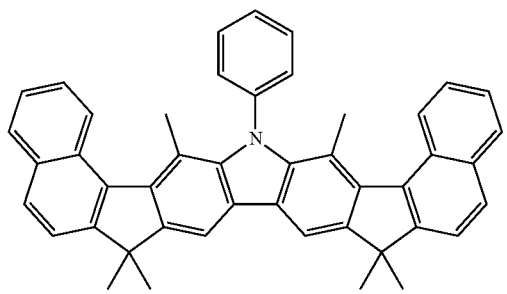
55
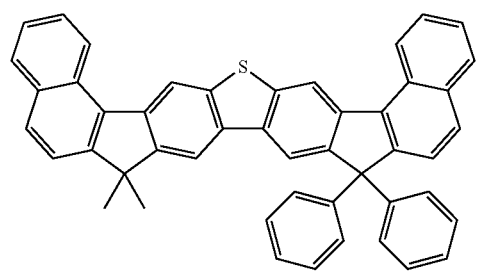
56
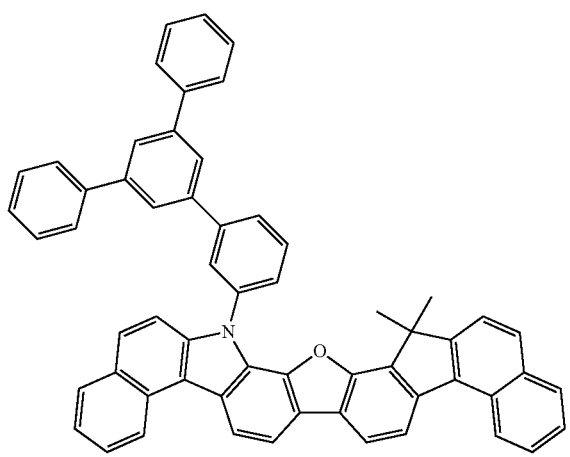

-continued
57
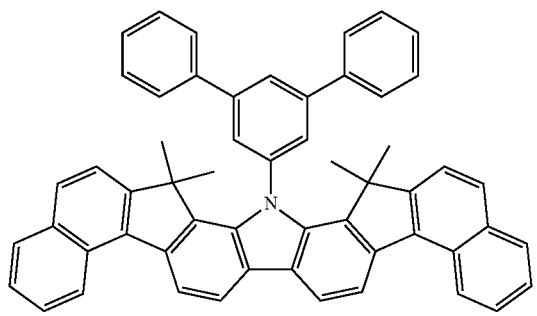
58
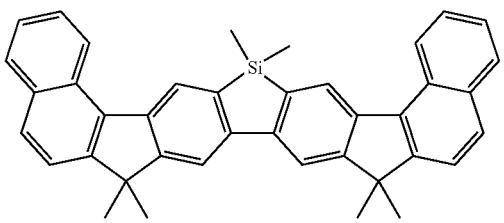
59
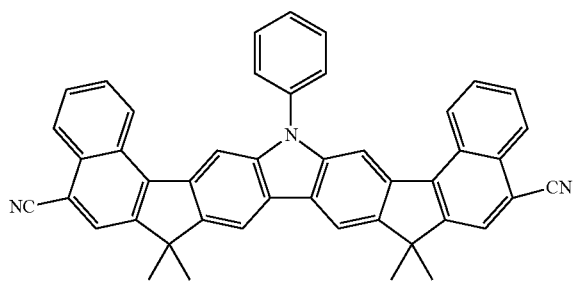
60
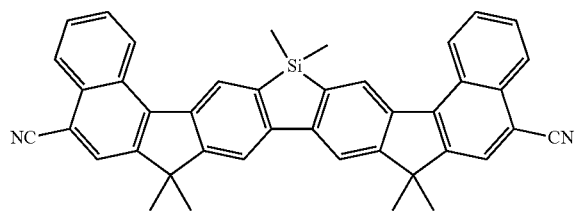
61
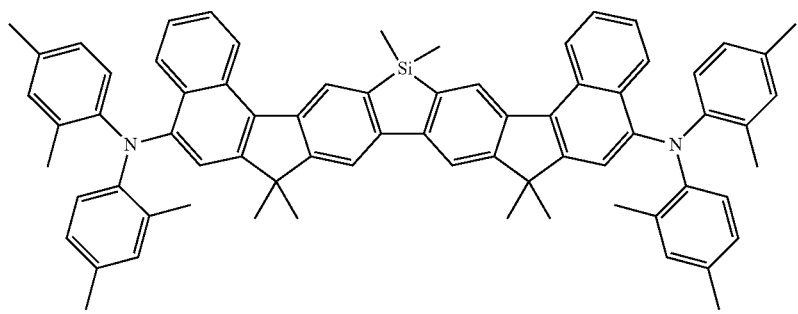
62
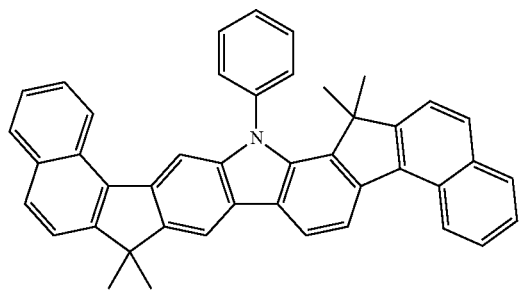
63
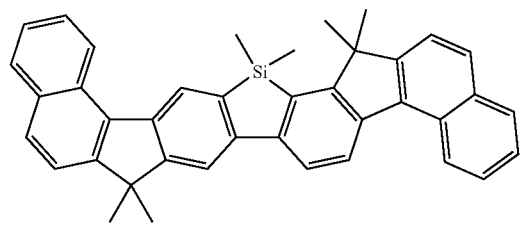
64
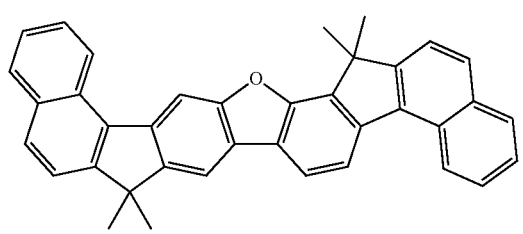
65
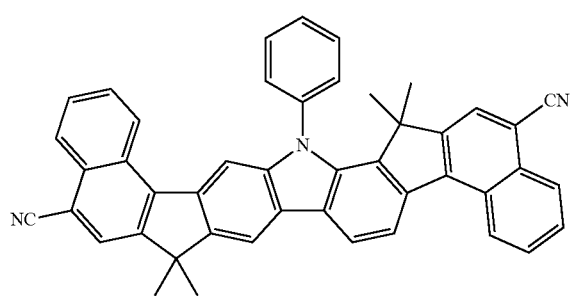

-continued
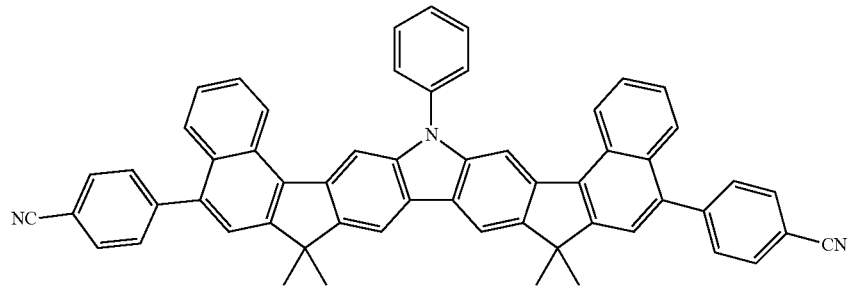
66
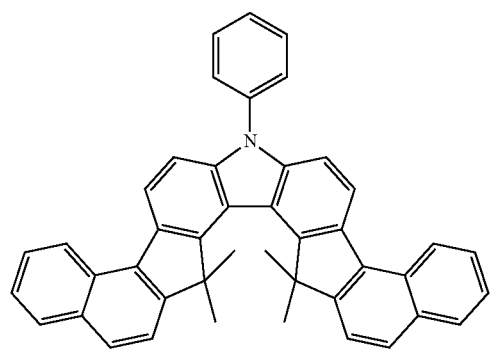
67
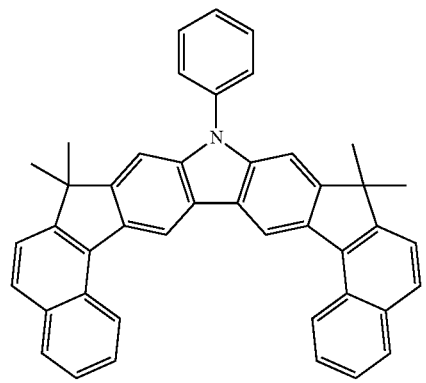
68
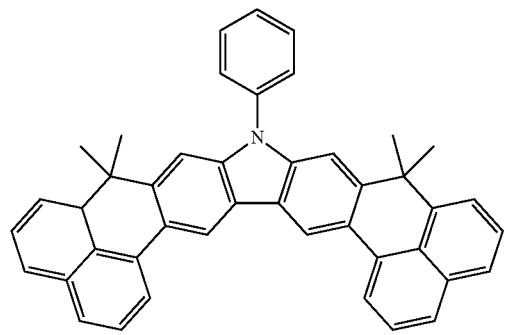
69
70
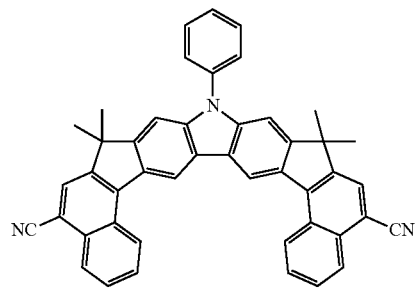
71
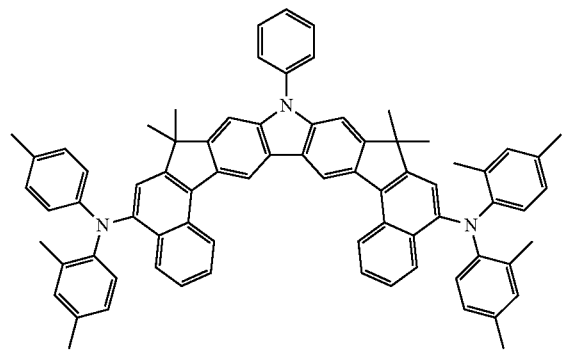
72

-continued
73
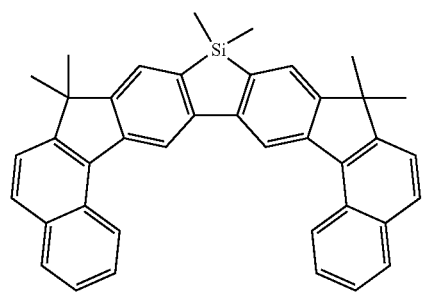
74
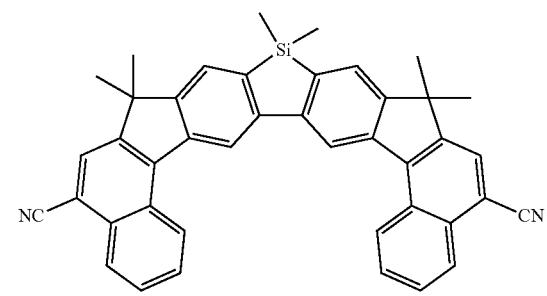
75
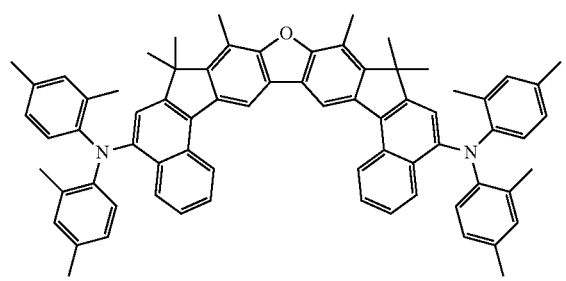
76
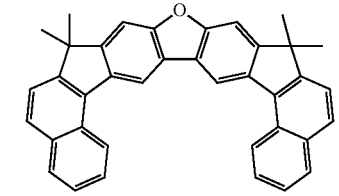
77
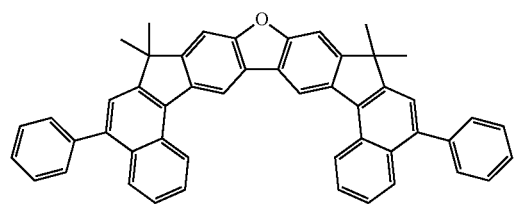
78
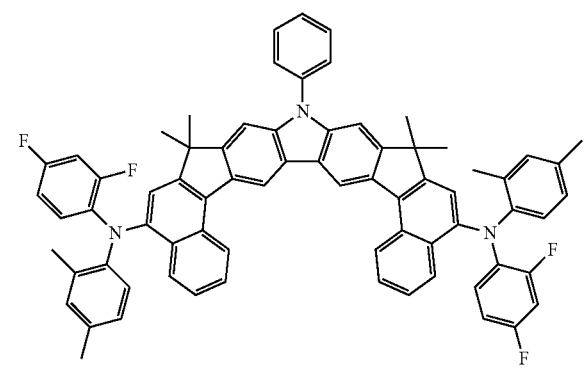
79
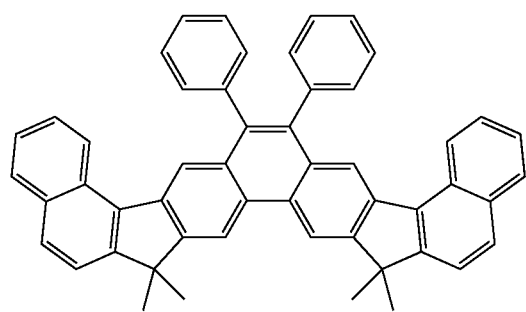
80
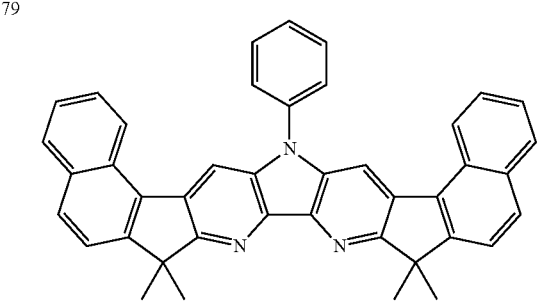

-continued
81
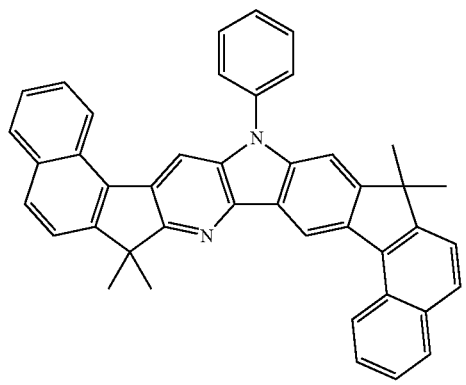
82
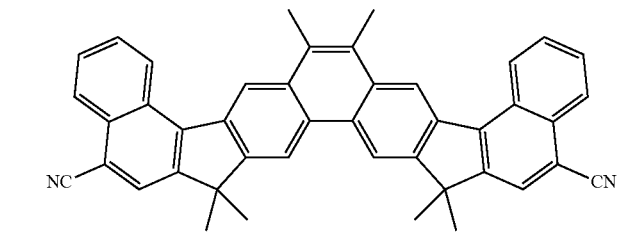
83
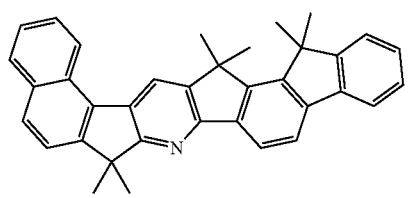
84
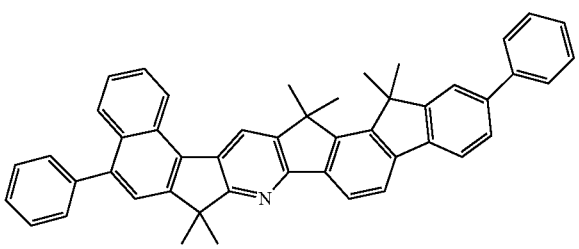
85
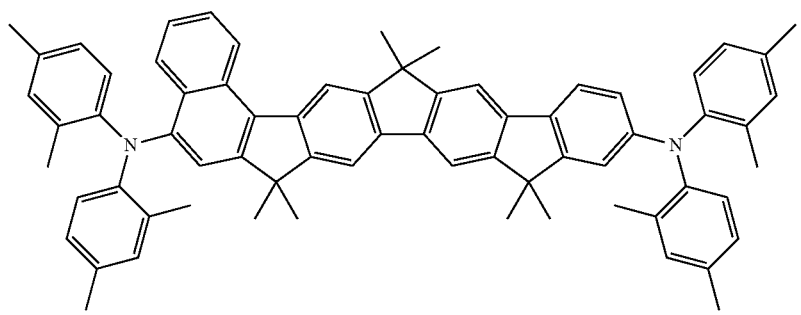
86
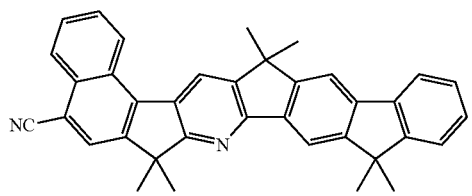
87
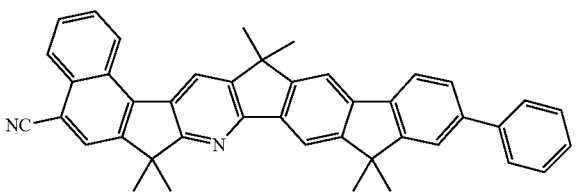
88
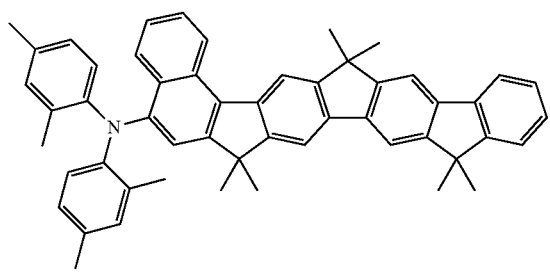
89
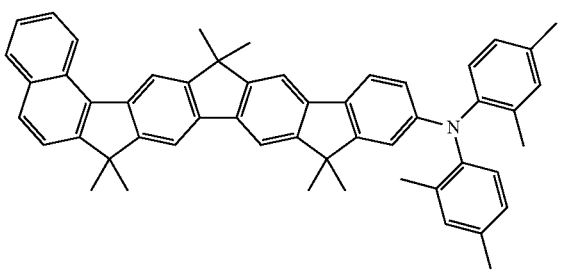

-continued
90
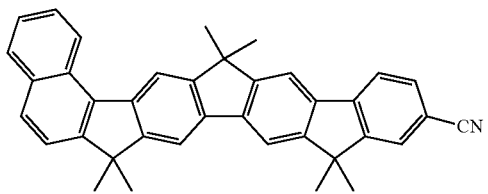
91
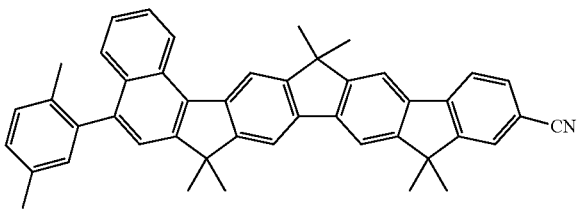
92
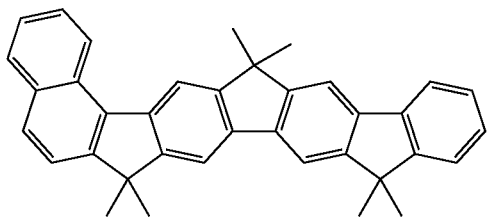
93
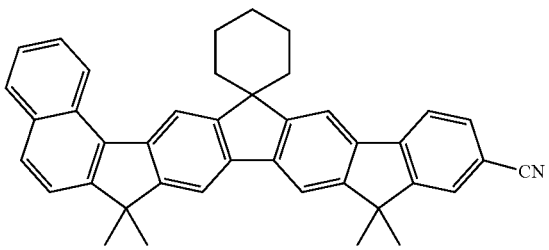
94
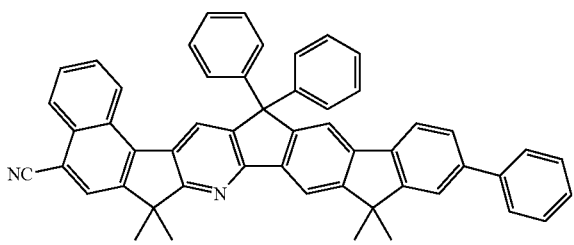
95
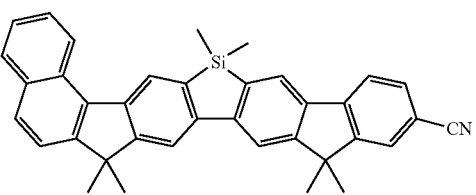
96
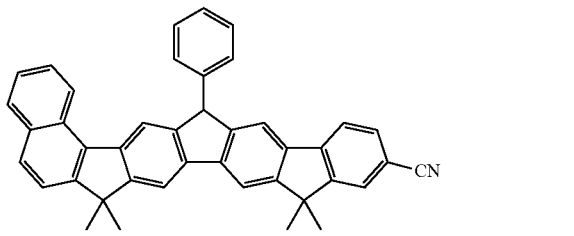
97
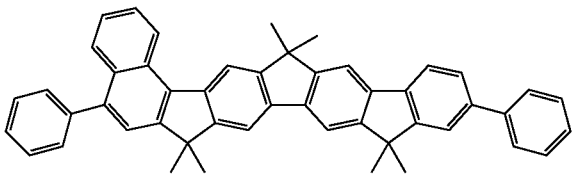
98
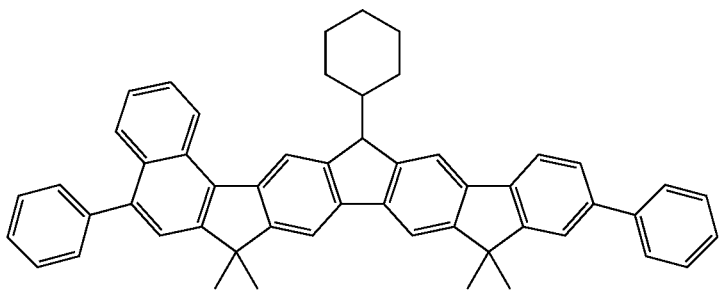
99
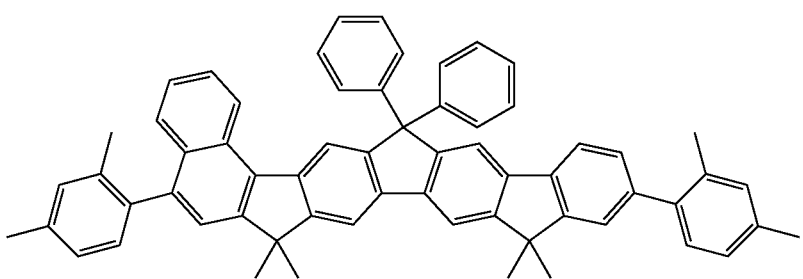

-continued
100 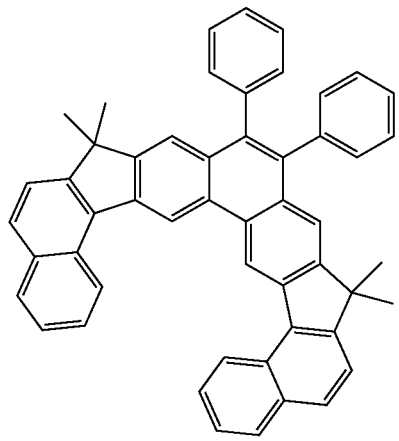 101 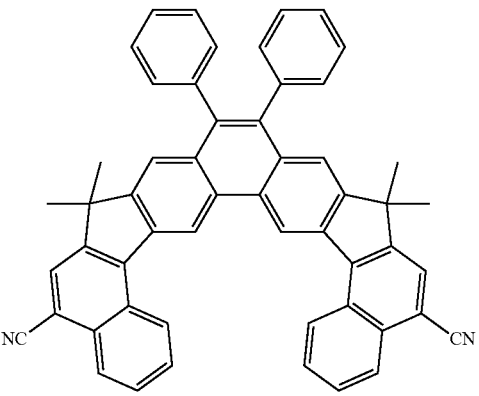
102 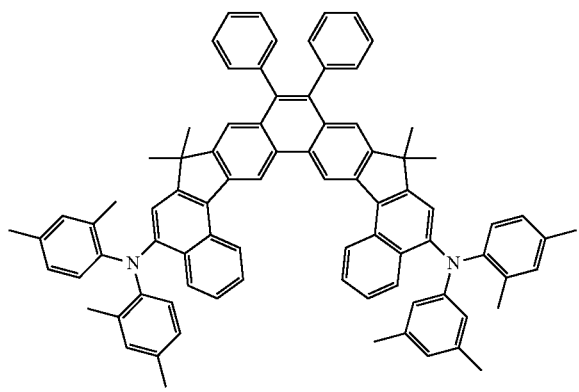 103 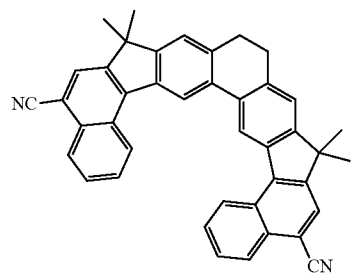
104 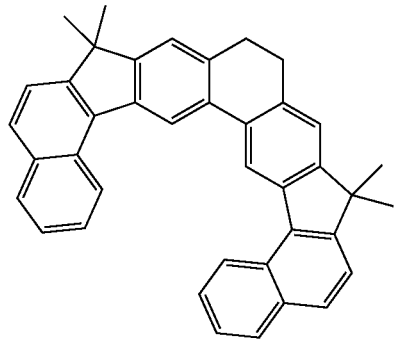 105 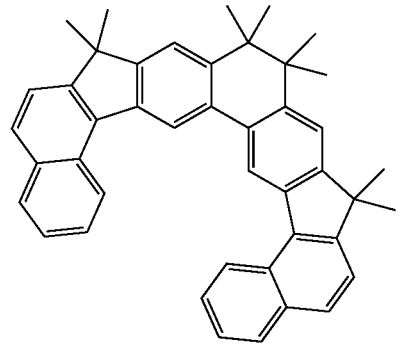
106 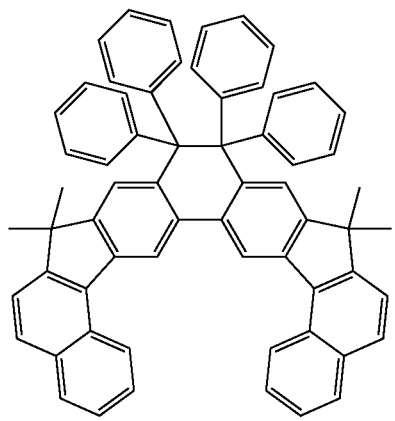 107 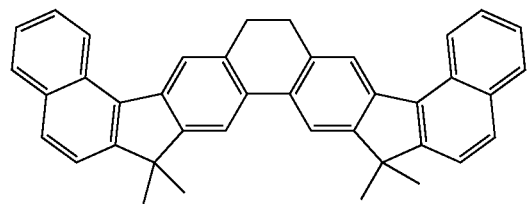

-continued
108 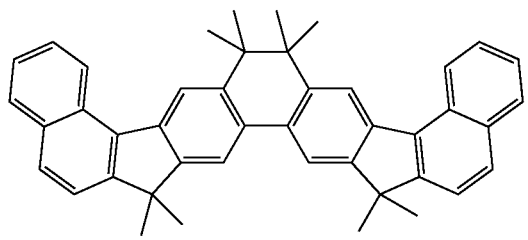
109 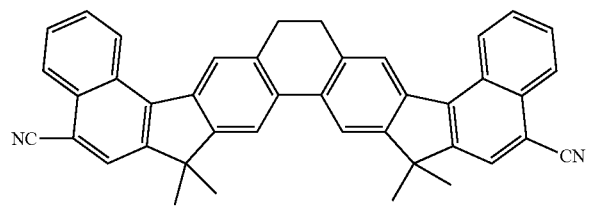
110 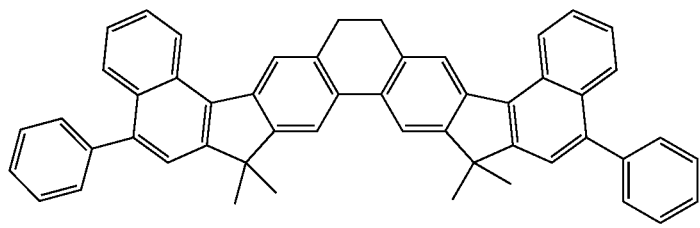
111 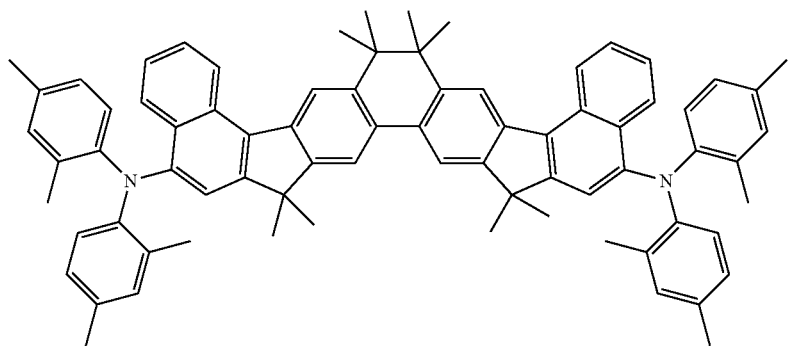
112 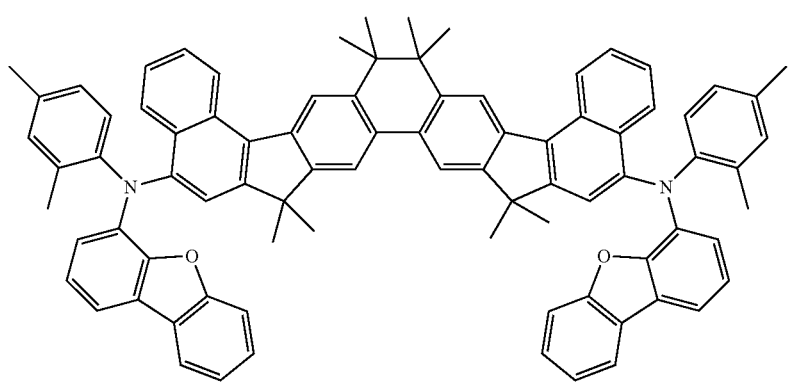
113 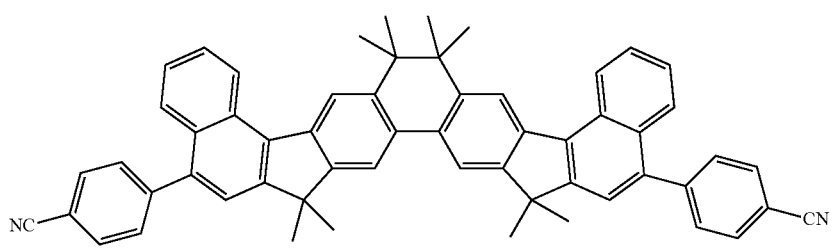

-continued
114
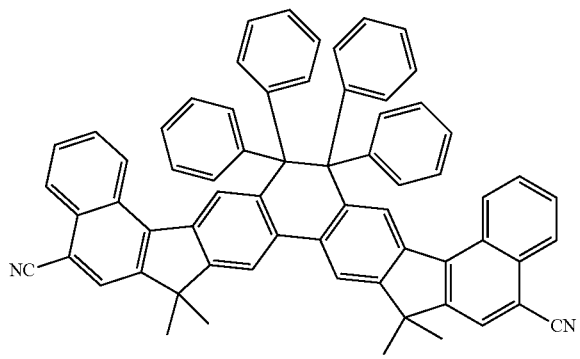
115
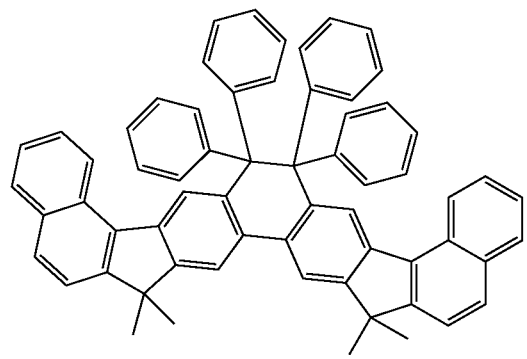
116
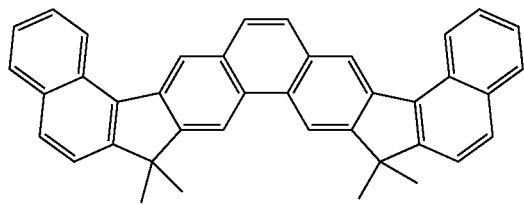
117
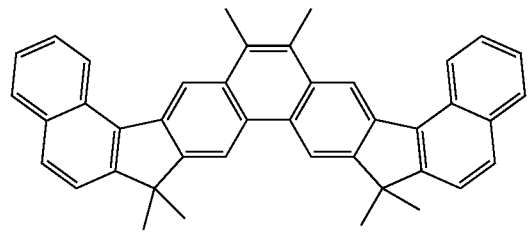
118
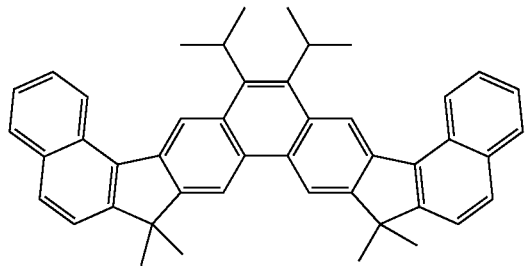
119
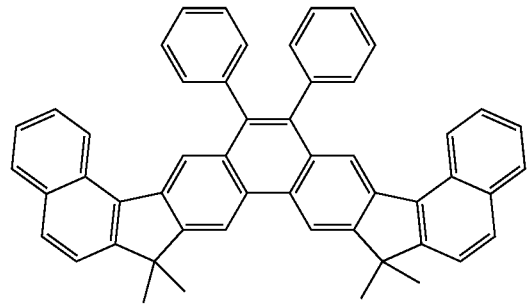
120
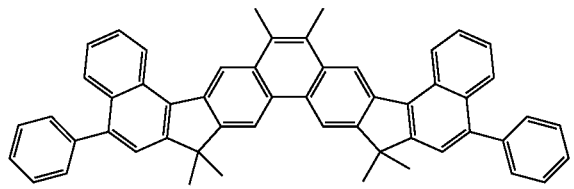
121
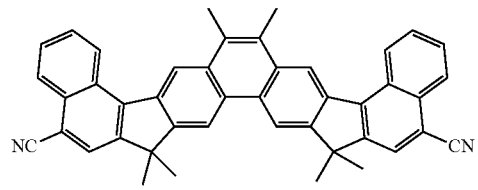
122
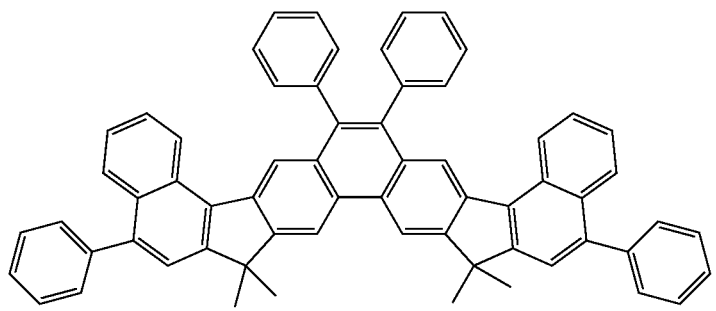

-continued
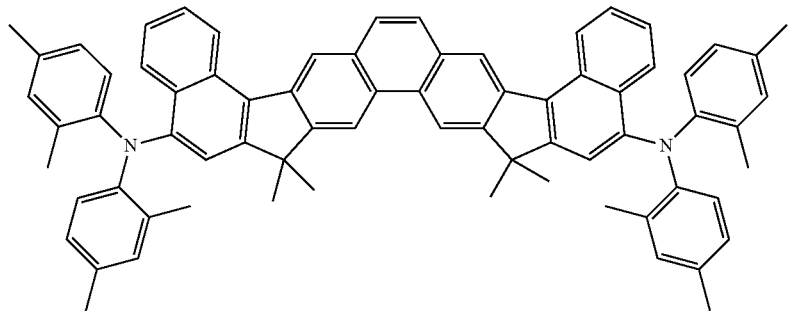
123
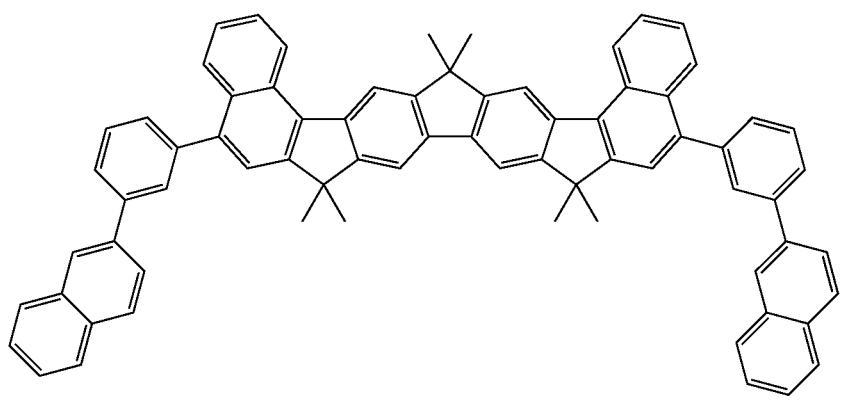
124
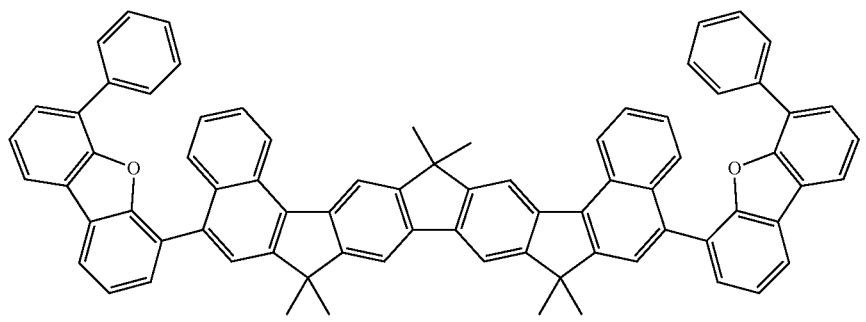
125
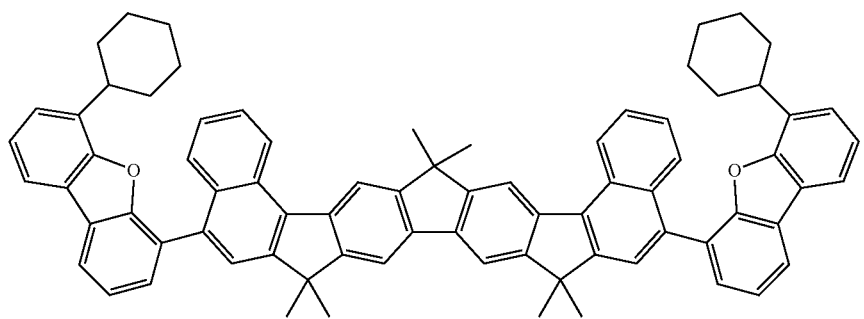
126

-continued
127
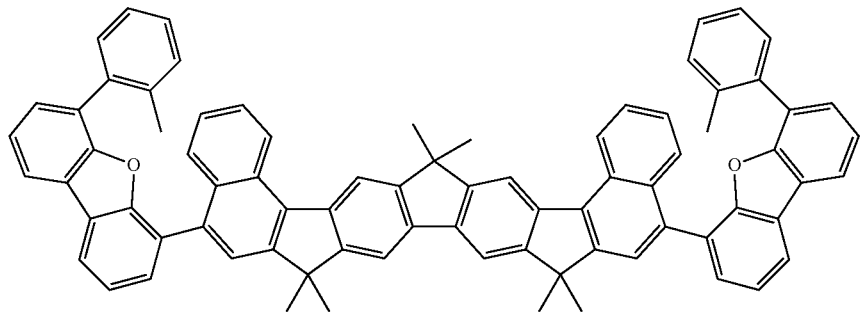
128
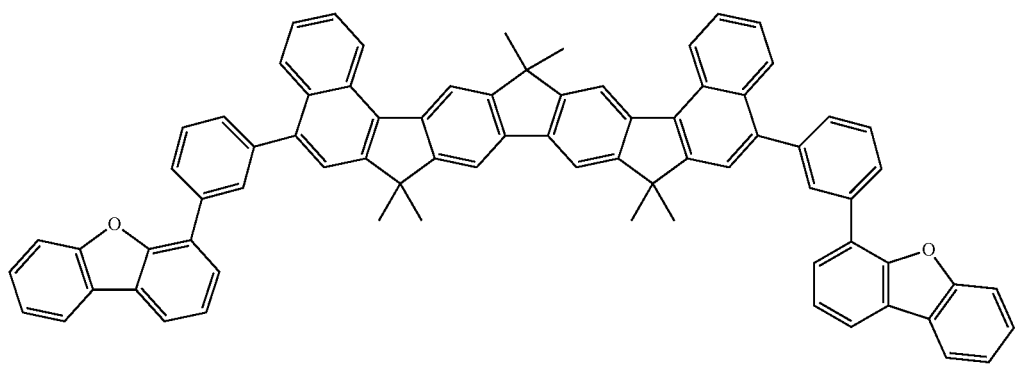
129
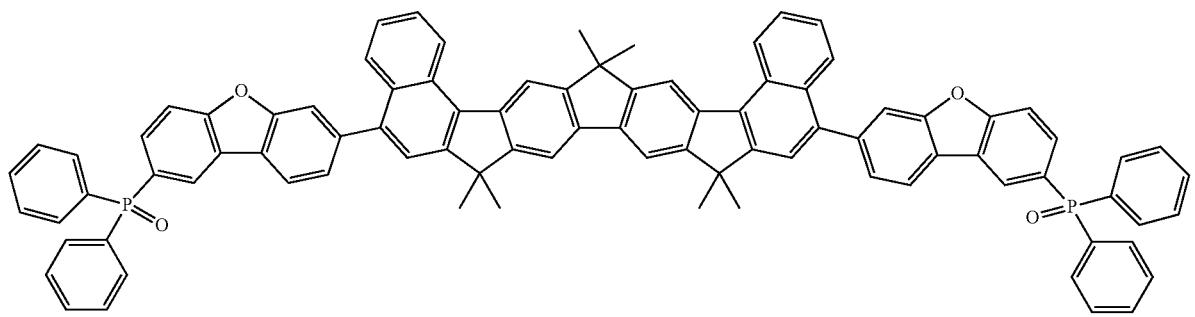
130
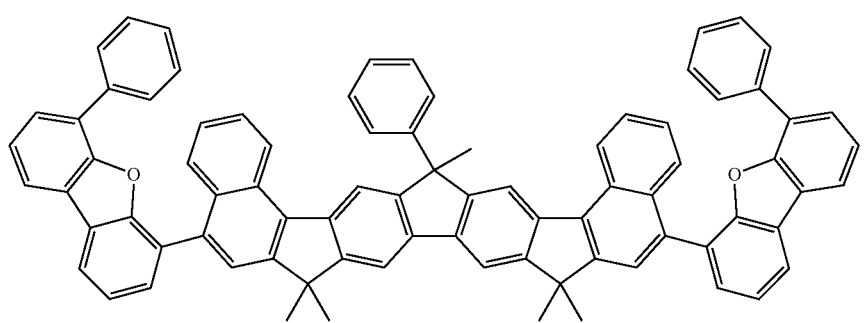

131
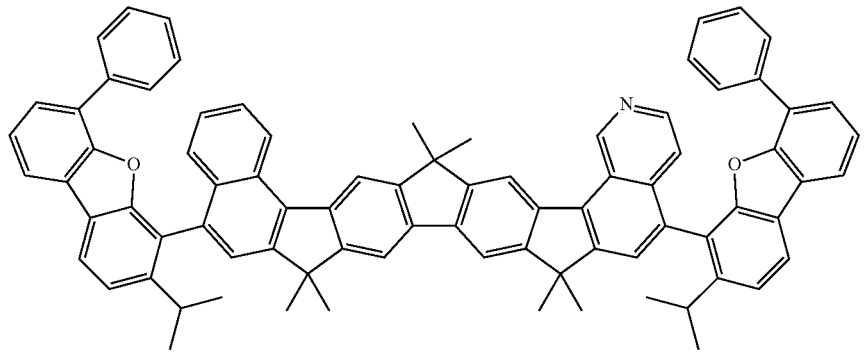
132
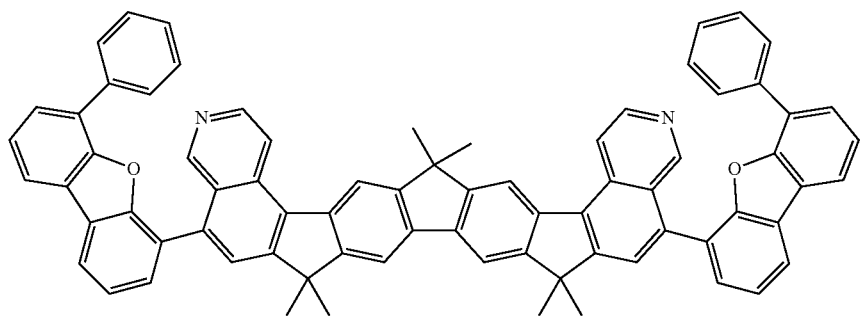
133
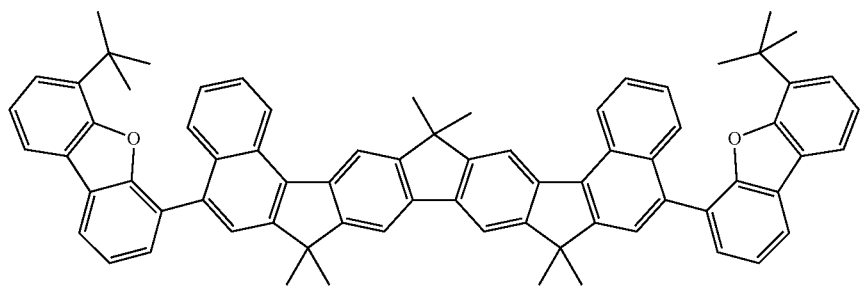
134
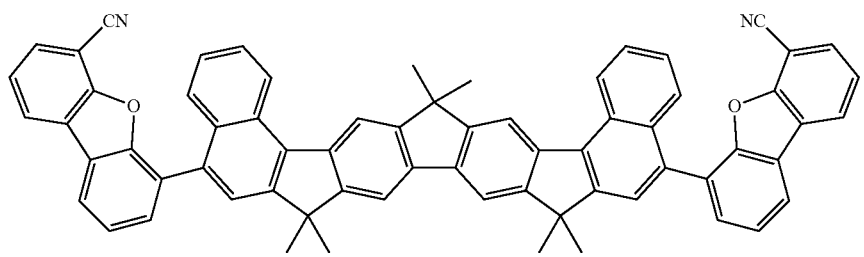
135
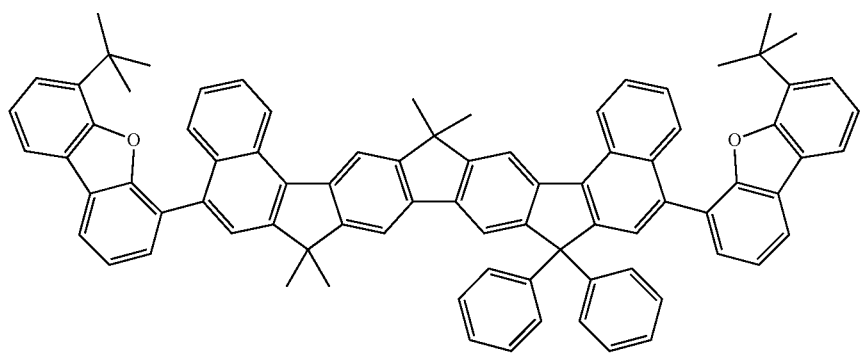

-continued
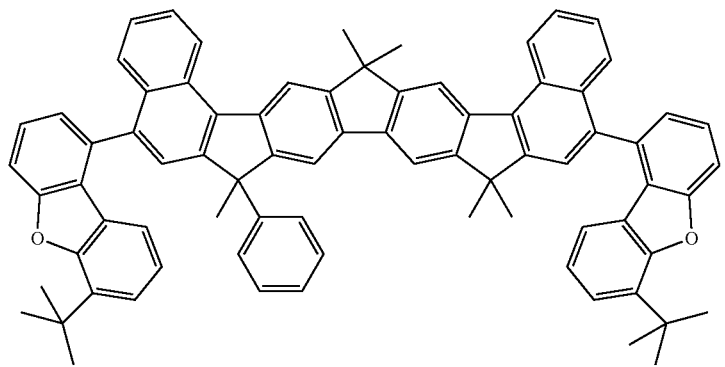
136
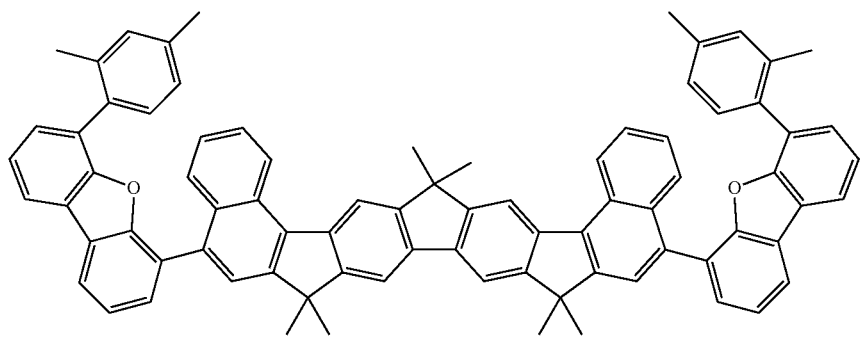
137
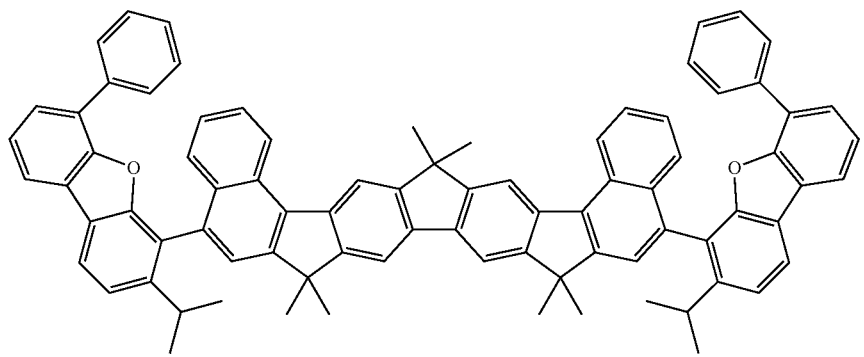
138
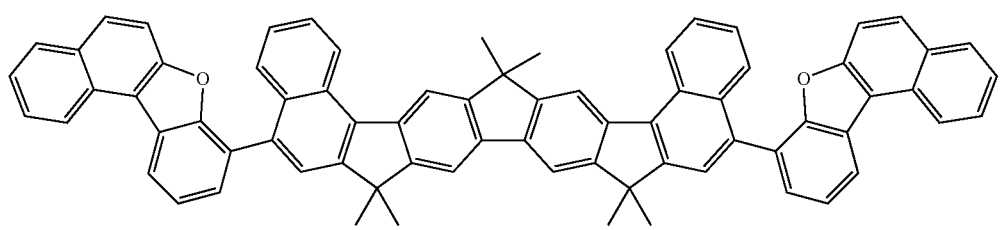
139
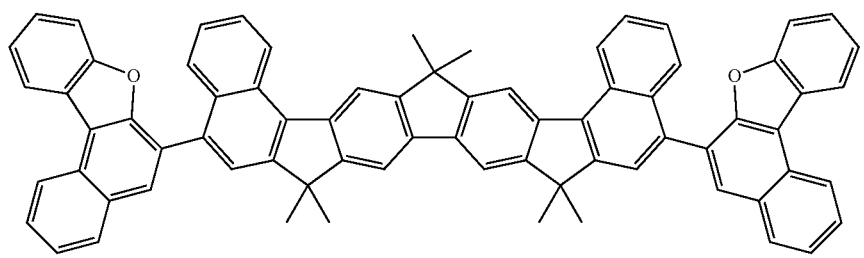
140

141
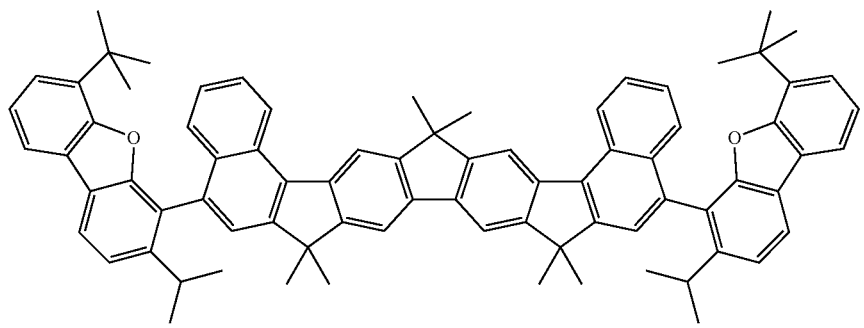
142
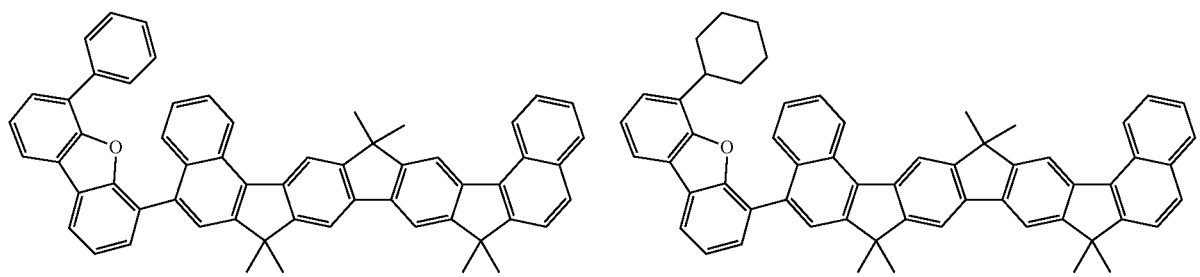
143
144
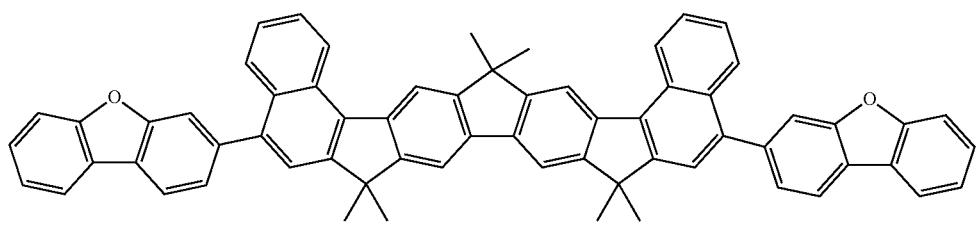
145
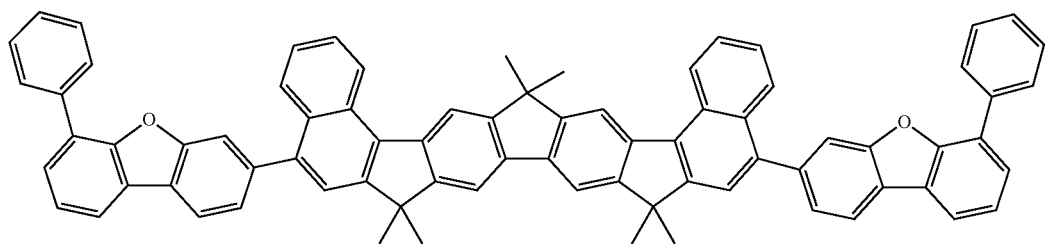
146
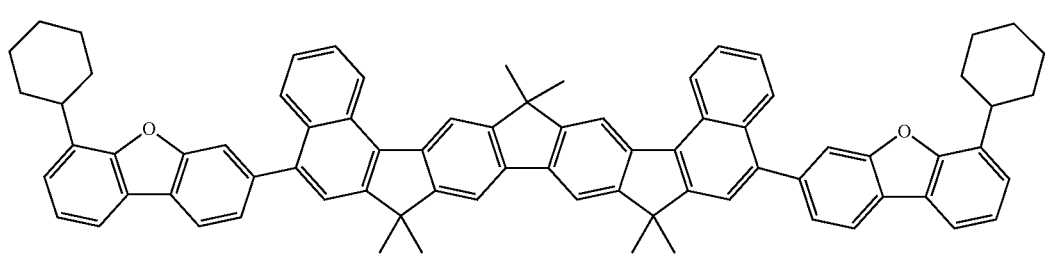
147
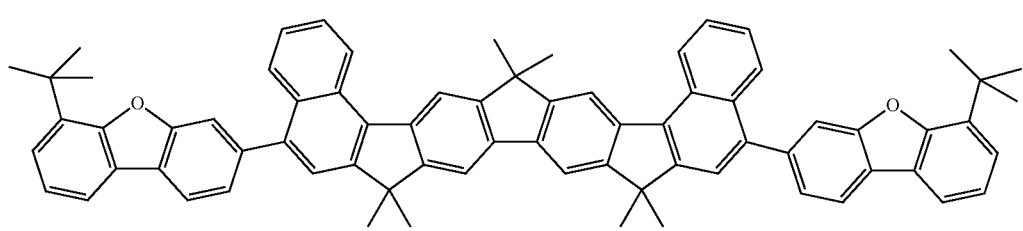

148
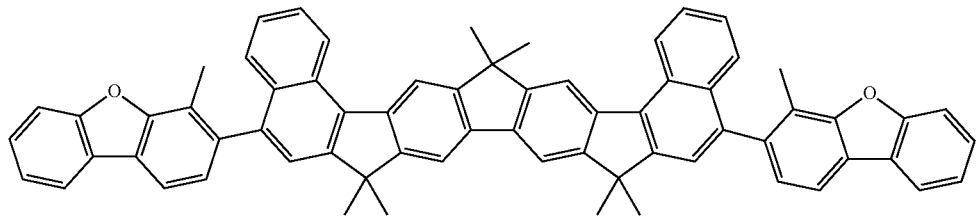
149
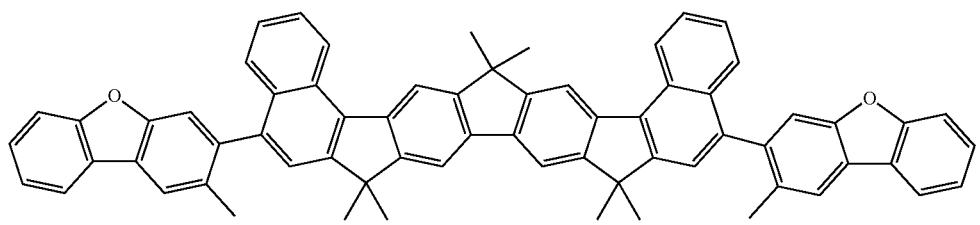
150
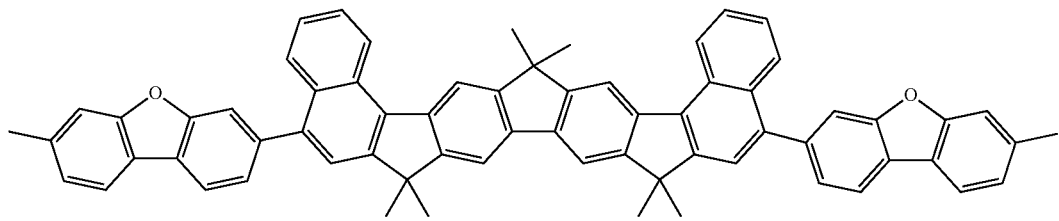
151
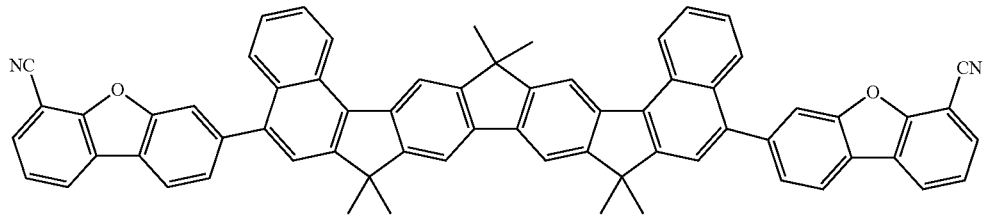
152
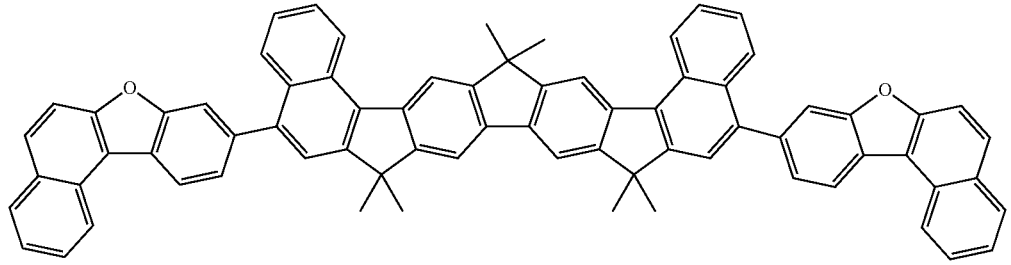
153
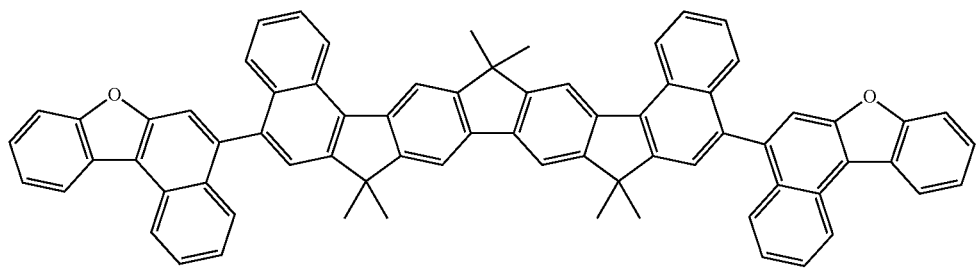

-continued
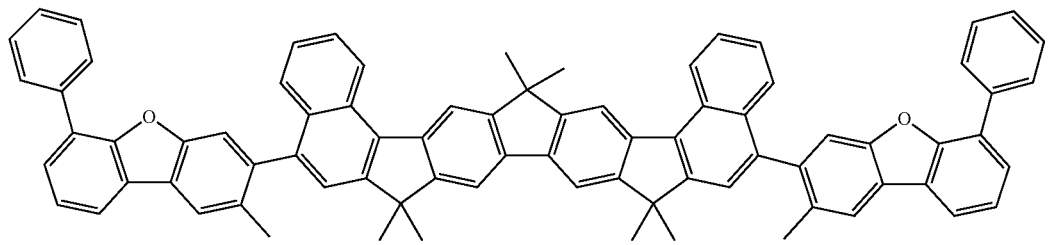
154
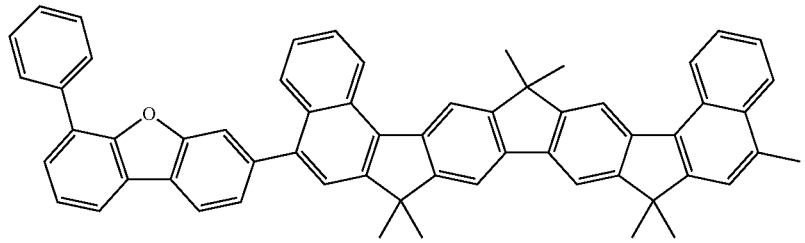
155
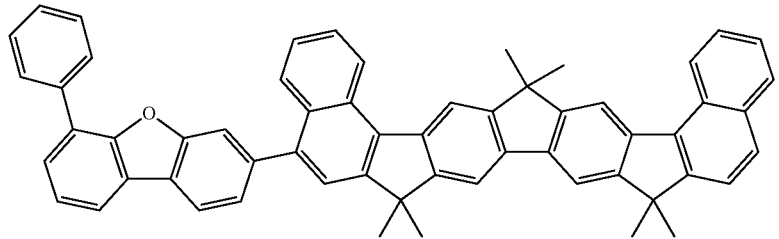
156
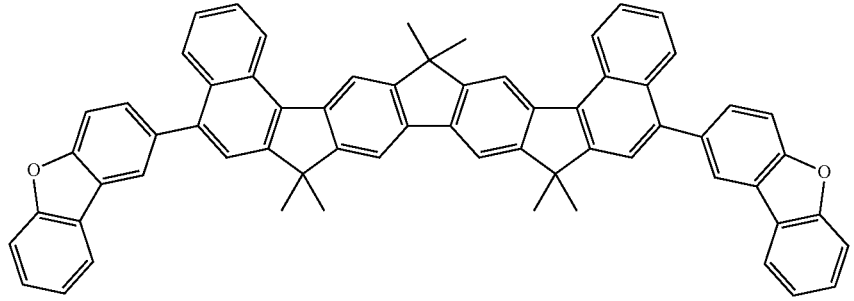
157
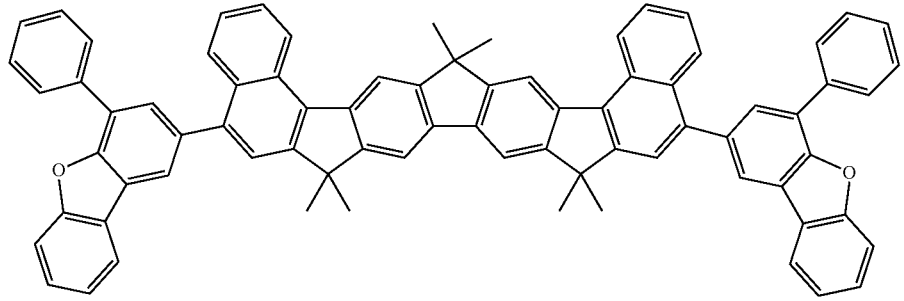
158

-continued
159
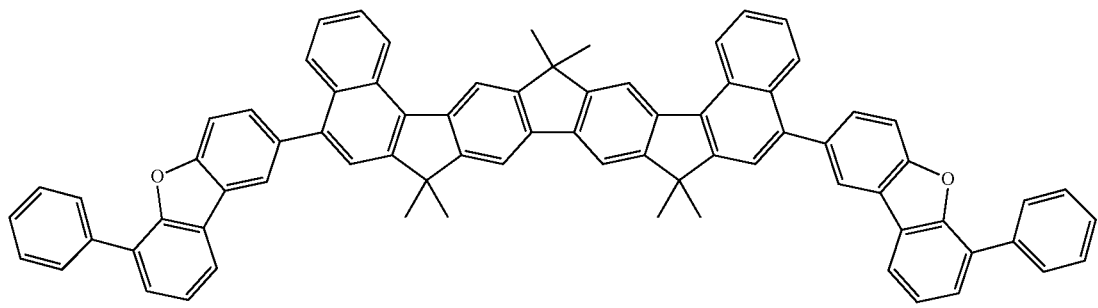
160
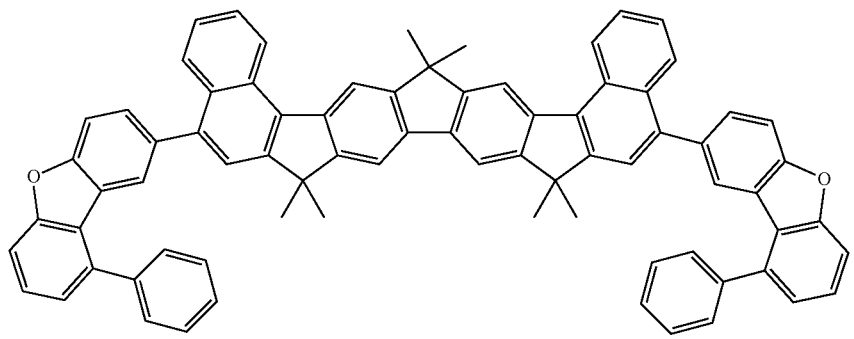
161
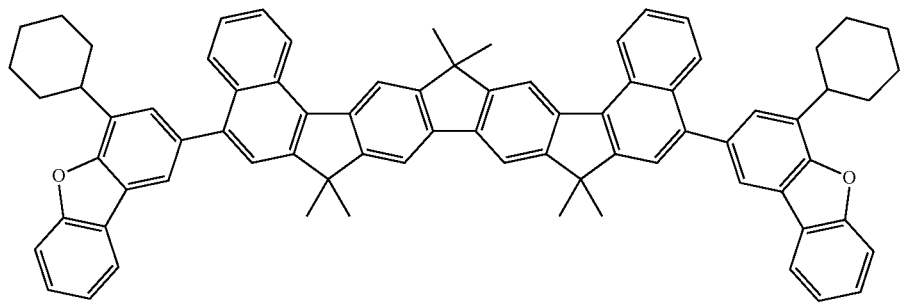
162
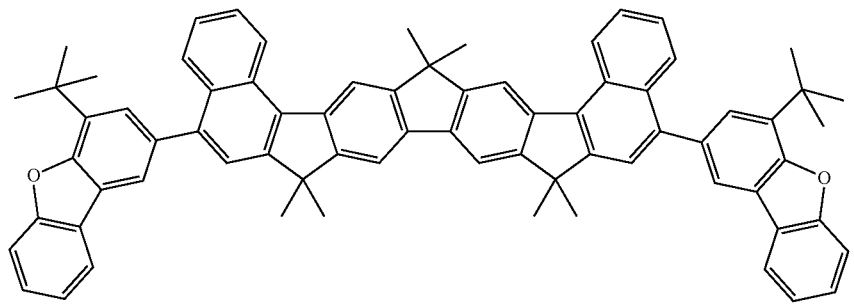
163
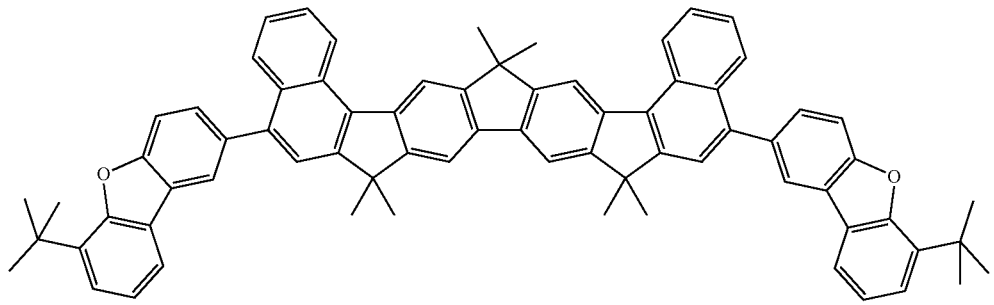

164
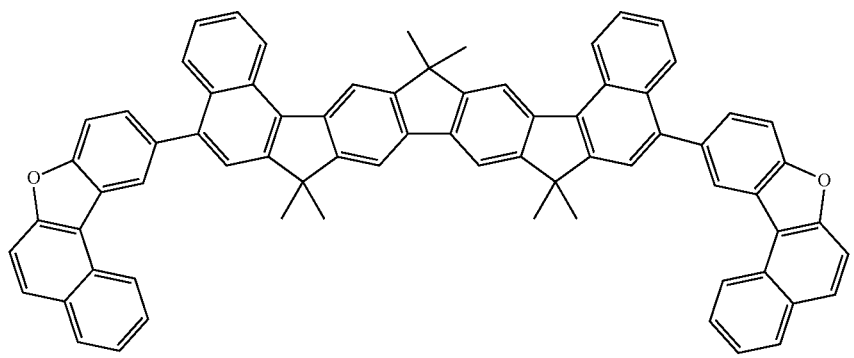
165
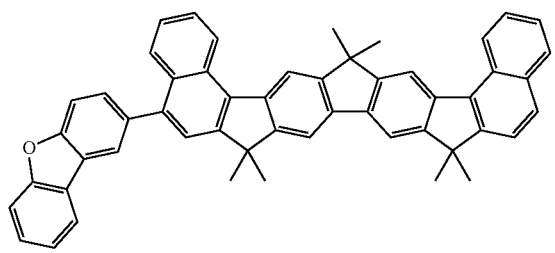
166
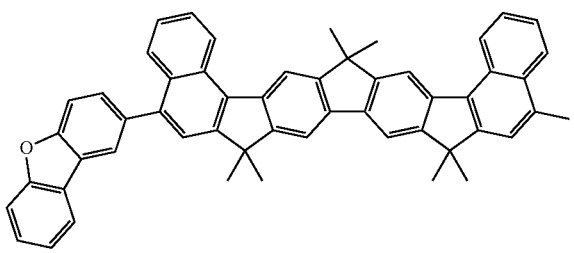
167
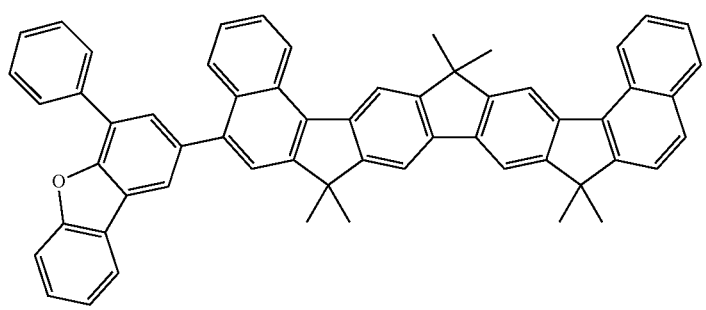
168
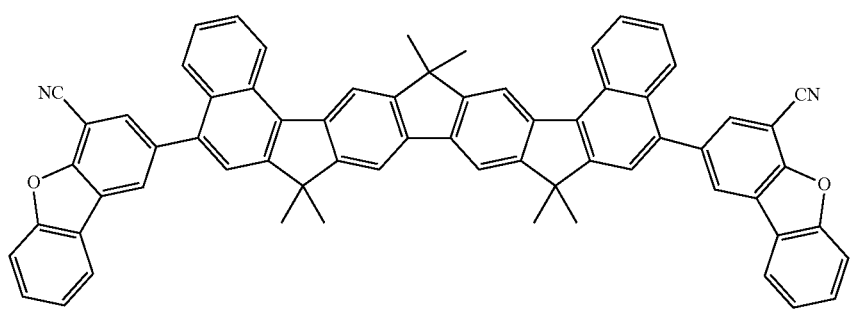
169
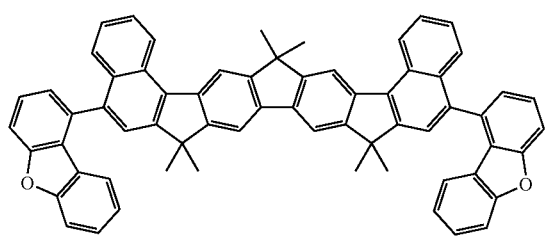
170
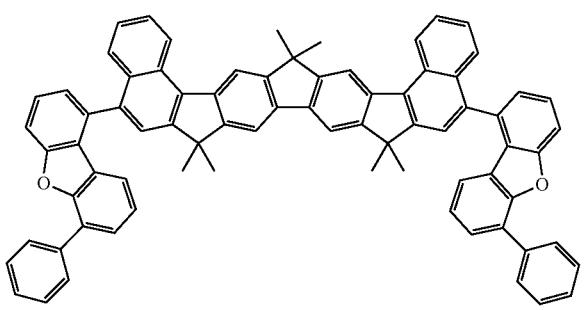

-continued
171
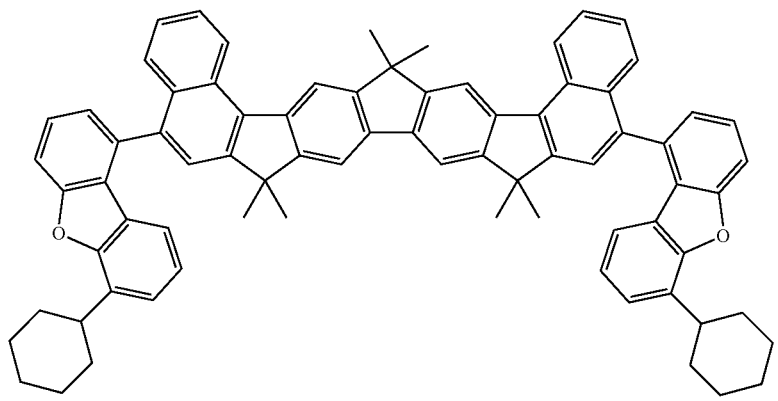
172
173
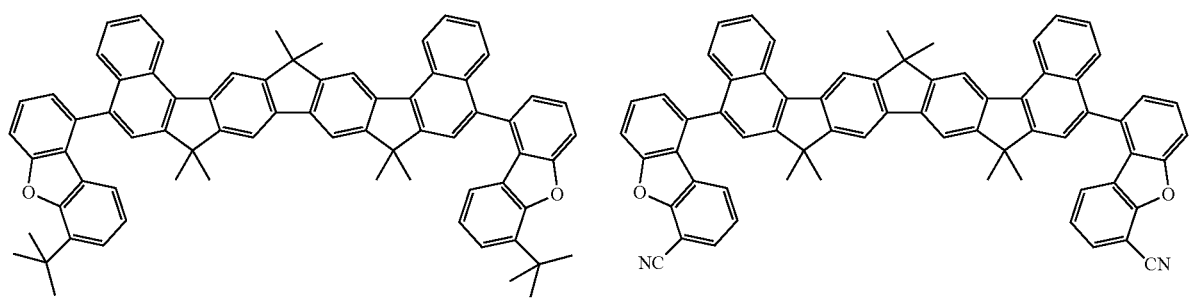
174
175
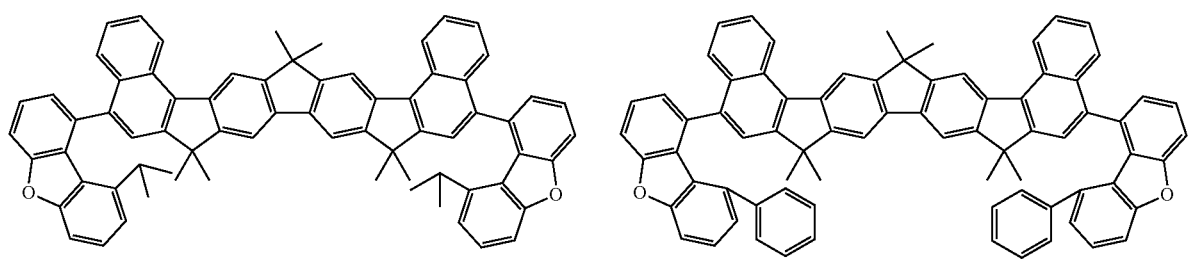
176
177
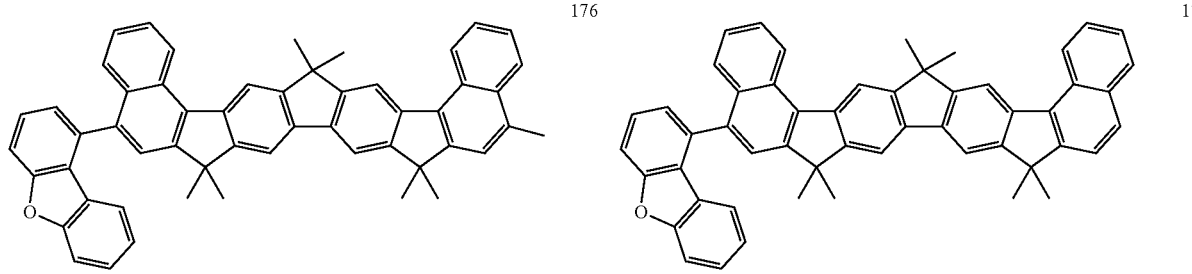
178
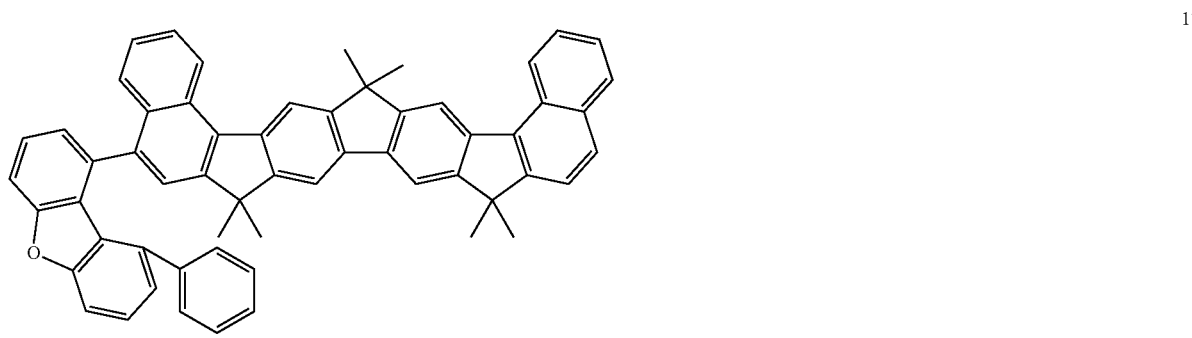

-continued
179
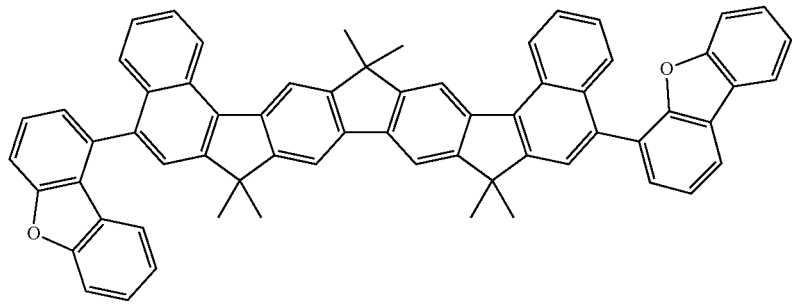
180
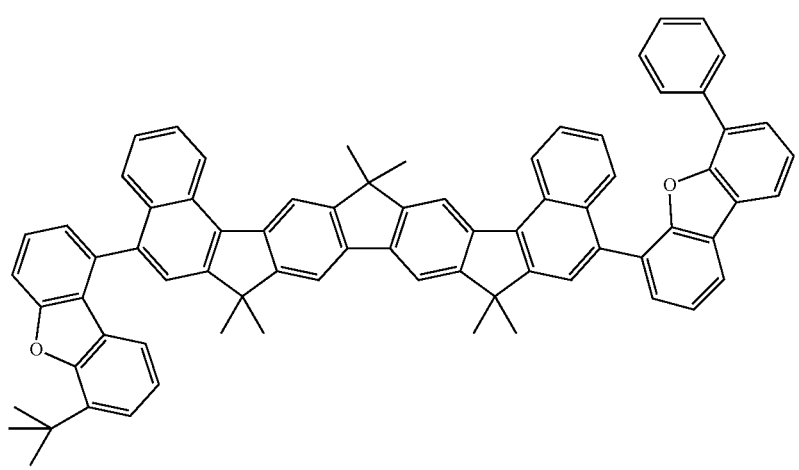
181
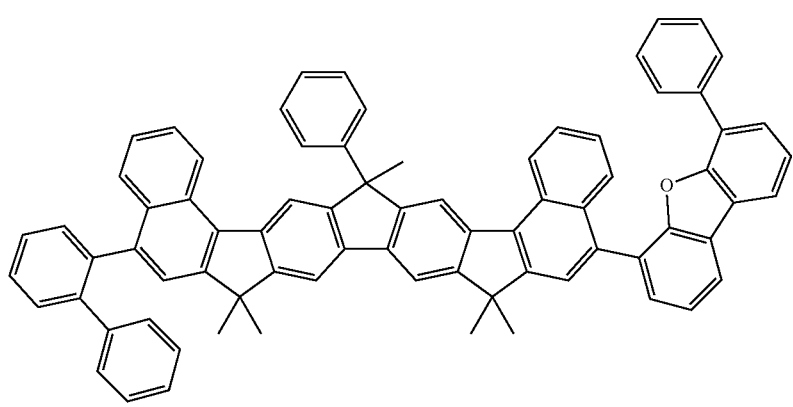
182
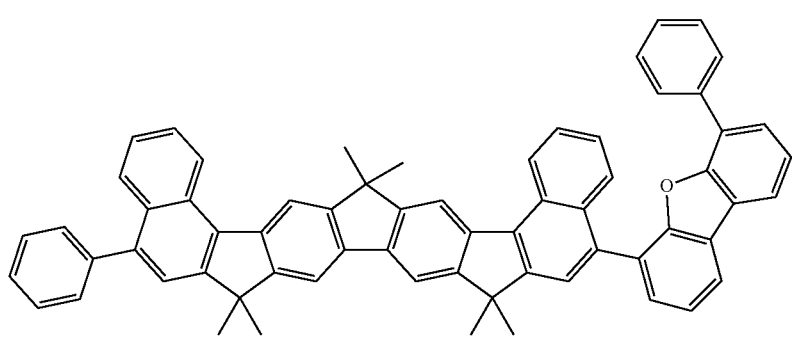

-continued
183
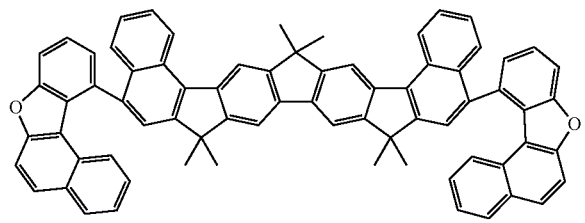
184
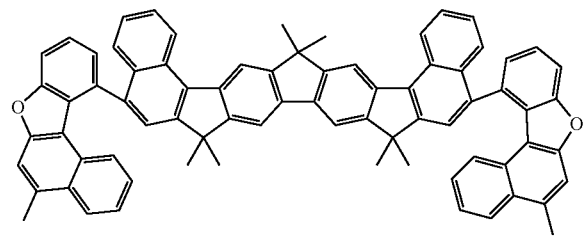
185
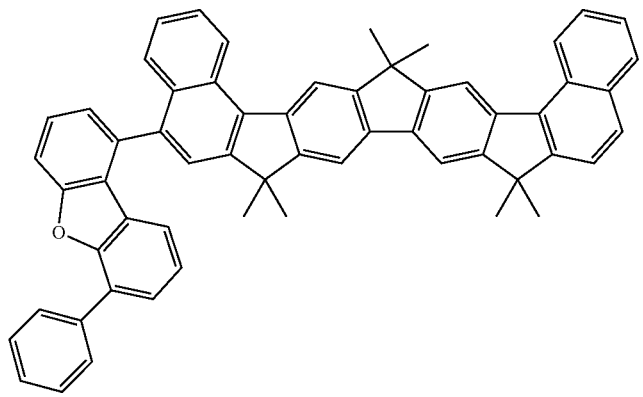
186
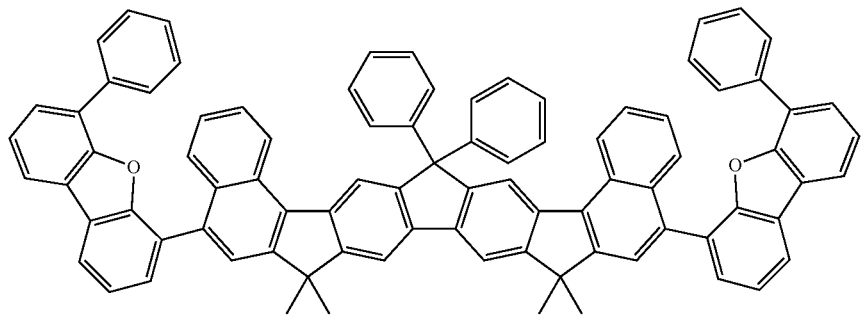
187
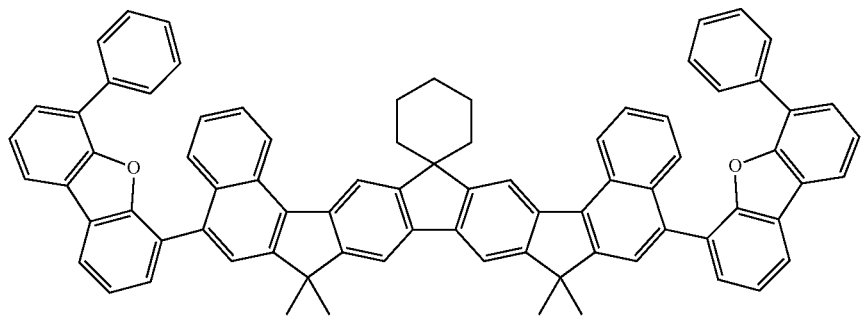
188
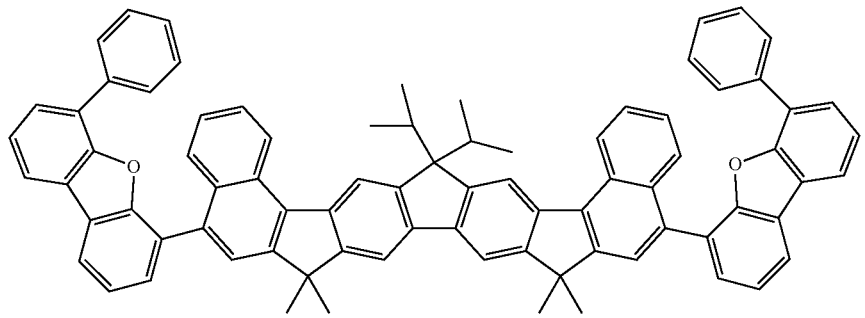

189
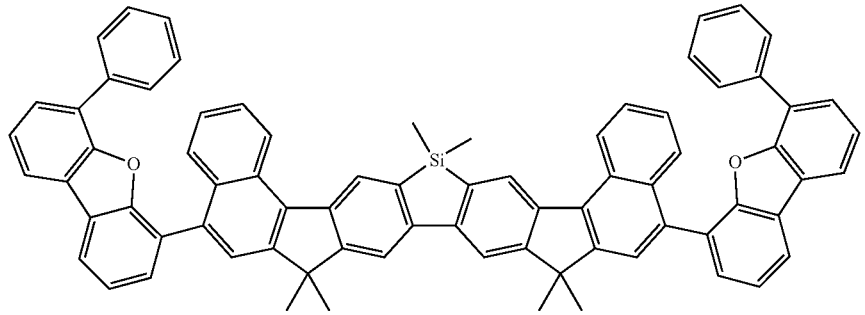
190
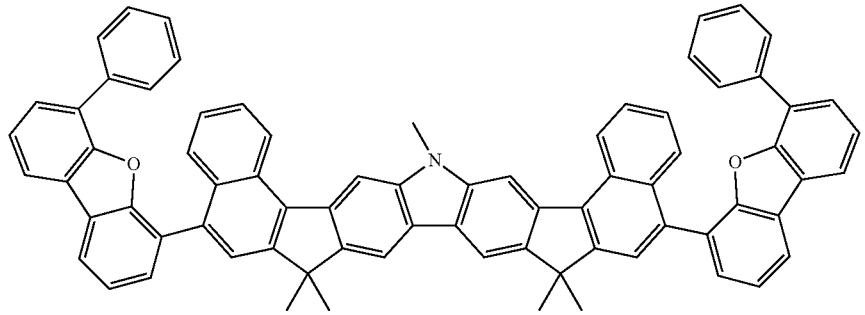
191
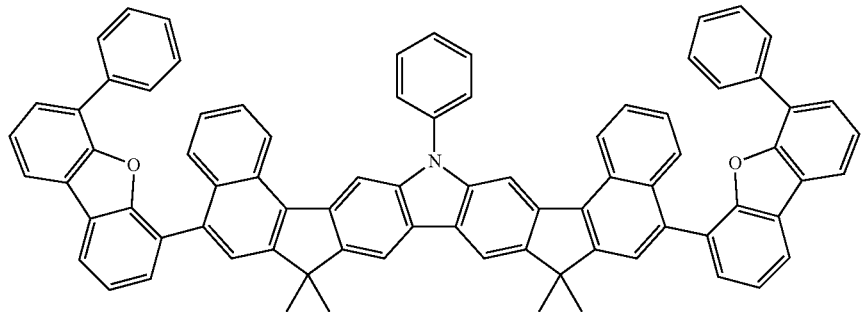
192
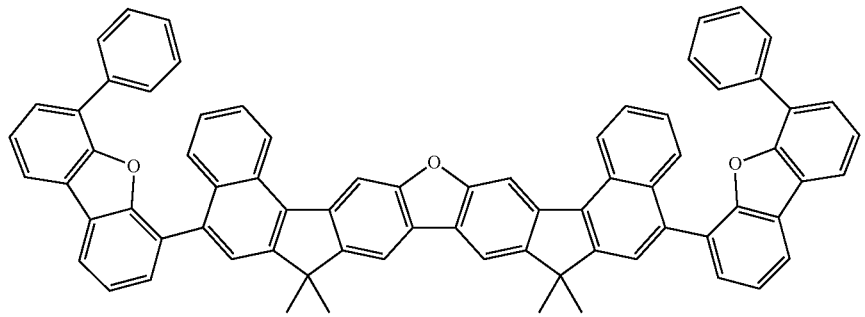
193 194
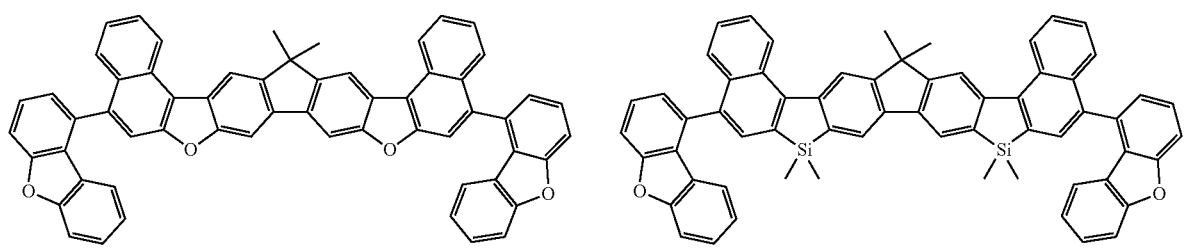

-continued
195
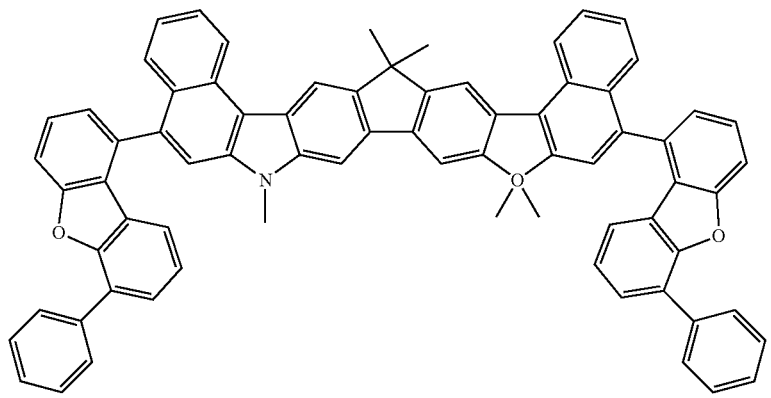
196
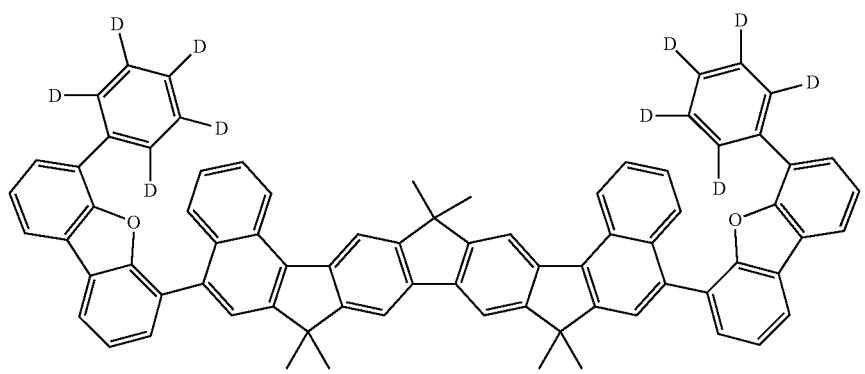
197
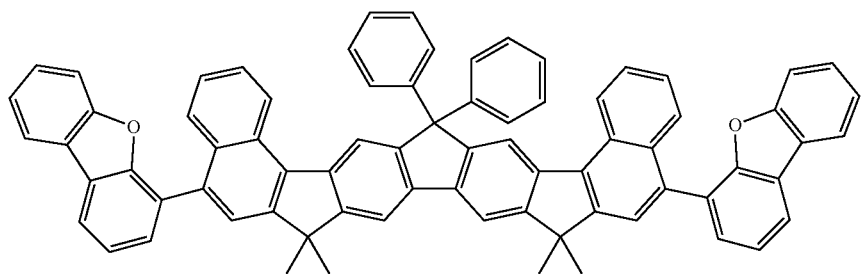
198
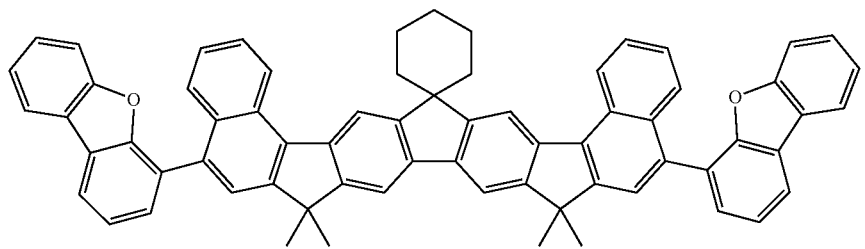
199
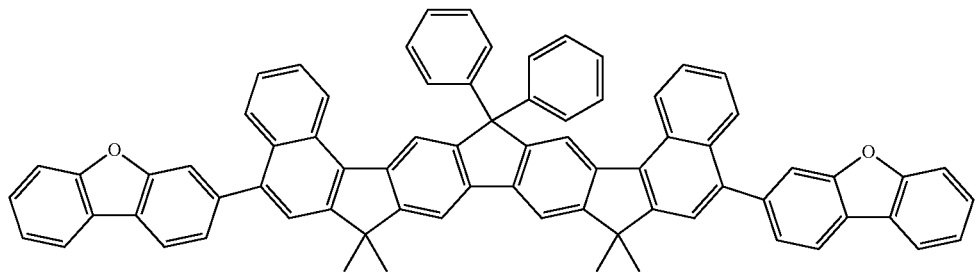

-continued
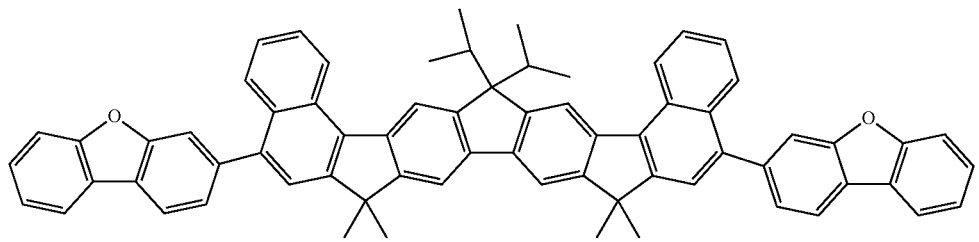
200
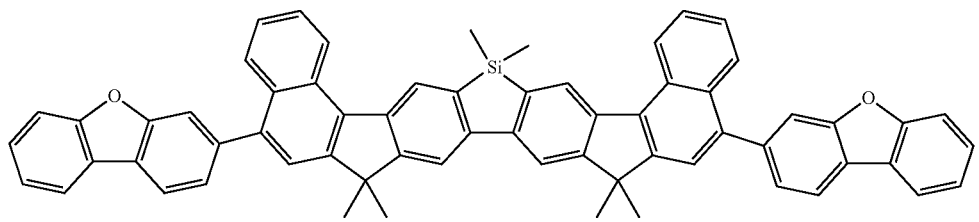
201
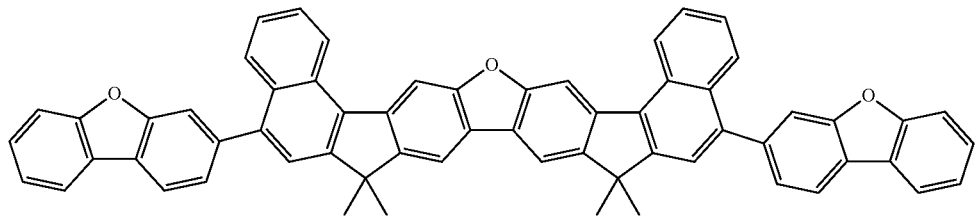
202
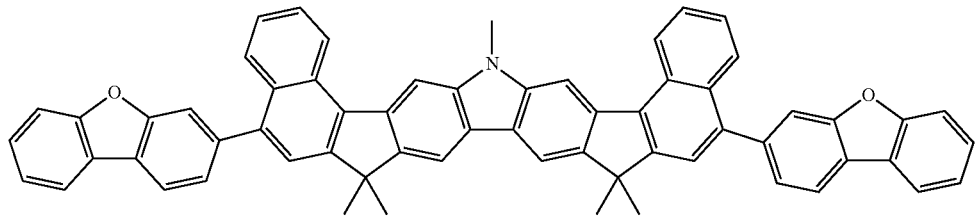
203
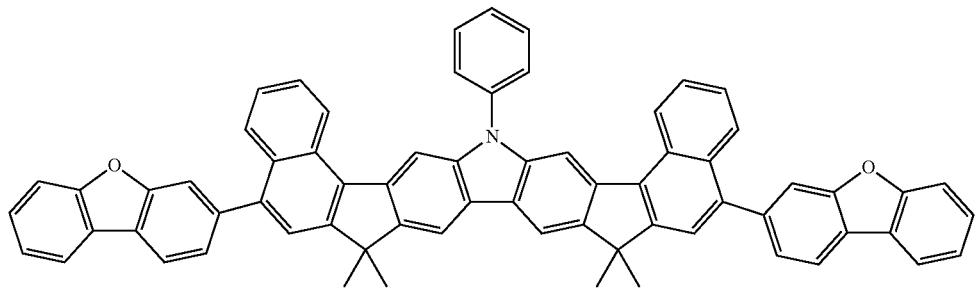
204
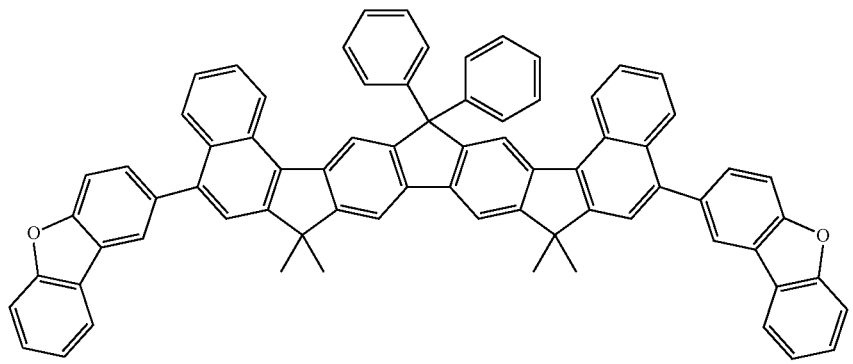
205

206
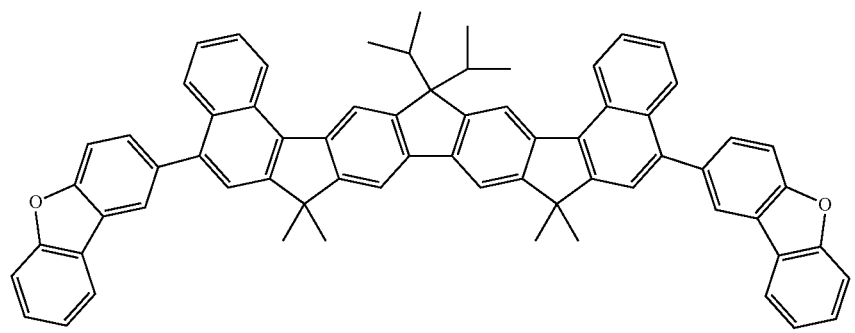
207
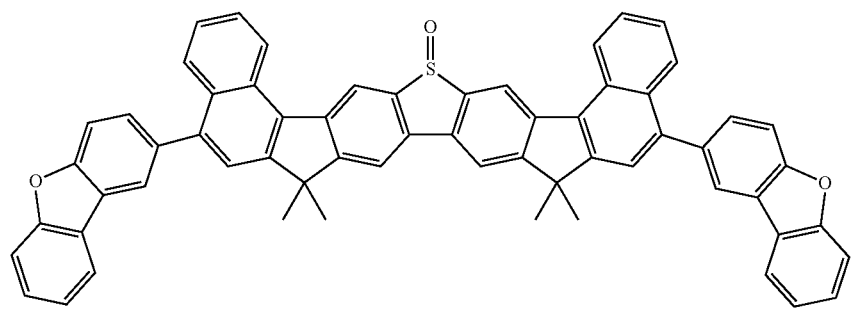
208
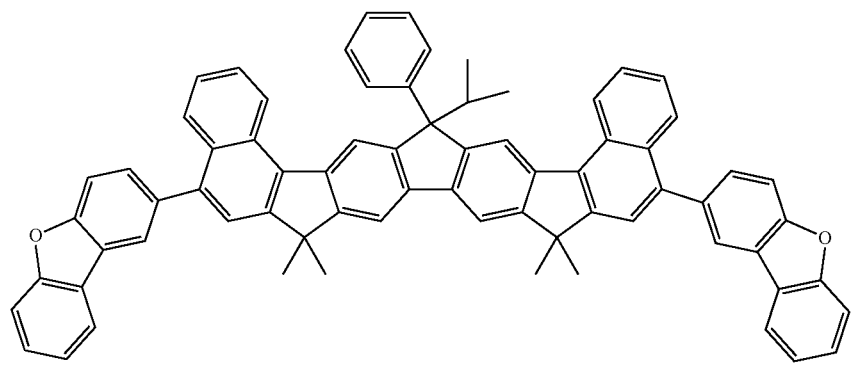
209
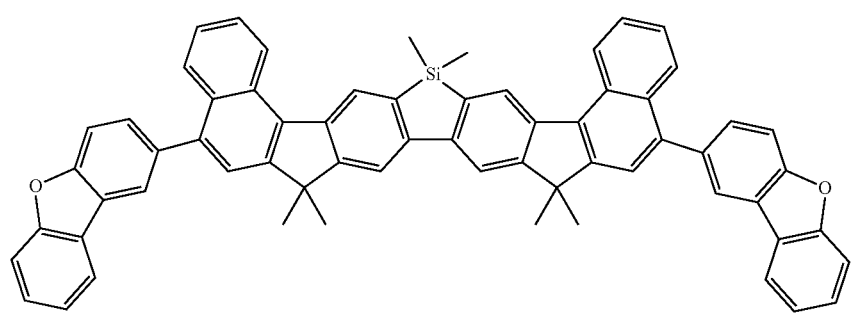

210
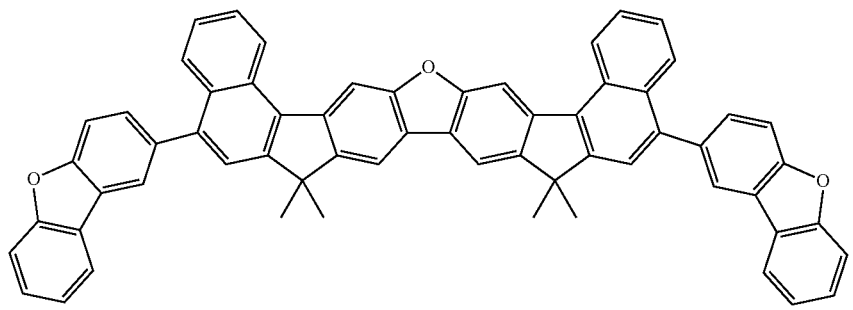
211
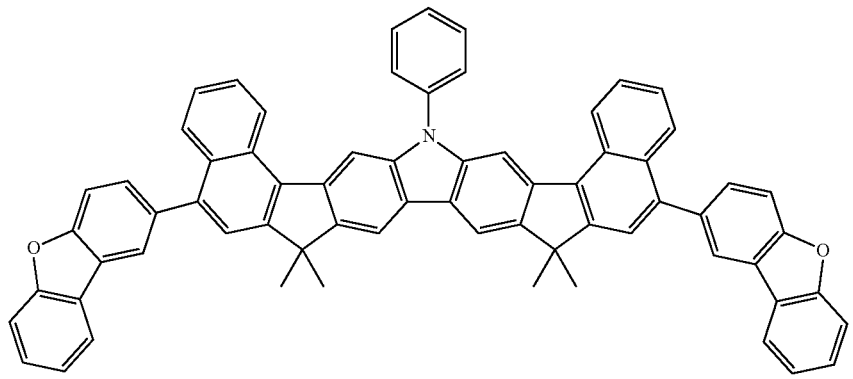
212
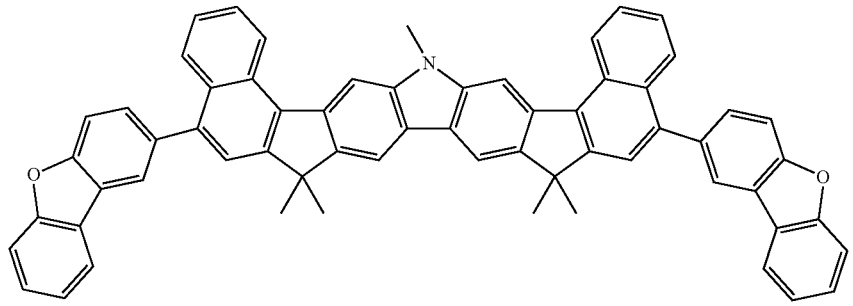
213 214
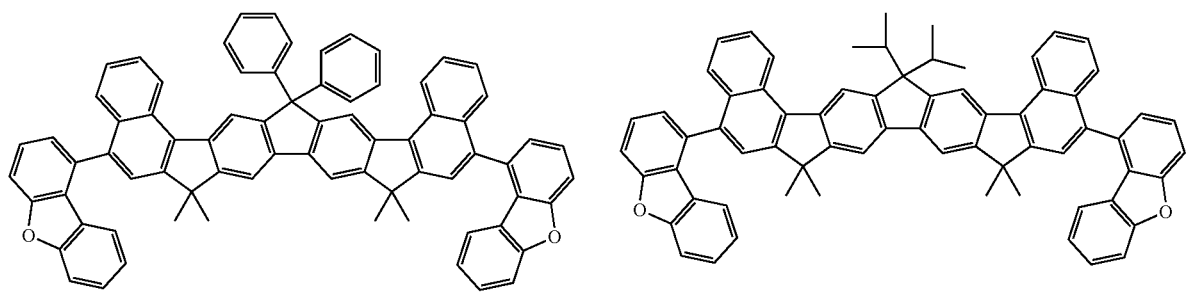
215 216
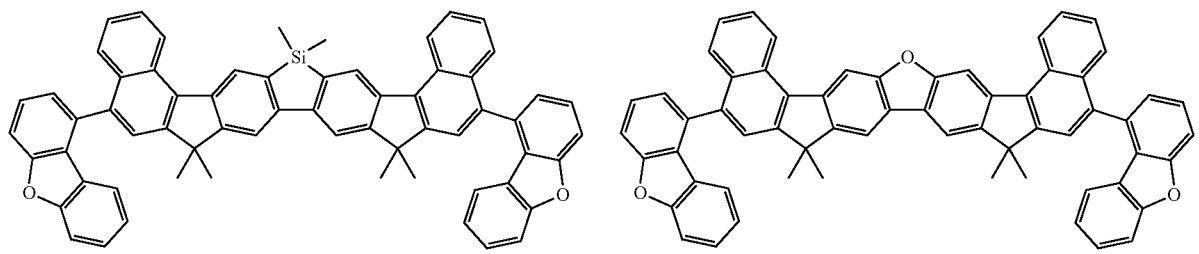

-continued
217
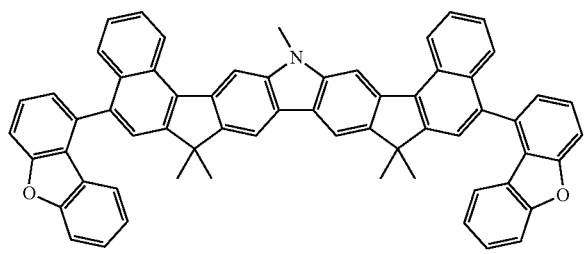
218
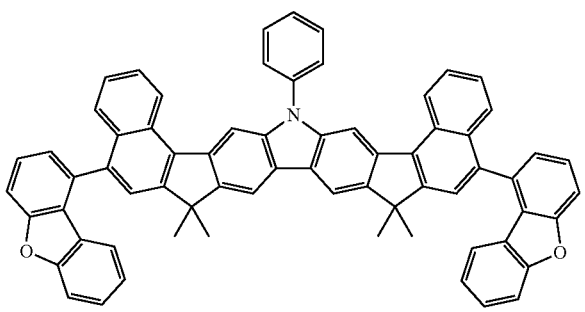
219
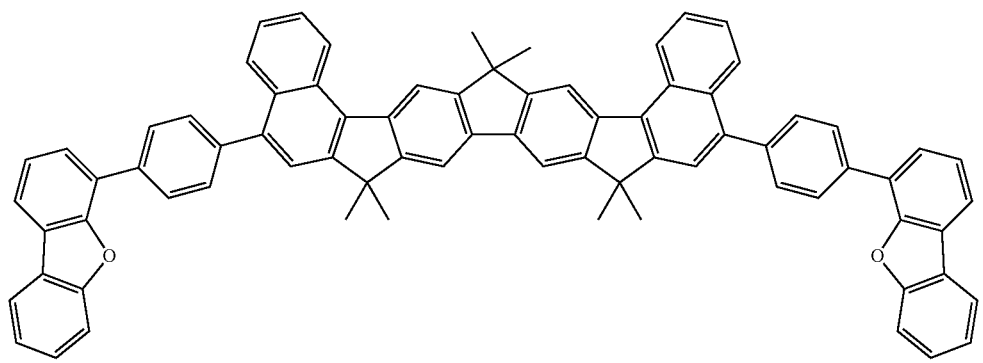
220
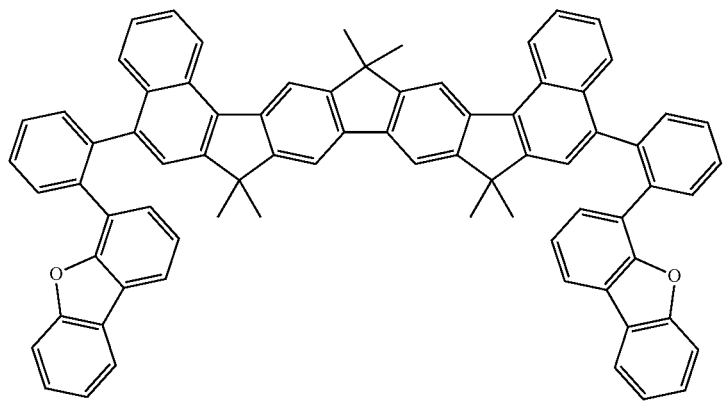
221
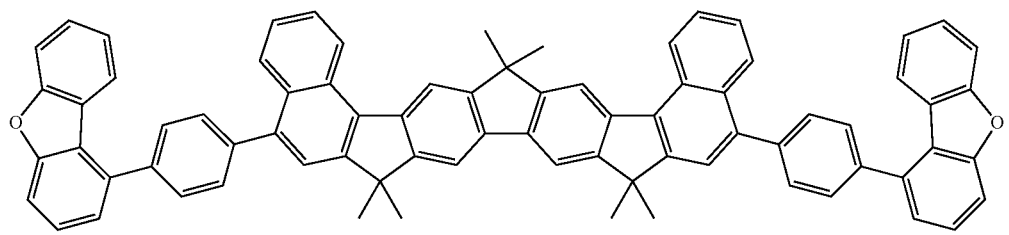
222
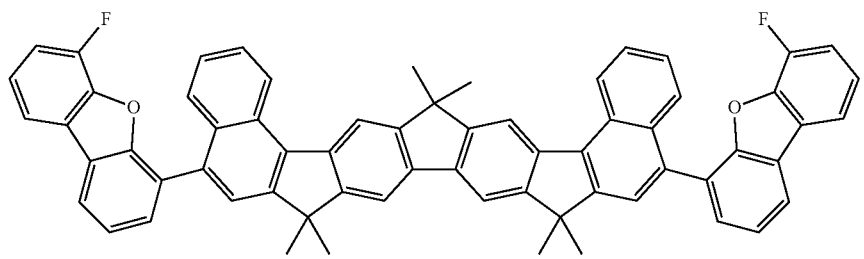

-continued
223
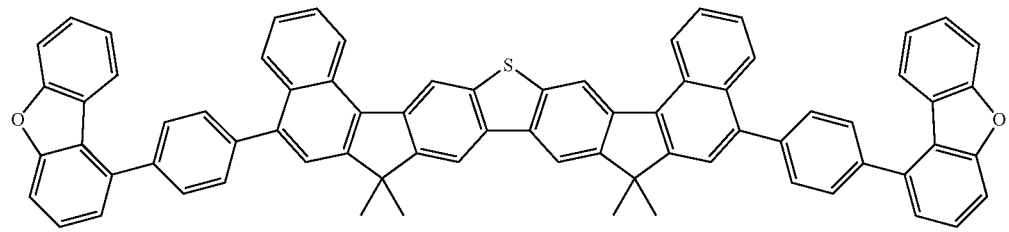
224
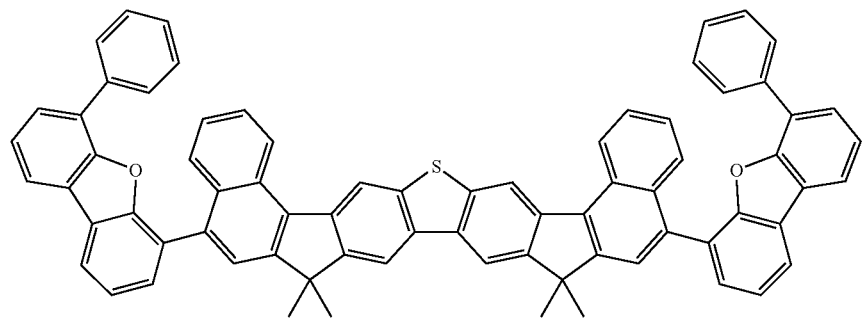
225
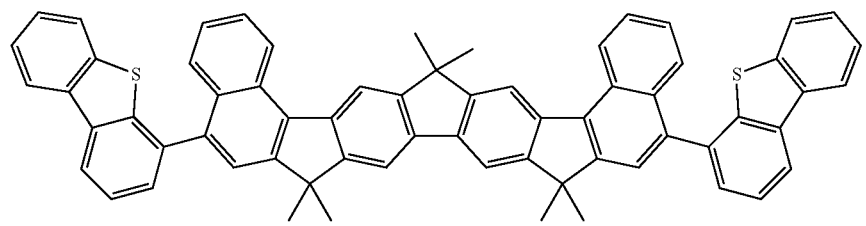
226
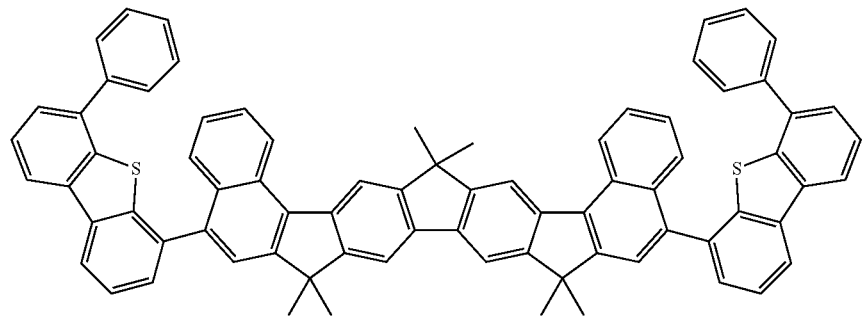
227
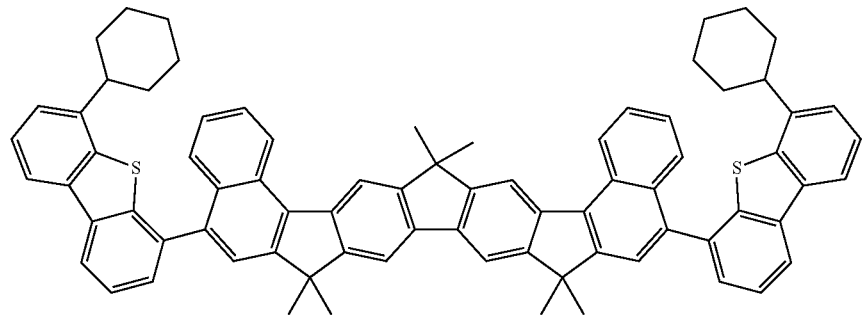

228
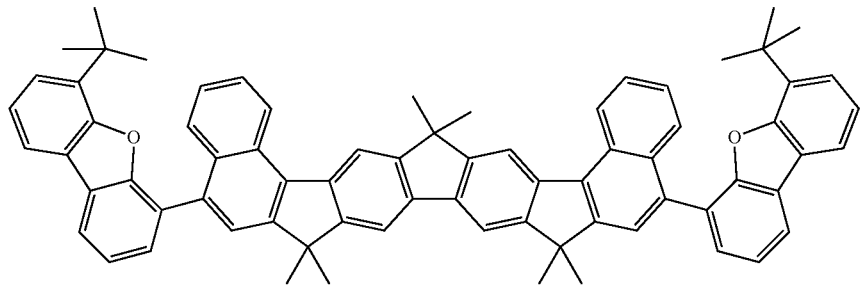
229
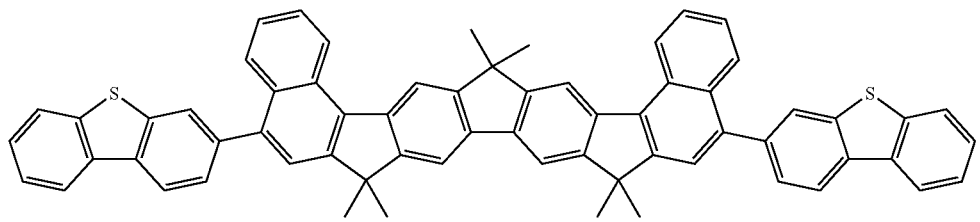
230
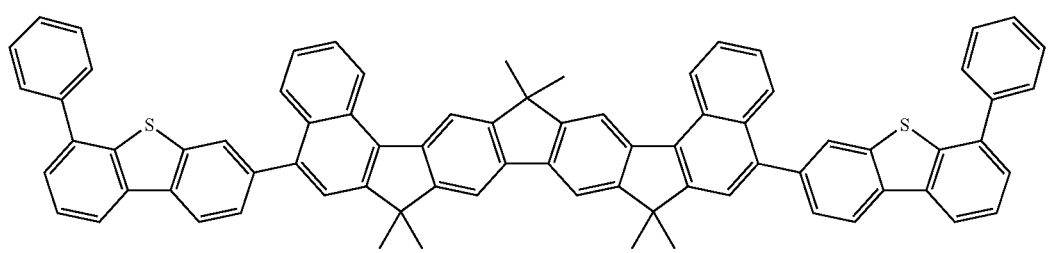
231
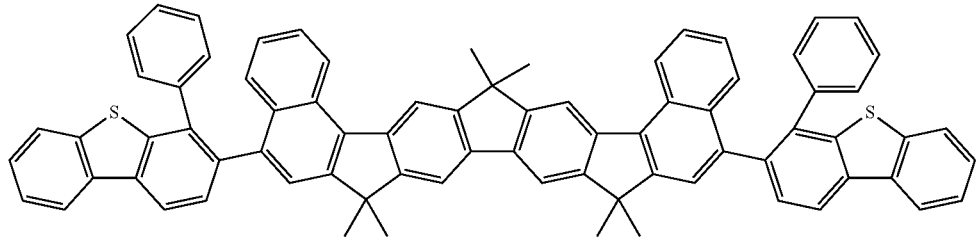
232
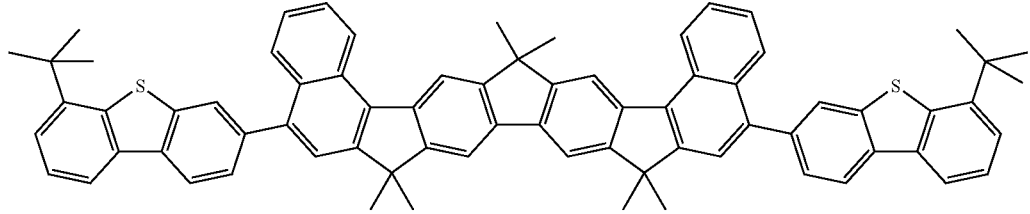
233
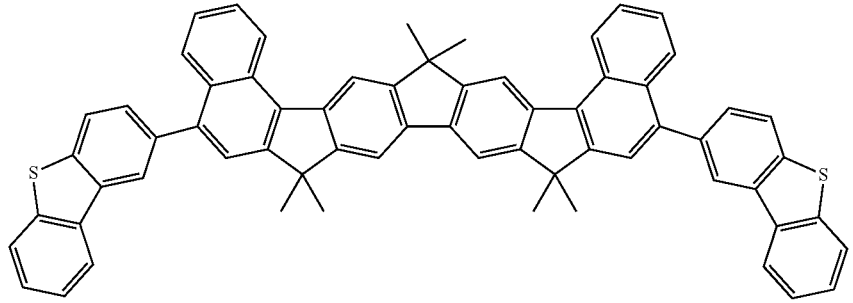

-continued
234
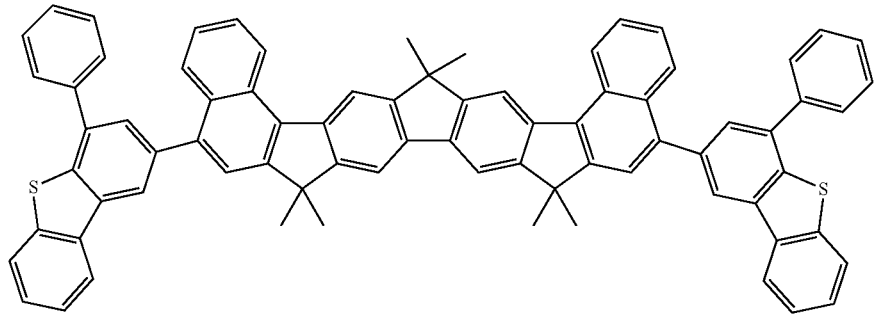
235
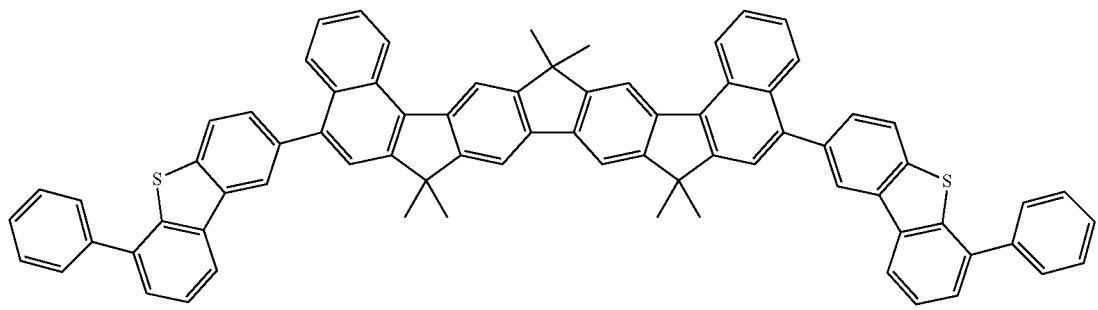
236
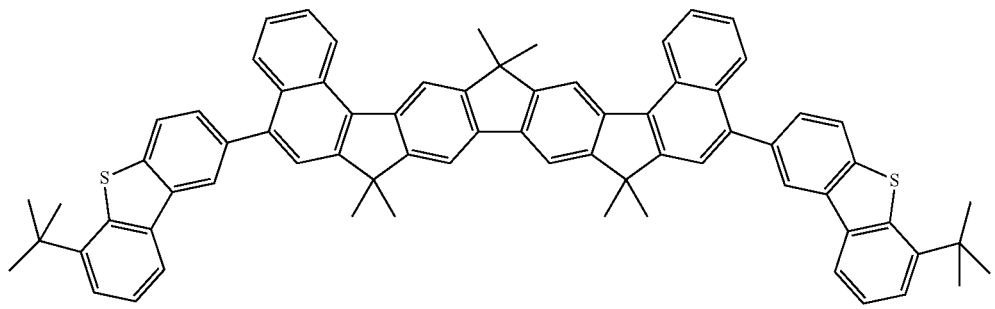
237 238
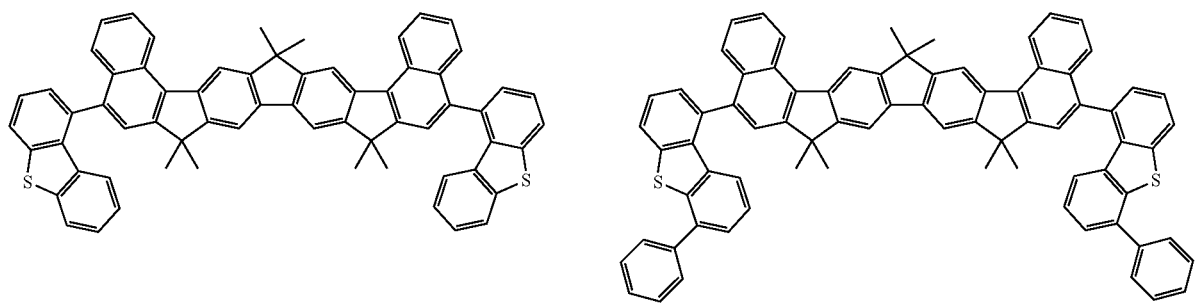
239 240
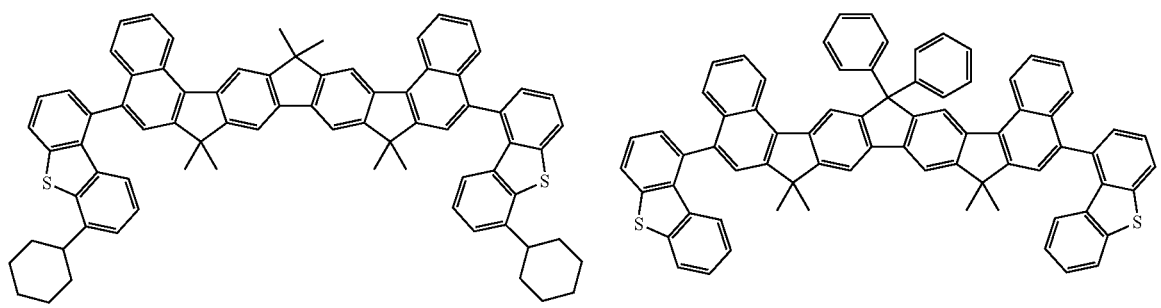

241
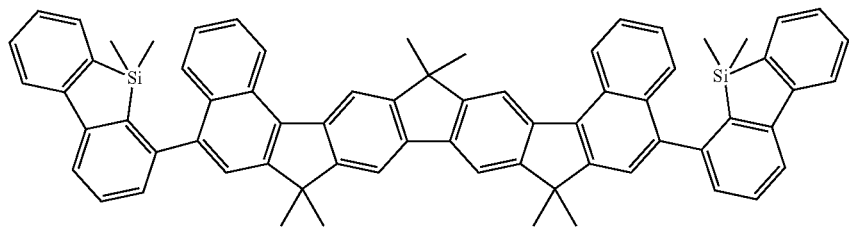
242
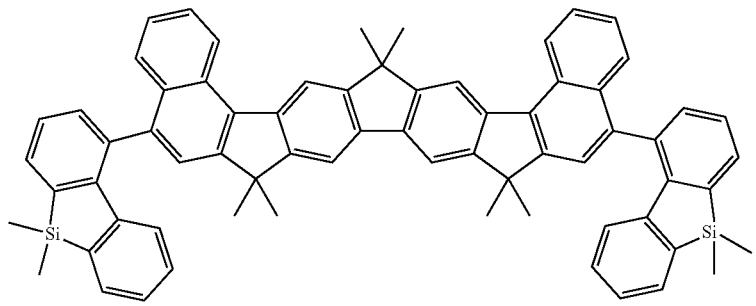
243
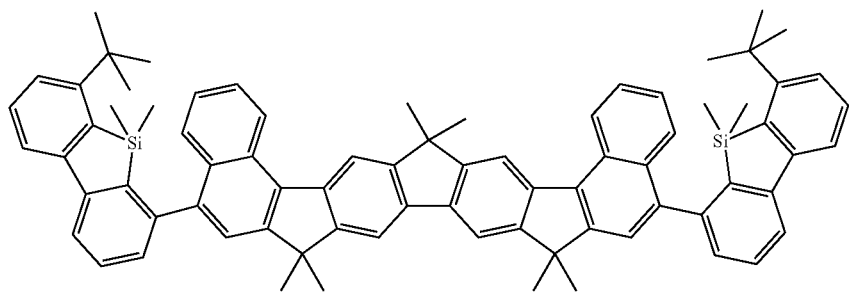
244
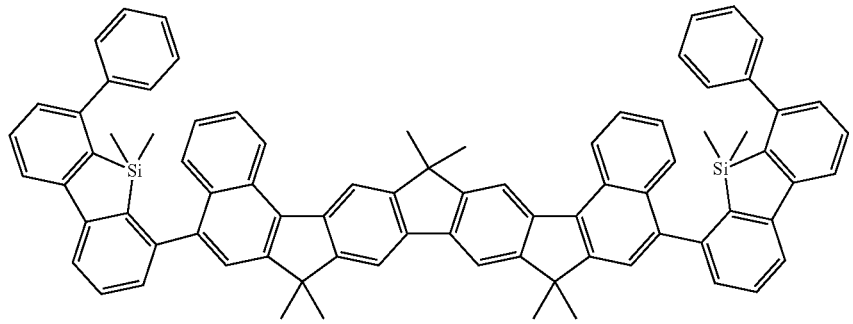
245
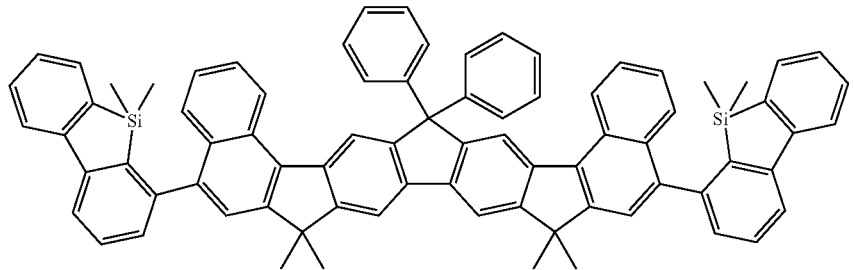

246
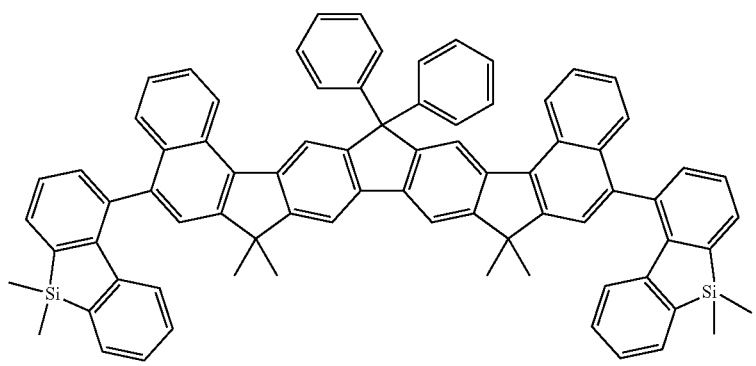
247
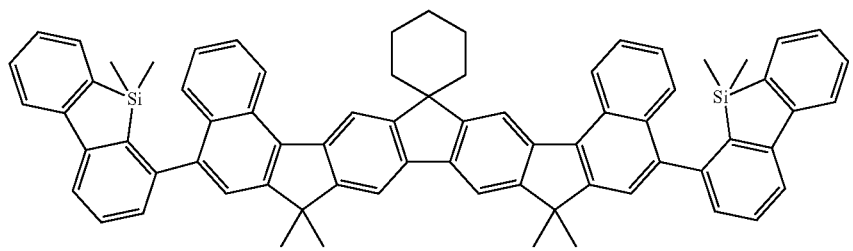
248
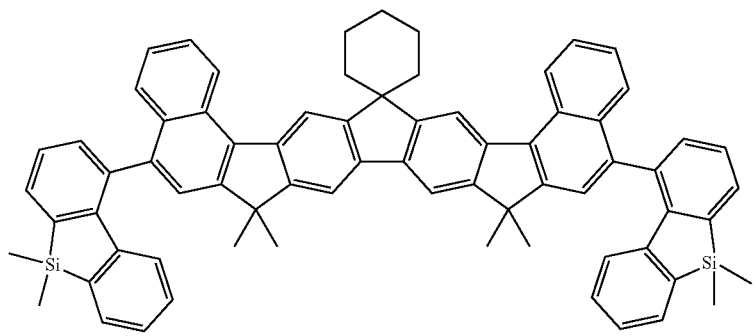
249
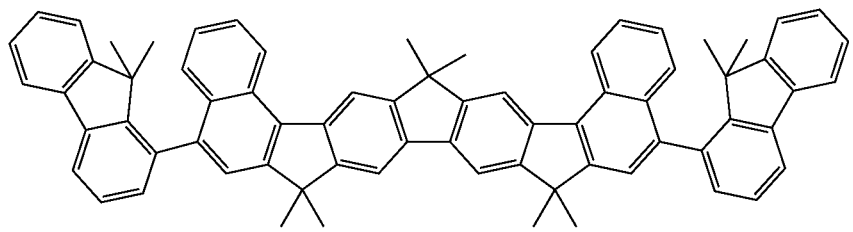
250
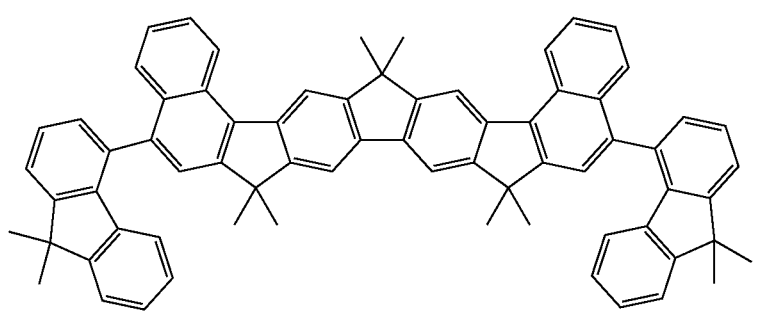

-continued
251
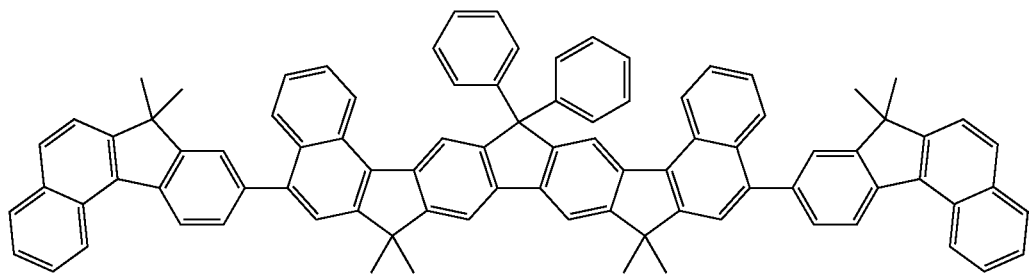
252
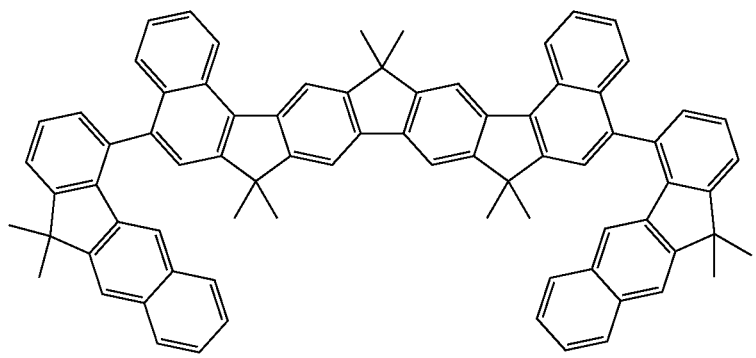
253
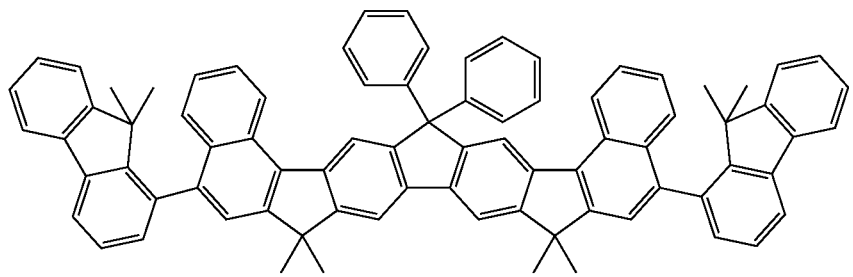
254
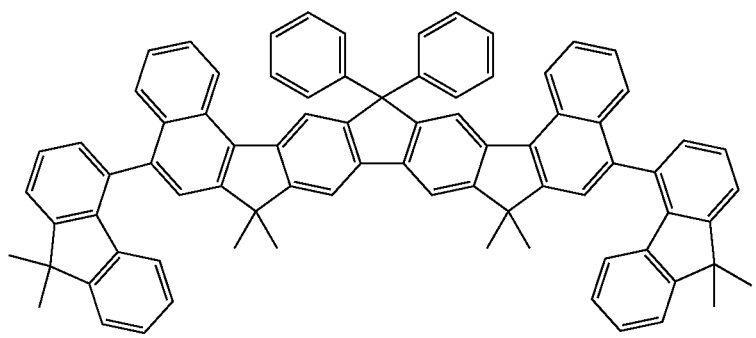
255
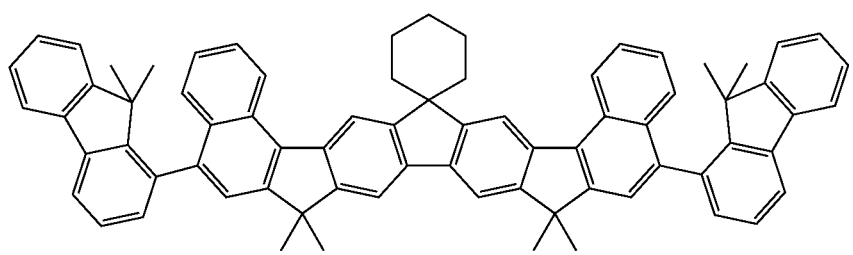

-continued
256
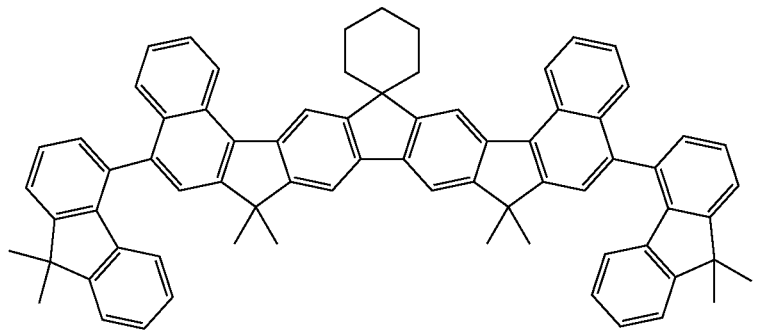
257
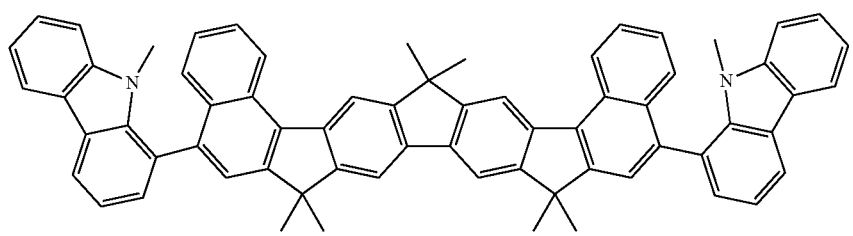
258
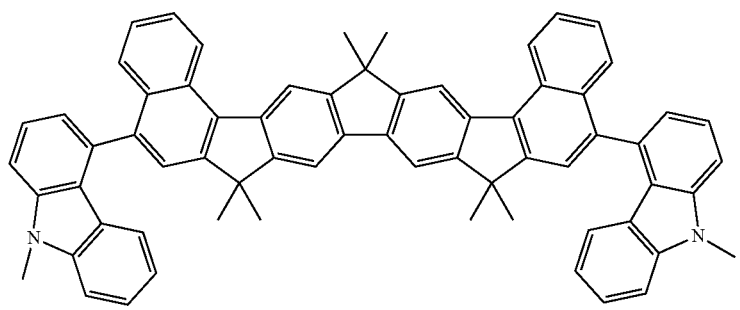
259
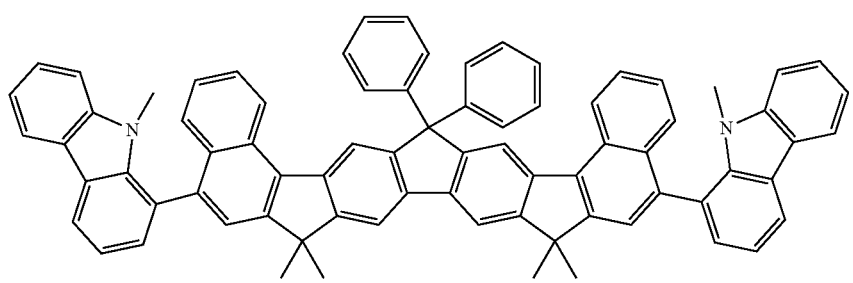
260
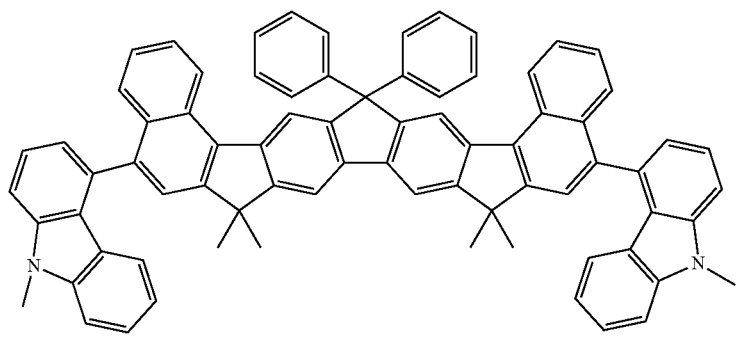

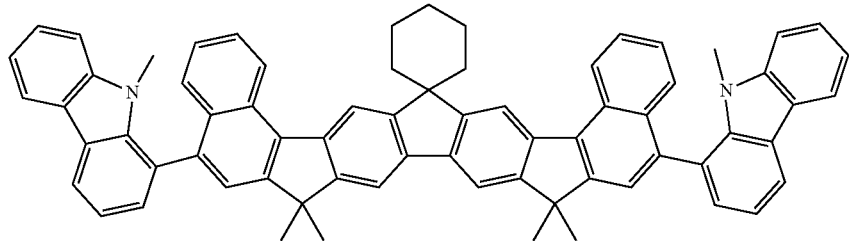
261
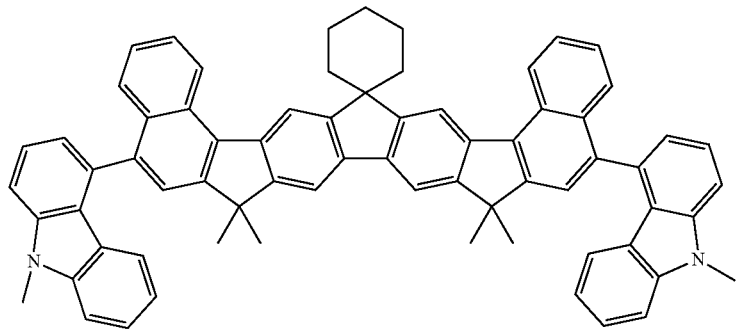
262
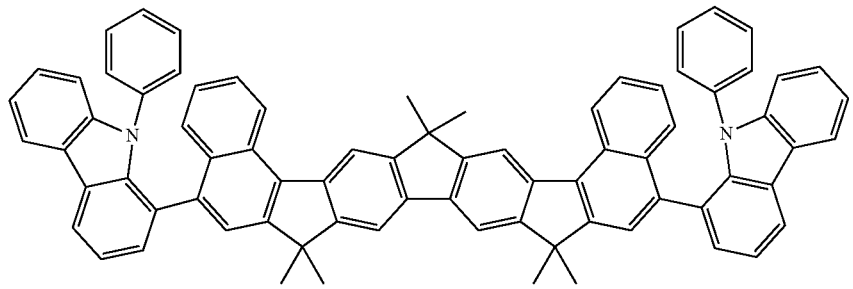
263
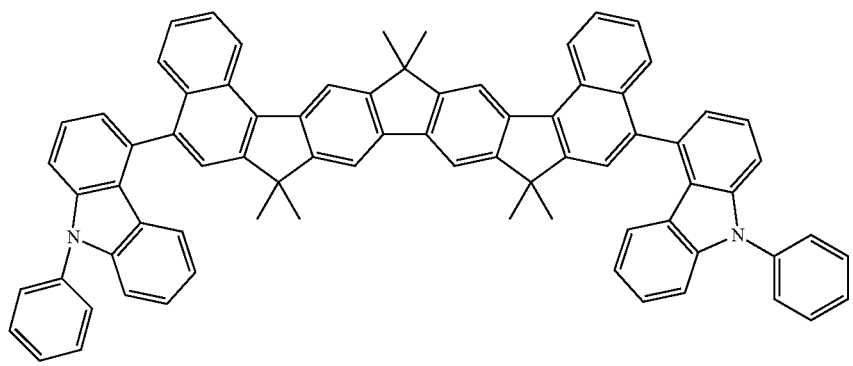
264
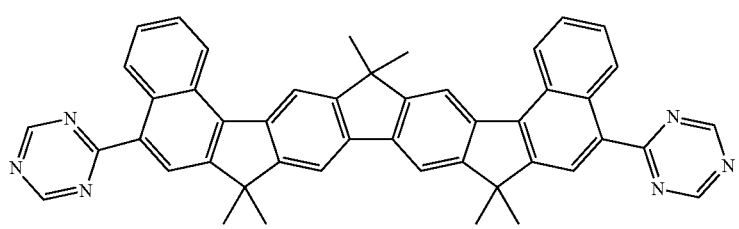
265

266
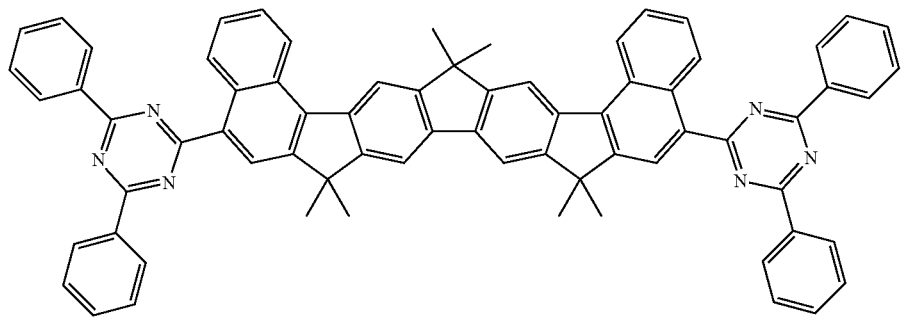
267
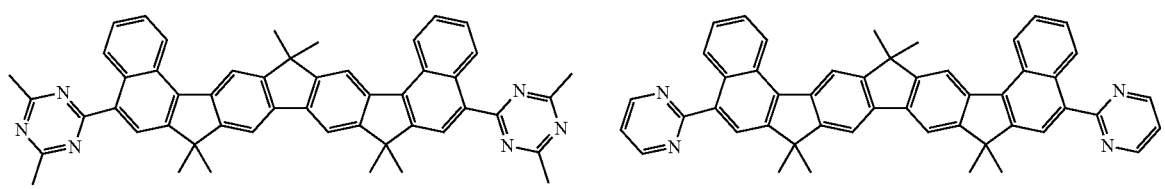
268
269
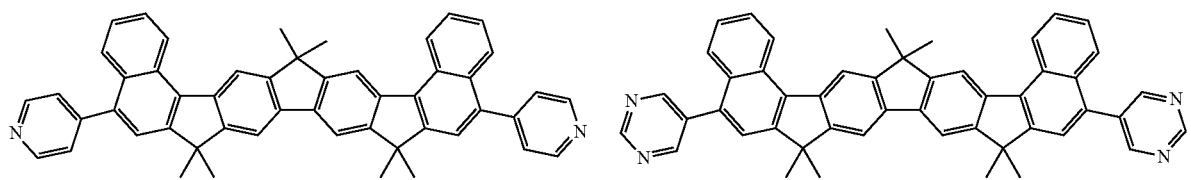
270
271
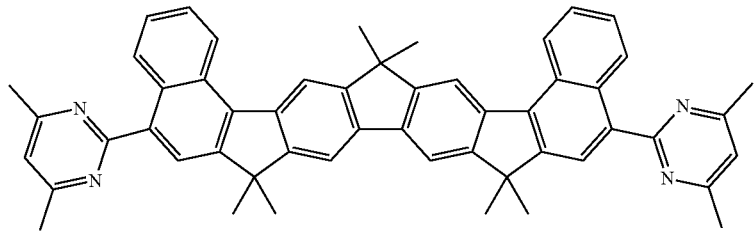
272
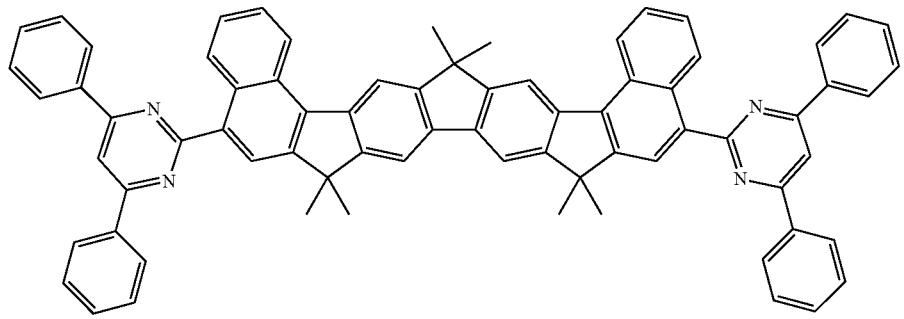
273
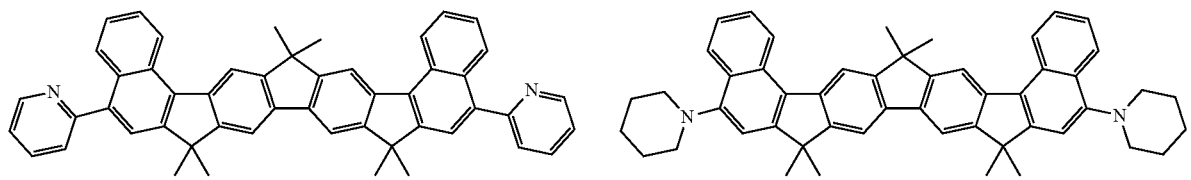
274

275
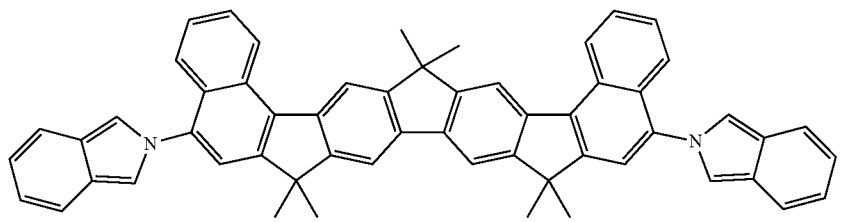
276
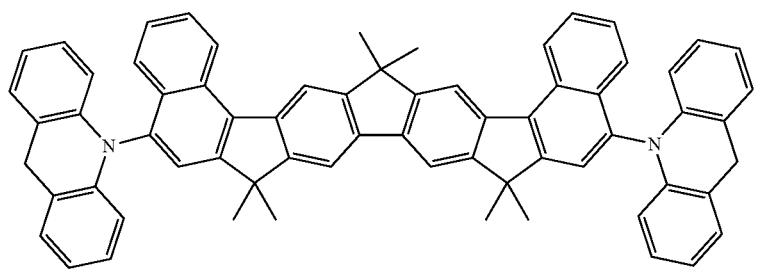
277
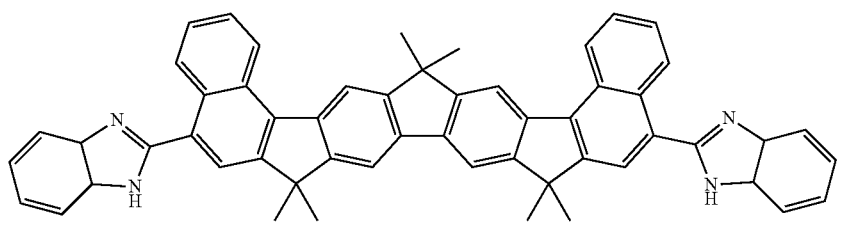
278
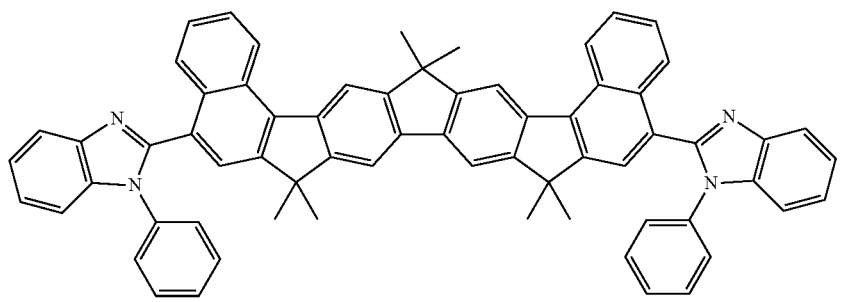
279
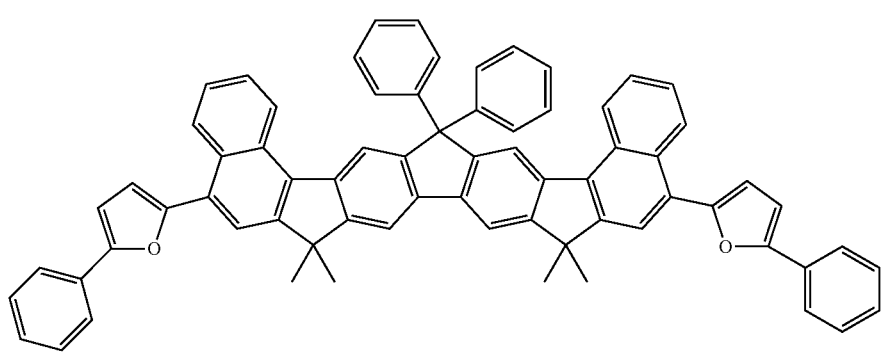

-continued
280
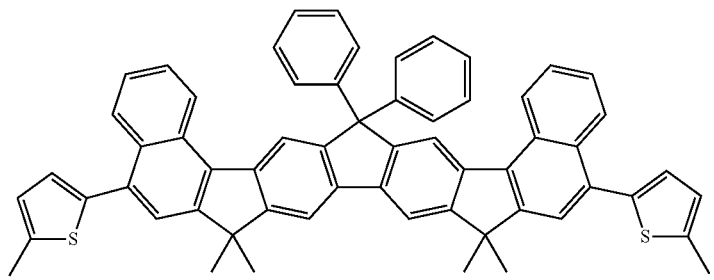
281
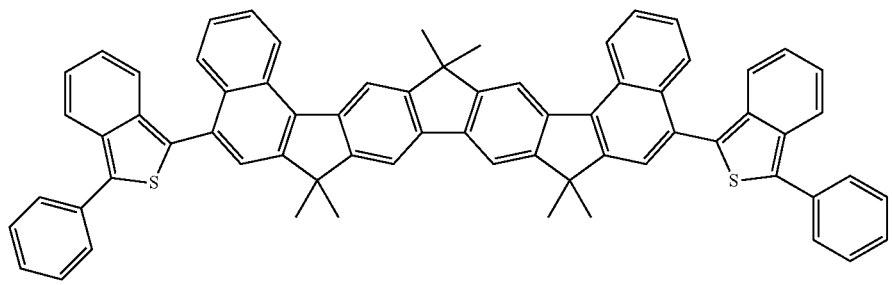
282
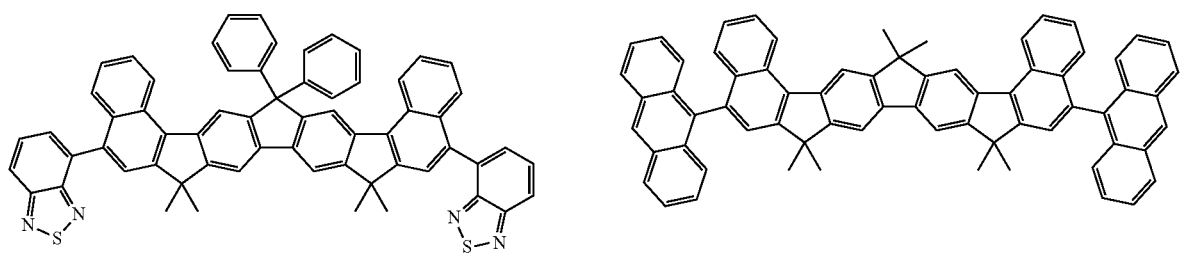
283
284
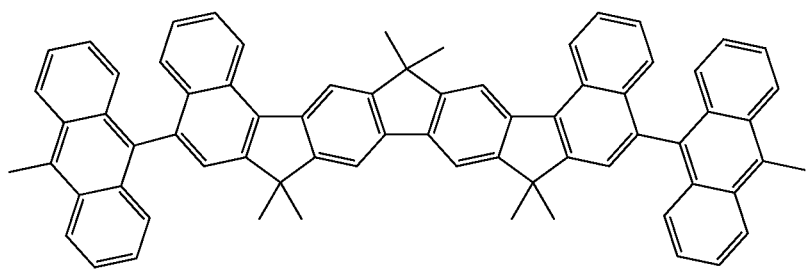
285
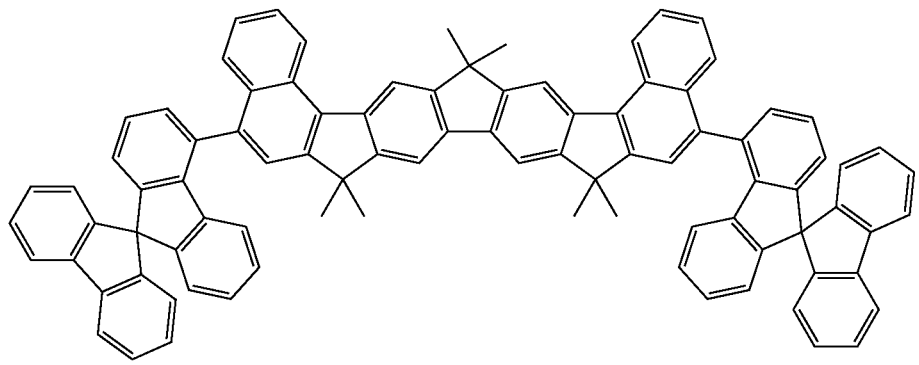

286
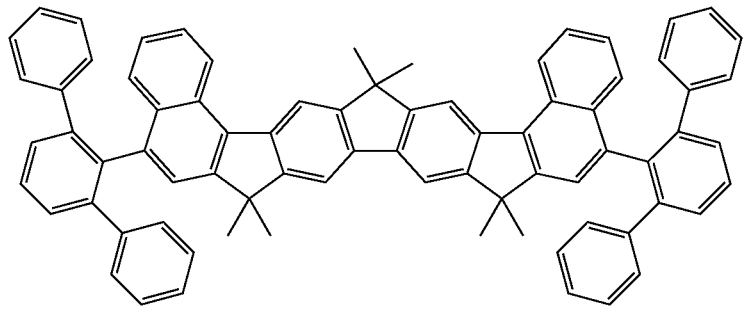
287
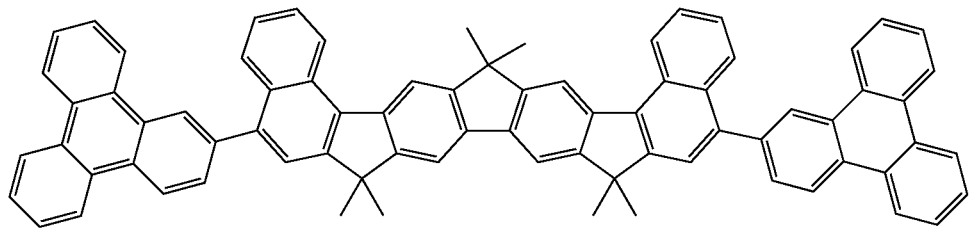
288
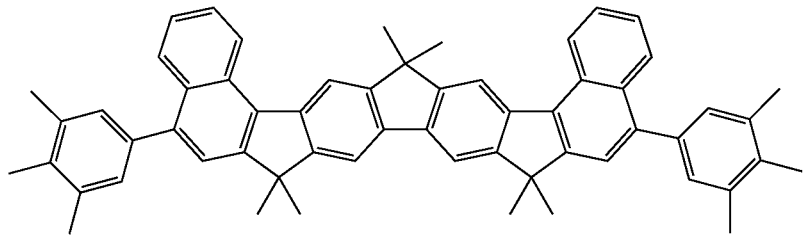
289
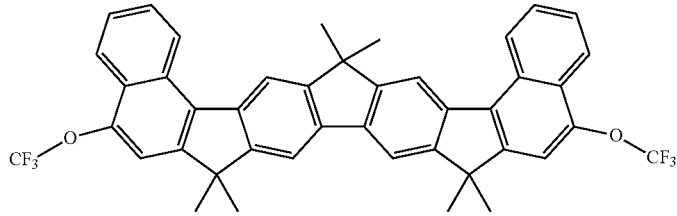
290
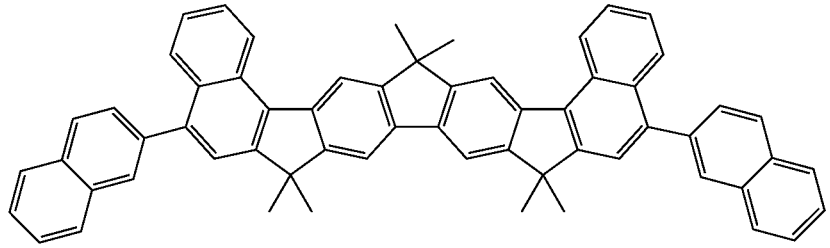
291
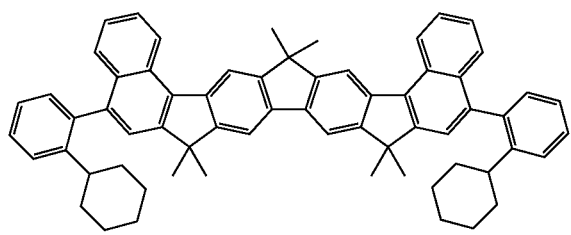
292
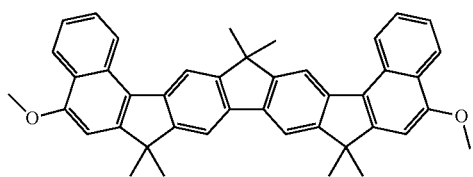

293
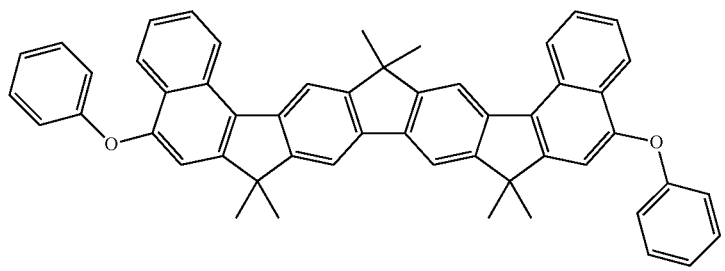
294
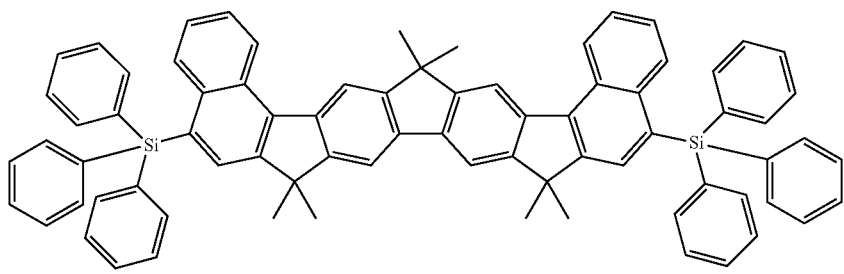
295
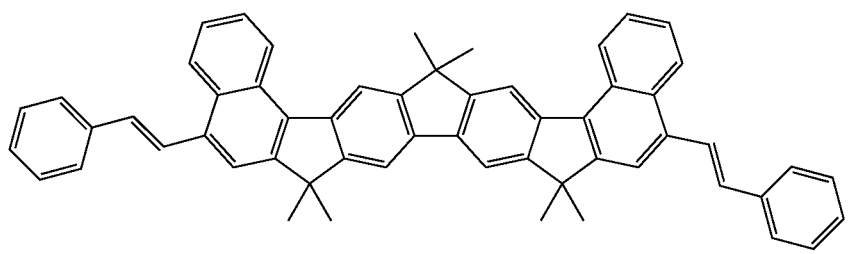
296
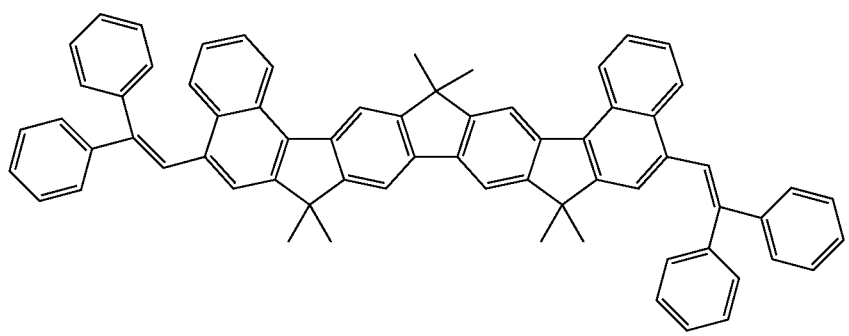
297
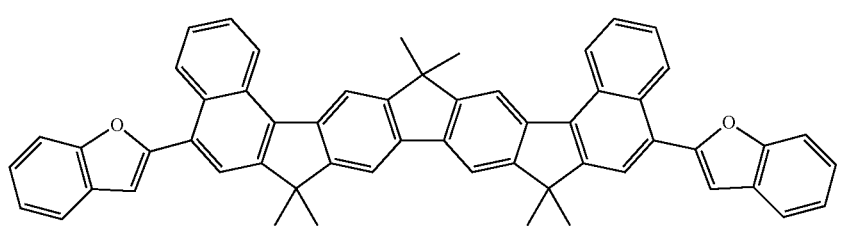
298
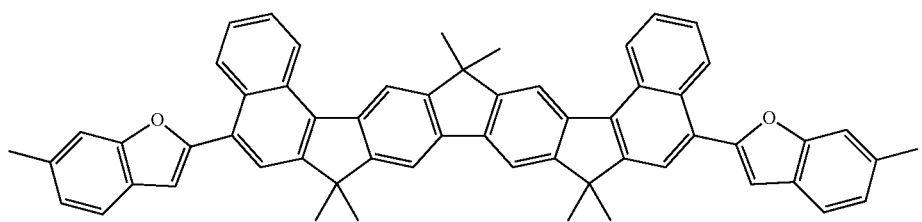

-continued
299
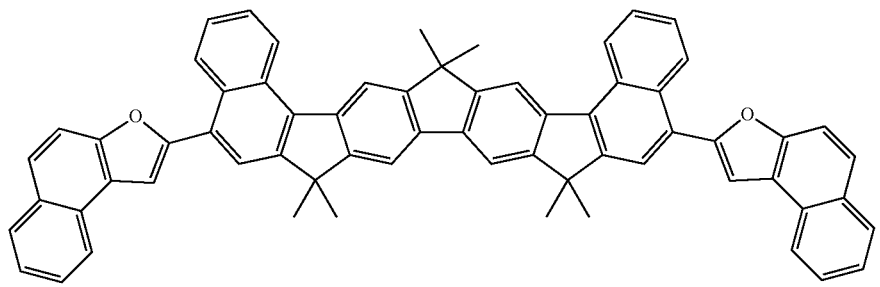
300
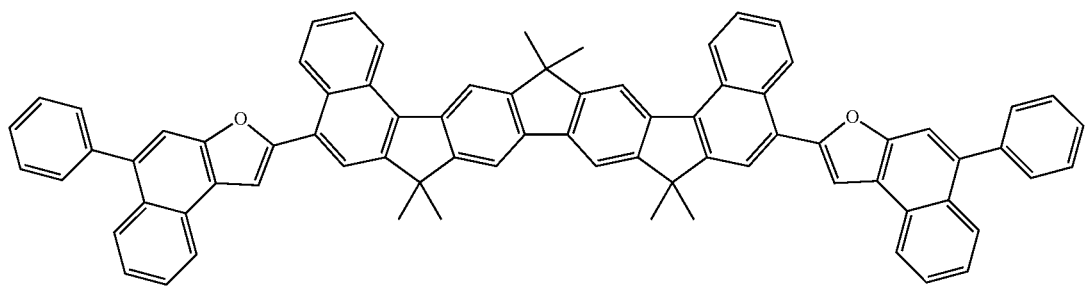
301
302
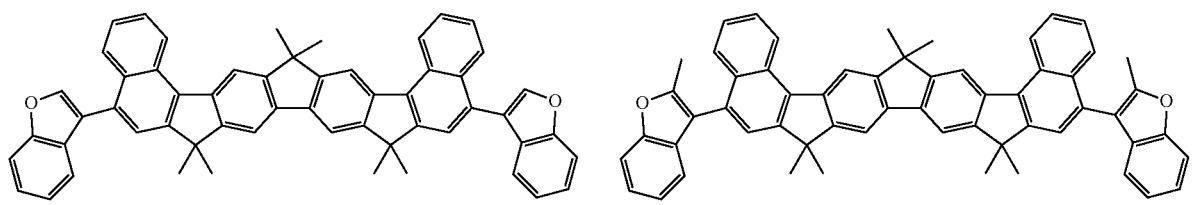
303
304
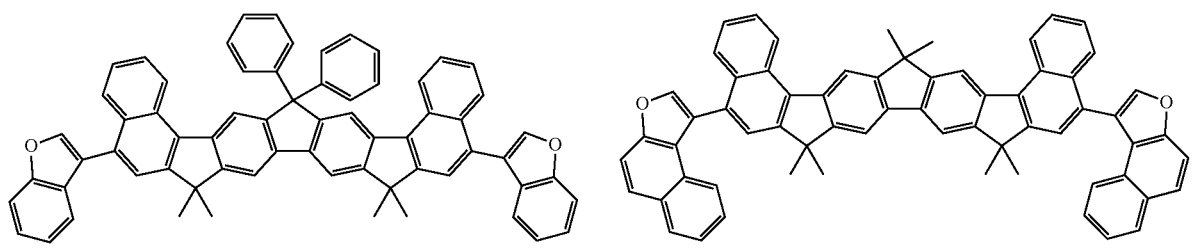
305
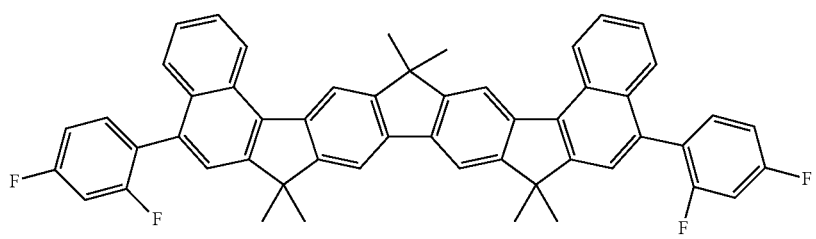
306
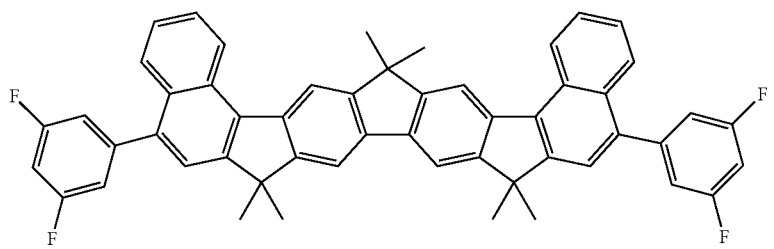

307
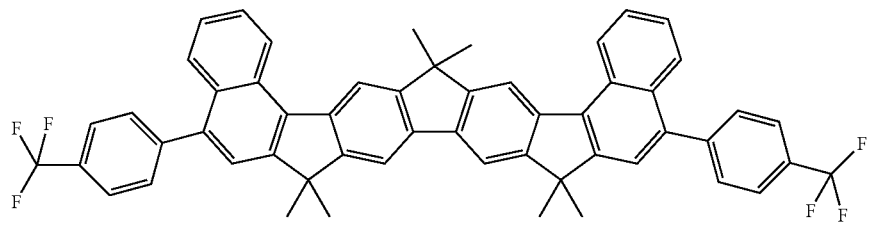
308
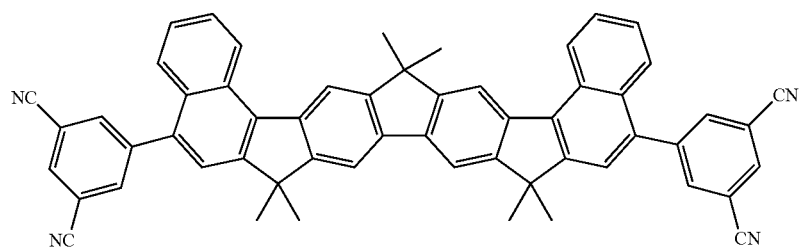
309
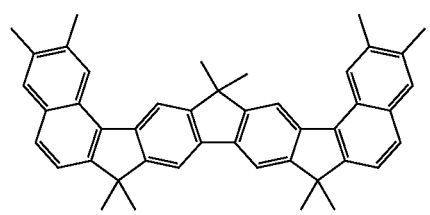
310
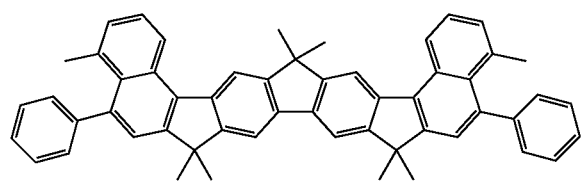
311
312
313
314
315
316
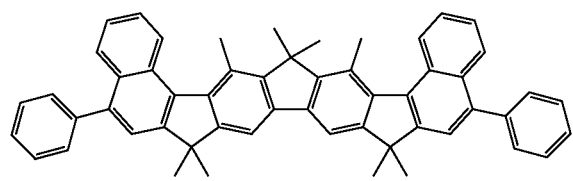
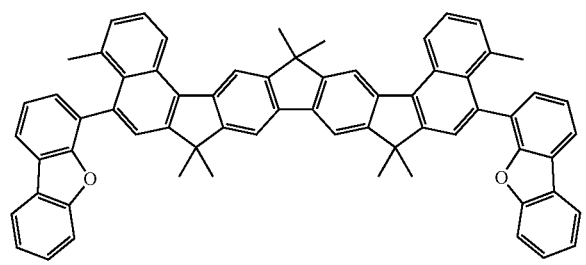
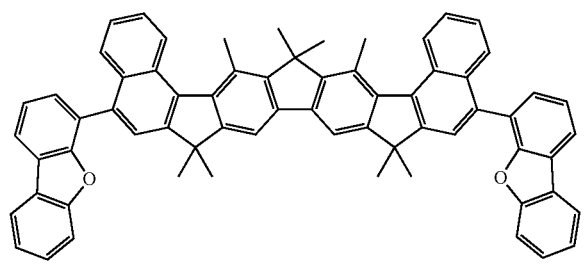

-continued
317
318
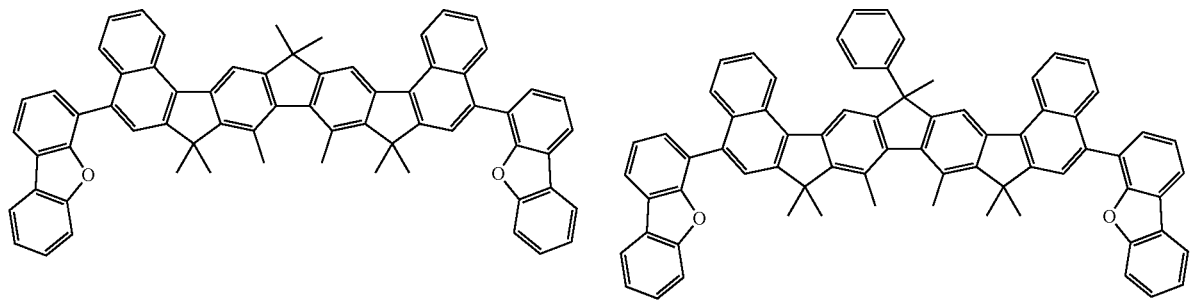
319
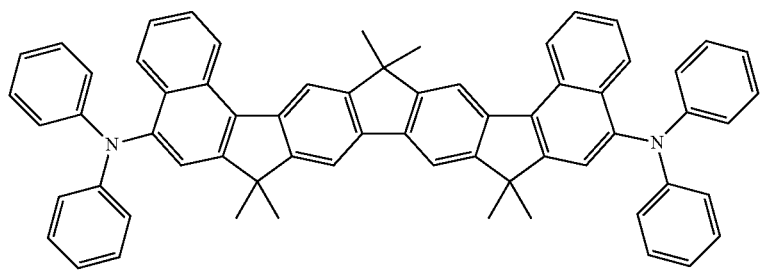
320
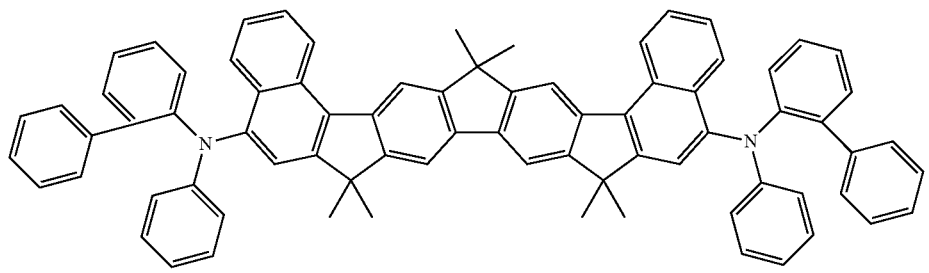
321
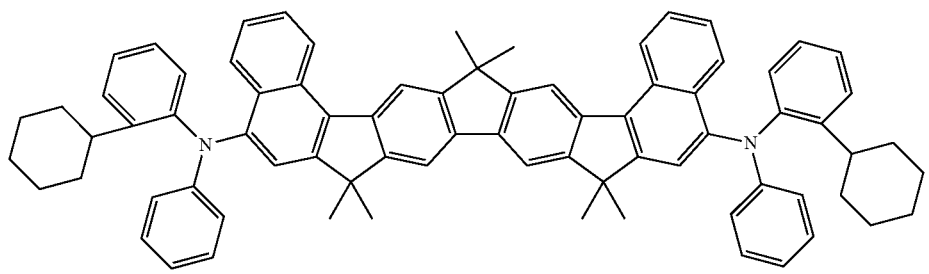
322
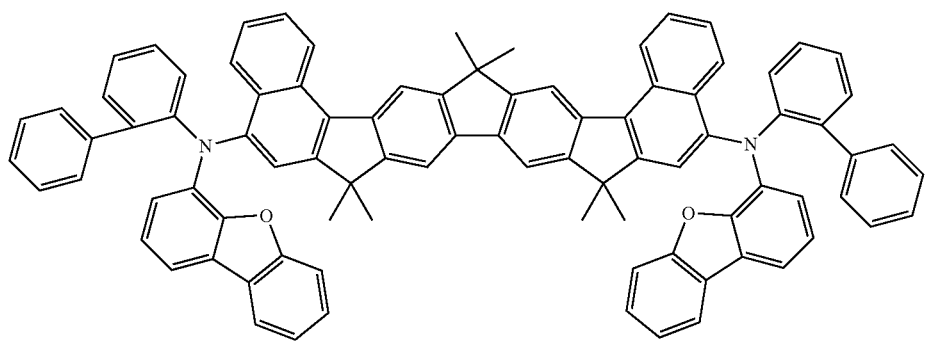

-continued
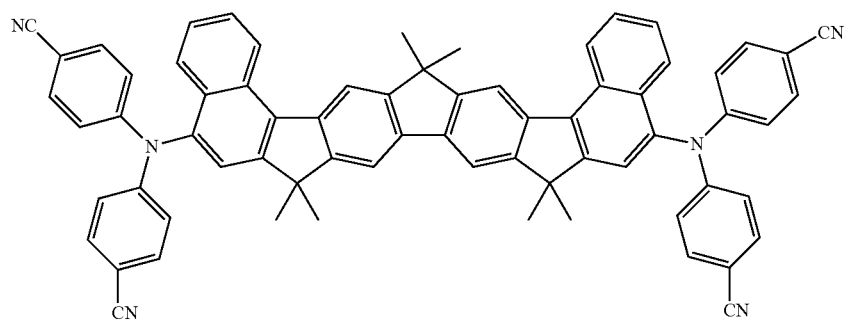
323
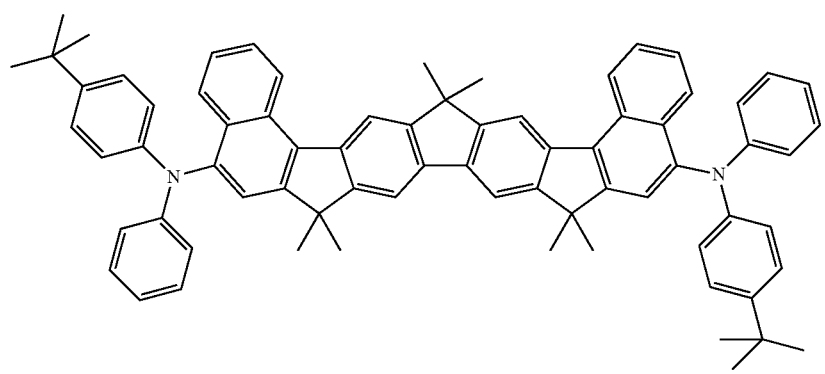
324
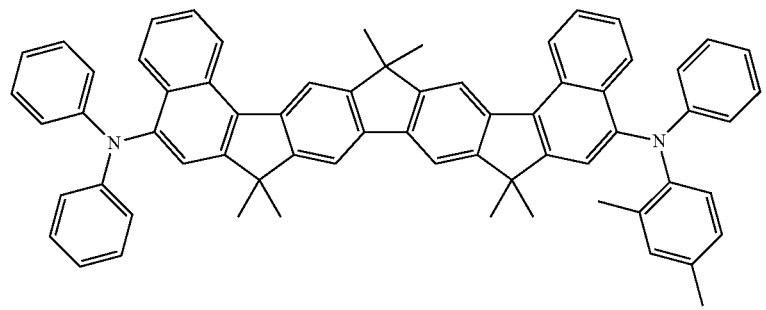
325
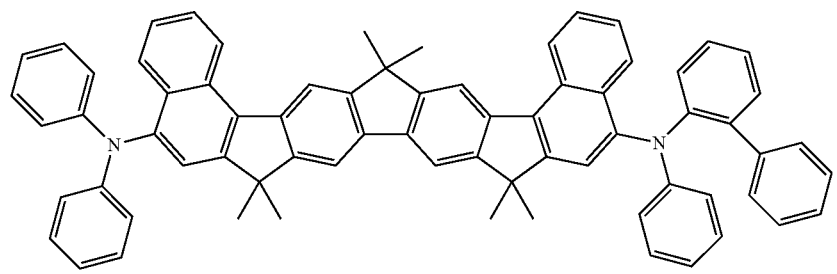
326
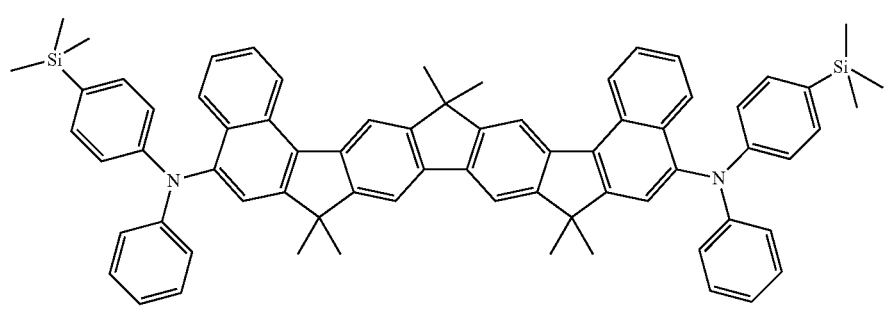
327

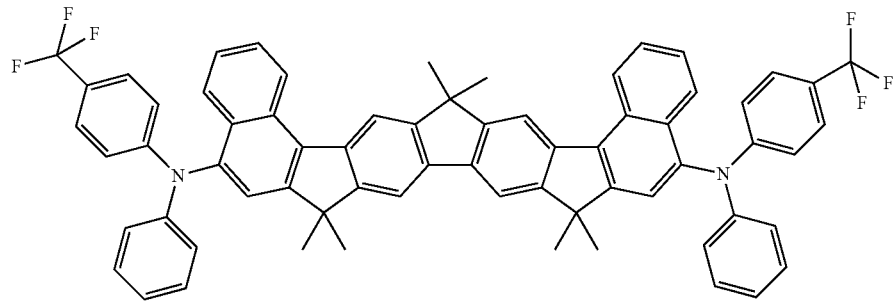 328
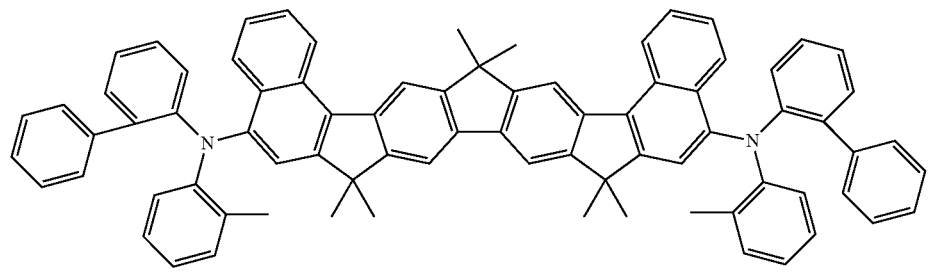 329
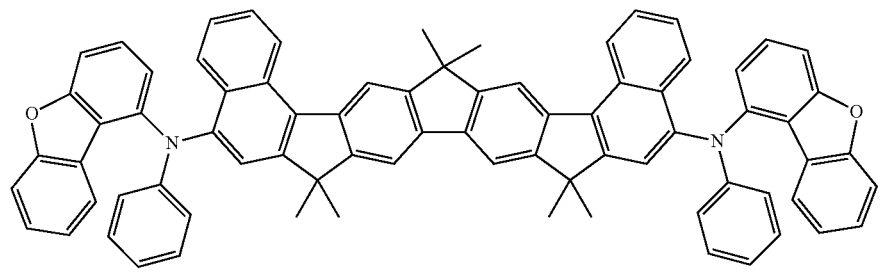 330
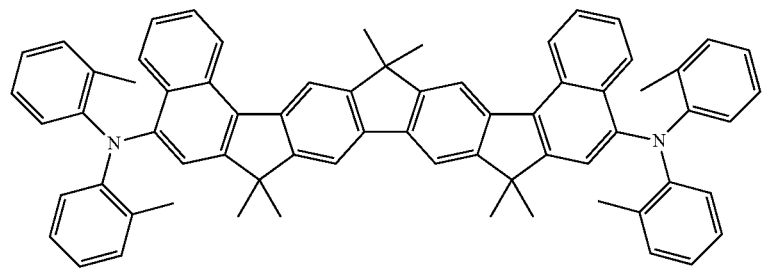 331
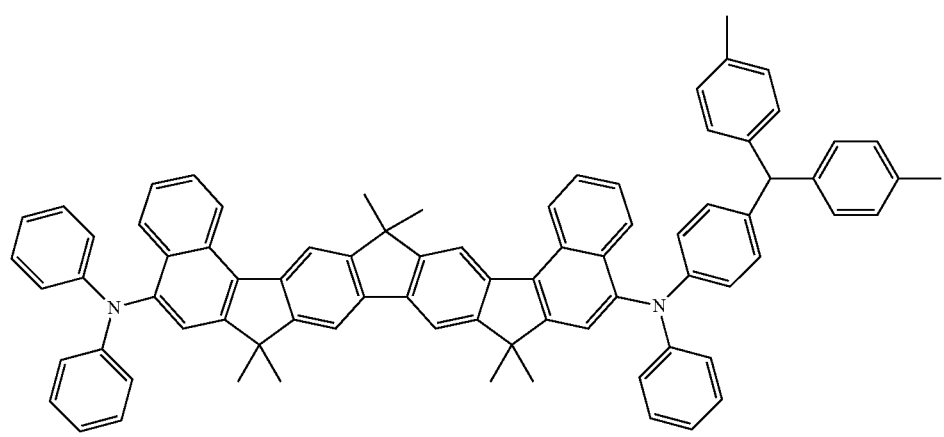 332

333
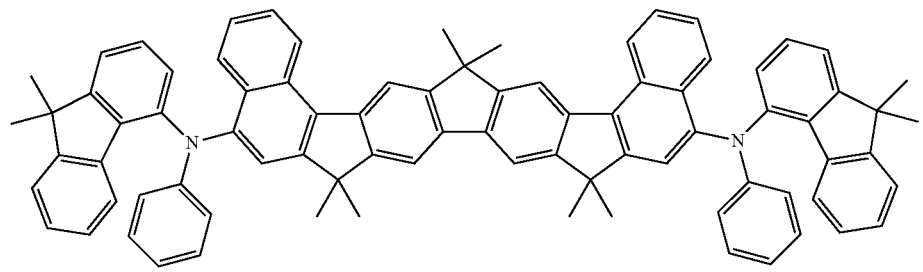
334
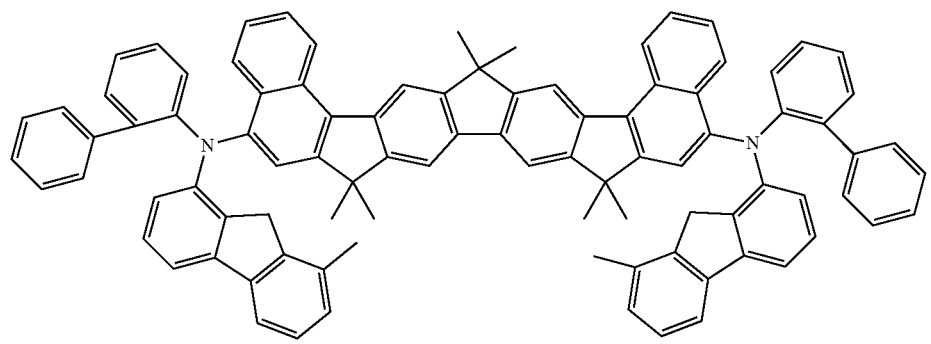
335
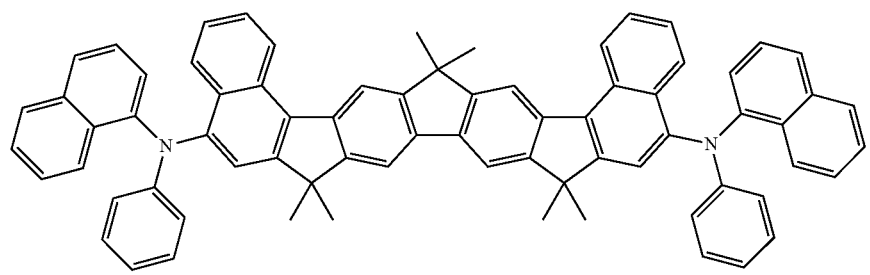
336
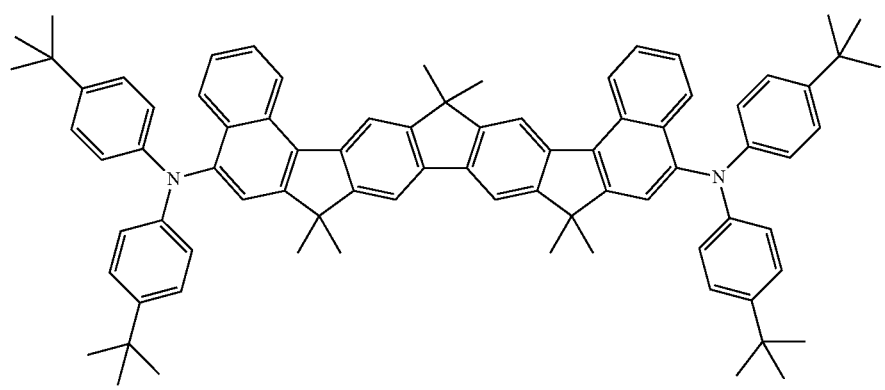
337
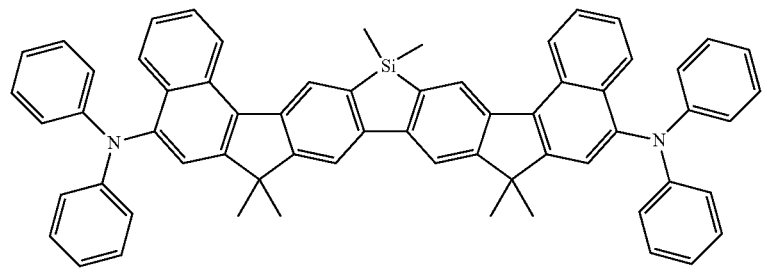

-continued
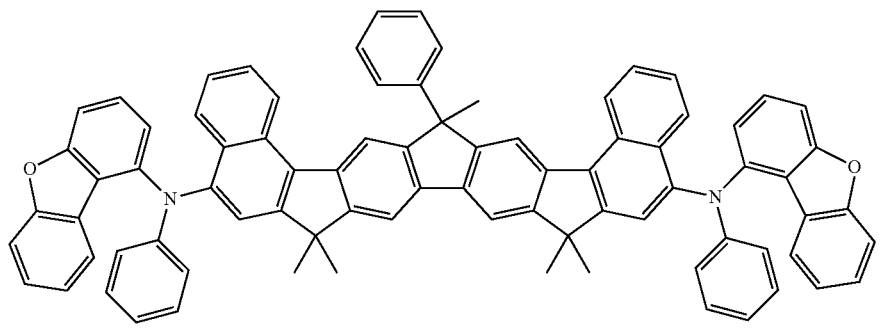
338
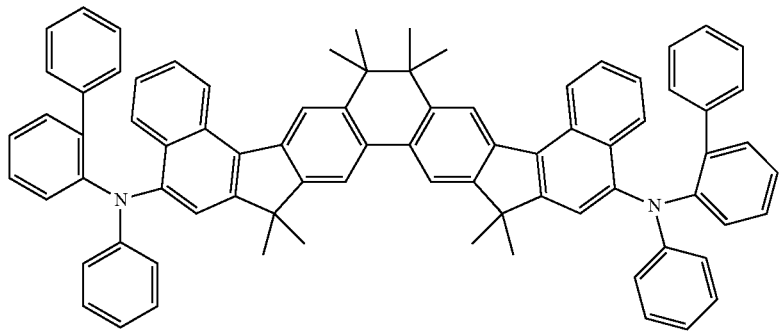
339
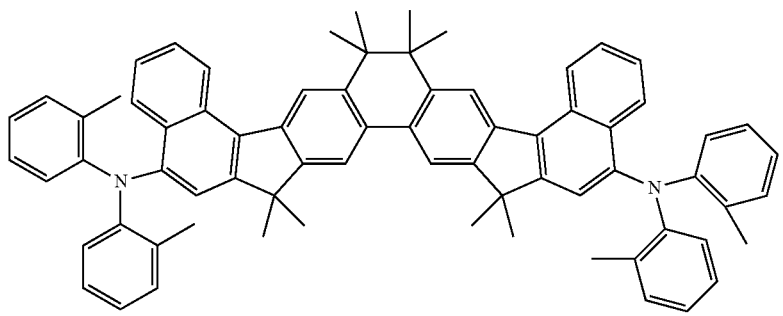
340
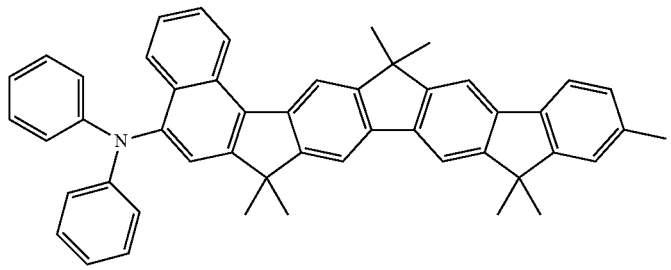
341
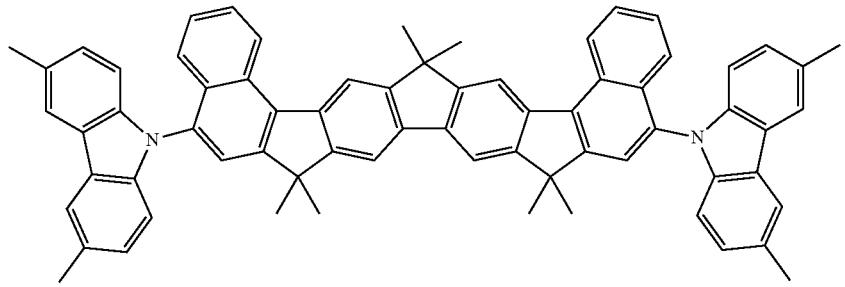
342

343
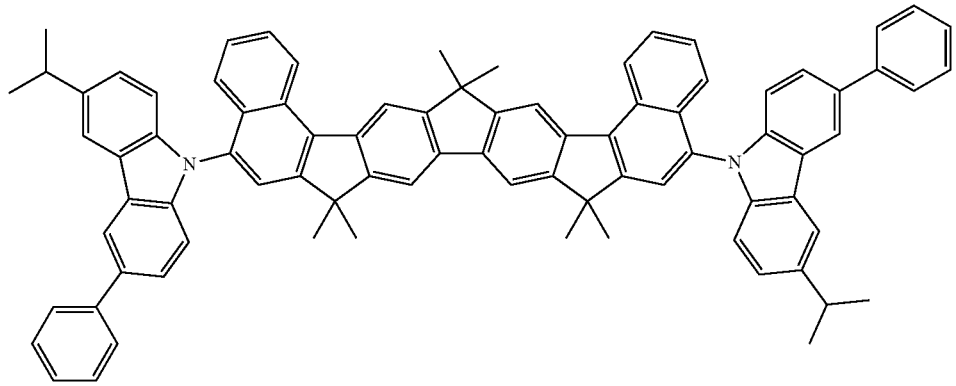
344
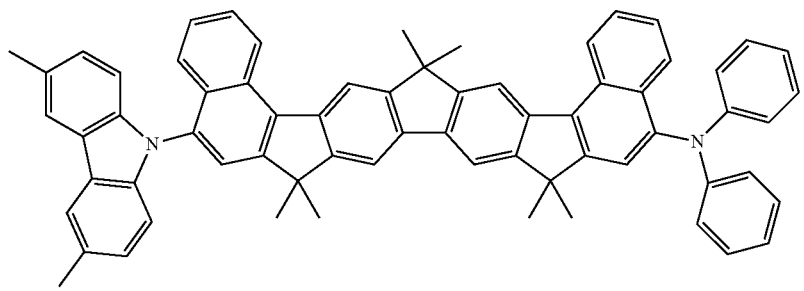
345
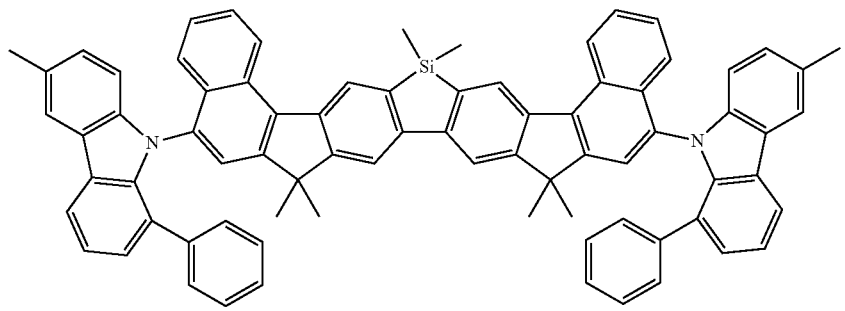
346
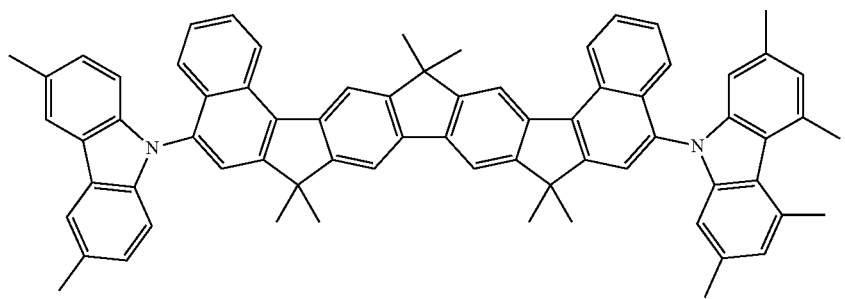
347
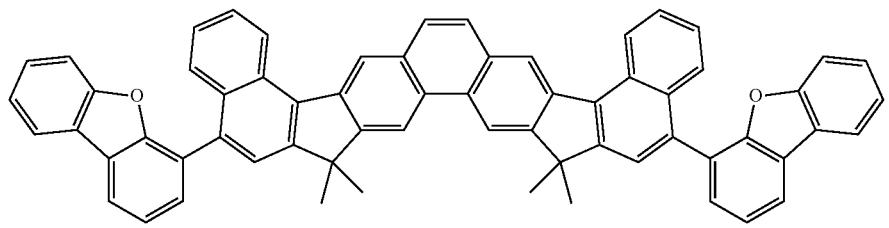

348
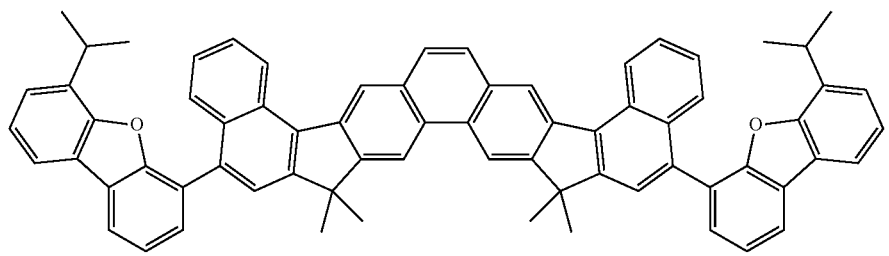
349
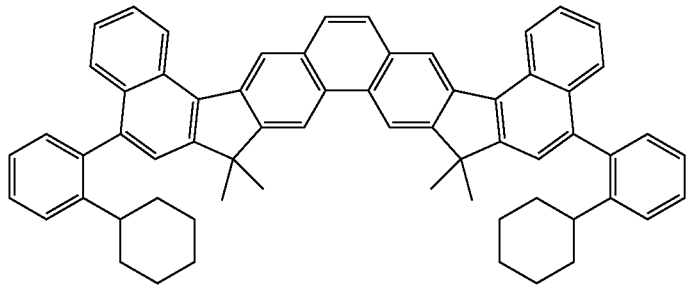
350
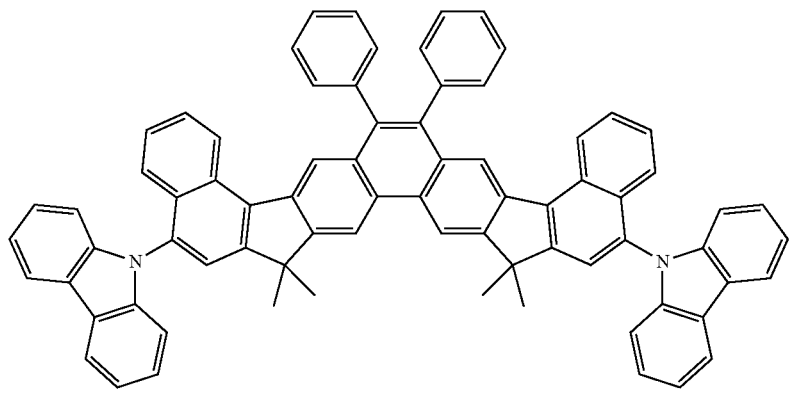
351
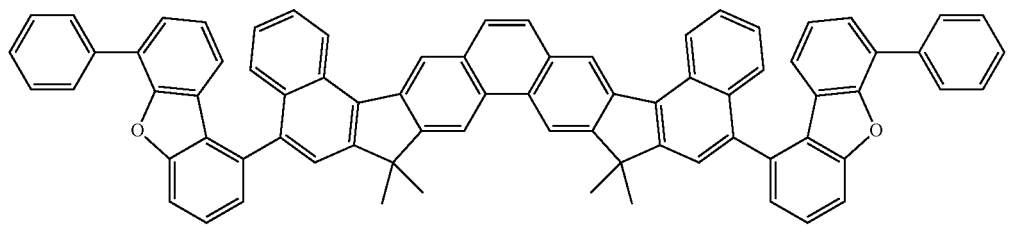
352
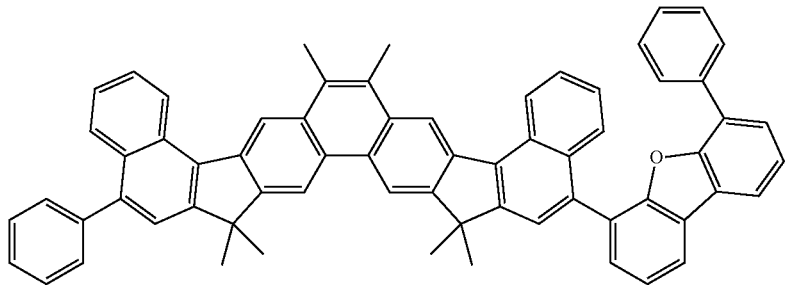

353
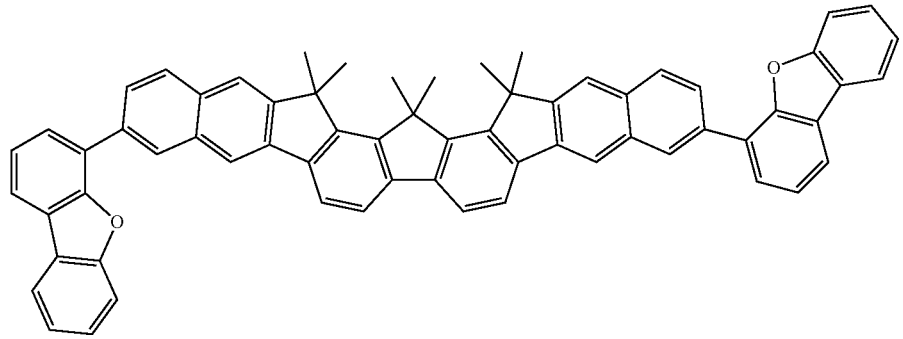
354
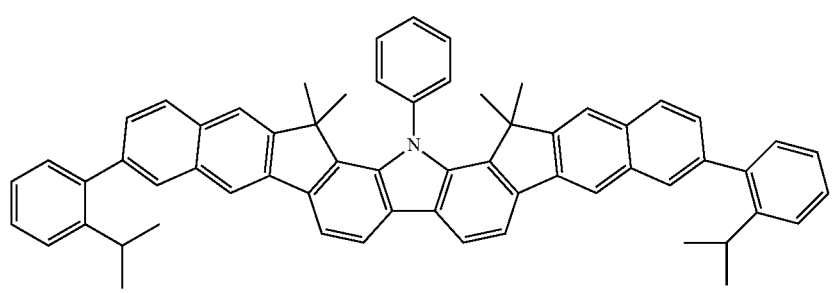
355
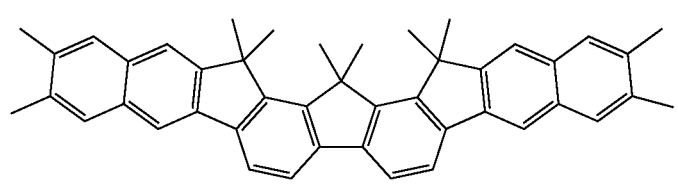
356
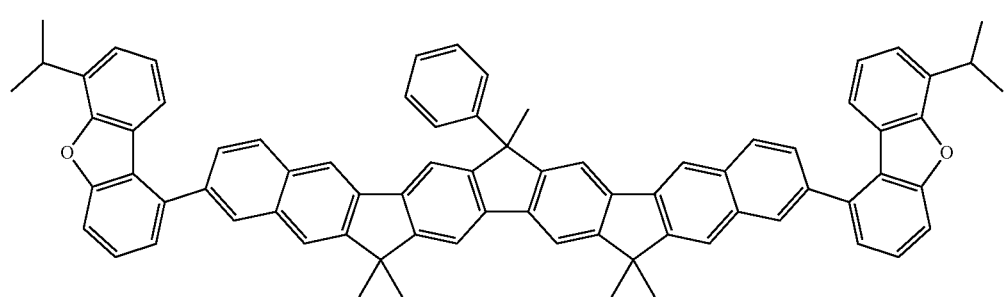
357
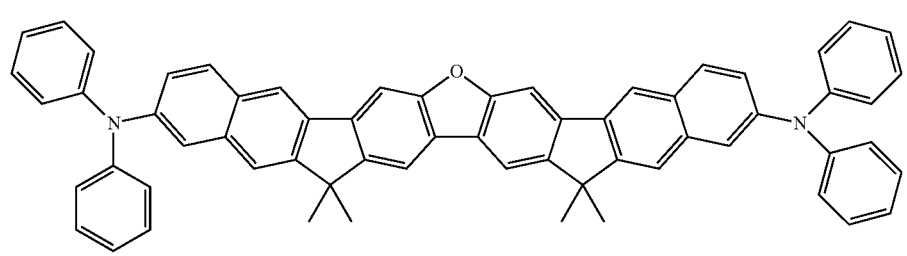

358
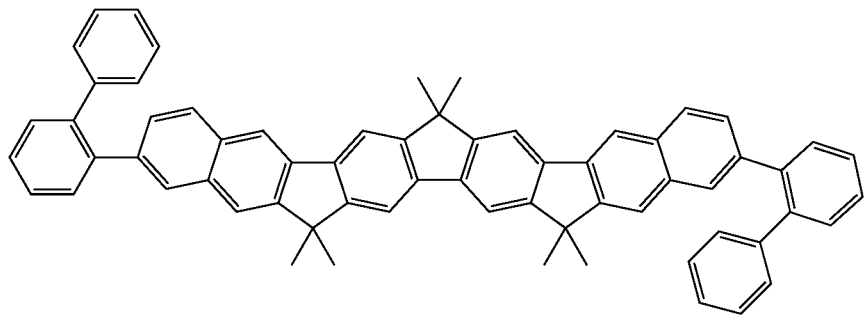
359
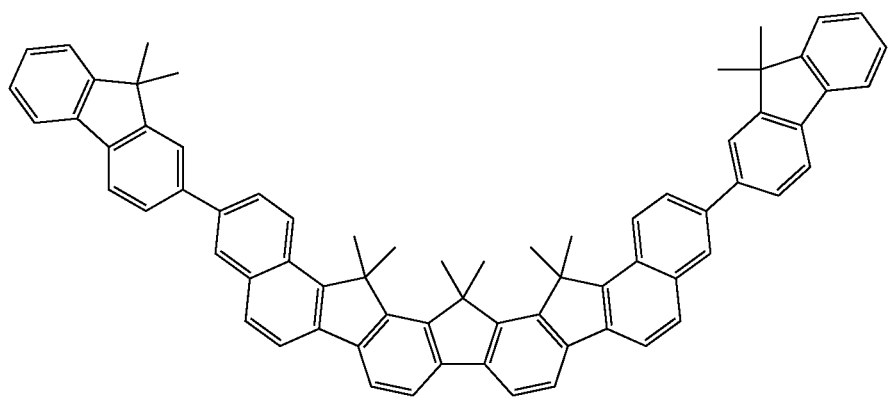
360
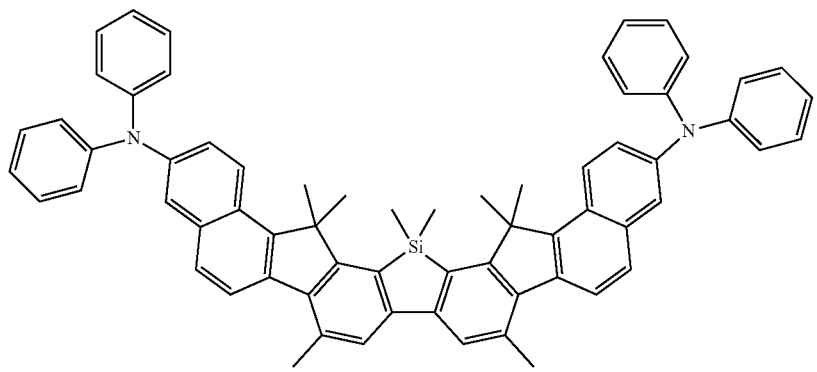
361
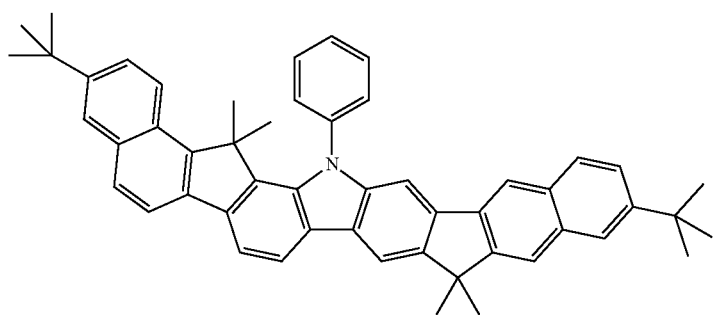

362
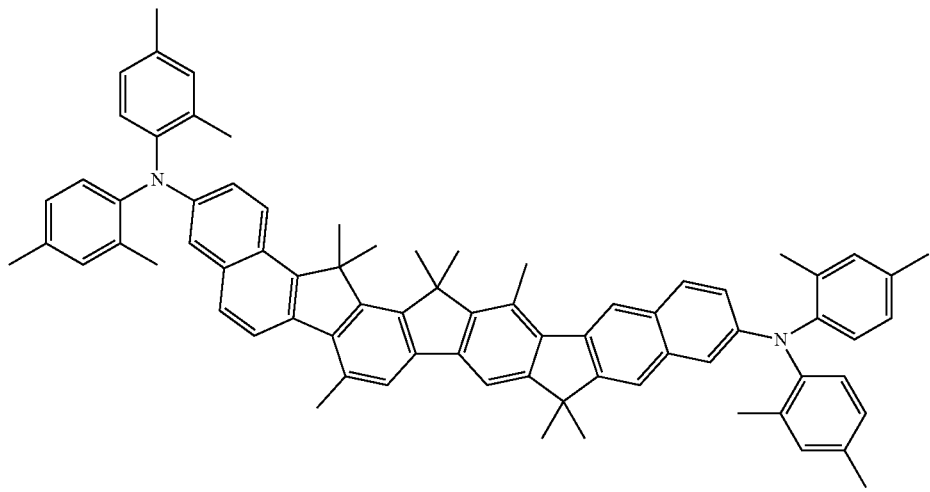
363
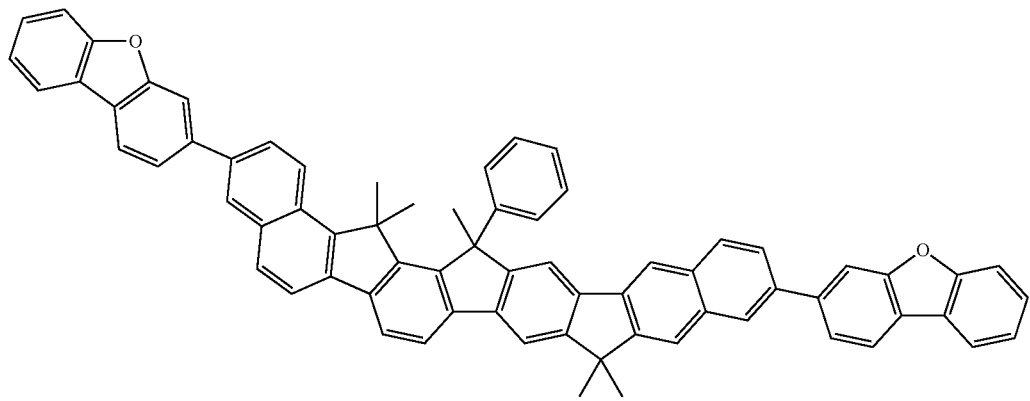
364
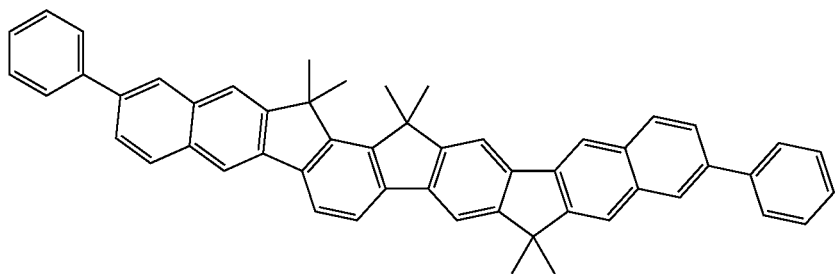
365
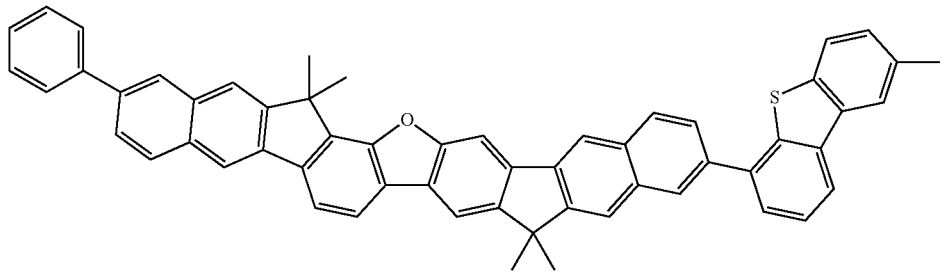

366
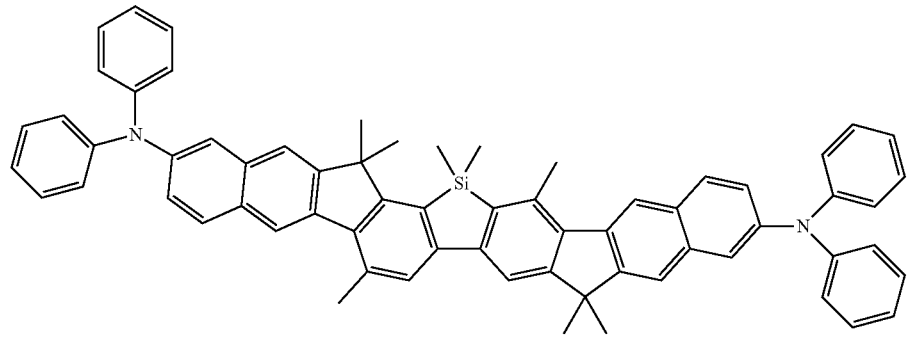
367
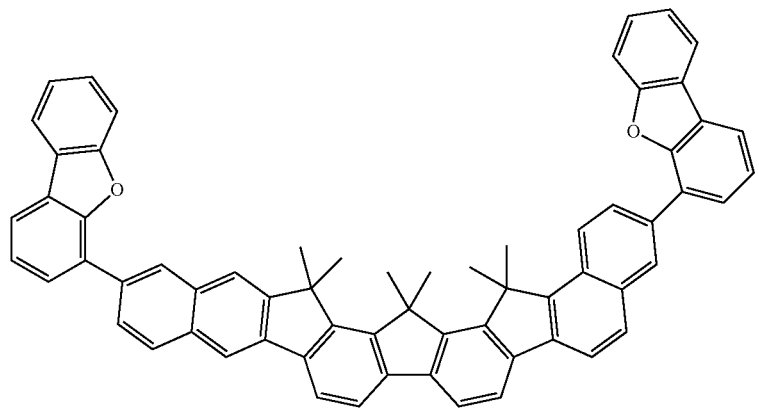
368
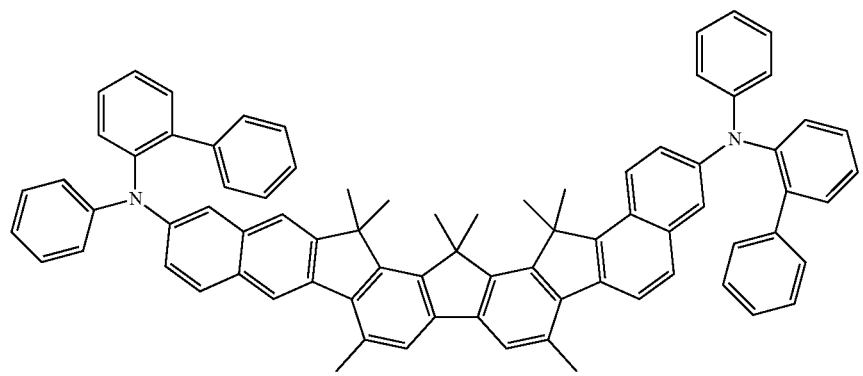
369
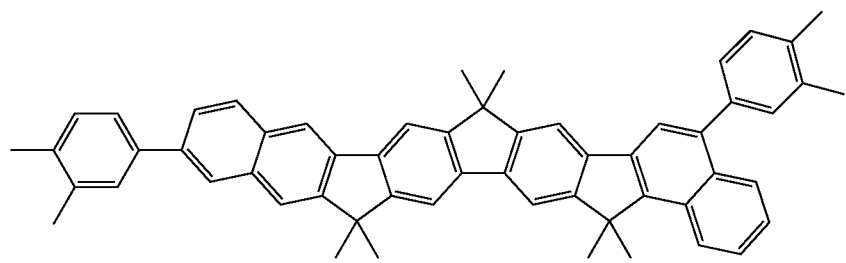

-continued
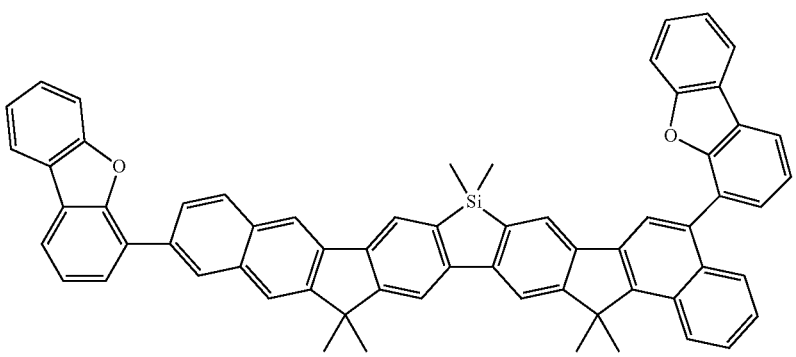
370
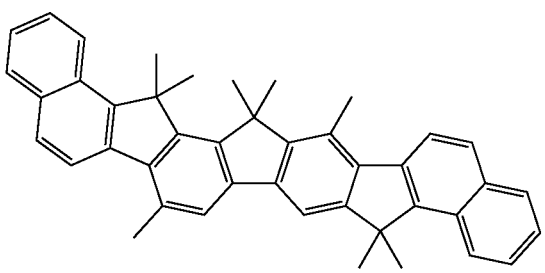
371
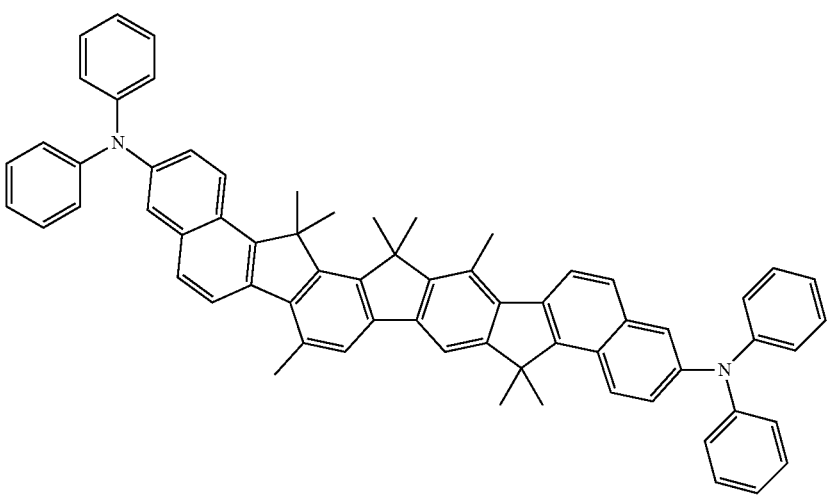
372
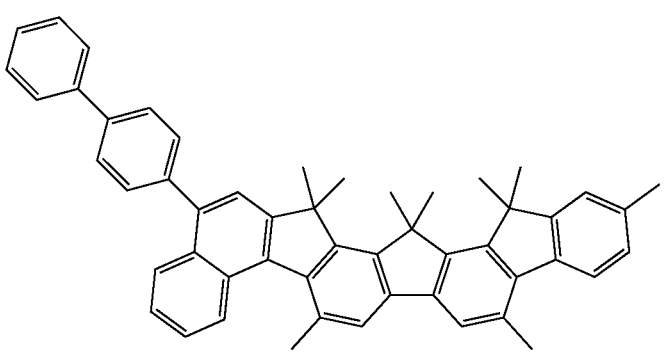
373

374
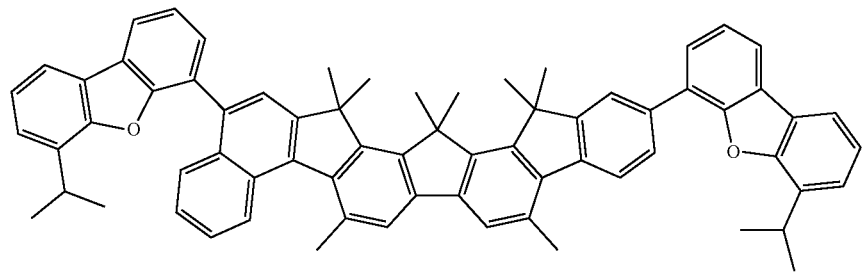
375
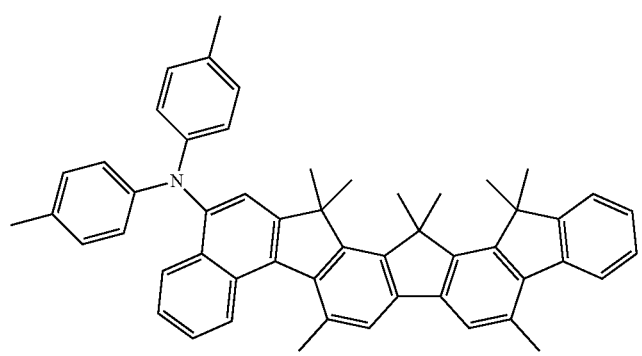
376
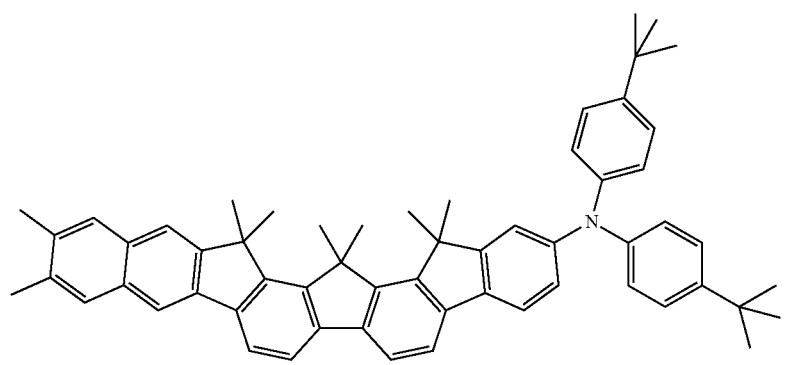
377
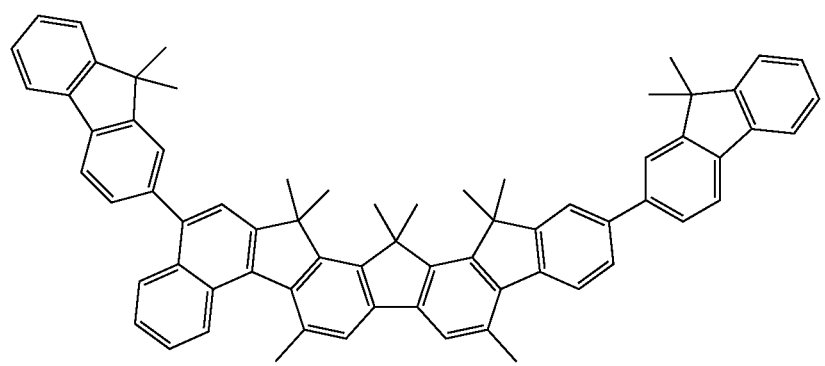
378
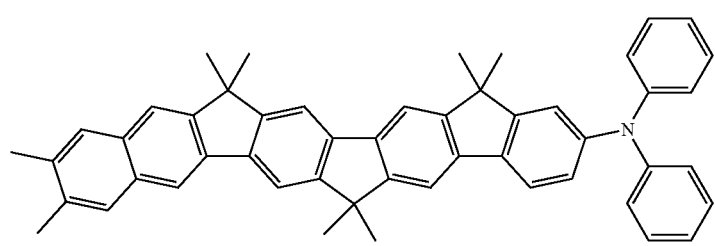

379
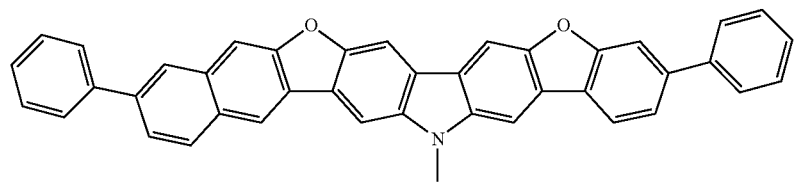
380
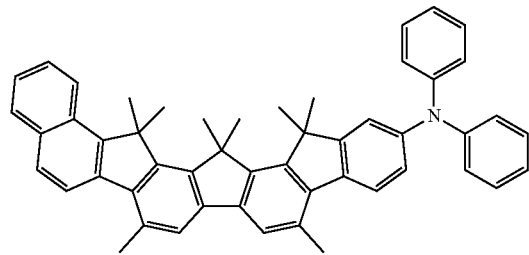
381
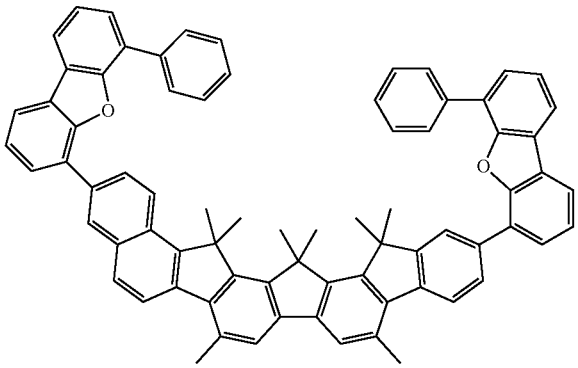
382
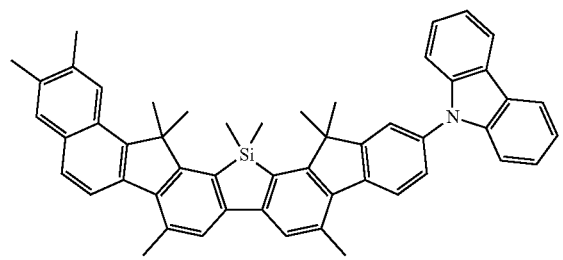
383
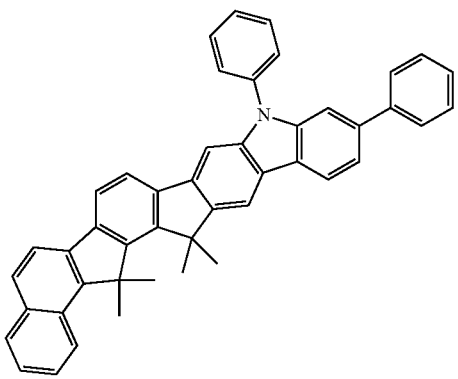
384
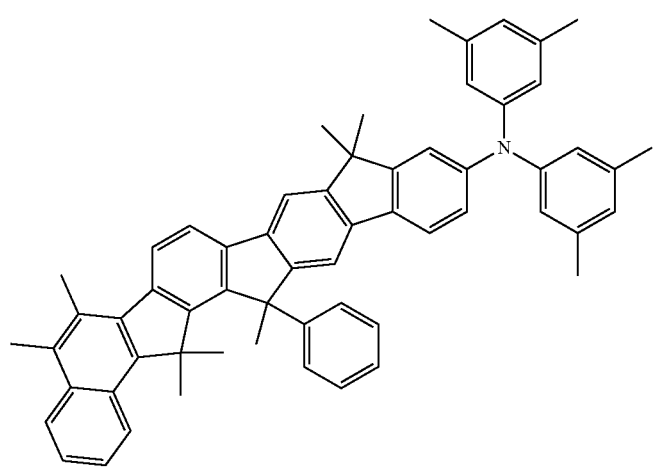

-continued
385
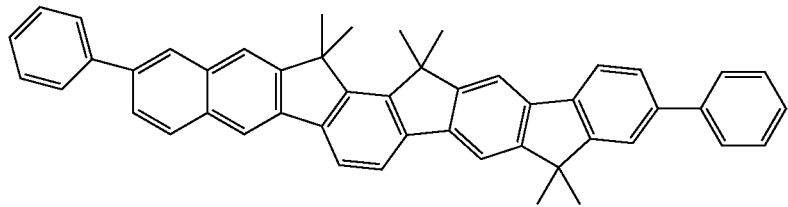
386
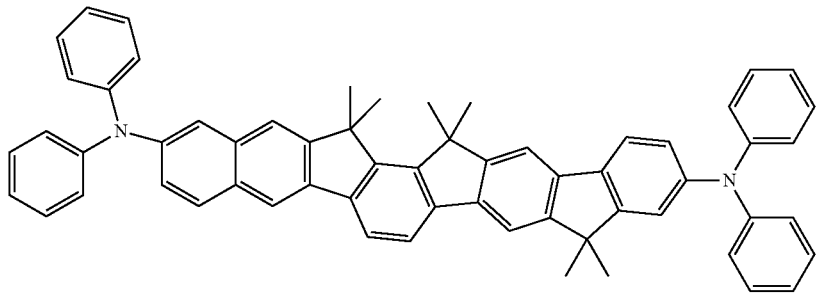
387
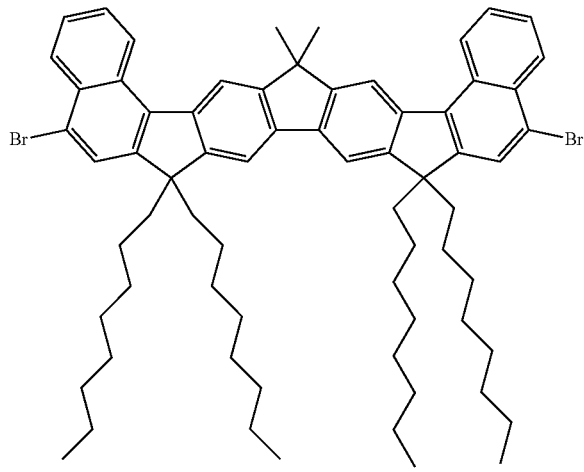
388
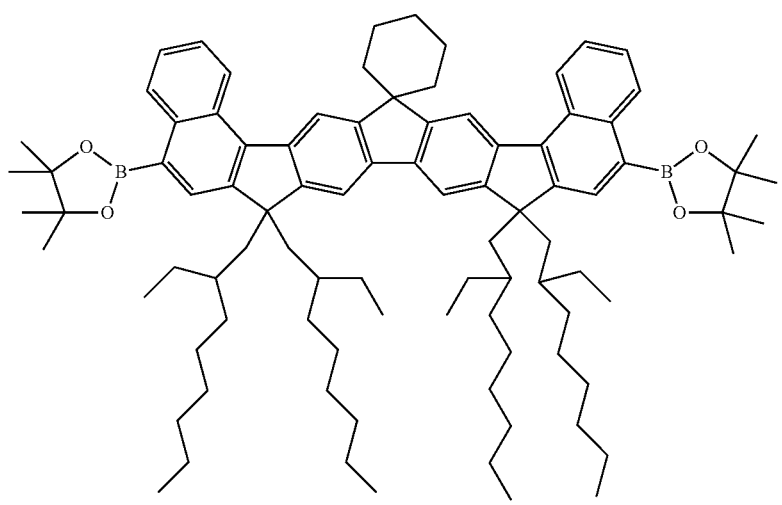

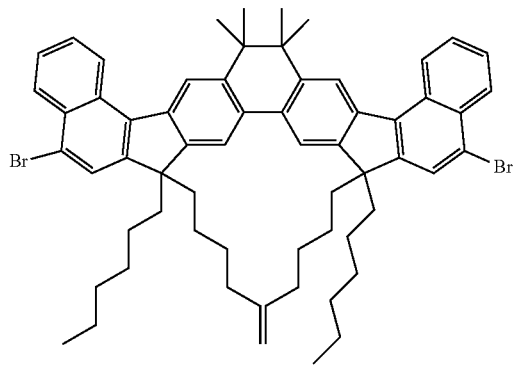

389

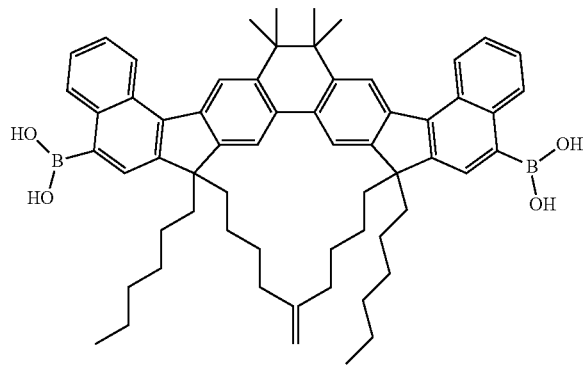

390

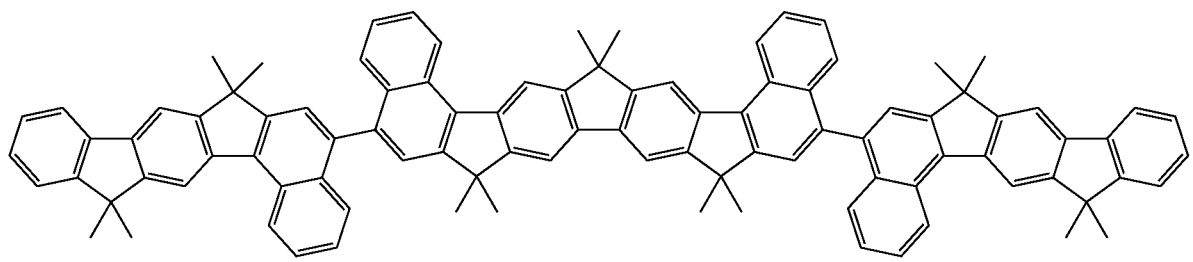

391

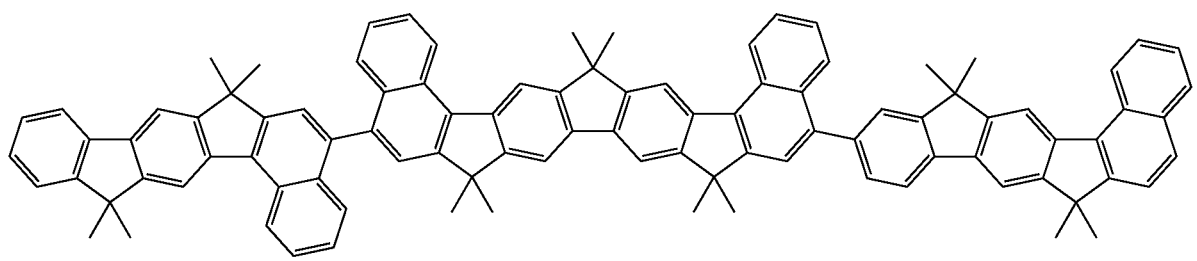

392

The compounds of the formula (I) can be prepared by known processes or reaction steps of organic chemistry.

A preferred process for the preparation of compounds of the formula (I) is shown below (Scheme 1):

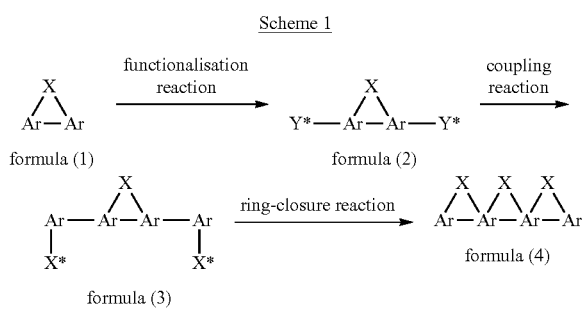

Ar: aromatic or heteroaromatic group
X: bridging group
X*: precursor group of the bridging group
Y*: reactive group, for example Cl, Br, I To this end, reactive groups are introduced into a starting compound (formula (1)), which is in many cases commercially available, for example by bromination, or by bromination and subsequent boronation. A double coupling reaction, for example a Suzuki coupling reaction, is subsequently carried out, by means of which two further aromatic groups are introduced. These further aromatic groups contain a functional group X*, which is able to carry out a ring closure with formation of a bridging group X. After the ring-closure reaction, a compound of the formula (I) (formula (4) in Scheme 1) is obtained, which can optionally be functionalised further.

Alternatively, as shown in Scheme 2, the starting material can be a compound which already contains two bridging groups X (formula (5) in Scheme 2). Processes for the preparation of such compounds are known to the person skilled in the art, for example from WO 2008/006449. The further steps correspond to those indicated in the case of Scheme 1.

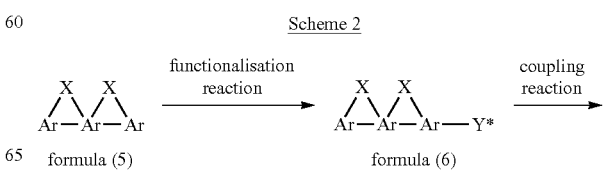

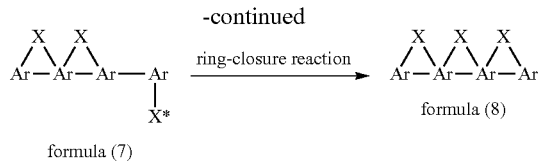

formula (7)

Ar: aromatic or heteroaromatic group
X: bridging group
X*: precursor group of the bridging group
Y*: reactive group, for example Cl, Br, I Details on the processes indicated schematically above can be obtained from the working examples.

The person skilled in the art will be able to deviate from the processes indicated schematically above or modify them in order to obtain compounds of the formula (I), if this is necessary. This is carried out within the scope of the usual abilities of the person skilled in the art.

The present application thus relates to a process for the preparation of a compound of the formula (I), characterised in that it comprises at least one metal-catalysed coupling reaction and at least one ring-closure reaction.

The metal-catalysed coupling reaction here is preferably a transition-metal-catalysed coupling reaction, particularly preferably a Suzuki reaction.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups containing a terminal C—C double or triple bond respectively, oxiranes, oxetanes, groups which undergo a cycloaddition, for example a 1,3-dipolar cycloaddition, such, as, for example, dienes or azides, carboxylic acid derivatives, alcohols and silanes.

The invention therefore furthermore relates to oligomers, polymers or dendrimers comprising one or more compounds of the formula (I), where the bond(s) to the polymer, oligomer or dendrimer may be localised at any desired positions in formula (I) which are substituted by $R^1$, $R^2$ or $R^3$. Depending on the linking of the compound of the formula (I), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (I) may, for example, be linked via a trivalent or polyvalent group, for example via a trivalent or polyvalent aromatic or heteroaromatic group, to give a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or at least one polymer, oligomer or dendrimer containing at least one unit of the formula (I), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (I) are suitable for use in electronic devices, in particular in organic electroluminescent devices (OLEDs). Depending on the substitution, the compounds are employed in various functions and layers.

The compound of the formula (I) can be employed in any function in the organic electroluminescent device, for example as hole-transporting material, as matrix material, as emitting material, or as electron-transporting material.

The invention therefore furthermore relates to the use of a compound of the formula (I) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (I). The electronic device is preferably selected from the devices indicated above. Particular preference is given to an organic electroluminescent device comprising anode, cathode and at least one emitting layer, characterised in that at least one organic layer comprises at least one compound of the formula (I).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, inter-layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device is preferably as follows: anode-hole-injection layer hole-transport layer-emitting layer-electron-transport layer-electron-injection layer-cathode. It is not necessary for all of the said layers to be present, and further layers may additionally be present, for example an electron-blocking layer adjacent to the emitting layer on the anode side, or a hole-blocking layer adjacent to the emitting layer on the cathode side The organic electroluminescent device according to the invention may comprise a plurality of emitting layers. In this case, these emission layers particularly preferably have in total a plurality of emission maxima between 380 nm and 750 nm, resulting overall in white emission, i.e. various emitting compounds which are able to fluoresce or phosphoresce and which emit blue, green, yellow, orange or red light are used in the emitting layers. Particular preference is given to three-layer systems, i.e. systems having three emitting layers, where at least one of these layers preferably comprises at least one compound of the formula (I) and where the three layers exhibit blue, green, yellow, orange or red emission (for the basic structure see, for example, WO 2005/011013). It should be noted that, for the generation of white light, an emitter compound used individually which emits in a broad wavelength range may also be suitable instead of a plurality of emitter compounds emitting in colour. Alternatively and/or additionally, the compounds according to the invention may also be present in the hole-transport layer or in another layer in an organic electroluminescent device of this type. The various emitting layers may be directly adjacent to one another, or they may be separated from one another by non-emitting layers. According to a preferred embodiment of the invention, a white-emitting OLED is a so-called tandem OLED, i.e. two or more complete OLED layer sequences are present in the OLED, where the OLED layer sequences in each case comprise hole-transport layer, emitting layer and electron-transport layer, which are each separated from one another by a charge-generation layer.

It is preferred for the compound of the formula (I) to be employed in an emitting layer. The compound of the formula (I) is particularly suitable for use as emitting compound or as matrix material in an emitting layer.

The compound according to the invention is particularly suitable for use as blue-emitting emitter compound or as matrix compound for a blue-emitting emitter compound.

If the compound according to the invention is employed as matrix material in an emitting layer of an OLED, it is preferred for none of the substituents $R^1$, $R^2$ and $R^3$ to be selected from groups which are conjugated with the basic structure of the formula (I), in particular for none of the substituents $R^1$, $R^2$ and $R^3$ to be selected from cyano groups, arylamino groups or aryl or heteroaryl groups. In the case of the use of the compound according to the invention as matrix material, $R^1$ and $R^2$ are particularly preferably selected from H, D, F and alkyl groups having 1 to 10 C atoms, particularly preferably from H and D, $R^1$ and $R^2$ are very particularly preferably equal to H.

If the compound according to the invention is employed as emitter compound in an emitting layer of an OLED, it is preferred for one or more substituents $R^1$, $R^2$ and $R^3$ to be selected from groups which are conjugated with the basic structure of the formula (I), for example cyano groups, arylamino groups or aryl or heteroaryl groups.

If the compound according to the invention is employed as emitting compound in an emitting layer, it is preferably employed in combination with one or more matrix materials. A matrix material here is taken to mean a material which is present in the emitting layer, preferably as the principal component, and which does not emit light on operation of the device.

The proportion of the emitting compound in the mixture of the emitting layer is between 0.1 and 50.0%, preferably between 0.5 and 20.0%, particularly preferably between 1.0 and 10.0%. Correspondingly, the proportion of the matrix material or matrix materials is between 50.0 and 99.9%, preferably between 80.0 and 99.5%, particularly preferably between 90.0 and 99.0%.

The specifications of the proportions in % are, for the purposes of the present application, taken to mean % by vol. if the compounds are applied from the gas phase and % by weight if the compounds are applied from solution.

If the compound according to the invention is employed as matrix material, it can be employed in combination with all known emitting compounds. It is preferably employed in combination with the preferred emitting compounds indicated below, particularly the preferred fluorescent compounds indicated below.

If the compound of the formula (I) is employed as matrix material in combination with a phosphorescent emitter in an emitting layer, the phosphorescent emitter is preferably selected from the embodiments of phosphorescent emitters indicated below. In this case, one or more further matrix materials are furthermore preferably present in the emitting layer.

So-called mixed-matrix systems of this type preferably comprise two or three different matrix materials, particularly preferably two different matrix materials. One of the two materials here is preferably a material having hole-transporting properties and the other material is a material having electron-transporting properties. The compound of the formula (I) preferably represents the material having hole-transporting properties.

However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

Particularly suitable matrix materials which can be used in combination with the compounds according to the invention as matrix components of a mixed-matrix system are selected from the preferred matrix materials indicated below for phosphorescent emitting compounds or the preferred matrix materials for fluorescent emitting compounds, depending on what type of emitting compound is employed in the mixed-matrix system.

The compounds according to the invention can also be employed in layers other than the emitting layer, for example as hole-transport materials in a hole-injection or hole-transport layer or electron-blocking layer.

If the compound of the formula (I) is employed as hole-transport material, for example in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (I) then additionally comprises one or more p-dopants. Preferred p-dopants employed in accordance with the present invention are organic electron-acceptor compounds which are able to oxidise one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

It is furthermore preferred in this case for the electronic device to have a plurality of hole-transporting layers between the anode and the emitting layer. The case may occur that all these layers comprise a compound of the formula (I), or that only individual layers thereof comprise a compound of the formula (I).

If the compound of the formula (I) is employed as hole-transport material, it is preferred for it to have a large separation between the HOMO and LUMO energy levels. It is furthermore preferred for it to contain no amino groups as substituents. It is furthermore preferred for it to contain absolutely no substituents on the aromatic rings, i.e. for $R^1$ and $R^2$ to be equal to H or D, particularly preferably equal to H.

The compound of the formula (I) can furthermore be employed as electron-transporting compound in an electron-transport layer, a hole-blocking layer or an electron-injection layer. It is preferred for this purpose for the compound of the formula (I) to contain one or more substituents selected from electron-deficient heteroaryl groups, such as, for example, triazine, pyrimidine or benzimidazole.

Generally preferred classes of material for use as corresponding functional materials in the organic electroluminescent devices according to the invention are indicated below.

Suitable phosphorescent emitting compounds are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitting compounds used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present invention.

Examples of the phosphorescent emitting compounds described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention. The person skilled in the art will also be able, without inventive step, to employ further phosphorescent complexes in combination with the compounds according to the invention in OLEDs.

Preferred fluorescent emitters, besides the compounds according to the invention, are selected from the class of the arylamines. An arylamine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and WO 2013/185871. Preference is likewise given to the benzoindenofluorenamines disclosed in WO 2014/037077, the benzofluorenamines disclosed in the as yet unpublished EP 13000012.8 and the indenofluorenes disclosed in the as yet unpublished EP13004921.6.

Preferred fluorescent emitting compounds are depicted in the following table:

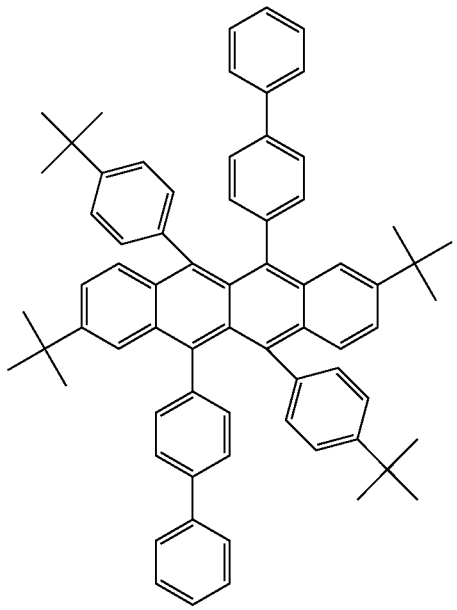 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

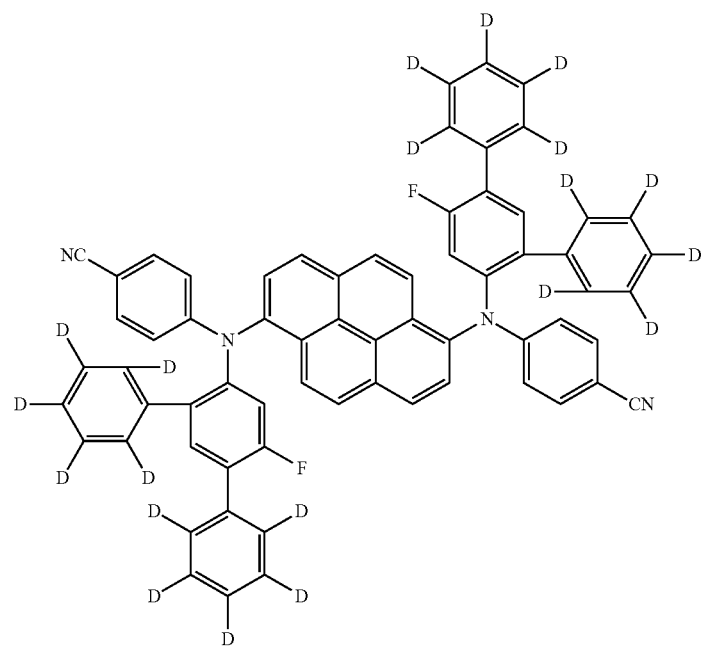 [SMILES: [2H]c1c([2H])c([2H])c(-c2cc(-c3c([2H])c([2H])c([2H])c([2H])c3[2H])c(N(c3ccc(C#N)cc3)c3ccc4ccc5c(N(c6ccc(C#N)cc6)c6cc(F)c(-c7c([2H])c([2H])c([2H])c([2H])c7[2H])cc6-c6c([2H])c([2H])c([2H])c([2H])c6[2H])ccc6ccc3c4c65)cc2F)c([2H])c1[2H]]

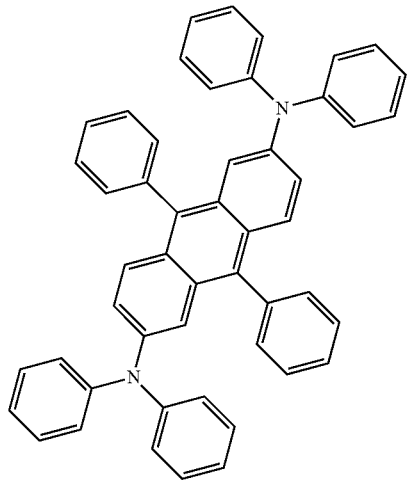 [SMILES: c1ccc(-c2c3ccc(N(c4ccccc4)c4ccccc4)cc3c(-c3ccccc3)c3ccc(N(c4ccccc4)c4ccccc4)cc23)cc1]
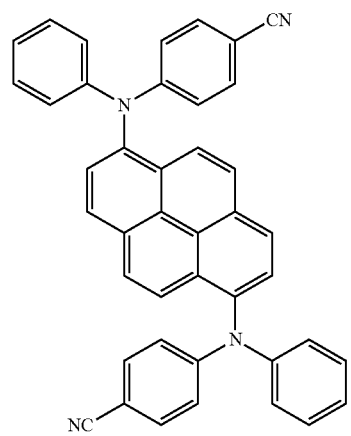 [SMILES: N#Cc1ccc(N(c2ccccc2)c2ccc3ccc4c(N(c5ccccc5)c5ccc(C#N)cc5)ccc5ccc2c3c54)cc1]
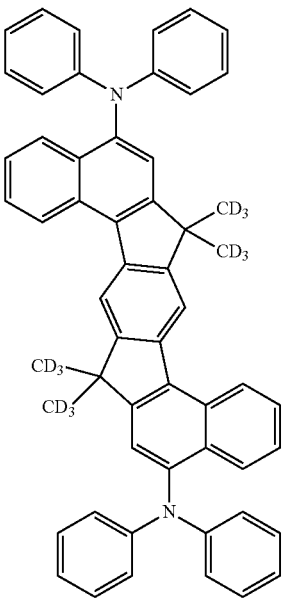 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]

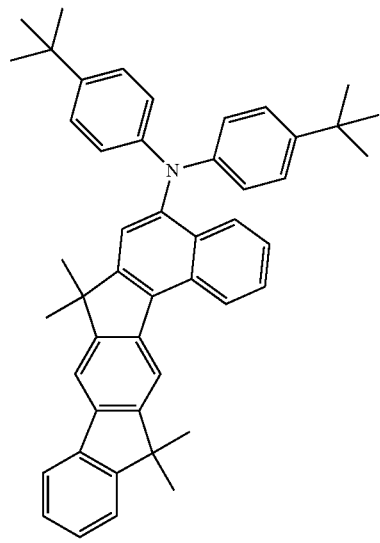 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
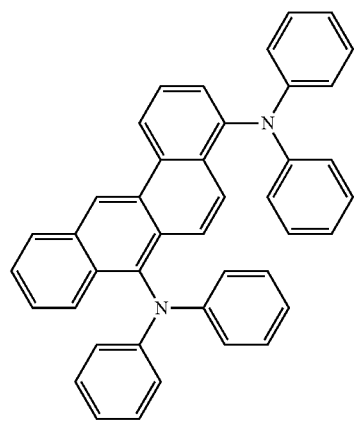 [SMILES: c1ccc(N(c2ccccc2)c2cccc3c2ccc2c(N(c4ccccc4)c4ccccc4)c4ccccc4cc23)cc1]
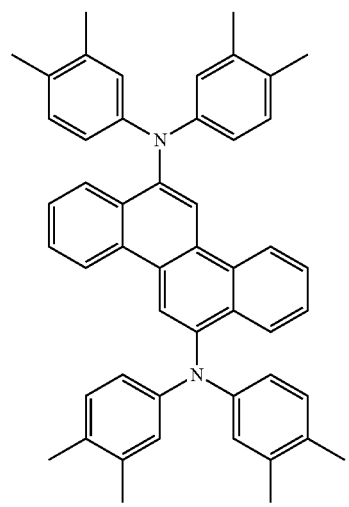

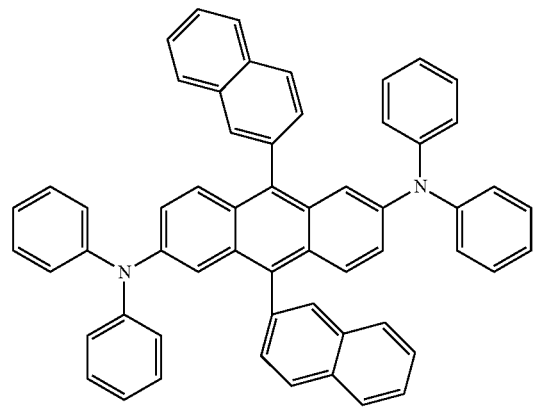 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
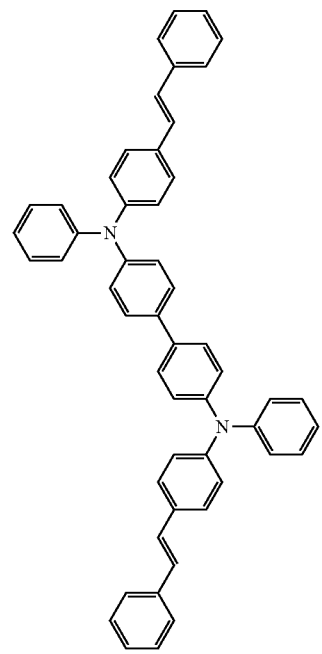 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
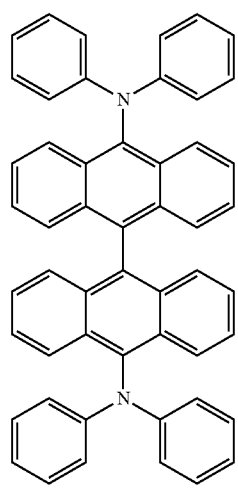 [SMILES: c1ccc(N(c2ccccc2)c2c3ccccc3c(-c3c4ccccc4c(N(c4ccccc4)c4ccccc4)c4ccccc34)c3ccccc23)cc1]

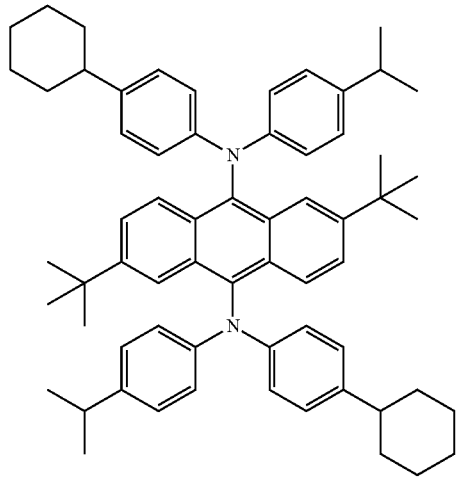 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
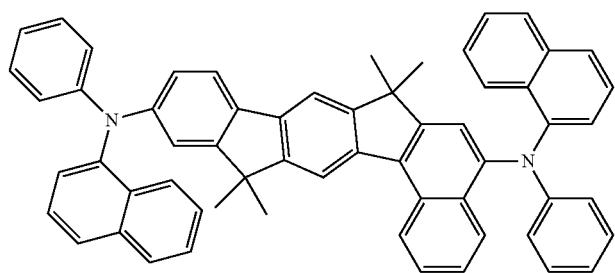 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
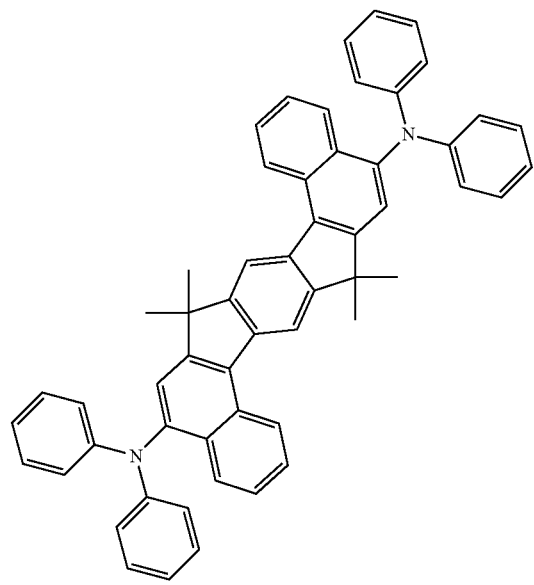 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]

-continued
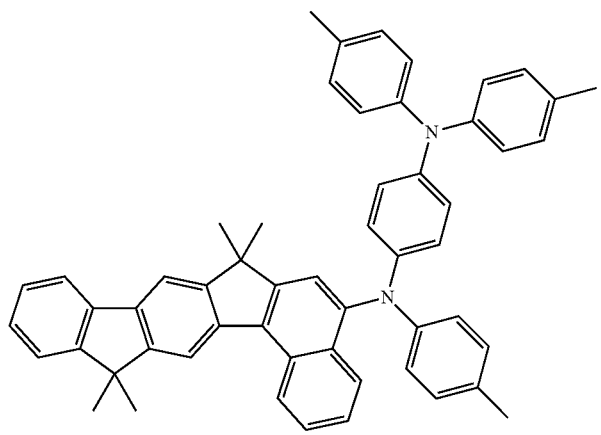 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
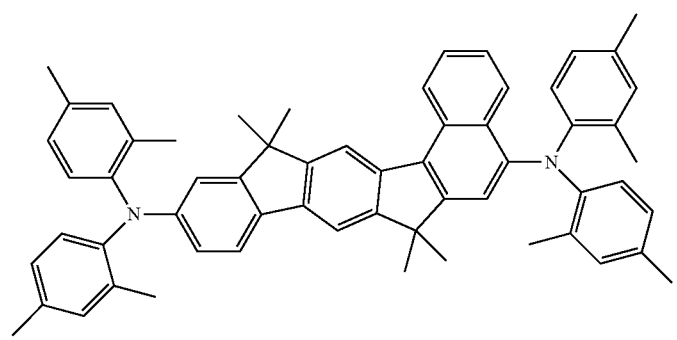
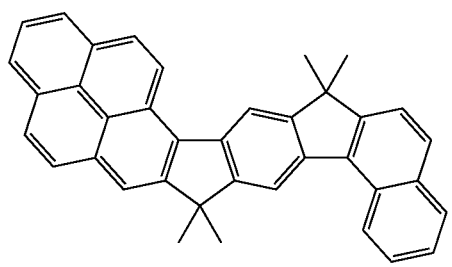 [SMILES: CC1(C)c2cc3c(cc2-c2c1ccc1ccccc21)C(C)(C)c1cc2ccc4cccc5ccc(c1-3)c2c45]
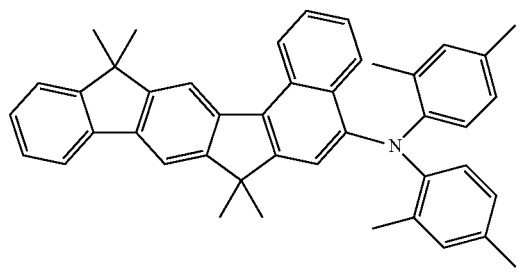 [SMILES: Cc1ccc(N(c2ccc(C)cc2C)c2cc3c(c4ccccc24)-c2cc4c(cc2C3(C)C)-c2ccccc2C4(C)C)c(C)c1]

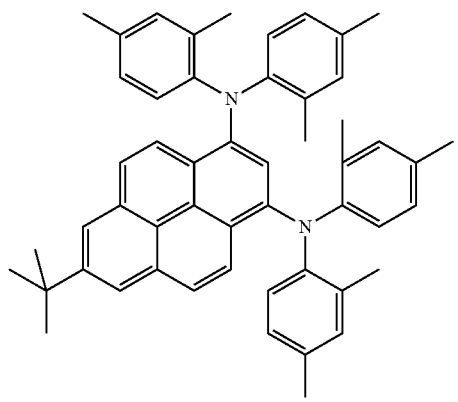 [SMILES: Cc1ccc(N(c2ccc(C)cc2C)c2cc(N(c3ccc(C)cc3C)c3ccc(C)cc3C)c3ccc4cc(C(C)(C)C)cc5ccc2c3c54)c(C)c1]
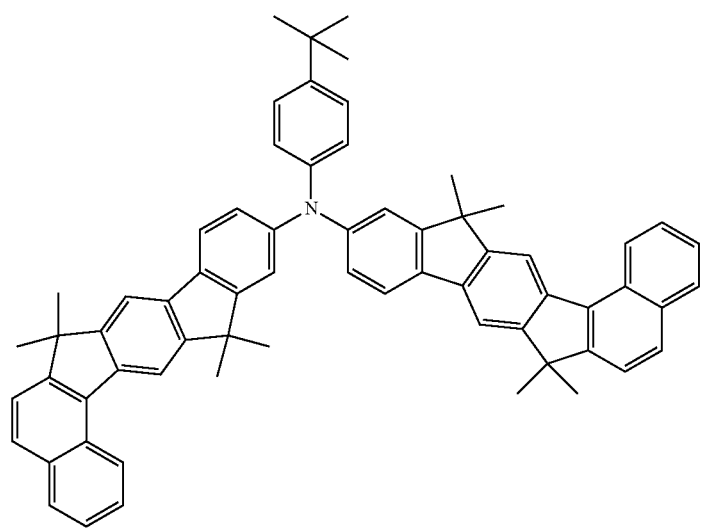 [SMILES: CC(C)(C)c1ccc(N(c2ccc3c(c2)C(C)(C)c2cc4c(cc2-3)C(C)(C)c2ccc3ccccc3c2-4)c2ccc3c(c2)C(C)(C)c2cc4c(cc2-3)C(C)(C)c2ccc3ccccc3c2-4)cc1]
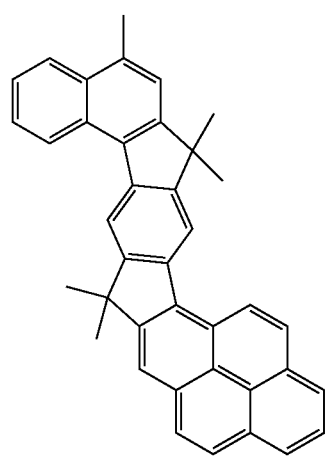 [SMILES: Cc1cc2c(c3ccccc13)-c1cc3c(cc1C2(C)C)-c1c(cc2ccc4cccc5ccc1c2c45)C3(C)C]

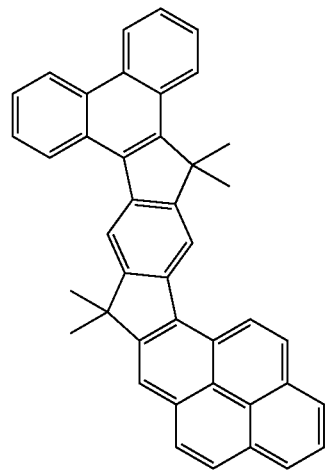 [SMILES: CC1(C)c2cc3c(cc2-c2c1cc1ccc4cccc5ccc2c1c45)C(C)(C)c1c-3c2ccccc2c2ccccc12]
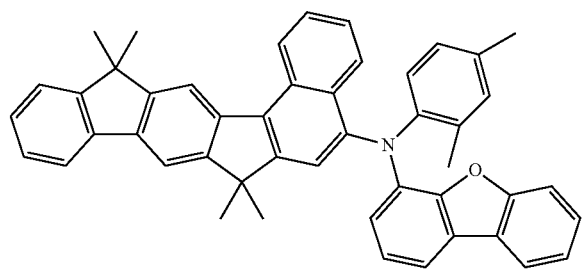 [SMILES: Cc1ccc(N(c2cc3c(c4ccccc24)-c2cc4c(cc2C3(C)C)-c2ccccc2C4(C)C)c2cccc3c2oc2ccccc23)c(C)c1]
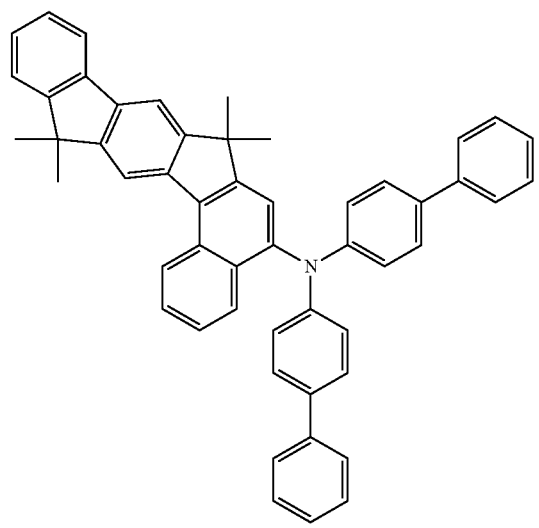 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]

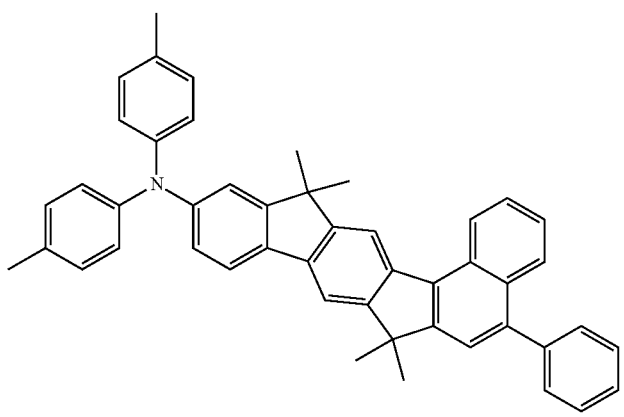 [SMILES: Cc1ccc(N(c2ccc(C)cc2)c2ccc3c(c2)C(C)(C)c2cc4c(cc2-3)C(C)(C)c2cc(-c3ccccc3)c3ccccc3c2-4)cc1]
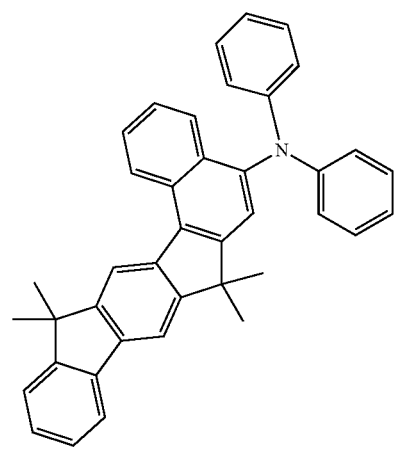 [SMILES: CC1(C)c2ccccc2-c2cc3c(cc21)-c1c(cc(N(c2ccccc2)c2ccccc2)c2ccccc12)C3(C)C]
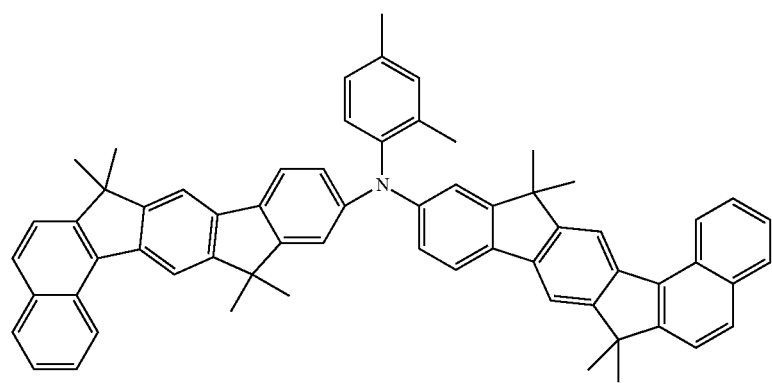 [SMILES: Cc1ccc(N(c2ccc3c(c2)C(C)(C)c2cc4c(cc2-3)C(C)(C)c2ccc3ccccc3c2-4)c2ccc3c(c2)C(C)(C)c2cc4c(cc2-3)C(C)(C)c2ccc3ccccc3c2-4)c(C)c1]

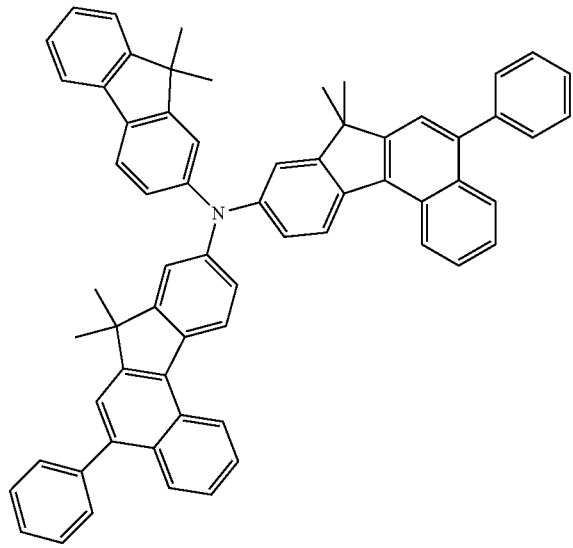 [SMILES: CC1(C)c2ccccc2-c2ccc(N(c3ccc4c(c3)C(C)(C)c3cc(-c5ccccc5)c5ccccc5c3-4)c3ccc4c(c3)C(C)(C)c3cc(-c5ccccc5)c5ccccc5c3-4)cc21]
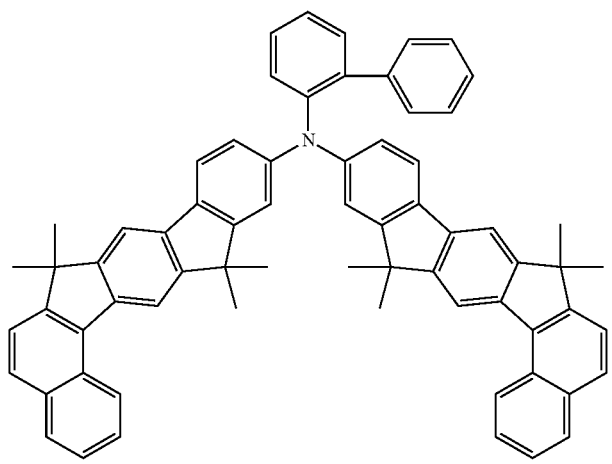 [SMILES: CC1(C)c2cc(N(c3ccc4c(c3)C(C)(C)c3cc5c(cc3-4)C(C)(C)c3ccc4ccccc4c3-5)c3ccccc3-c3ccccc3)ccc2-c2cc3c(cc21)-c1c(ccc2ccccc12)C3(C)C]
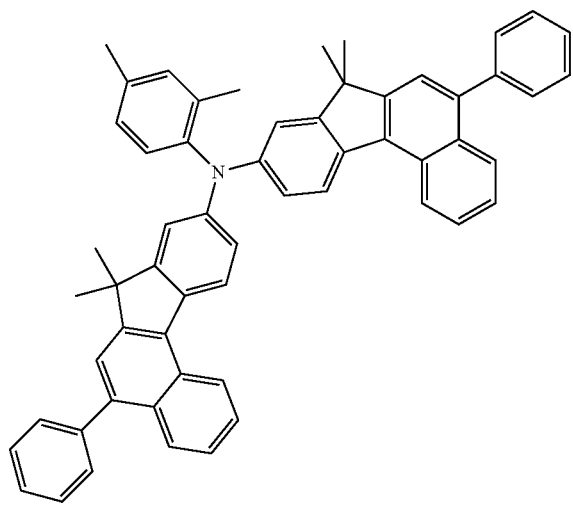 [SMILES: Cc1ccc(N(c2ccc3c(c2)C(C)(C)c2cc(-c4ccccc4)c4ccccc4c2-3)c2ccc3c(c2)C(C)(C)c2cc(-c4ccccc4)c4ccccc4c2-3)c(C)c1]

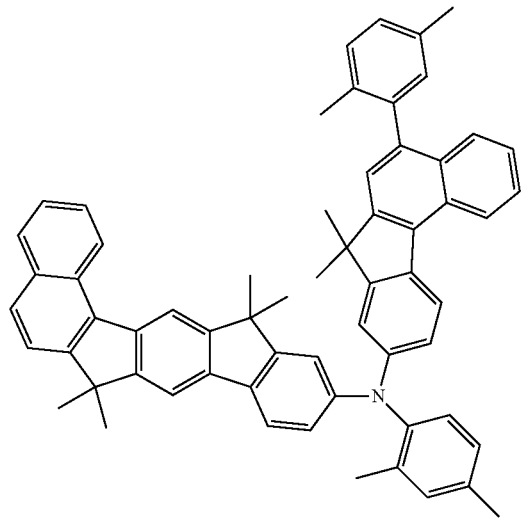 [SMILES: Cc1ccc(N(c2ccc3c(c2)C(C)(C)c2cc4c(cc2-3)C(C)(C)c2ccc3ccccc3c2-4)c2ccc3c(c2)C(C)(C)c2cc(-c4cc(C)ccc4C)c4ccccc4c2-3)c(C)c1]
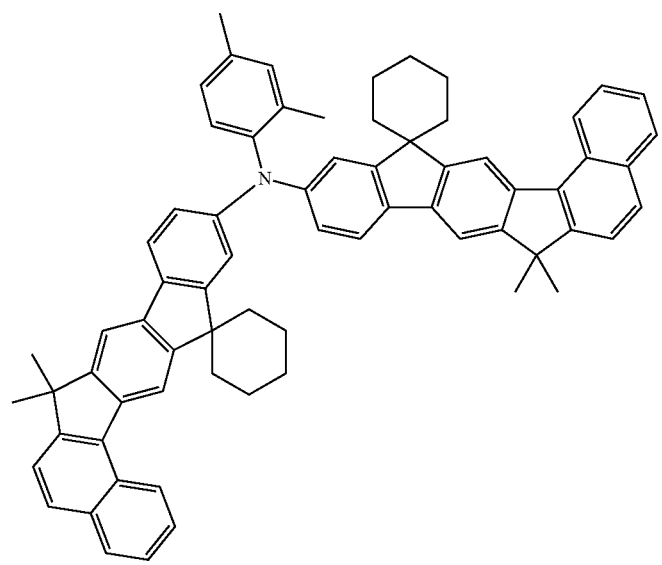 [SMILES: Cc1ccc(N(c2ccc3c(c2)C2(CCCCC2)c2cc4c(cc2-3)C(C)(C)c2ccc3ccccc3c2-4)c2ccc3c(c2)C2(CCCCC2)c2cc4c(cc2-3)C(C)(C)c2ccc3ccccc3c2-4)c(C)c1]
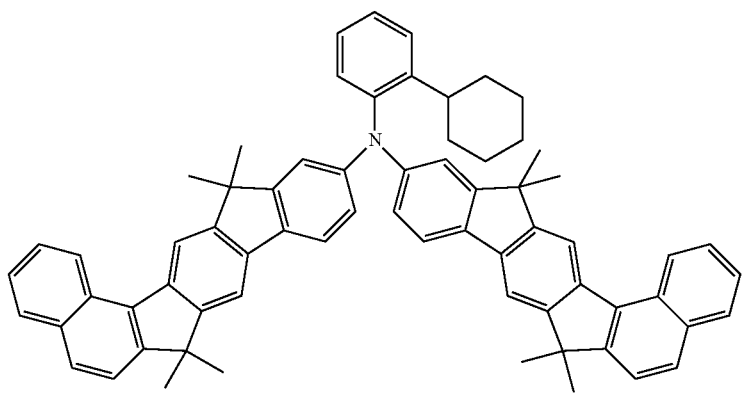 [SMILES: CC1(C)c2cc(N(c3ccc4c(c3)C(C)(C)c3cc5c(cc3-4)C(C)(C)c3ccc4ccccc4c3-5)c3ccccc3C3CCCCC3)ccc2-c2cc3c(cc21)-c1c(ccc2ccccc12)C3(C)C]

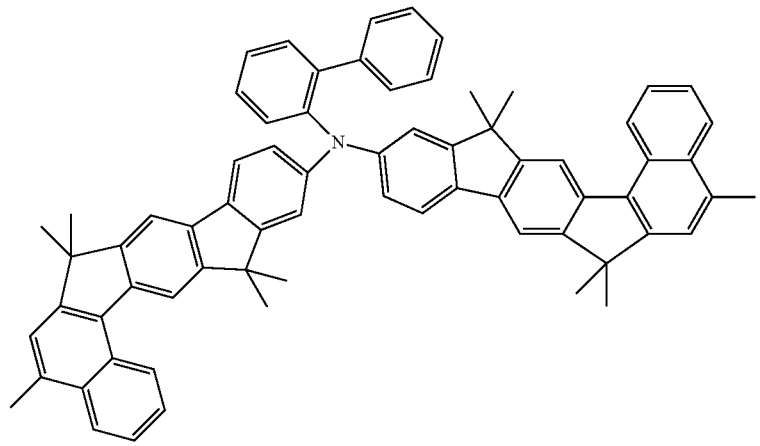
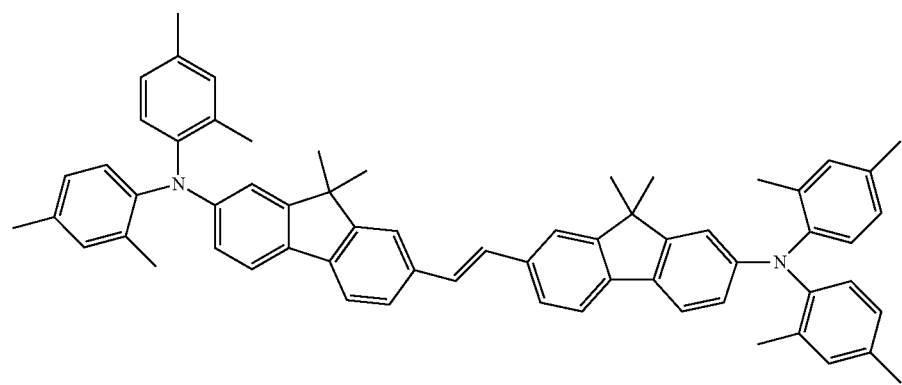
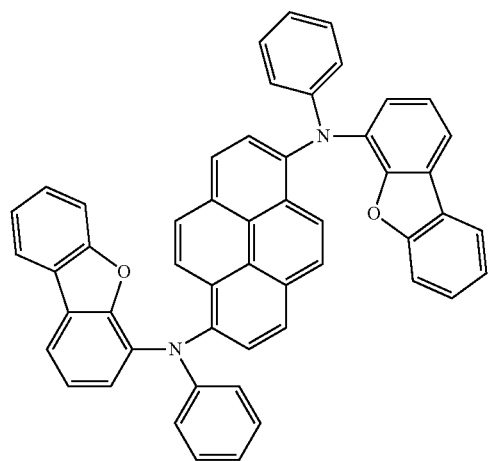 [SMILES: c1ccc(N(c2ccc3ccc4c(N(c5ccccc5)c5cccc6c5oc5ccccc56)ccc5ccc2c3c54)c2cccc3c2oc2ccccc23)cc1]

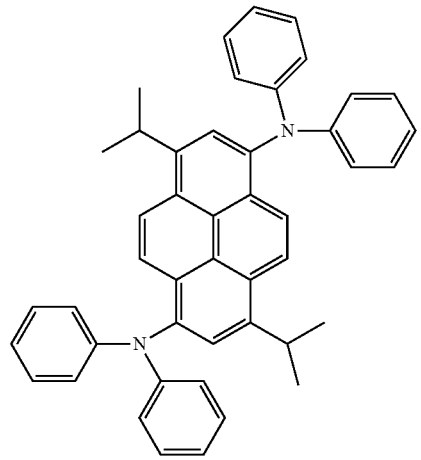 [SMILES: CC(C)c1cc(N(c2ccccc2)c2ccccc2)c2ccc3c(C(C)C)cc(N(c4ccccc4)c4ccccc4)c4ccc1c2c34]
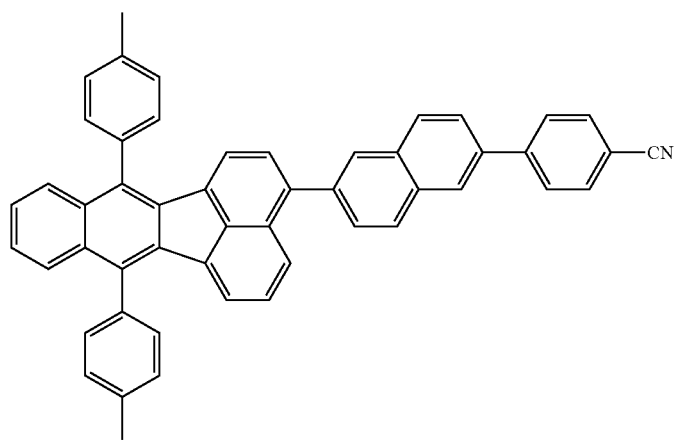 [SMILES: Cc1ccc(-c2c3c(c(-c4ccc(C)cc4)c4ccccc24)-c2ccc(-c4ccc5cc(-c6ccc(C#N)cc6)ccc5c4)c4cccc-3c24)cc1]
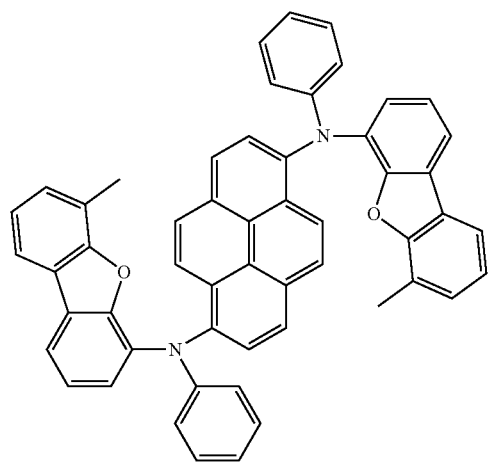 [SMILES: Cc1cccc2c1oc1c(N(c3ccccc3)c3ccc4ccc5c(N(c6ccccc6)c6cccc7c6oc6c(C)cccc67)ccc6ccc3c4c65)cccc12]

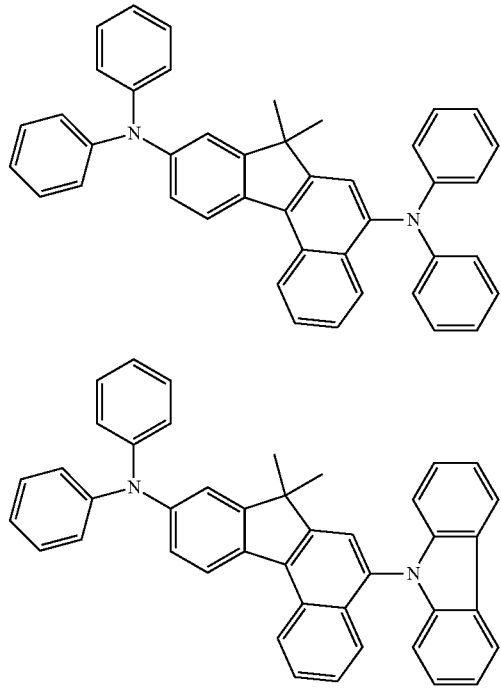

Preferred matrix materials for use in combination with fluorescent emitting compounds are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Particularly preferred matrix materials for use in combination with the compounds of the formula (I) in the emitting layer are depicted in the following table.

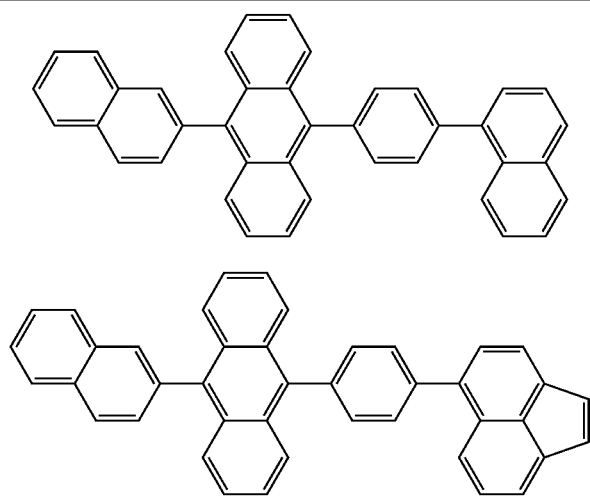

-continued
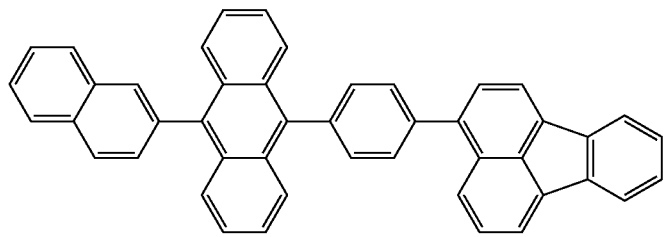 [SMILES: c1ccc2c(c1)-c1cccc3c(-c4ccc(-c5c6ccccc6c(-c6ccc7ccccc7c6)c6ccccc56)cc4)ccc-2c13]
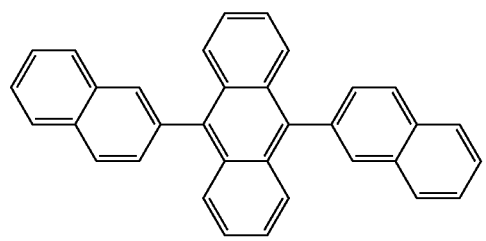 [SMILES: c1ccc2cc(-c3c4ccccc4c(-c4ccc5ccccc5c4)c4ccccc34)ccc2c1]
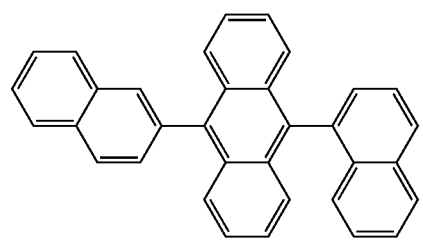 [SMILES: c1ccc2cc(-c3c4ccccc4c(-c4cccc5ccccc45)c4ccccc34)ccc2c1]
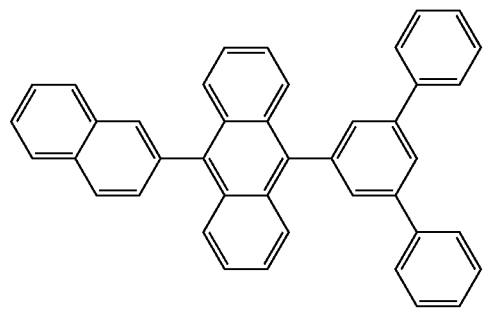 [SMILES: c1ccc(-c2cc(-c3ccccc3)cc(-c3c4ccccc4c(-c4ccc5ccccc5c4)c4ccccc34)c2)cc1]
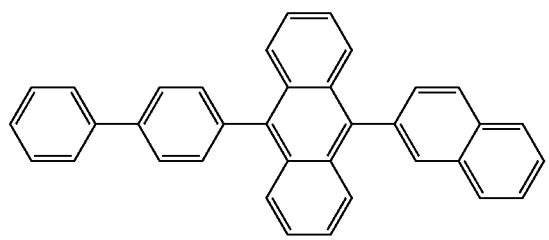 [SMILES: c1ccc(-c2ccc(-c3c4ccccc4c(-c4ccc5ccccc5c4)c4ccccc34)cc2)cc1]
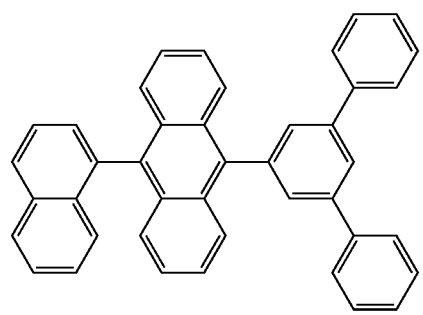 [SMILES: c1ccc(-c2cc(-c3ccccc3)cc(-c3c4ccccc4c(-c4cccc5ccccc45)c4ccccc34)c2)cc1]

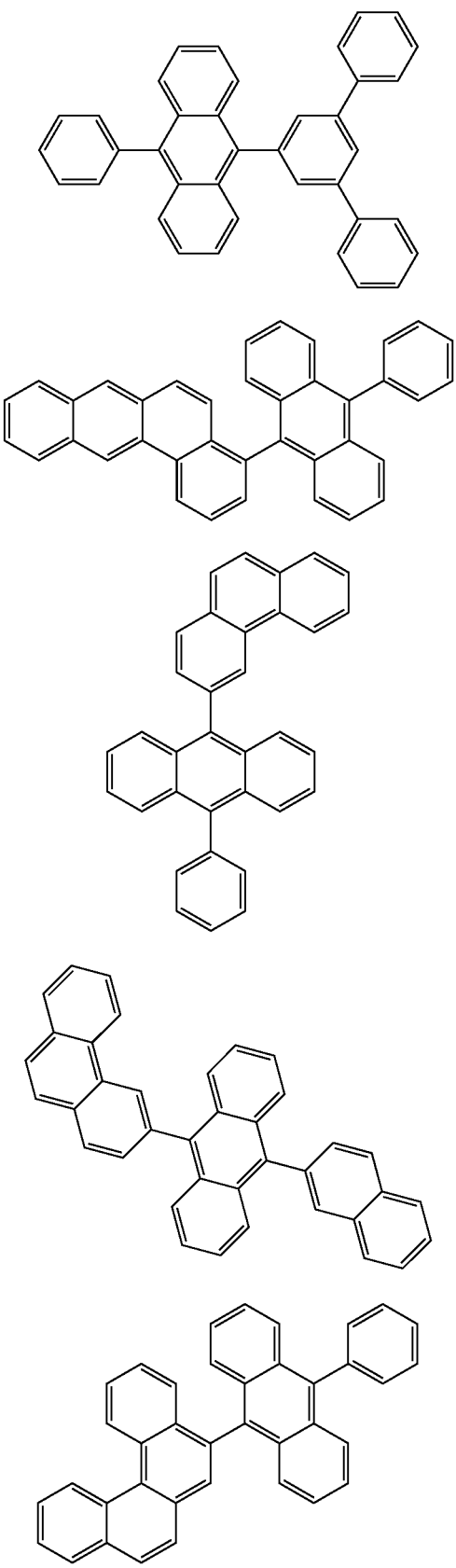

-continued
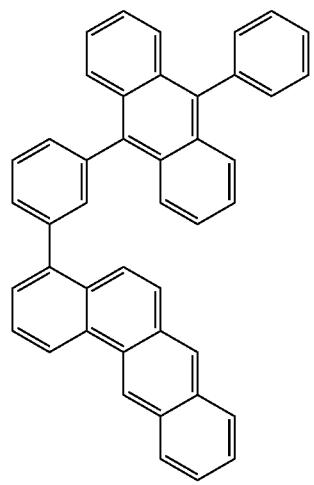 [SMILES: c1ccc(-c2c3ccccc3c(-c3cccc(-c4cccc5c4ccc4cc6ccccc6cc45)c3)c3ccccc23)cc1]
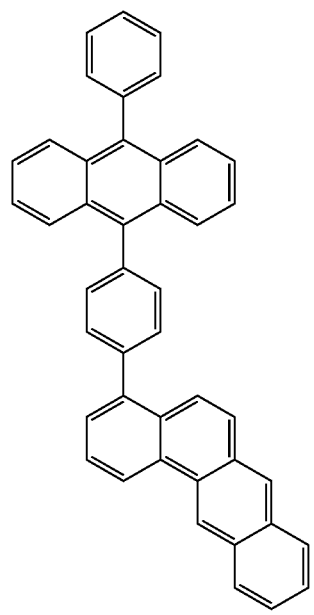 [SMILES: c1ccc(-c2c3ccccc3c(-c3ccc(-c4cccc5c4ccc4cc6ccccc6cc45)cc3)c3ccccc23)cc1]
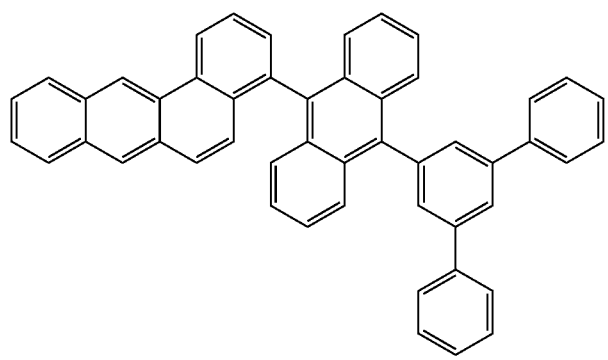 [SMILES: c1ccc(-c2cc(-c3ccccc3)cc(-c3c4ccccc4c(-c4cccc5c4ccc4cc6ccccc6cc45)c4ccccc34)c2)cc1]

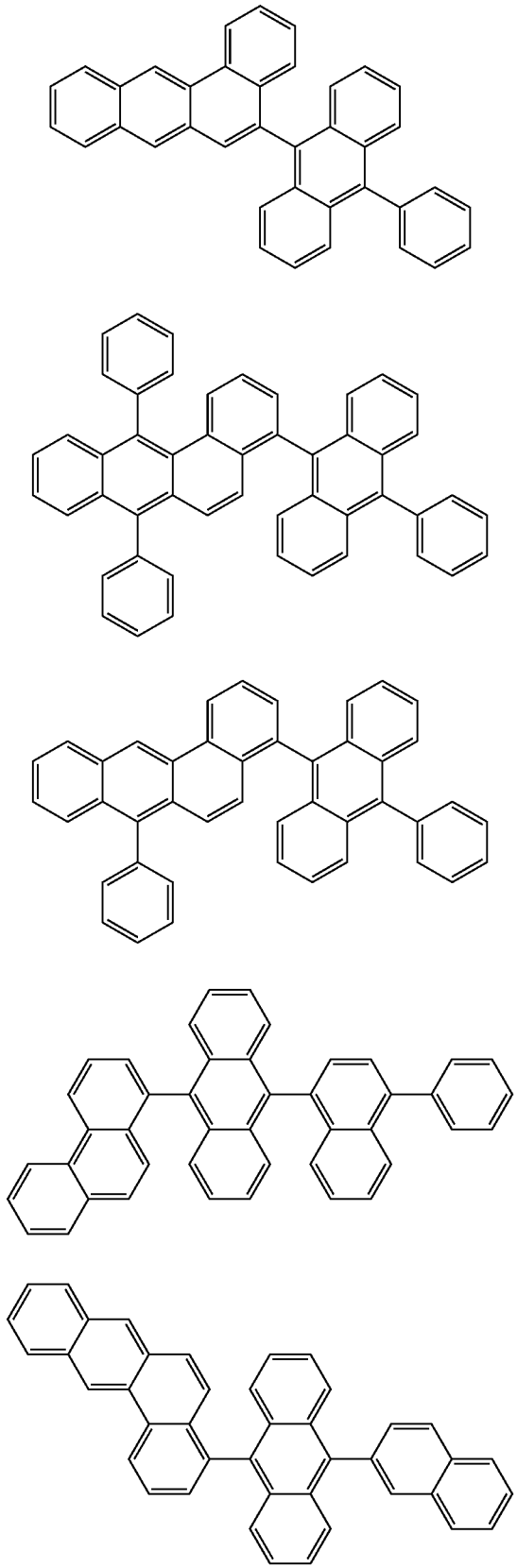

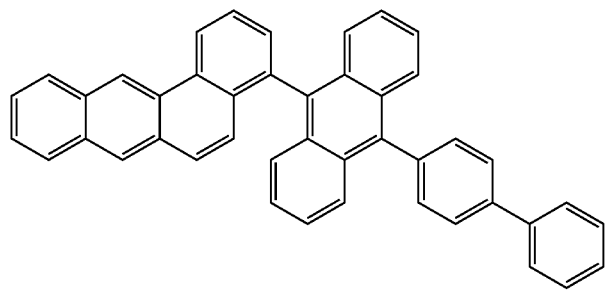 [SMILES: c1ccc(-c2ccc(-c3c4ccccc4c(-c4cccc5c4ccc4cc6ccccc6cc45)c4ccccc34)cc2)cc1]
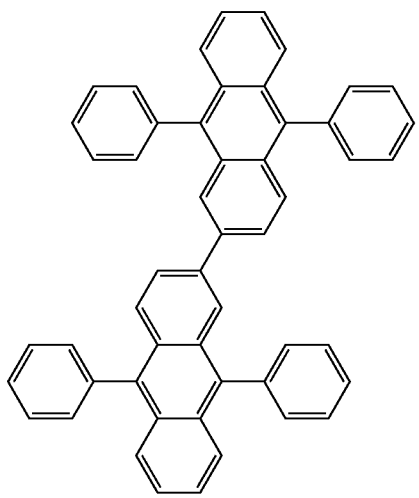 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
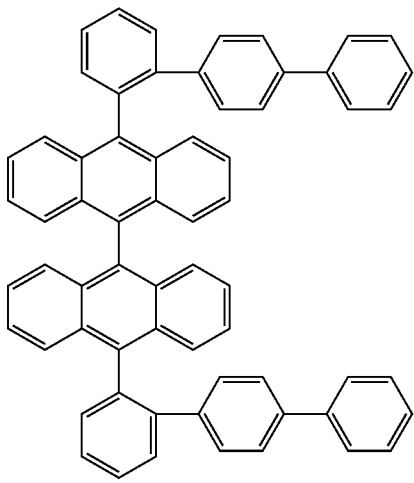 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]
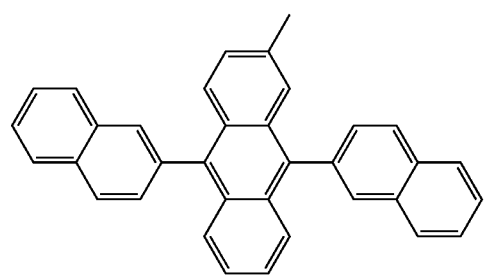 [SMILES: Cc1ccc2c(-c3ccc4ccccc4c3)c3ccccc3c(-c3ccc4ccccc4c3)c2c1]

-continued
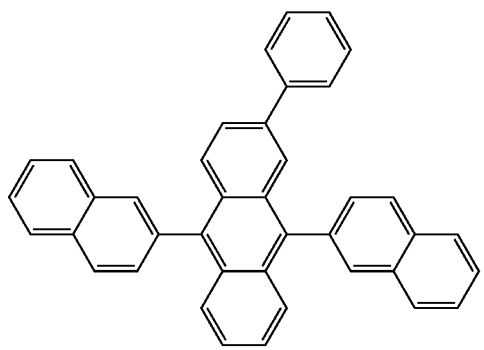 [SMILES: c1ccc(-c2ccc3c(-c4ccc5ccccc5c4)c4ccccc4c(-c4ccc5ccccc5c4)c3c2)cc1]
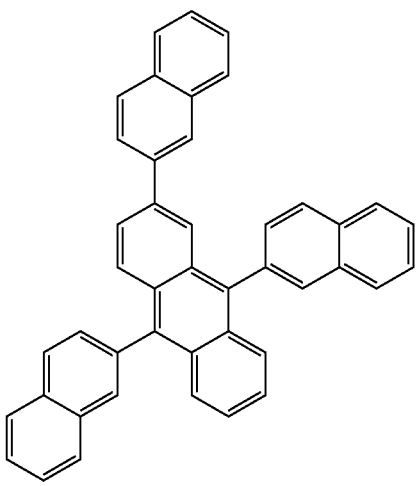 [SMILES: c1ccc2cc(-c3ccc4c(-c5ccc6ccccc6c5)c5ccccc5c(-c5ccc6ccccc6c5)c4c3)ccc2c1]
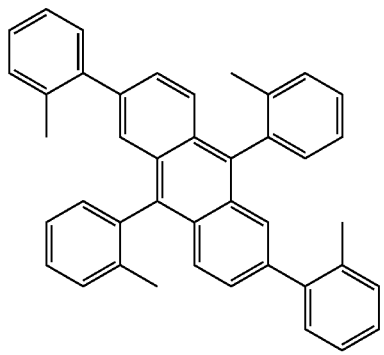 [SMILES: Cc1ccccc1-c1ccc2c(-c3ccccc3C)c3cc(-c4ccccc4C)ccc3c(-c3ccccc3C)c2c1]
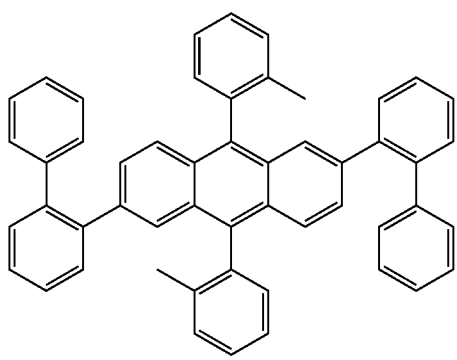 [SMILES: Cc1ccccc1-c1c2ccc(-c3ccccc3-c3ccccc3)cc2c(-c2ccccc2C)c2ccc(-c3ccccc3-c3ccccc3)cc12]

-continued
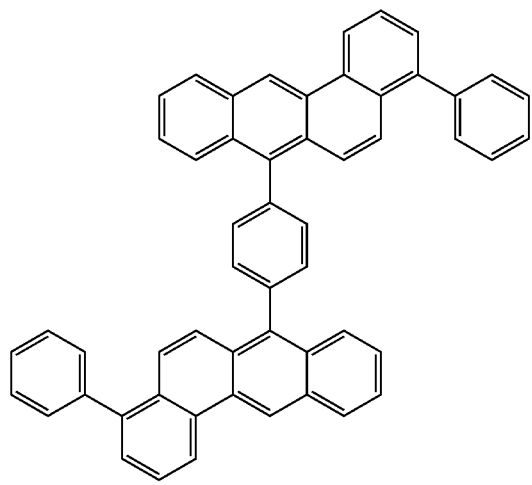 [SMILES: c1ccc(-c2cccc3c2ccc2c(-c4ccc(-c5c6ccccc6cc6c5ccc5c(-c7ccccc7)cccc56)cc4)c4ccccc4cc23)cc1]
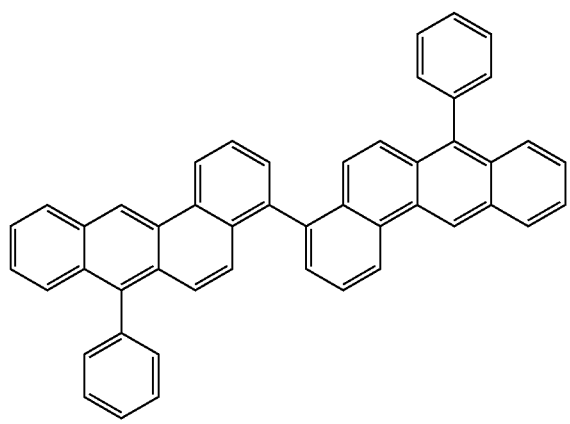 [SMILES: c1ccc(-c2c3ccccc3cc3c2ccc2c(-c4cccc5c4ccc4c(-c6ccccc6)c6ccccc6cc45)cccc23)cc1]
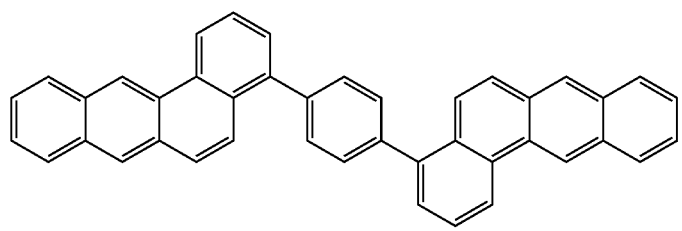 [SMILES: c1ccc2cc3c(ccc4c(-c5ccc(-c6cccc7c6ccc6cc8ccccc8cc67)cc5)cccc43)cc2c1]

-continued
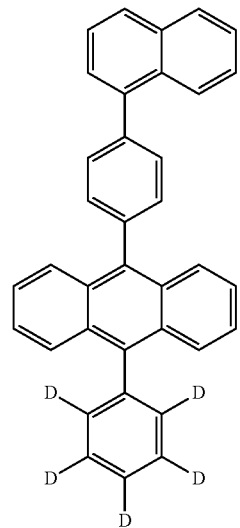 [SMILES: [2H]c1c([2H])c([2H])c(-c2c3ccccc3c(-c3ccc(-c4cccc5ccccc45)cc3)c3ccccc23)c([2H])c1[2H]]
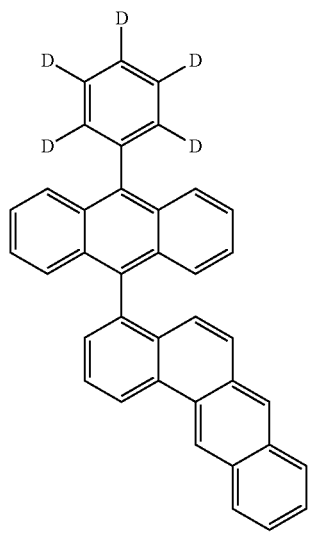 [SMILES: [2H]c1c([2H])c([2H])c(-c2c3ccccc3c(-c3cccc4c3ccc3cc5ccccc5cc34)c3ccccc23)c([2H])c1[2H]]
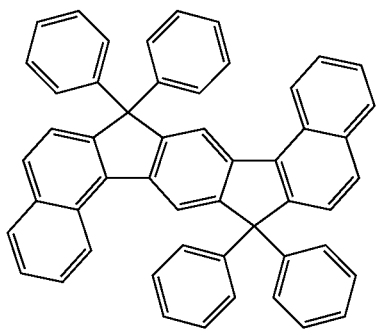 [SMILES: c1ccc(C2(c3ccccc3)c3cc4c(cc3-c3c2ccc2ccccc32)C(c2ccccc2)(c2ccccc2)c2ccc3ccccc3c2-4)cc1]
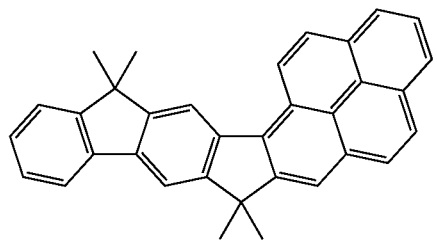 [SMILES: CC1(C)c2ccccc2-c2cc3c(cc21)-c1c(cc2ccc4cccc5ccc1c2c45)C3(C)C]

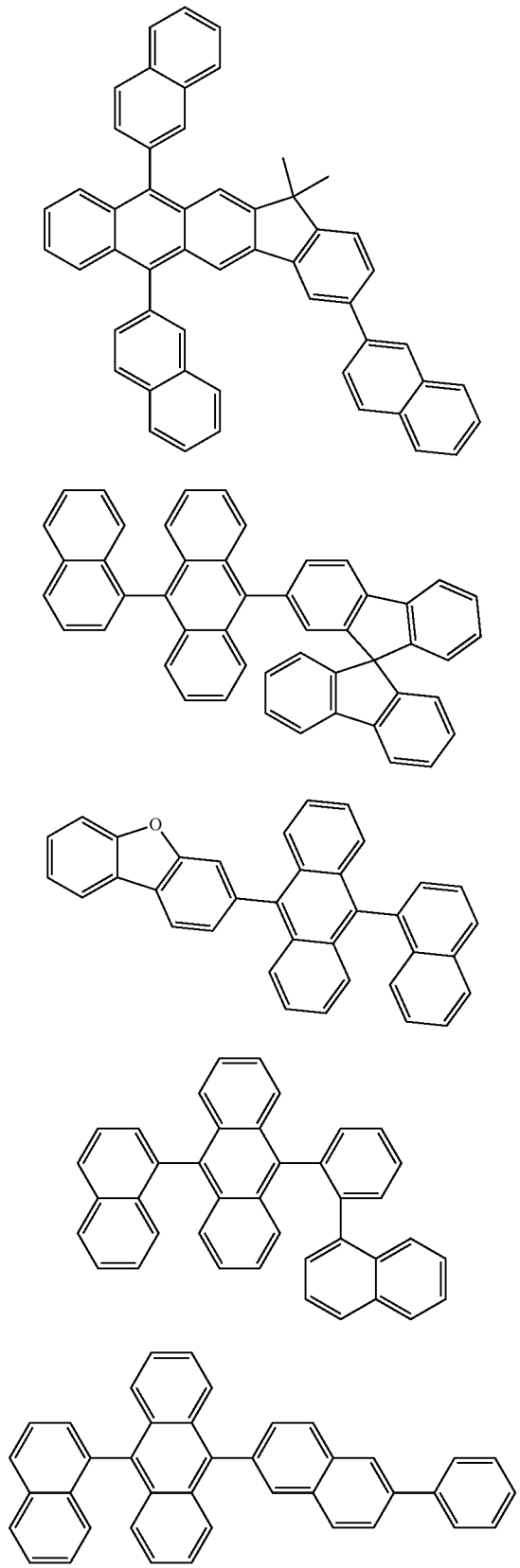

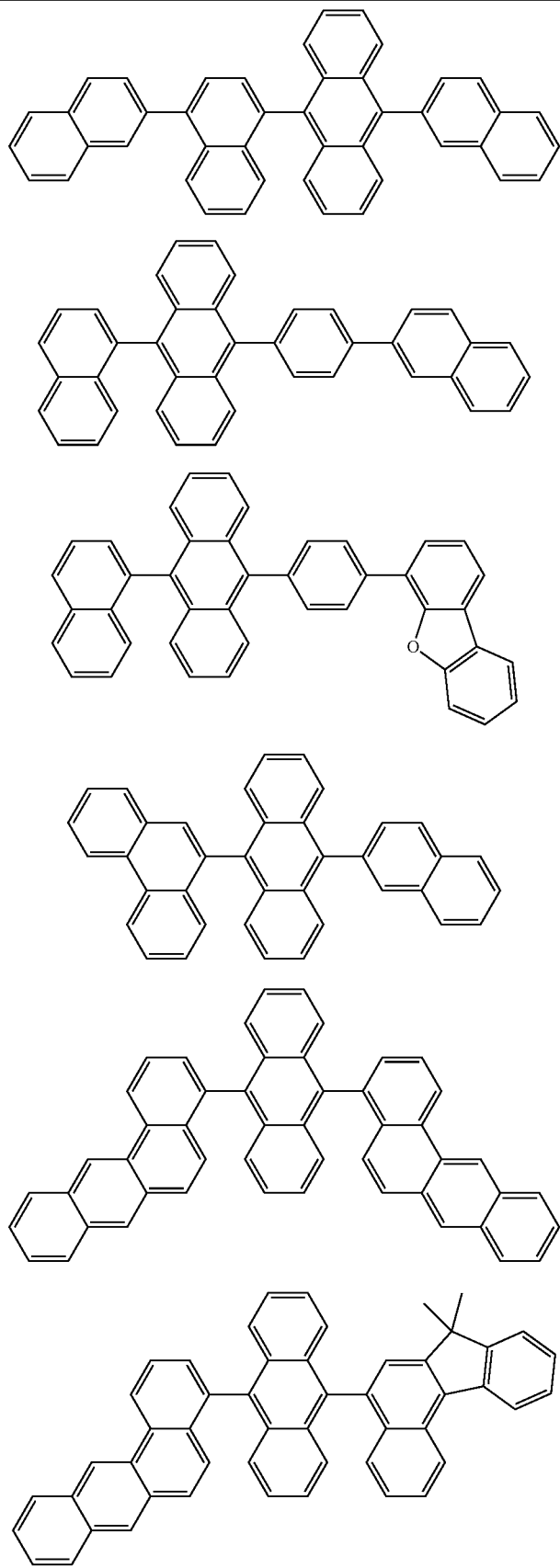

-continued
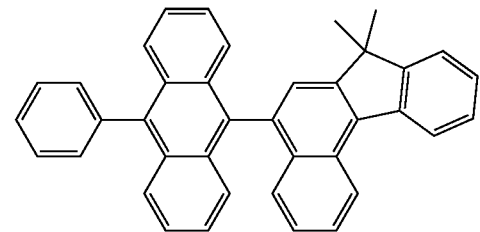 [SMILES: CC1(C)c2ccccc2-c2c1cc(-c1c3ccccc3c(-c3ccccc3)c3ccccc13)c1ccccc21]
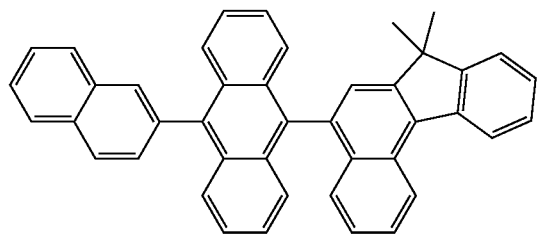 [SMILES: CC1(C)c2ccccc2-c2c1cc(-c1c3ccccc3c(-c3ccc4ccccc4c3)c3ccccc13)c1ccccc21]
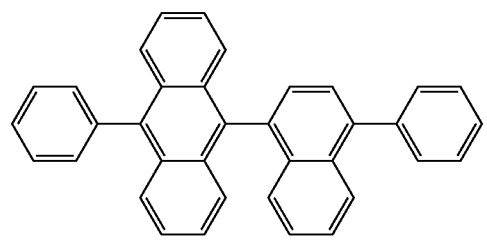 [SMILES: c1ccc(-c2ccc(-c3c4ccccc4c(-c4ccccc4)c4ccccc34)c3ccccc23)cc1]
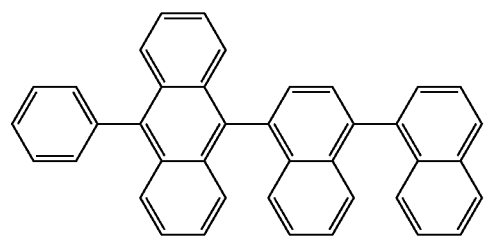 [SMILES: c1ccc(-c2c3ccccc3c(-c3ccc(-c4cccc5ccccc45)c4ccccc34)c3ccccc23)cc1]
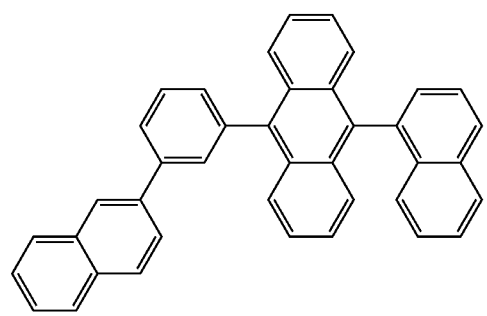 [SMILES: c1cc(-c2ccc3ccccc3c2)cc(-c2c3ccccc3c(-c3cccc4ccccc34)c3ccccc23)c1]
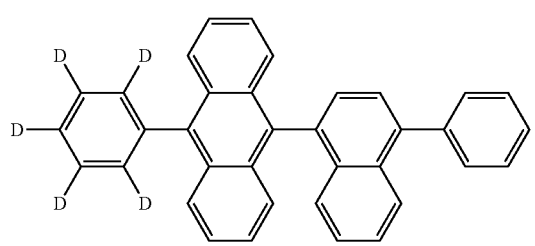 [SMILES: [2H]c1c([2H])c([2H])c(-c2c3ccccc3c(-c3ccc(-c4ccccc4)c4ccccc34)c3ccccc23)c([2H])c1[2H]]

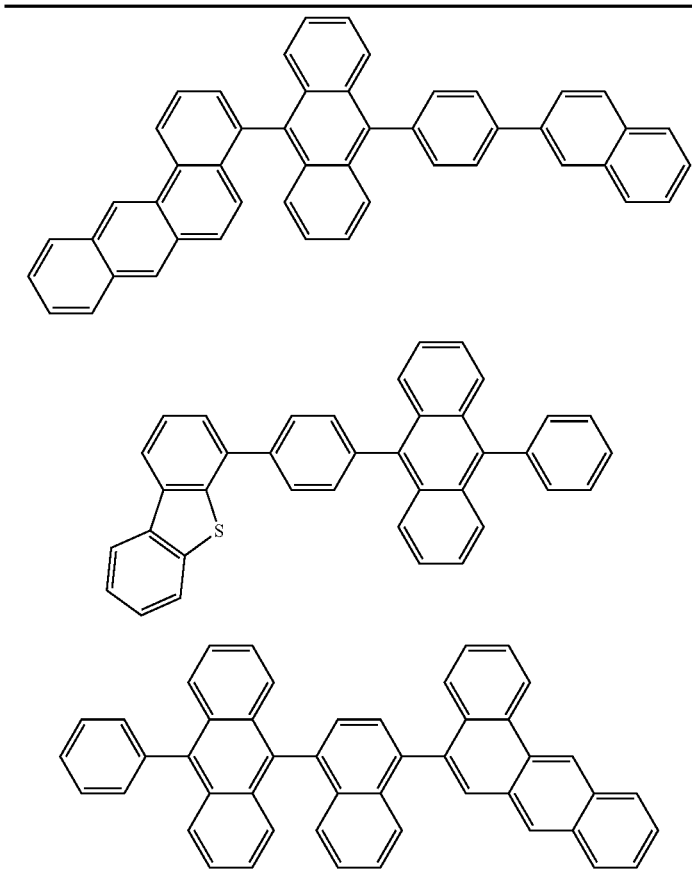

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Examples of preferred hole-transport materials which can be used besides the compounds of the formula (I) in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with the as yet unpublished applications EP 12005369.9, EP 12005370.7 and EP 12005371.5), spiro-dibenzopyranamines (for example in accordance with WO 2013/083216) and dihydroacridine derivatives (for example in accordance with WO 2012/150001).

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds according to the invention can be employed in displays, as light sources in lighting applications and as light sources in medical and/or cosmetic applications (for example light therapy).

WORKING EXAMPLES

A) Synthesis Examples

A-1) Variant I

The procedure is in accordance with the following general scheme:

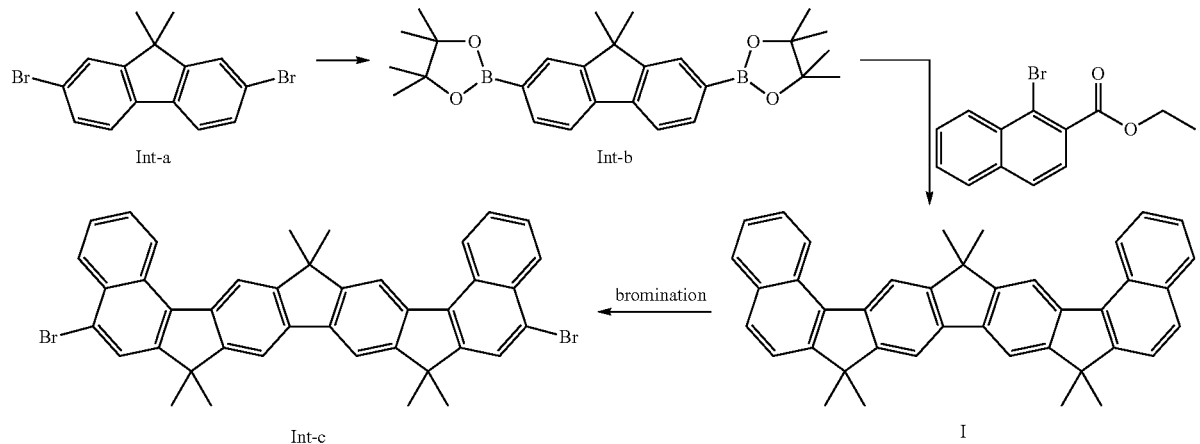

| Compound | | Synthesis/yield |
|---|---|---|
| Int-a1 | | Commercially available |
| Int-a2 | | Commercially available |
| Int-a3 | | Bioorg. & Med. Chem. Lett., 2012, 22, 5108-5113 |

-continued

| Compound | | Synthesis/yield |
|---|---|---|
| | 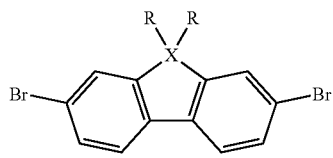 | |
| | 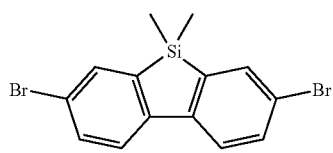 [SMILES: C[Si]1(C)c2cc(Br)ccc2-c2ccc(Br)cc21] | |
| Int-a4 |  | Tetrahedron 2001, 57, 10047-10053 |
| Int-a5 | | Synthesis 2003, 16, 2470-2472 |
| Int-a6 | 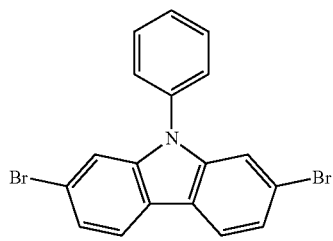 | J. Mat. Chem. 2009, 19, 4148-4156 |

-continued

| Compound | | Synthesis/yield |
|---|---|---|
| | 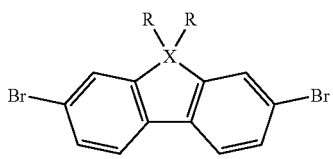 | |
| | 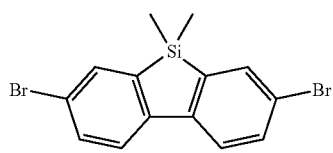 [SMILES: C[Si]1(C)c2cc(Br)ccc2-c2ccc(Br)cc21] | |
| Int-a7 | 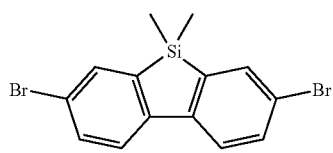 [SMILES: C[Si]1(C)c2cc(Br)ccc2-c2ccc(Br)cc21] | Org. Lett. 2008, 10, 773-776 |
| Int-a8 | 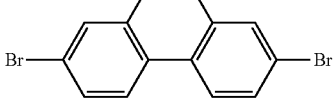 | WO 2012/ 60283 A1 |

Compound Int-b 2,7-Dibromo-9,9-dimethyl-9H-fluorene (130 g, 369 mmol), bis(pinacolato)-diborane (225 g, 886 mmol) and potassium acetate (217 g, 2.22 mol) are suspended in 1.4 l of dioxane. The solution is degassed and saturated with argon. PdCl$_2$(dppf)-CH$_2$Cl$_2$ (15 g, 18 mmol) is then added. The reaction mixture is heated at the boil under a protective-gas atmosphere for 4 h. The mixture is filtered and washed with dioxane. After filtration of the crude product, the residue remaining is extracted with THF in a Soxhlet extractor, then filtered. The yield is 137 g (83% of theory) as a grey solid. Purity>95% (NMR in CDCl$_3$).

The following compounds are prepared analogously:

| Compound | Structure | Yield |
|---|---|---|
| Int-b1 | 9,9-dimethylfluorene-2,7-diboronic acid bis(pinacol) ester | 83% |
| Int-b2 | 9,9-cyclohexylidenefluorene-2,7-diboronic acid bis(pinacol) ester | 80% |
| Int-b3 | 4,6-dimethyldibenzofuran-3,7-diboronic acid bis(pinacol) ester | 50% |
| Int-b4 | 9,9-dimethyl-9-siladibenzofluorene-diboronic acid bis(pinacol) ester | 75% |
| Int-b5 | 9-phenylcarbazole-2,7-diboronic acid bis(pinacol) ester | 85% |
| Int-b6 | 9,10-dihydrophenanthrene-2,7-diboronic acid bis(pinacol) ester | 90% |

-continued

| Compound | | Yield |
|---|---|---|
| Int-b7 | 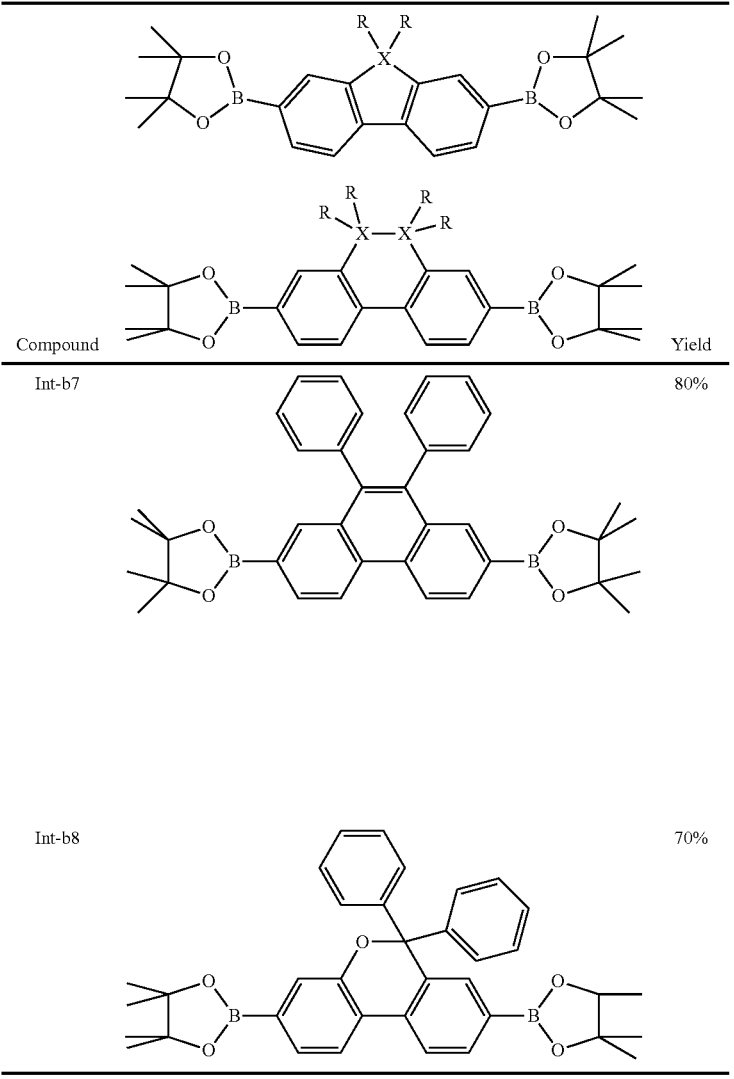 | 80% |
| Int-b8 | | 70% |

Compound I 2,7-Bispinacolato-9,9-dimethyl-9H-fluorene (137 g, 307 mmol), 1-bromonaphthalene-2-carboxylic acid (173 g, 620 mmol) and tripotassium phosphate monohydrate (283 g, 1.23 mol) are suspended in a water/toluene/dioxane mixture (1:1:1, 1.5 l). The solution is degassed and saturated with argon. Tri(o-tolyl)phosphine (22.4 g, 73 mmol) and palladium(II) acetate (2.76 g, 12.3 mmol) are then added. The reaction mixture is heated at the boil under a protective-gas atmosphere for 5.5 h. The phases are separated, and the aqueous phase is washed with toluene. The organic phase is dried over $Na_2SO_4$ and evaporated in a rotary evaporator. The mixture is filtered through silica gel and AlOx with toluene and evaporated in a rotary evaporator. The yellow oil is dried in a vacuum drying cabinet and is not purified.

The yellow oil in 500 ml of THF is added dropwise to a mixture of cerium(III) trichloride (166 g, 670 mmol) and 500 ml of THF. The reaction mixture is stirred at room temperature for 1 h, then cooled to 0° C. Methyl-magnesium chloride (813 ml, 3M in THF) is added dropwise at this temperature. The reaction mixture is stirred overnight. 500 ml of water are added to the batch, which is then filtered with THF. The phases of the mother liquor are separated. The organic phase is dried over $Na_2SO_4$ and evaporated in a rotary evaporator. The yellow oil is dried in a vacuum drying cabinet and is not purified further.

The yellow oil and polyphosphoric acid (446 g, 4.56 mol) are suspended in 1 l of dichloromethane. Methanesulfonic acid (296 ml, 4.56 mol) is slowly added dropwise. The reaction mixture is stirred for 1 h. 700 ml of ethanol are added. The batch is filtered, and the residue remaining is recrystallised from toluene. The yield is 109 g (68% of theory) as a yellow solid. Purity 99.7% (HPLC).

The following compounds are prepared analogously:
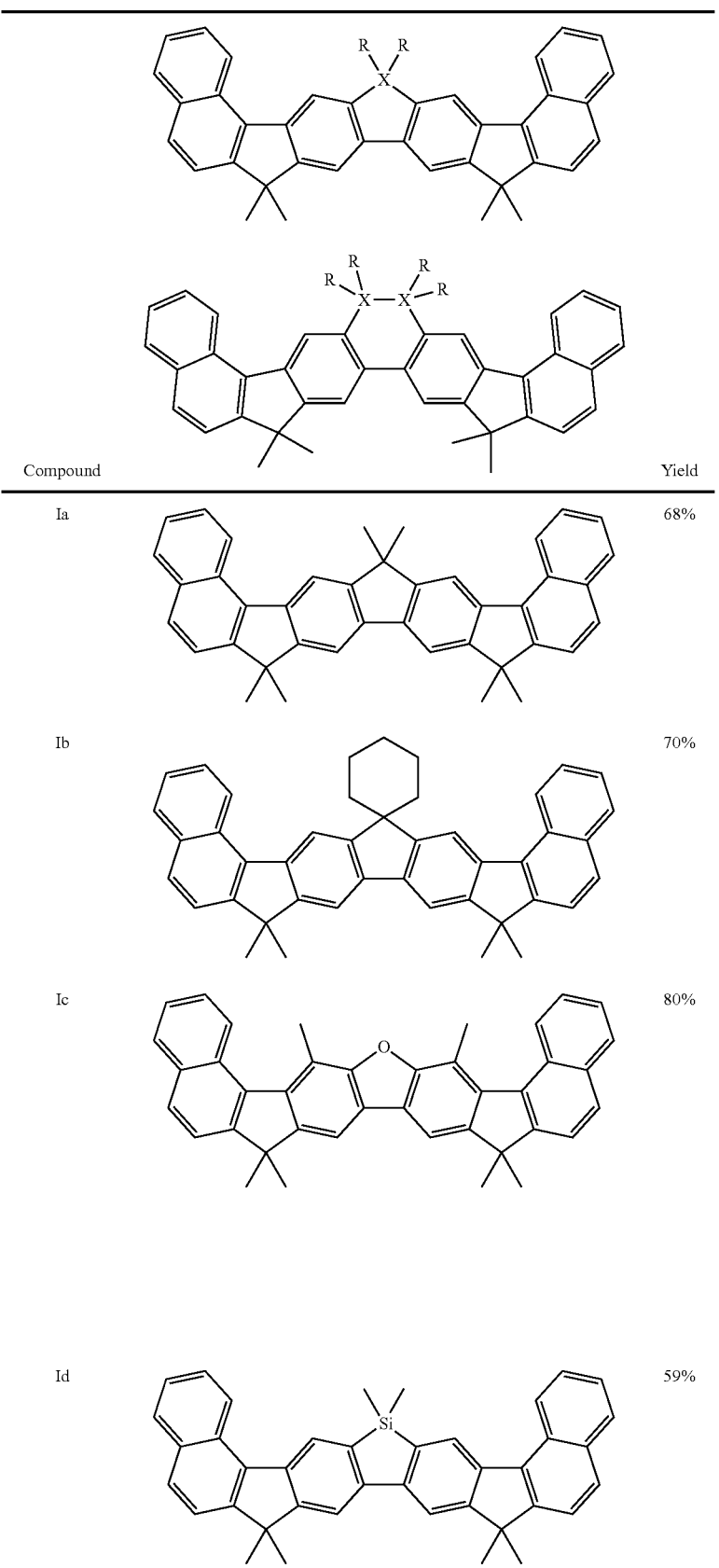
| Compound | Yield |
|---|---|
| Ia | 68% |
| Ib | 70% |
| Ic | 80% |
| Id | 59% |

-continued

| Compound | | Yield |
|---|---|---|
| Ie | | 52% |
| If | | 64% |
| Ig | | 45% |
| Ih | | 48% |

Compound Int-c

Ia (80 g, 152 mmol) is dissolved in 500 ml of DCM. Br$_2$ (16 ml, 311 mmol) in 300 ml of DCM is added dropwise at 0° C. The reaction mixture is stirred at room temperature overnight. 20 ml of sodium thiosulfate solution are added, and the mixture is stirred for 15 min. The batch is filtered with ethanol. The residue remaining is recrystallised three times from toluene. The yield is 60 g (57% of theory) as a grey solid. Purity 96.3% (HPLC).

The following compounds are prepared analogously:

| Compound | | Yield |
|---|---|---|
| Int-c1 | | 57% |
| Int-c2 | | 65% |
| Int-c3 | | 58% |
| Int-c4 | | 50% |

-continued
| Compound | | Yield |
|---|---|---|
| | 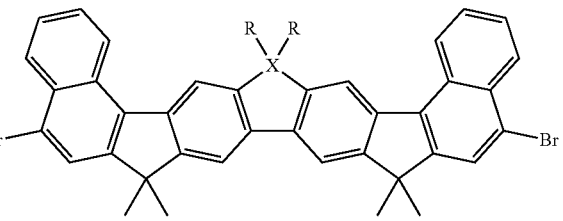 | |
| Int-c5 | 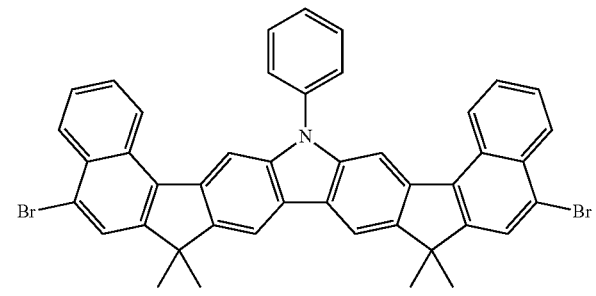 [SMILES: CC1(C)c2cc3c4cc5c(cc4n(-c4ccccc4)c3cc2-c2c1cc(Br)c1ccccc21)-c1c(cc(Br)c2ccccc12)C5(C)C] | 65% |
| Int-c6 | | 69% |
| Int-c7 | 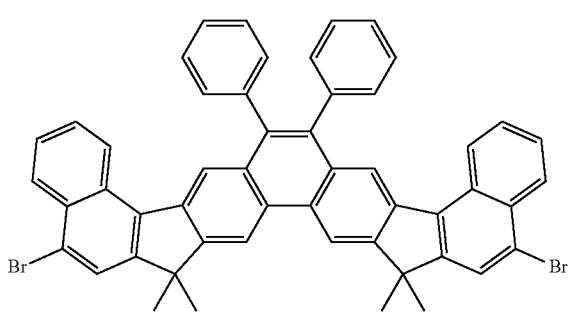 [SMILES: CC1(C)c2cc3c(cc2-c2c1cc(Br)c1ccccc21)c(-c1ccccc1)c(-c1ccccc1)c1cc2c(cc13)C(C)(C)c1cc(Br)c3ccccc3c1-2] | 48% |
| Int-c8 | 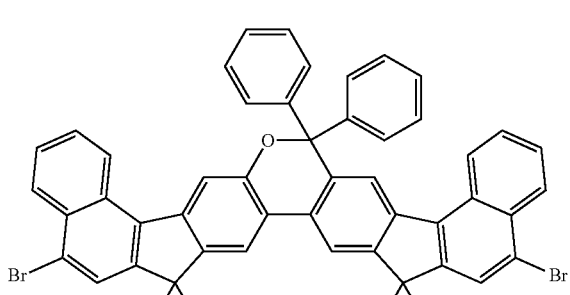 | 52% |

Compound II

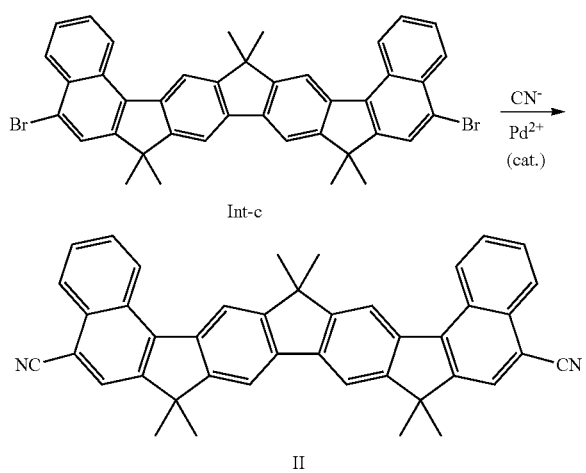

Int-c (17 g, 24 mmol), K$_4$[Fe(CN)$_6$]*3H$_2$O (10.5 g, 24 mmol) and sodium carbonate (7.9 g, 75 mmol) are suspended in 400 ml of DMF. The solution is degassed and saturated with argon. S-Phos (816 mg, 2 mmol) and palladium(II) acetate (223 mg, 1 mmol) are then added. The reaction mixture is heated at the boil under a protective-gas atmosphere overnight. The reaction mixture is cooled, then evaporated in a rotary evaporator. The resultant solid is extracted with toluene over aluminium oxide in a Soxhlet extractor, then recrystallised 7× from chloroform. The yield is 2.5 g (17.5% of theory) as a grey solid. Purity 99.9% (HPLC).

The following compounds are prepared analogously:

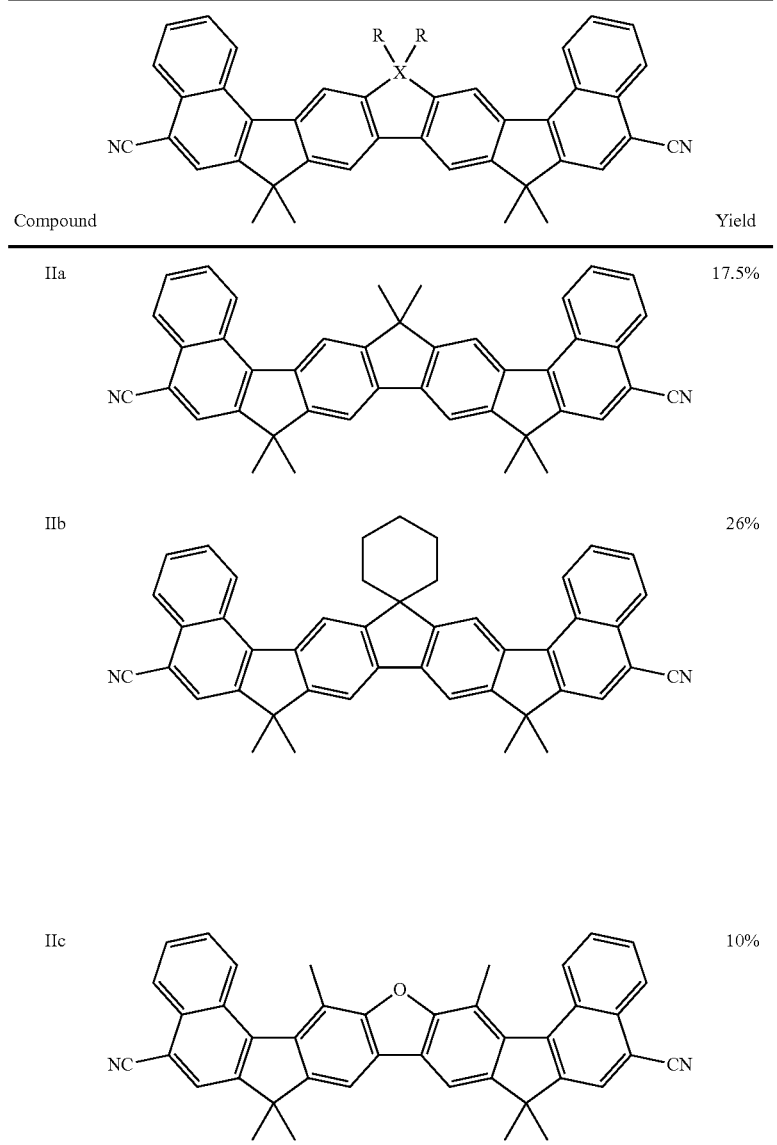

-continued
| Compound | | Yield |
|---|---|---|
| | 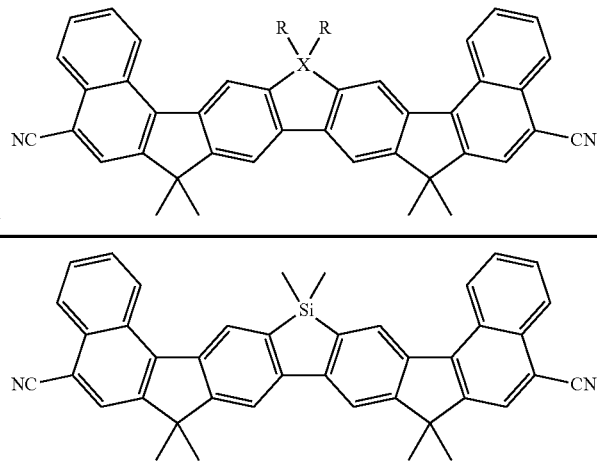 | |
| IId | 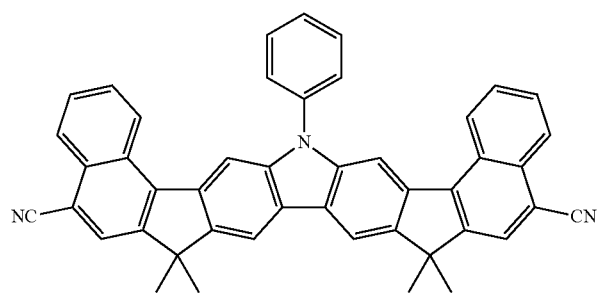 [SMILES: CC1(C)c2cc3c4cc5c(cc4n(-c4ccccc4)c3cc2-c2c1cc(C#N)c1ccccc21)-c1c(cc(C#N)c2ccccc12)C5(C)C] | 11% |
| IIe | 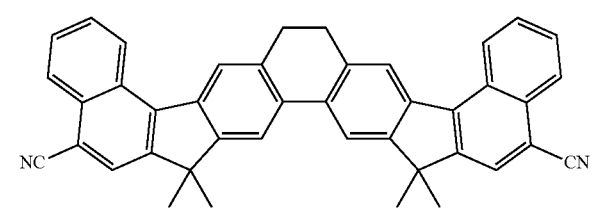 [SMILES: CC1(C)c2cc3c(cc2-c2c1cc(C#N)c1ccccc21)CCc1cc2c(cc1-3)C(C)(C)c1cc(C#N)c3ccccc3c1-2] | 8% |
| IIf | 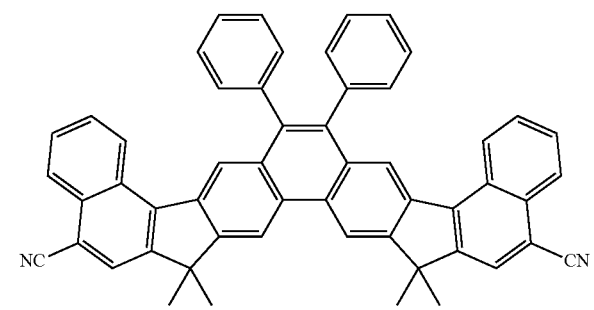 [SMILES: CC1(C)c2cc3c(cc2-c2c1cc(C#N)c1ccccc21)c(-c1ccccc1)c(-c1ccccc1)c1cc2c(cc13)C(C)(C)c1cc(C#N)c3ccccc3c1-2] | 21% |
| IIg | 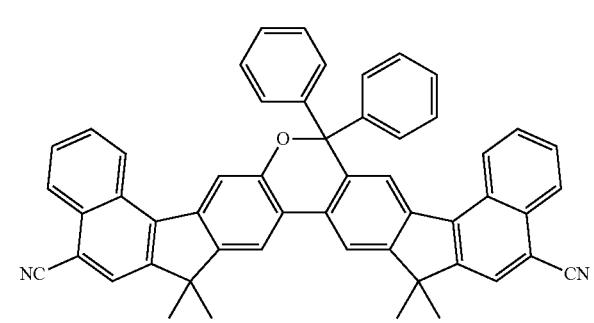 [SMILES: CC1(C)c2cc3c(cc2-c2c1cc(C#N)c1ccccc21)OC(c1ccccc1)(c1ccccc1)c1cc2c(cc1-3)C(C)(C)c1cc(C#N)c3ccccc3c1-2] | 8% |
| IIh | | 10% |

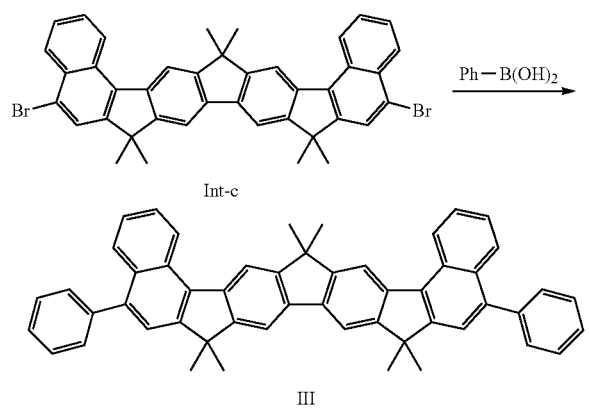

Compound III

Int-c (800 mg, 1.5 mmol), benzeneboronic acid (342 mg, 3 mmol) and tripotassium phosphate monohydrate (1.08 g, 4.7 mmol) are suspended in a water/toluene/dioxane mixture (1:1:1, 6 ml). The solution is degassed and saturated with argon. Tri(o-tolyl)phosphine (43 mg, 0.14 mmol) and palladium(II) acetate (10 mg, 0.05 mmol) are then added. The reaction mixture is heated at the boil under a protective-gas atmosphere overnight. The phases are separated, and the aqueous phase is washed with toluene. The organic phase is dried over $Na_2SO_4$ and evaporated in a rotary evaporator. The mixture is filtered through silica gel and AlOx with toluene and evaporated in a rotary evaporator. The solid is recrystallised from toluene. The yield is 505 mg (64% of theory) as a yellow solid. Purity 99% (HPLC).

The following compounds are prepared analogously:

| Compound | | Yield |
|---|---|---|
| IIIa | | 64% |
| IIIb | | 42% |
| IIIc | | 59% |
| IIId | | 5% |

-continued

| Compound | | Yield |
|---|---|---|
| IIIe | | 12% |
| IIIf | | 26% |
| IIIg | | 46% |
| IIIh | | 8% |
| IIIi | | 12% |

-continued

| Compound | | Yield |
|---|---|---|
| IIIj | | 83% |
| IIIk | | 21% |
| IIIl | | 28% |
| IIIm | | 25% |
| IIIn | | 15% |

-continued
| Compound | | Yield |
|---|---|---|
| | 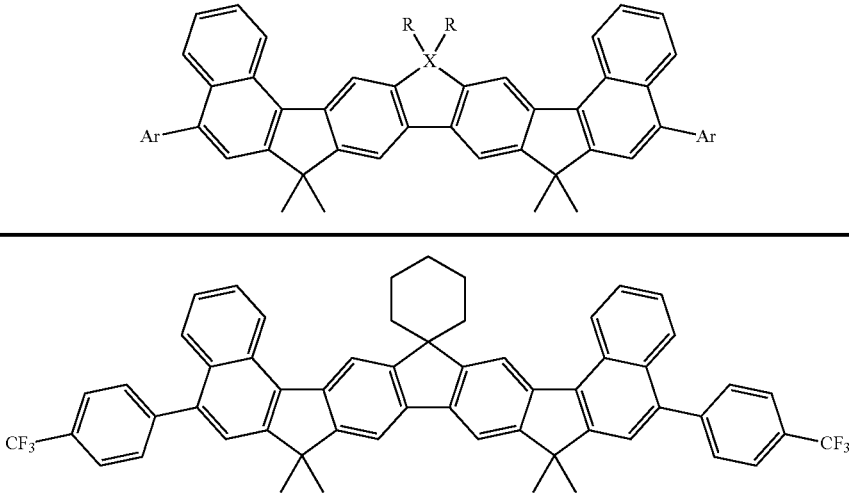 | |
| IIIo | 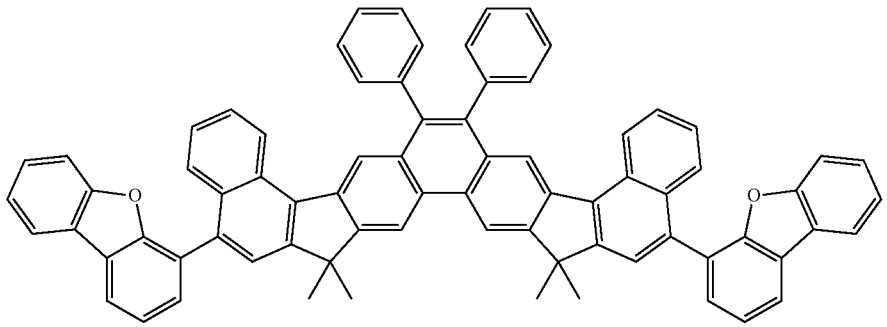 [SMILES: CC1(C)c2cc3c(cc2-c2c1cc(-c1cccc4c1oc1ccccc14)c1ccccc21)c(-c1ccccc1)c(-c1ccccc1)c1cc2c(cc13)C(C)(C)c1cc(-c3cccc4c3oc3ccccc34)c3ccccc3c1-2] | 78% |
| IIIq | 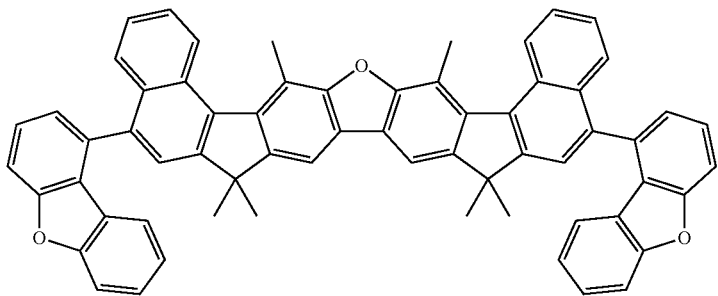 [SMILES: Cc1c2c(cc3c1oc1c(C)c4c(cc13)C(C)(C)c1cc(-c3cccc5oc6ccccc6c35)c3ccccc3c1-4)C(C)(C)c1cc(-c3cccc4oc5ccccc5c34)c3ccccc3c1-2] | 18% |
| IIIr | | 51% |

Compound Int-d 2,4-Dimethylphenylamine (1.12 ml, 8.9 mmol), 4-bromodibenzofuran (2 g, 8.1 mmol) and sodium tert-butoxide (1.9 g, 20 mmol) are suspended in 150 ml of toluene. The solution is degassed and saturated with argon. PdCl$_2$(dppf)-CH$_2$Cl$_2$ (132 mg, 162 mmol) is then added. The reaction mixture is heated at the boil under a protective-gas atmosphere overnight. The mixture is filtered through silica gel and AlOx with toluene and evaporated in a rotary evaporator. The oil is purified over a silica-gel column with heptane. The yield is 1.9 g (82% of theory) as a pale-brown oil. Purity 94% (HPLC).

The following compounds are prepared analogously:

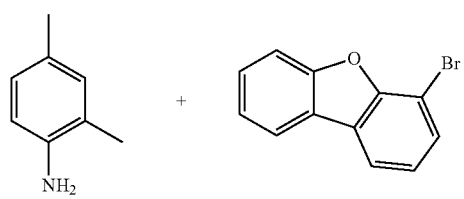

| Compound | Ar–NH–Ar | Yield |
|---|---|---|
| Int-d1 | 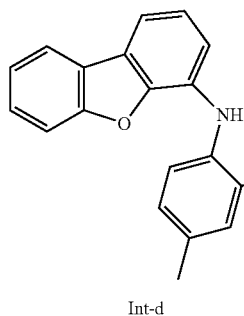 | 82% |

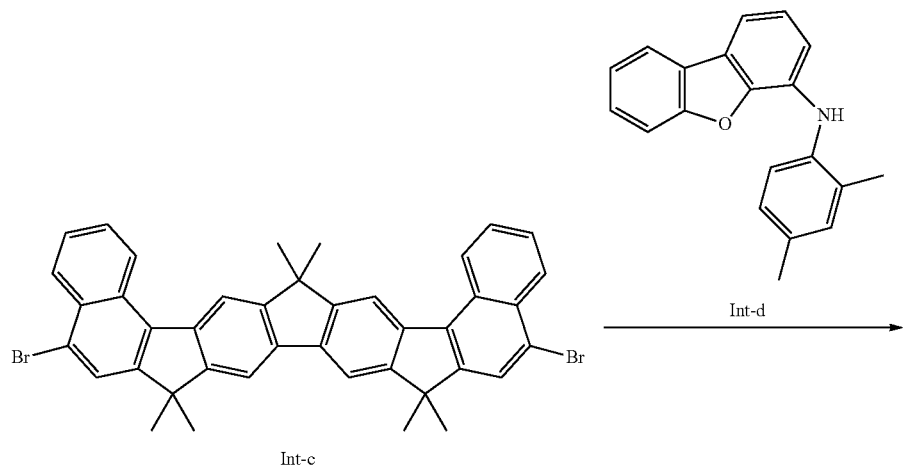

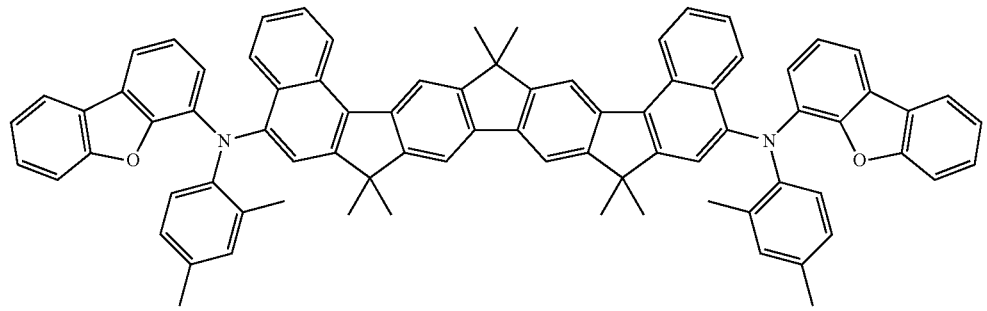

IV

| Compound | Ar–NH–Ar | Yield |
|---|---|---|
| Int-d2 | (bis-dibenzofuran-4-yl amine) | 30% |
| Int-d3 | (2-biphenyl)(phenyl)amine | 80% |
| Int-d4 | (2-biphenyl)(2-methylphenyl)amine | 85% |

| Compound | Ar–NH–Ar | Yield |
|---|---|---|
| Int-d5 | diphenylamine | 90% |
| Int-d6 | bis(2-methylphenyl)amine | 88% |

Compounds IVa and IVb

Int-c (1 g, 1.46 mmol), the dibenzofuran compound (903 mg, 3.14 mmol) and sodium tert-butoxide (421 mg, 4.38 mmol) are suspended in 40 ml of toluene. The solution is degassed and saturated with argon. Tri-tert-butyl-phosphine (117 µl, 1M in toluene) and palladium(II) acetate (48 mg, 0.06 mmol) are then added. The reaction mixture is heated at the boil under a protective-gas atmosphere for 4 h. The mixture is filtered through silica gel and AlOx with toluene and evaporated in a rotary evaporator. The product is recrystallised three times from toluene. The yield is 200 mg (13% of theory) as a pale-brown oil. Purity 96.7% (HPLC).

| Compound | | Yield |
|---|---|---|
| IVa | | 13% |

-continued

| Compound | | Yield |
|---|---|---|
| | (general structure with Ar, N, R, X substituents) | |
| IVb | | 16% |
| IVc | | 8% |
| IVd | | 12% |
| IVe | | 80% |

-continued
| Compound | | Yield |
|---|---|---|
| IVf | 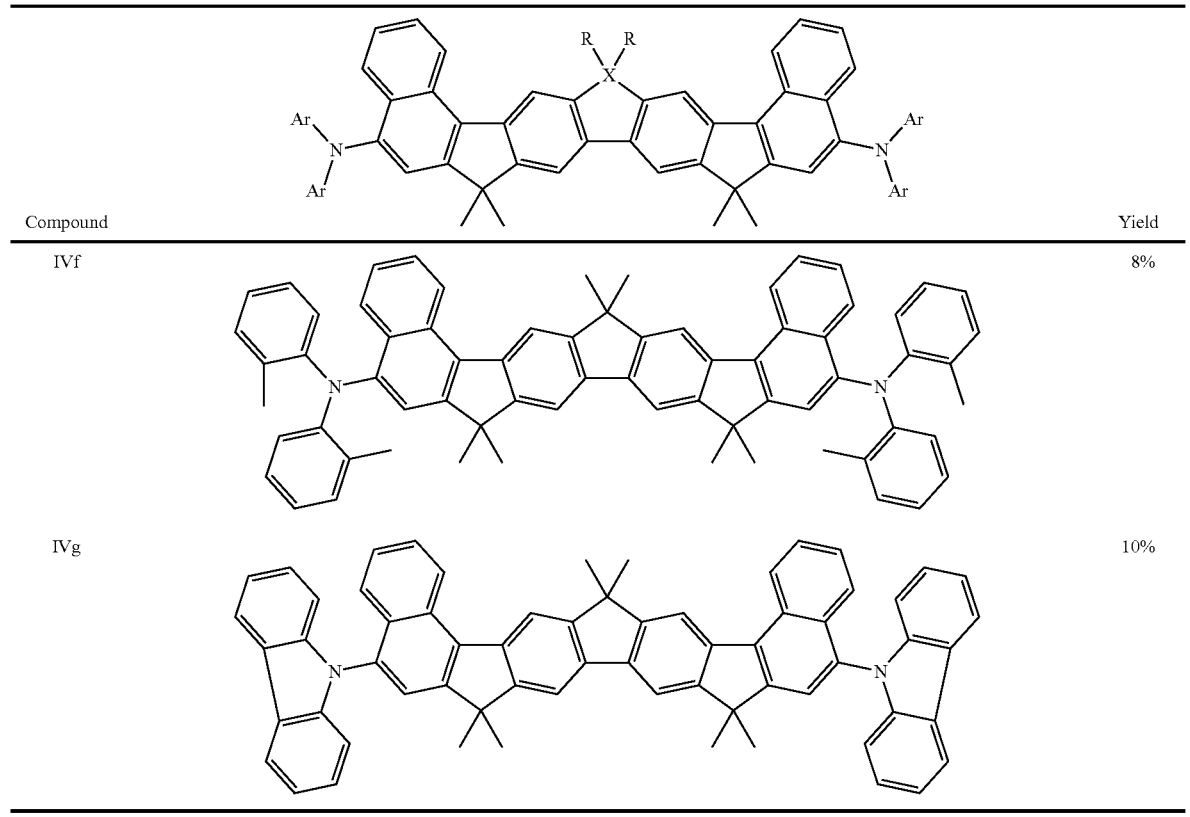 | 8% |
| IVg | | 10% |
A-2) Variant II
The procedure is in accordance with the following general scheme:

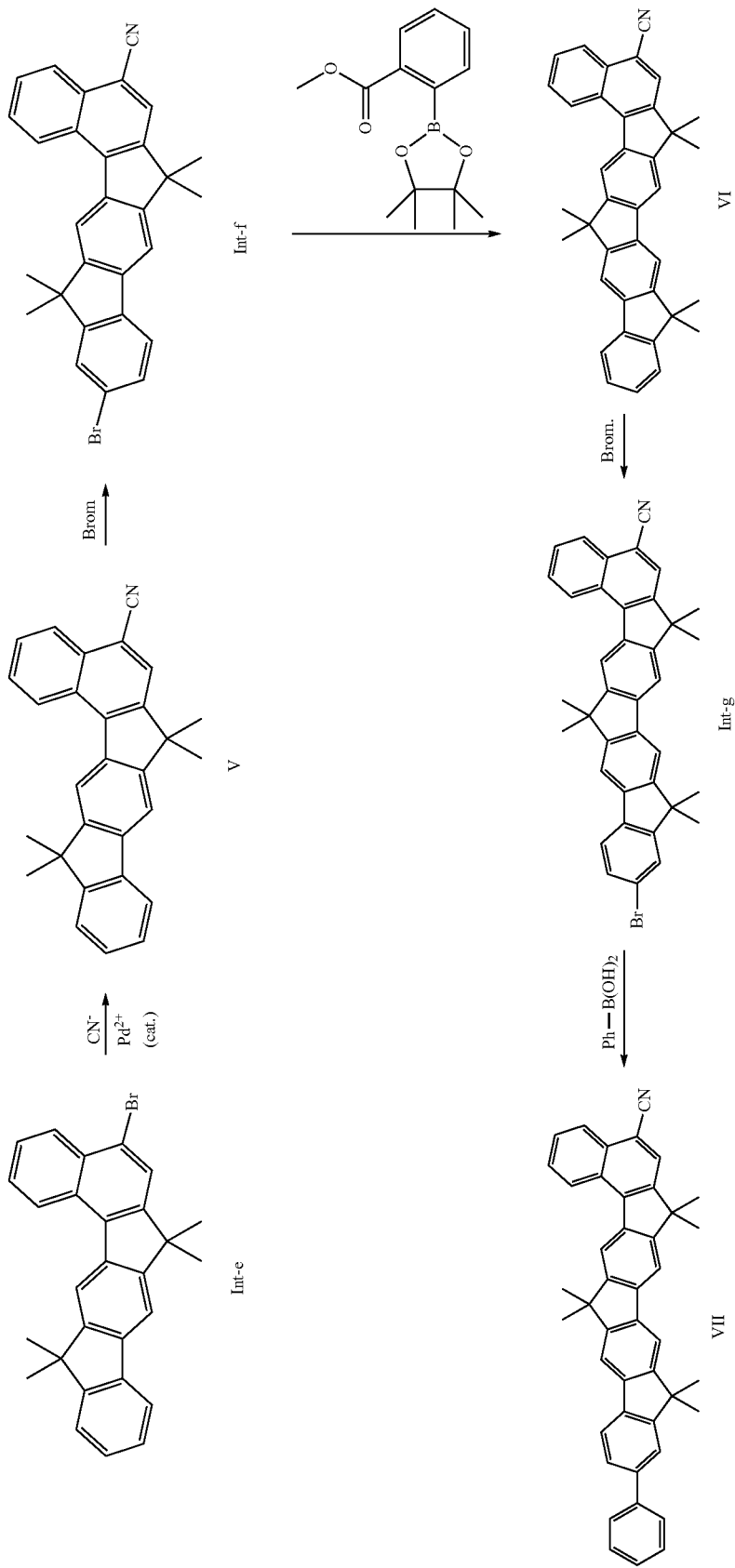

Compound V

Int-e (10 g, 20 mmol), K₄[Fe(CN)₆]*3H₂O (4.3 g, 10 mmol) and sodium carbonate (3.3 g, 31 mmol) are suspended in 150 ml of DMF. The solution is degassed and saturated with argon. S-Phos (336 mg, 0.82 mmol) and palladium(II) acetate (92 mg, 0.41 mmol) are then added. The reaction mixture is heated at the boil under a protective-gas atmosphere overnight. The reaction mixture is cooled, then evaporated in a rotary evaporator. The resultant solid is extracted with toluene over aluminium oxide in a Soxhlet extractor, then recrystallised 7× from chloroform. The yield is 5.3 g (67% of theory) as a yellow solid. Purity 99.6% (HPLC).

Compound Int-f

Compound V (3 g, 7.7 mmol) is dissolved in 25 ml of DCM. Br₂ (394 µl, 7.7 mmol) in 25 ml of DCM is added dropwise at 0° C. The reaction mixture is stirred at room temperature overnight. 10 ml of sodium thiosulfate solution are added, and the mixture is stirred for 15 min. The batch is filtered with ethanol. The residue remaining is recrystallised three times from heptane/toluene 1:1. The yield is 1.7 g (44% of theory) as a yellow solid. Purity 94% (HPLC).

Compound VI

Compound Int-f (1 g, 2.2 mmol), 1-bromonaphthalene-2-carboxylic acid (649 mg, 2.5 mmol) and tripotassium phosphate monohydrate (1.5 g, 6.5 mmol) are suspended in a water/toluene/dioxane mixture (1:1:1, 30 ml). The solution is degassed and saturated with argon. Trio-tolyl)-phosphine (79 mg, 0.3 mmol) and palladium(II) acetate (9.7 mg, 0.04 mmol) are then added. The reaction mixture is heated at the boil under a protective-gas atmosphere for 7 h. The phases are separated, and the aqueous phase is washed with toluene. The organic phase is dried over Na₂SO₄ and evaporated in a rotary evaporator. The mixture is filtered through silica gel and AlOx with toluene and evaporated in a rotary evaporator. The yellow solid is dried in a vacuum drying cabinet and is not purified further.

The yellow solid in 20 ml of THF is added dropwise to a mixture of cerium(III) trichloride (600 mg, 2.37 mmol) and 20 ml of THF. The reaction mixture is stirred at room temperature for 1 h, then cooled to 0° C. Methyl-magnesium chloride (1.25 ml, 3M in THF) is added dropwise at this temperature. The reaction mixture is stirred overnight. 20 ml of water are added to the batch, which is then filtered with THF. The phases of the mother liquor are separated. The organic phase is dried over Na₂SO₄ and evaporated in a rotary evaporator. The yellow solid is dried in a vacuum drying cabinet and is not purified.

The yellow solid and polyphosphoric acid (2.1 g, 21.5 mol) are suspended in 30 ml of dichloromethane. Methanesulfonic acid (1.4 ml, 21.5 mol) is slowly added dropwise. The reaction mixture is stirred for 1 h. 30 ml of ethanol are added. The batch is filtered, and the residue remaining is recrystallised from toluene. The yield is 809 mg (75% of theory) as a yellow solid. Purity 97% (HPLC).

Compound Int-g

Compound VI (809 mg, 1.6 mmol) is dissolved in 25 ml of DCM. Br₂ (83 µl, 1.6 mmol) in 25 ml of DCM is added dropwise at 0° C. The reaction mixture is stirred at room temperature overnight. 10 ml of sodium thiosulfate solution are added, and the mixture is stirred for 15 min. The batch is filtered with ethanol. The residue remaining is recrystallised three times from heptane/toluene 1:1. The yield is 790 mg (85% of theory) as a yellow solid. Purity 96% (HPLC).

Compound VII

Int-g (790 mg, 1.3 mmol), benzeneboronic acid (342 mg, 3 mmol) and tripotassium phosphate monohydrate (1.08 g, 4.7 mmol) are suspended in a water toluene/dioxane mixture (1:1:1, 6 ml). The solution is degassed and saturated with argon, Tri(o-tolyl)phosphine (43 mg, 0.14 mmol) and palladium(II) acetate (10 mg, 0.05 mmol) are then added. The reaction mixture is heated at the boil under a protective-gas atmosphere overnight. The phases are separated, and the aqueous phase is washed with toluene. The organic phase is dried over Na₂SO₄ and evaporated in a rotary evaporator. The mixture is filtered through silica gel and AlOx with toluene and evaporated in a rotary evaporator. The solid is recrystallised from toluene. The yield is 675 mg (73% of theory) as a yellow solid. Purity 97% (HPLC).

The following compounds are prepared analogously:

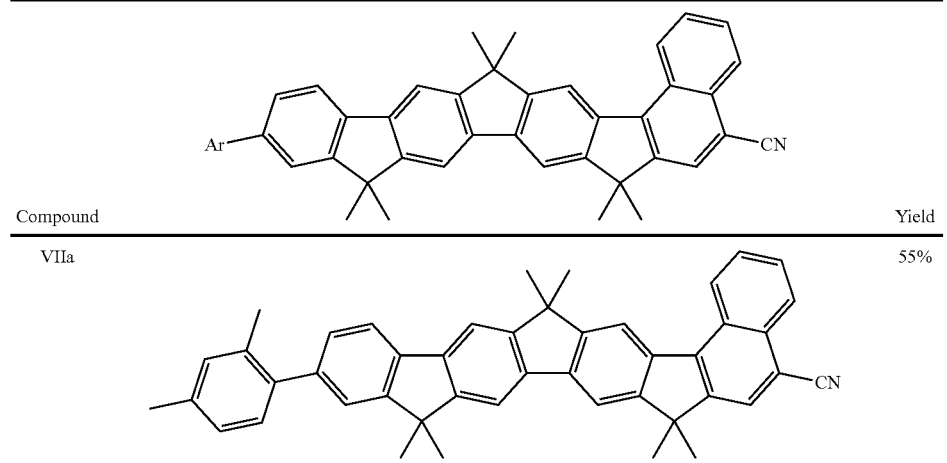

| Compound | | Yield |
|---|---|---|
| VIIa | | 55% |

| Compound | | Yield |
|---|---|---|
| VIIb | (structure with Ar and CN groups) | 69% |
| | (structure with biphenyl and CN groups) | |

B) Device Examples: Production of the OLEDs

OLEDs according to the invention and OLEDs in accordance with the prior art are produced by a general process in accordance with WO 04/058911, which is adapted to the circumstances described here (layer-thickness variation, materials).

The data for various OLEDs are presented in the following examples (see Tables 1 to 3). The substrates used are glass substrates which have been coated with structured ITO (indium tin oxide) in a thickness of 50 nm. The OLEDs have in principle the following layer structure: substrate/hole-injection layer1 (95% of HTL1+5% of HIL, 20 nm)/hole-transport layer (HTL, thickness indicated in Table 1)/emission layer (EML, 20 nm) electron-transport layer (ETL, 20 nm)/electron-injection layer (EIL, 3 nm) and finally a cathode. The cathode is formed by an aluminium layer with a thickness of 100 nm. A layer of Clevios P VP AI 4083 (purchased from Heraeus Clevios GmbH, Leverkusen) with a thickness of 20 nm is applied as buffer by spin coating. All remaining materials are applied by thermal vapour deposition in a vacuum chamber. The structure of the OLEDs is shown in Table 1. The materials used are shown in Table 3.

The emission layer (EML) always consists of at least one matrix material (host=H) and an emitting compound (dopant=D), which is admixed with the matrix material in a certain proportion by volume by co-evaporation. An expression such as H1:D1 (97%:3%) here means that material H1 is present in the layer in a proportion by volume of 97% and D1 is present in the layer in a proportion of 3%.

The OLEDs are characterised by standard methods. For this purpose, the electroluminescence spectra are recorded, the current efficiency (measured in cd/A) and the external quantum efficiency (EQE, measured in percent as a function of the luminous density assuming Lambert emission characteristics are calculated from current/voltage/luminous density characteristic lines (IUL characteristic lines), and finally the lifetime of the components is determined. The electroluminescence spectra are recorded at a luminous density of 1000 cd/m$^2$, and the CIE 1931 x and y colour coordinates are calculated therefrom. The expression EQE @ 1000 cd/m$^2$ denotes the external quantum efficiency at an operating luminous density of 1000 cd/m$^2$. The lifetime LT95 @ 1000 cd/m$^2$ is the time which passes until the initial luminance has dropped by 5% from 1000 cd/m$^2$. The data obtained for the various OLEDs are summarised in Table 2.

Use of the Compounds According to the Invention as Emitters in Fluorescent OLEDs Compounds D3, D4, D5, D6, D7, D8, D9, D10, D11 and D12 according to the invention are employed individually as emitters in the emitting layer of OLEDs (structure see Table 3). The matrix material used in the emitting layer here is compound V-H2. The OLEDs obtained are E4 to E6 and E9 to E15. They exhibit a very good lifetime in the case of deep-blue emission (Table 2). Compared with emitter materials known from the prior art (V-D1 and V-D2, cf. V1 to V3), the lifetime is considerably improved, with constant quantum efficiency.

In particular the comparison with material V-D1 shows the improvement achieved by the bisindenofluorene basic structure according to the invention compared with the indenofluorene basic structure known from the prior art.

Use of the Compounds According to the Invention as Matrix Materials in Fluorescent OLEDs Example E7, in which compound H3 according to the invention is employed as matrix material, likewise exhibits a good lifetime and quantum efficiency in the case of deep-blue emission (Table 2). This confirms the good suitability of the compounds according to the invention as matrix materials in the emitting layer.

Use of the Compounds According to the Invention as Hole-Transport Materials in OLEDs Example E8, in which compound H3 according to the invention is employed as hole-transport material in the hole-transport layer, likewise exhibits a good lifetime and quantum efficiency in the case of deep-blue emission (Table 2). This confirms the good suitability of the compounds according to the invention as hole-transporting compounds.

TABLE 1

Structure of the OLEDs

| Ex. | HTL Material Thickness/nm | EML Material |
|---|---|---|
| V1 | HTL3 195 nm | V-H1(97%):V-D1(3%) |
| V2 | HTL3 195 nm | V-H2(97%):V-D1(3%) |
| V3 | HTL3 195 nm | V-H2(97%):V-D2(3%) |

TABLE 1-continued

Structure of the OLEDs

| Ex. | HTL Material Thickness/nm | EML Material |
|---|---|---|
| E4 | HTL3 195 nm | V-H2(97%):D3(3%) |
| E5 | HTL3 195 nm | V-H2(97%):D4(3%) |
| E6 | HTL3 195 nm | V-H2(97%):D5(3%) |
| E7 | HTL2 20 nm | H3(95%):D3(1%) |
| E8 | D3 20 nm | V-H2(95%)V-D2(5%) |
| E9 | HTL3 195 nm | V-H2(97%):D6(3%) |
| E10 | HTL3 195 nm | V-H2(97%):D7(3%) |
| E11 | HTL3 195 nm | V-H2(97%):D8(3%) |
| E12 | HTL3 195 nm | V-H2(97%):D9(3%) |
| E13 | HTL3 195 nm | V-H2(97%):D10(3%) |
| E14 | HTL3 195 nm | V-H2(97%):D11(3%) |
| E15 | HTL3 195 nm | V-H2(97%):D12(3%) |

TABLE 2

Data of the OLEDs

| Ex. | EQE @ 1000 cd/m$^2$ % | LT95 @ 1000 cd/m$^2$ [h] | CIE x | CIE y |
|---|---|---|---|---|
| V1 | 7.5 | 90 | 0.13 | 0.13 |
| V2 | 7.8 | 110 | 0.13 | 0.14 |
| V3 | 7.9 | 90 | 0.13 | 0.10 |
| E4 | 7.4 | 350 | 0.14 | 0.11 |
| E5 | 7.6 | 320 | 0.14 | 0.14 |
| E6 | 6.9 | 150 | 0.14 | 0.13 |
| E7 | 6.9 | 120 | 0.13 | 0.13 |
| E8 | 7.3 | 140 | 0.13 | 0.14 |
| E9 | 7.0 | 140 | 0.14 | 0.11 |
| E10 | 7.2 | 370 | 0.14 | 0.14 |
| E11 | 7.8 | 140 | 0.13 | 0.10 |
| E12 | 7.6 | 280 | 0.14 | 0.25 |
| E13 | 7.5 | 270 | 0.13 | 0.09 |
| E14 | 7.3 | 280 | 0.14 | 0.11 |
| E15 | 7.8 | 350 | 0.14 | 0.26 |

TABLE 3

Structures of the materials used

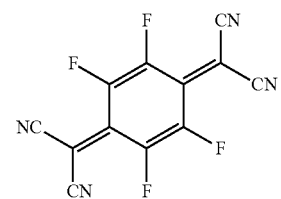 [SMILES: N#CC(C#N)=c1c(F)c(F)c(=C(C#N)C#N)c(F)c1F]

HIL

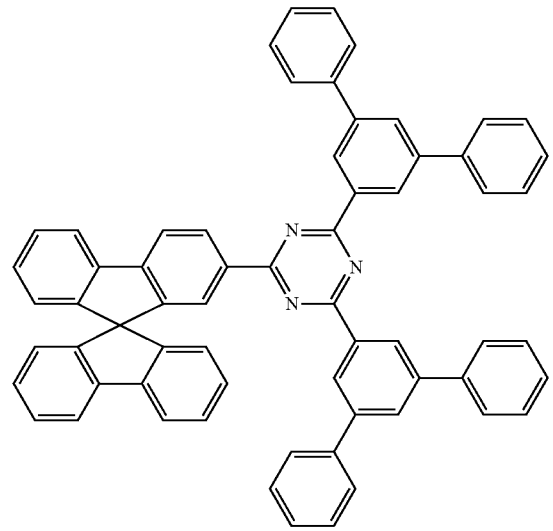 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

ETL

TABLE 3-continued
Structures of the materials used
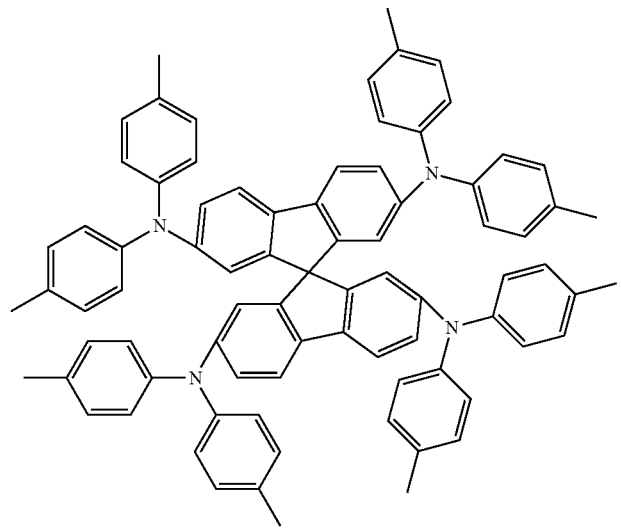
HTL1
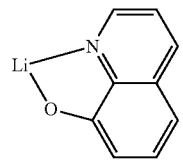
EIL
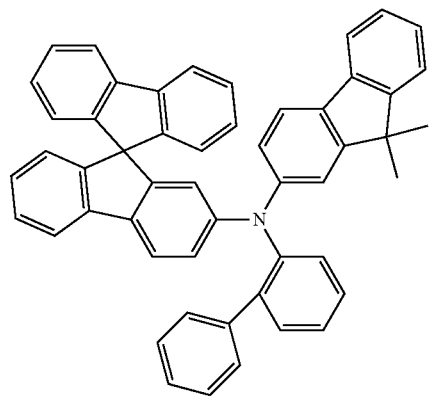 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HTL2

TABLE 3-continued
Structures of the materials used
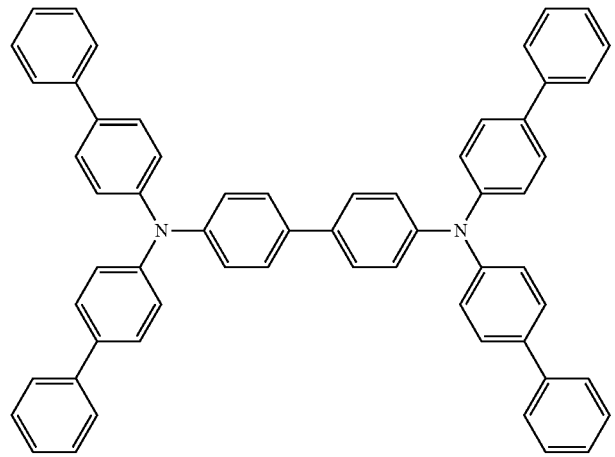 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
HTL3
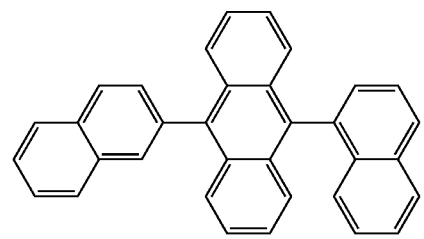 [SMILES: c1ccc2cc(-c3c4ccccc4c(-c4cccc5ccccc45)c4ccccc34)ccc2c1]
V-H1
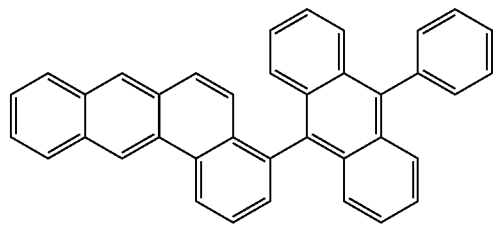 [SMILES: c1ccc(-c2c3ccccc3c(-c3cccc4c3ccc3cc5ccccc5cc34)c3ccccc23)cc1]
V-H2
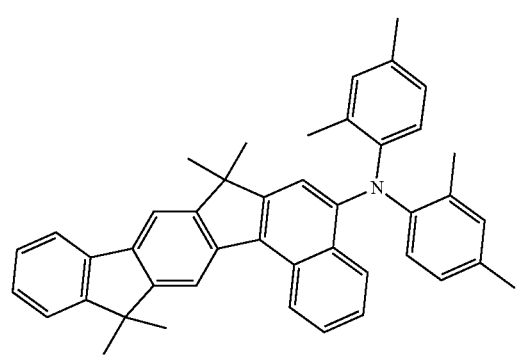 [SMILES: Cc1ccc(N(c2ccc(C)cc2C)c2cc3c(c4ccccc24)-c2cc4c(cc2C3(C)C)-c2ccccc2C4(C)C)c(C)c1]
V-D1

TABLE 3-continued
Structures of the materials used
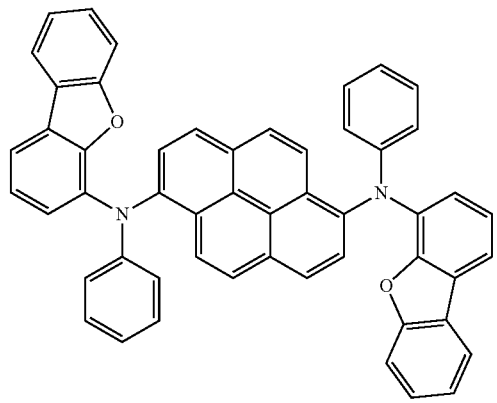 [SMILES: c1ccc(N(c2ccc3ccc4c(N(c5ccccc5)c5cccc6c5oc5ccccc56)ccc5ccc2c3c54)c2cccc3c2oc2ccccc23)cc1]
V-D2
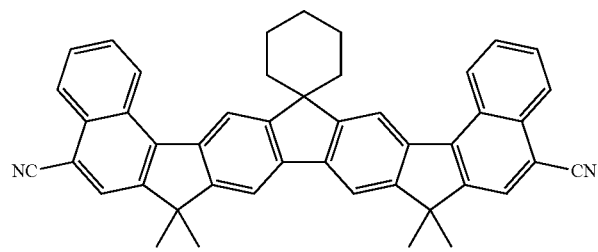 [SMILES: CC1(C)c2cc3c(cc2-c2c1cc(C#N)c1ccccc21)C1(CCCCC1)c1cc2c(cc1-3)C(C)(C)c1cc(C#N)c3ccccc3c1-2]
D3
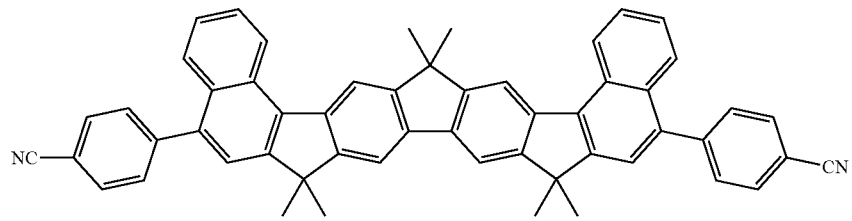 [SMILES: CC1(C)c2cc3c(cc2-c2cc4c(cc21)-c1c(cc(-c2ccc(C#N)cc2)c2ccccc12)C4(C)C)C(C)(C)c1cc(-c2ccc(C#N)cc2)c2ccccc2c1-3]
D4
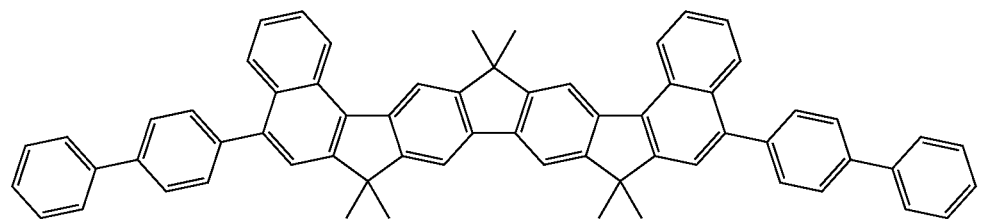 [SMILES: CC1(C)c2cc3c(cc2-c2cc4c(cc21)-c1c(cc(-c2ccc(-c5ccccc5)cc2)c2ccccc12)C4(C)C)C(C)(C)c1cc(-c2ccc(-c4ccccc4)cc2)c2ccccc2c1-3]
D5
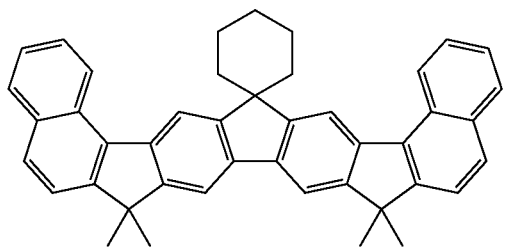 [SMILES: CC1(C)c2cc3c(cc2-c2c1ccc1ccccc21)C1(CCCCC1)c1cc2c(cc1-3)C(C)(C)c1ccc3ccccc3c1-2]
H3

TABLE 3-continued
Structures of the materials used
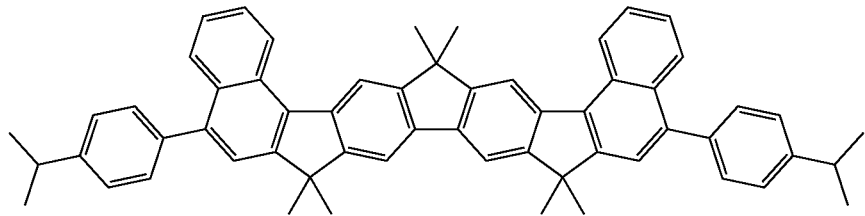 [SMILES: CC(C)c1ccc(-c2cc3c(c4ccccc24)-c2cc4c(cc2C3(C)C)-c2cc3c(cc2C4(C)C)-c2c(cc(-c4ccc(C(C)C)cc4)c4ccccc24)C3(C)C)cc1]
D6
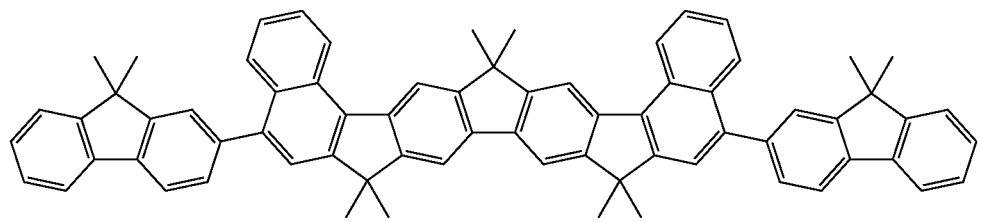 [SMILES: CC1(C)c2ccccc2-c2ccc(-c3cc4c(c5ccccc35)-c3cc5c(cc3C4(C)C)-c3cc4c(cc3C5(C)C)-c3c(cc(-c5ccc6c(c5)C(C)(C)c5ccccc5-6)c5ccccc35)C4(C)C)cc21]
D7
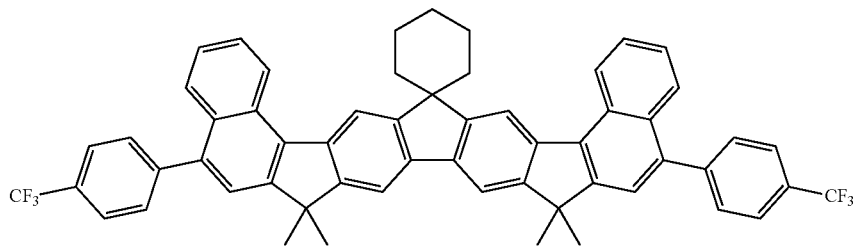 [SMILES: CC1(C)c2cc3c(cc2-c2c1cc(-c1ccc(C(F)(F)F)cc1)c1ccccc21)C1(CCCCC1)c1cc2c(cc1-3)C(C)(C)c1cc(-c3ccc(C(F)(F)F)cc3)c3ccccc3c1-2]
D8
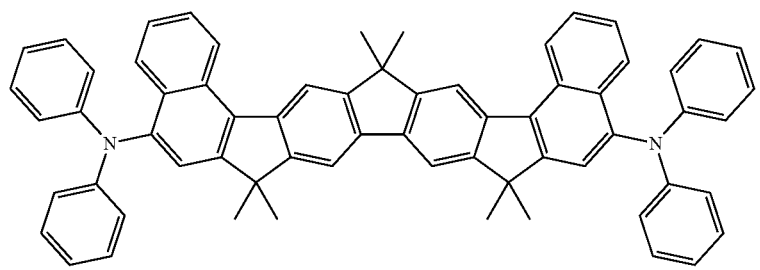 [SMILES: CC1(C)c2cc3c(cc2-c2cc4c(cc21)-c1c(cc(N(c2ccccc2)c2ccccc2)c2ccccc12)C4(C)C)C(C)(C)c1cc(N(c2ccccc2)c2ccccc2)c2ccccc2c1-3]
D9
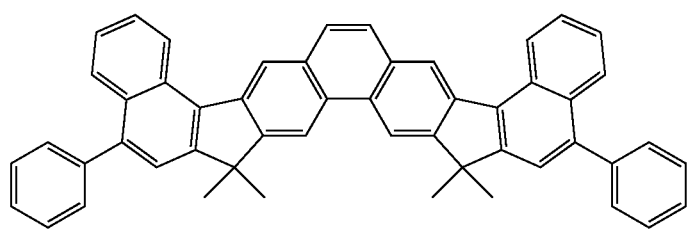 [SMILES: CC1(C)c2cc3c(ccc4cc5c(cc43)C(C)(C)c3cc(-c4ccccc4)c4ccccc4c3-5)cc2-c2c1cc(-c1ccccc1)c1ccccc21]
D10

TABLE 3-continued

Structures of the materials used

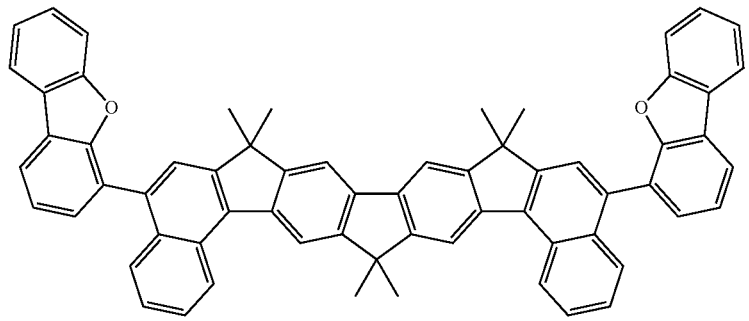 [SMILES: CC1(C)c2cc3c(cc2-c2cc4c(cc21)-c1c(cc(-c2cccc5c2oc2ccccc25)c2ccccc12)C4(C)C)C(C)(C)c1cc(-c2cccc4c2oc2ccccc24)c2ccccc2c1-3]

D11

D12

The invention claimed is:

1. A compound of formula (I):

$$Ar^1\!\!-\!\!\overset{X^1}{\triangle}\!\!-\!\!Ar^2\!\!-\!\!\overset{X^1}{\triangle}\!\!-\!\!Ar^2\!\!-\!\!\overset{X^1}{\triangle}\!\!-\!\!Ar^1 \qquad (I)$$

wherein the groups $Ar^1$ are naphthyl groups, which are optionally substituted by one or more radicals $R^1$, and the groups $Ar^2$ are phenyl groups, which are optionally substituted by one or more radicals $R^2$; or one of the two groups $Ar^1$ is a phenyl group, which is optionally substituted by one or more radicals $R^1$, and the other of the two groups $Ar^1$ is a naphthyl group, which is optionally substituted by one or more radicals $R^1$, and the groups $Ar^1$ are phenyl groups, which are optionally substituted by one or more radicals $R^2$ $X^1$ is on each occurrence, identically or differently, $BR^3$, $C(R^3)_2$, —$C(R^3)_2$—$C(R^3)_2$—, —$C(R^3)_2$—O—, —$C(R^3)_2$—S—, —$R^3C$=$CR^3$—, —$R^3C$=$N$—, $Si(R^3)_2$, —$Si(R^3)_2$—$Si(R^3)_2$—, C=O, O, S, S=O, $SO_2$, $NR^3$, $PR^3$, or P(=O)$R^3$;

$R^1$, $R^2$, and $R^3$ are on each occurrence, identically or differently, H, D, F, Cl, Br, I, C(=O)$R^4$, CN, Si($R^4$)$_3$, N($R^4$)$_2$, P(=O) ($R^4$)$_2$, O$R^4$, S(=O)$R^4$, S(=O)$_2R^4$, a straight-chain alkyl or alkoxy group having 1 to 20 C atoms, a branched or cyclic alkyl or alkoxy group having 3 to 20 C atoms, or an alkenyl or alkynyl group having 2 to 20 C atoms, wherein the above-mentioned groups are optionally substituted by one or more radicals $R^4$ and wherein one or more $CH_2$ groups in the above-mentioned groups are optionally replaced by —$R^4C$=$CR^4$—, —C≡C—, Si($R^4$)$_2$, C=O, C=$NR^4$, —C(=O)O—, —C(=O)$NR^4$—, $NR^4$, P(=O)($R^4$), —O—, —S—, SO, or $SO_2$, or an aromatic or heteroaromatic ring system having 5 to 30 aromatic ring atoms, which is optionally substituted by one or more radicals $R^4$, and wherein two or more radicals $R^3$ are optionally linked to one another so as to define a ring;

$R^4$ is on each occurrence, identically or differently, H, D, F, Cl, Br, I, C(=O)$R^5$, CN, Si($R^5$)$_3$, N($R^5$)$_2$, P(=O) ($R^5$)$_2$, O$R^5$, S(=O)$R^5$, S(=O)$_2R^5$, a straight-chain alkyl or alkoxy group having 1 to 20 C atoms, a branched or cyclic alkyl or alkoxy group having 3 to 20 C atoms, or an alkenyl or alkynyl group having 2 to 20 C atoms, wherein the above-mentioned groups are optionally substituted by one or more radicals $R^5$ and wherein one or more $CH_2$ groups in the above-mentioned groups are optionally replaced by —$R^5C$=$CR^5$—, —C≡C—, Si($R^5$)$_2$, C=O, C=$NR^5$, —C(=O)O—, —C(=O)$NR^5$—, $NR^5$, P(=O)($R^5$), —O—, —S—, SO, or $SO_2$, or an aromatic or heteroaromatic ring system having 5 to 30 aromatic ring atoms, which is optionally substituted by one or more radicals $R^5$, and wherein two or more radicals $R^4$ are optionally linked to one another so as to define a ring;

$R^5$ is on each occurrence, identically or differently, H, D, F, or an aliphatic, aromatic, or heteroaromatic organic radical having 1 to 20 C atoms, wherein one or more H atoms are optionally replaced by D or F, and wherein two or more substituents $R^5$ are optionally linked to one another so as to define a ring.

2. The compound of claim 1, wherein the bonds from the groups $Ar^2$ to the adjacent group $Ar^1$ or $Ar^2$ are each present in the para-position to one another.

3. The compound of claim 1, wherein $X^1$ is selected on each occurrence, identically or differently, from the group consisting of $C(R^3)_2$, —$C(R^3)_2$—$C(R^3)_2$—, —$C(R^3)_2$—O—, $Si(R^3)_2$, O, S, and $NR^3$.

4. The compound of claim 1, wherein $X^1$ is $C(R^3)_2$.

5. The compound of claim 1, wherein $R^2$ is H or D.

6. An oligomer, polymer, or dendrimer comprising one or more compounds of claim 1, wherein the bond(s) to the polymer, oligomer, or dendrimer are optionally localised at any position in formula (I) substituted by $R^1$, $R^2$, or $R^3$.

7. A formulation comprising at least one compound of claim 1 and at least one solvent.

8. A formulation comprising at least one oligomer, polymer, or dendrimer of claim 6 and at least one solvent.

9. An electronic device comprising at least one oligomer, polymer, or dendrimer of claim 6, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices.

10. The electronic device of claim 9, wherein the electronic device is selected from the group consisting of organic electroluminescent devices comprising a cathode, an anode, and at least one organic layer, wherein the at least one organic layer comprises the at least one oligomer, polymer, or dendrimer.

11. The electronic device of claim 10, wherein the at least one oligomer, polymer, or dendrimer is present as a hole-transport material in a hole-transport layer, as an emitting compound in an emitting layer, or as a matrix compound in an emitting layer.

12. An electronic device comprising at least one compound of claim 1, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices.

13. The electronic device of claim 12, wherein the electronic device is selected from the group consisting of organic electroluminescent devices comprising a cathode, an anode, and at least one organic layer, wherein the at least one organic layer comprises the at least one compound.

14. The electronic device of claim 13, wherein the at least one compound is present as a hole-transport material in a hole-transport layer, as an emitting compound in an emitting layer, or as a matrix compound in an emitting layer.

15. A process for preparing a compound of claim 1, comprising the steps of performing at least one metal-catalysed coupling reaction and performing at least one ring-closure reaction.

* * * * *